United States Patent
Legrand et al.

(10) Patent No.: US 9,409,895 B2
(45) Date of Patent: Aug. 9, 2016

(54) AUTOTAXIN INHIBITORS

(71) Applicants: Darren Mark Legrand, East Grinstead (GB); Vikki Furminger, Horsham (GB); Christopher Thomson, Horsham (GB); Owen Rhys Hughes, Derbyshire (GB); Emily Stanley, Horsham (GB)

(72) Inventors: Darren Mark Legrand, East Grinstead (GB); Vikki Furminger, Horsham (GB); Christopher Thomson, Horsham (GB); Owen Rhys Hughes, Derbyshire (GB); Emily Stanley, Horsham (GB)

(73) Assignee: Novartis AG, Basel (CH)

( * ) Notice: Subject to any disclaimer, the term of this patent is extended or adjusted under 35 U.S.C. 154(b) by 42 days.

(21) Appl. No.: 13/833,460

(22) Filed: Mar. 15, 2013

(65) Prior Publication Data

US 2014/0171403 A1    Jun. 19, 2014

Related U.S. Application Data

(60) Provisional application No. 61/739,214, filed on Dec. 19, 2012.

(51) Int. Cl.

| | | |
|---|---|---|
| C07D 249/08 | (2006.01) | |
| C07D 401/12 | (2006.01) | |
| C07D 403/12 | (2006.01) | |
| C07D 413/12 | (2006.01) | |
| A61K 31/4192 | (2006.01) | |
| A61K 31/454 | (2006.01) | |
| A61K 31/55 | (2006.01) | |
| C07D 211/34 | (2006.01) | |
| C07D 295/185 | (2006.01) | |
| A61K 31/337 | (2006.01) | |
| A61K 31/4174 | (2006.01) | |
| A61K 31/4245 | (2006.01) | |
| A61K 31/426 | (2006.01) | |

(52) U.S. Cl.
CPC ............ *C07D 413/12* (2013.01); *A61K 31/337* (2013.01); *A61K 31/4174* (2013.01); *A61K 31/4192* (2013.01); *A61K 31/426* (2013.01); *A61K 31/4245* (2013.01); *A61K 31/454* (2013.01); *A61K 31/55* (2013.01); *C07D 211/34* (2013.01); *C07D 295/185* (2013.01); *C07D 401/12* (2013.01); *C07D 403/12* (2013.01); *C07D 249/08* (2013.01)

(58) Field of Classification Search
CPC .. C07D 401/12; C07D 403/12; C07D 413/12; C07D 249/08
See application file for complete search history.

(56) References Cited

U.S. PATENT DOCUMENTS

| 5,547,978 A | 8/1996 | Christensen et al. |
|---|---|---|
| 6,159,938 A | 12/2000 | Gyorkos et al. |
| 2004/0224901 A1 | 11/2004 | Chaturvedula et al. |

FOREIGN PATENT DOCUMENTS

| EP | 093379 A2 | 11/1983 |
|---|---|---|
| EP | 1564213 | 8/2005 |
| EP | 1698626 | 9/2006 |
| EP | 1340757 | 10/2006 |
| WO | 00/09542 | 2/2000 |
| WO | 02/080928 | 10/2002 |
| WO | 02/100352 | 12/2002 |
| WO | WO 03024946 A2 * | 3/2003 |
| WO | 2004/098589 | 11/2004 |
| WO | 2005/016883 | 2/2005 |
| WO | 2006/077419 | 7/2006 |
| WO | 2006/134318 | 12/2006 |
| WO | 2007/003962 | 1/2007 |
| WO | 2007/020194 | 2/2007 |
| WO | 2007/061862 | 5/2007 |
| WO | 2007/103719 | 9/2007 |
| WO | 2009/046804 A1 | 4/2009 |
| WO | 2009/046841 A2 | 4/2009 |
| WO | 2009/080226 | 7/2009 |
| WO | 2010/060532 A1 | 6/2010 |
| WO | 2010/063352 | 6/2010 |
| WO | 2010/097374 A1 | 9/2010 |
| WO | 2010/112116 A1 | 10/2010 |
| WO | 2010/112124 | 10/2010 |
| WO | 2010/115491 A2 | 10/2010 |
| WO | 2011/006569 | 1/2011 |
| WO | 2011/044978 A1 | 4/2011 |
| WO | 2011/116867 A1 | 9/2011 |
| WO | 2012/024620 A2 | 2/2012 |
| WO | 2012/068589 A2 | 5/2012 |
| WO | 2013/186159 A1 | 12/2013 |
| WO | 2014/048865 | 4/2014 |

OTHER PUBLICATIONS

Fulp et al., J. of Med. Chem., 55(6):2820-2834 (2012).
Brotherton-Pleiss, Bioorg. Med. Chem. Letters, 20(3):1031-1036 (2010).
McMasters et al., Bioorg. Med. Chem. Letters, 19(11):2965-2968 (2009).
Tsutsumi et al., J. Med. Chem., 37(21):3492-3502 (1994).
Tsutsumi et al., Bioorg. Med. Chem. Letters, 4(6):831-834 (1994).
Adang et al., Bioorganic Medicinal Chemistry Letters, 9(9):1227-1232 (1999).
Zheng et al., Tetrahedron Letters, 47(44):7793-7796 (2006).
Timmons et al., Bioorganic Medicinal Chemistry Letters, 18(6):2109-2113 (2008).
Whitby et al., Journal of the American Chemical Society, 133(26):10184-10194 (2011).

* cited by examiner

*Primary Examiner* — Samira Jean-Louis
(74) *Attorney, Agent, or Firm* — Shawn D. Britt

(57) ABSTRACT

The present invention relates to novel compounds that are autotaxin inhibitors, processes for their preparation, pharmaceutical compositions and medicaments containing them and to their use in diseases and disorders mediated by autotaxin.

11 Claims, No Drawings

AUTOTAXIN INHIBITORS

TECHNICAL FIELD

The present invention relates to novel compounds that are autotaxin inhibitors, processes for their preparation, pharmaceutical compositions and medicaments containing them and to their use in diseases and disorders mediated by autotaxin.

BACKGROUND

Autotaxin (ATX), also known as ectonucleotide pyrophosphatase/phosphodiesterase (ENPP2), is a secreted ectoenzyme known to possess lysophospholipase D activity (Umezu-Goto et al., 2002), and is responsible for producing the bioactive lipid mediator lysophosphatidic acid (LPA) by the hydrolysis of lysophosphatidylcholine (LPC) (Tokumura et al., 2002). LPA is highly implicated in the pathogenesis of a number of physio-pathological diseases, including cancer (Liu et al., 2009; Mills & Moolenaar, 2003), neuropathic pain (Inoue et al., 2004) and fibrosis (Tager et al., 2008). Following the production of LPA, the lipid binds to specific G protein-coupled receptors of which there are seven known isoforms (Noguchi et al., 2009). Binding of LPA activates multiple signalling pathways (Mills & Moolenaar, 2003) including cell migration (van Dijk et al., 1998), proliferation and survival (Brindley, 2004). Other cellular responses include smooth muscle contraction, apoptosis and platelet aggregation (Tigyi & Parrill, 2003).

ATX was originally identified as a cell motility-stimulating factor following isolation from human A2058 melanoma cells (Stracke et al., 1992). Subsequent work on the enzyme was focused towards its role as a motility factor due to its aberrant expression in many cancer types including breast and renal cancer (Stassar et al., 2001), Hodgkin's lymphoma (Baumforth et al., 2005), follicular lymphoma (Masuda et al., 2008), as well as fibrosis of the lung and kidney (Hama et al., 2004). Ten years following its discovery, ATX was characterised as a secreted lysophospholipase (lysoPLD) (Tokumura et al., 2002; Gesta et al., 2002). Since then ATX gene knockout mice have shown that the ATX-LPA signalling axis plays a vital role during embryonic development of the cardiovascular and neural system (Tanaka et al., 2006; van Meeteren et al., 2006), resulting in early embryonic lethality (Bachner et al., 1999).

ATX belongs to a family of proteins called nucleotide pyrophosphatase/phosphodiesterase (NPP), encoded for by the gene ENPP. The family consists of seven structurally related enzymes (ENPP 1-7) conserved within vertebrates which are numbered according to their discovery. They were originally defined by their ability to hydrolyse pyrophosphate or phosphodiester bonds of various nucleotides and nucleotides derivatives in vitro (Stefan et al., 1999; Goding et al., 1998; Gijsbers et al., 2001), though ENPP2 and choline phosphate esters (ENPP6 & 7) have specific activity for other extracellular non-nucleotide molecules. ENPP2 (ATX) is unique within the family as it is the only secreted protein, whereas other ENPP members are transmembrane proteins (Stefan et al., 2005).

WO02/100352 (Merck) and WO 02/080928 (Merck) relate to N-substituted nonaryl-heterocyclo amidyl NMDA/NR2B receptor antagonists for the treatment or prevention of migraines.

WO2010/115491 (Merck) and WO 2009/046841 (Merck) relate to piperidine and piperazine derivatives as ATX inhibitors.

WO2010/112116 (Merck) and WO 2010/112124 (Merck) relate to heterocyclic compounds as ATX inhibitors and WO 2011/044978 (Merck) relates to sulfoxide derivatives for treating tumours.

Hence, there is a need for further potent inhibitors of ATX.

DESCRIPTION OF THE EMBODIMENTS

In an embodiment 1 of the invention, there is provided a compound of formula (I)

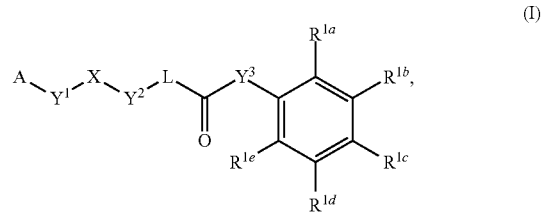

or a pharmaceutically acceptable salt thereof, wherein
A is selected from

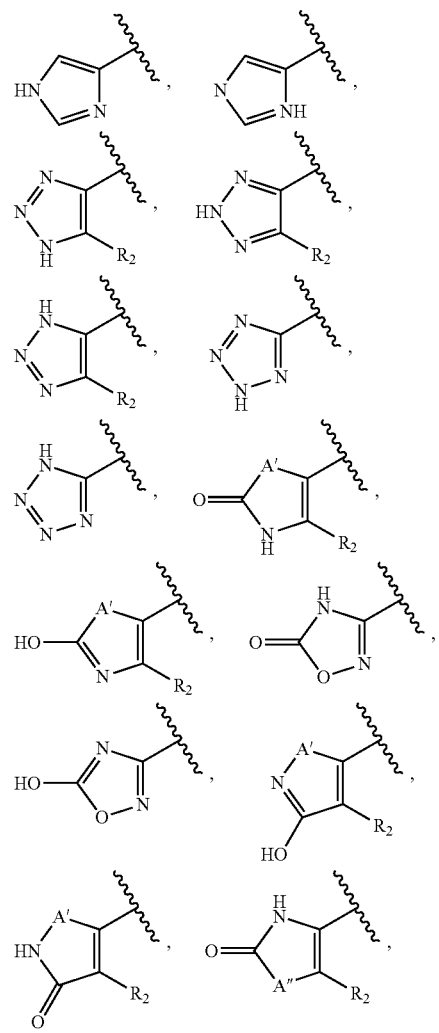

-continued

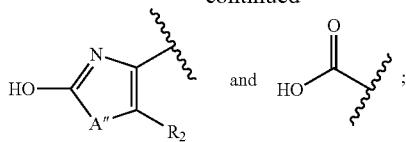 and 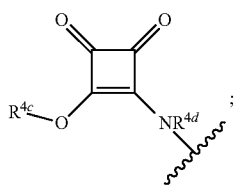;

A' is selected from O, S and NR$^{2a}$;
A" is selected from O and S;
Y$^1$ is —(CR$^{2b}$R$^{2c}$)$_m$— or —CH=CH—;
X is selected from —C(=O)—, —N(R$^3$)—C(=O)— and —C(=O)—N(R$^3$)—;
Y$^2$ is —(CR$^{4a}$R$^{4b}$)$_n$—,
m is selected from 0, 1, 2, 3, 4 and 5;
n is selected from 0, 1, 2, 3, 4 and 5;
wherein when Y$^1$ is —(CR$^{2b}$R$^{2c}$)$_m$— and A is not HO—C(=O)—, the sum of m and n is not less than 2 and no more than 5; and
wherein when Y$^1$ is —(CR$^{2b}$R$^{2c}$)$_m$— and A is HO—C(=O)—, the sum of m and n is not less than 2 and no more than 7; or
A-Y$^1$—X— is

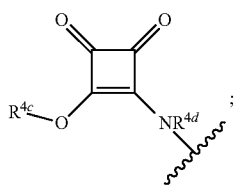;

L is selected from

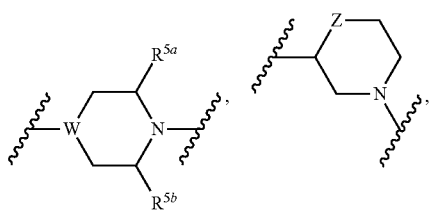

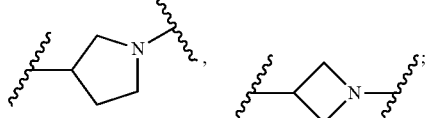

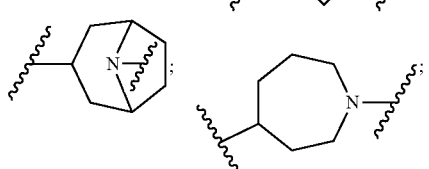

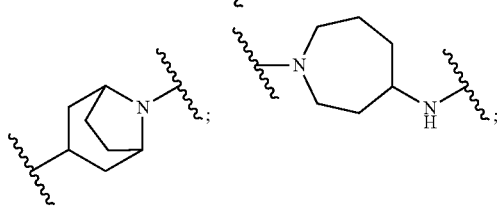

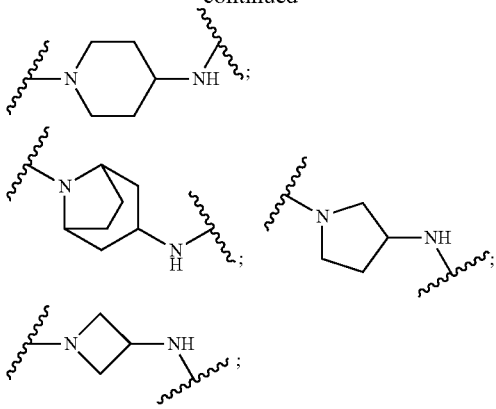

W is CH or N;
Z is selected from CH$_2$, O and NR$^{6c}$;
Y$^3$ is selected from —O—(CR$^{6a}$R$^{6b}$)—, —(CR$^{6c}$R$^{6d}$)—O—, —CH=CH—, —CR$^{6e}$R$^{6f}$—CR$^{6g}$R$^{6h}$—, and —O—(CR$^{6i}$R$^{6j}$—CR$^{6k}$R$^{6l}$)—;
R$^{1a}$, R$^{1b}$, R$^{1c}$, R$^{1d}$ and R$^{1e}$ are defined according to any one of
(a) R$^{1b}$ is halogen; R$^{1d}$ is halogen, CN, C$_{1-4}$haloalkyl or C$_{1-4}$haloalkoxy; and R$^{1a}$, R$^{1c}$ and R$^{1e}$ are H;
(b) R$^{1b}$ is halogen; R$^{1d}$ is halogen, CN, C$_{1-4}$haloalkyl or C$_{1-4}$haloalkoxy; R$^{1c}$ is halogen; and R$^{1a}$ and R$^{1e}$ are H;
(c) R$^{1b}$ is C$_{1-4}$alkyl; R$^{1d}$ is C$_{1-4}$alkyl, C$_{1-4}$haloalkoxy or CN; R$^{1a}$, R$^{1c}$ and R$^{1e}$ are H;
(d) R$^{1b}$ is CN; R$^{1d}$ is C$_{1-4}$ haloalkyl or C$_{1-4}$haloalkoxy; and R$^{1a}$, R$^{1c}$ and R$^{1e}$ are H;
(e) R$^{1b}$ is C$_{1-4}$haloalkyl or C$_{1-4}$haloalkoxy; R$^{1a}$, R$^{1c}$ and R$^{1e}$ are H; and R$^{1d}$ is H or CN;
(f) R$^{1a}$ is halogen; R$^{1c}$ is halogen, CN, C$_{1-4}$haloalkyl or C$_{1-4}$haloalkoxy; and R$^{1b}$, R$^{1d}$ and R$^{1e}$ are H;
(g) R$^{1c}$ is halogen, CN, C$_{1-4}$haloalkyl or C$_{1-4}$haloalkoxy; R$^{1a}$, R$^{1b}$ and R$^{1e}$ are H; and R$^{1d}$ is halogen, CN, C$_{1-4}$haloalkoxy, or H;
R$^2$ is selected from H, C$_{1-4}$alkyl and halogen;
R$^{2a}$, R$^{2b}$, R$^{2c}$, R$^3$, R$^{4a}$, R$^{4b}$, R$^{4c}$, R$^{4d}$, R$^{5a}$, R$^{5b}$, R$^{5c}$, R$^{6a}$, R$^{6b}$, R$^{6c}$, R$^{6d}$, R$^{6e}$, R$^{6f}$, R$^{6g}$, R$^{6h}$, R$^{6i}$, R$^{6j}$, R$^{6k}$ and R$^{6l}$ are independently selected from H and C$_{1-4}$alkyl.

In an embodiment 1.1 of the invention, there is provided a compound of formula (I)

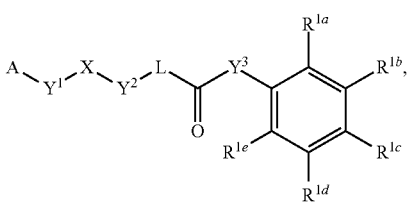

(I)

or a pharmaceutically acceptable salt thereof, wherein A is selected from

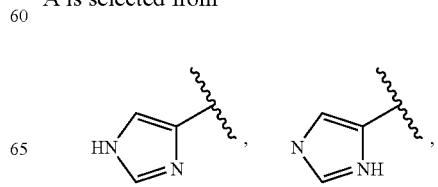

-continued

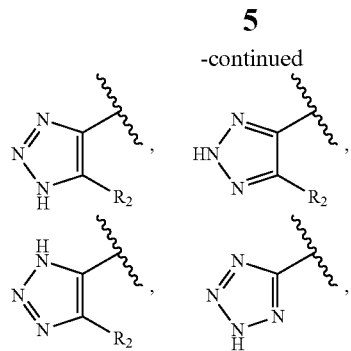

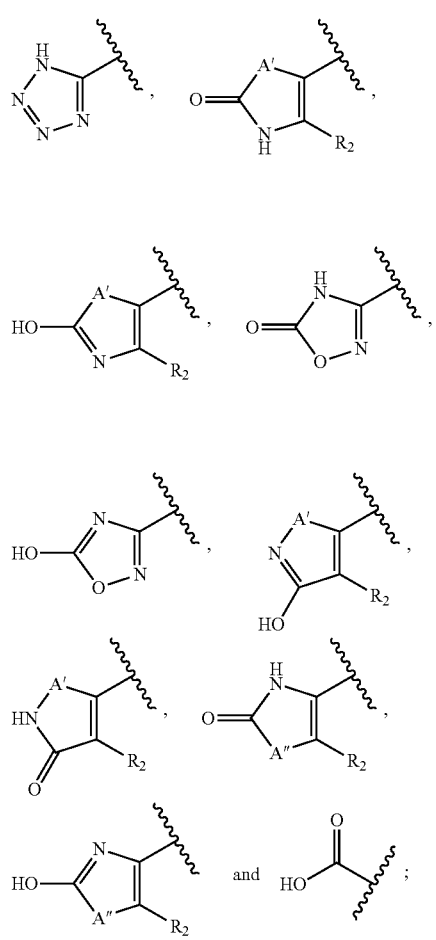

A-Y¹—X— is

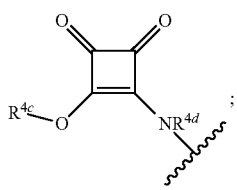

L is selected from

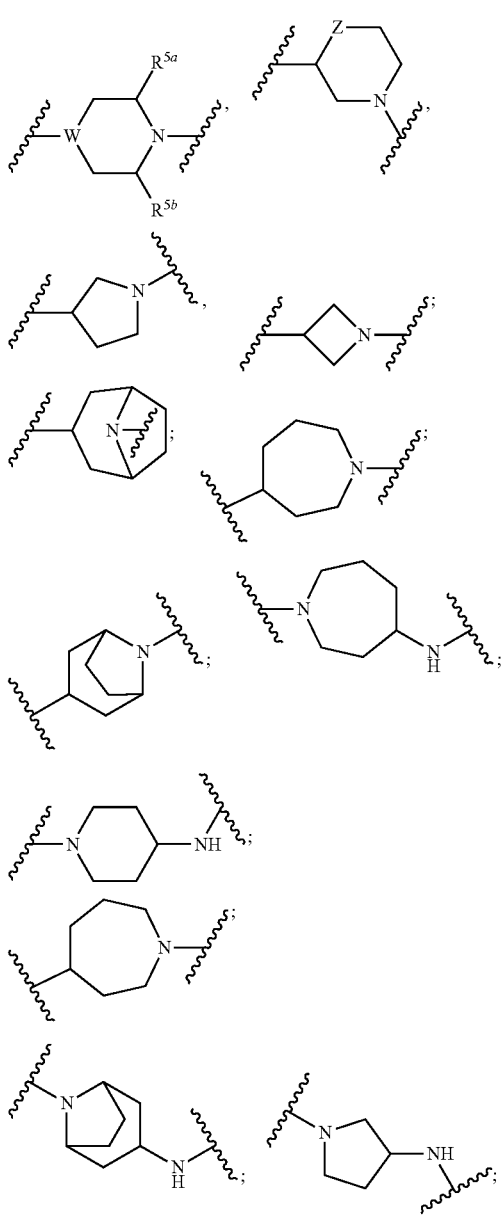

A' is selected from O, S and NR$^{2a}$;
A" is selected from O and S;
Y¹ is —(CR$^{2b}$R$^{2c}$)$_m$— or —CH=CH—;
X is selected from —C(=O)—, —N(R³)—C(=O)— and —C(=O)—N(R³)—;
Y² is —(CR$^{4a}$R$^{4b}$)$_n$—,
m is selected from 0, 1, 2, 3, 4 and 5;
n is selected from 0, 1, 2, 3, 4 and 5;
wherein when Y¹ is —(CR$^{2b}$R$^{2c}$)$_m$— and A is not HO—C(=O)—, the sum of m and n is not less than 2 and no more than 5; and
wherein when Y¹ is —(CR$^{2b}$R$^{2c}$)$_m$— and A is HO—C(=O)—, the sum of m and n is not less than 2 and no more than 7; or W is CH or N;

Z is selected from $CH_2$, O and $NR^{6d}$;

$Y^3$ is selected from $-O-(CR^{6a}R^{6b})-$, $-(CR^{6c}R^{6d})-O-$, $-CH=CH-$, $-CR^{6e}R^{6f}-CR^{6g}R^{6h}-$, and $-O-(CR^{6i}R^{6j}-CR^{6k}R^{6l})-$;

$R^{1a}, R^{1b}, R^{1c}, R^{1d}$ and $R^{1e}$ are defined according to any one of (a) $R^{1b}$ is halogen; $R^{1d}$ is halogen, CN, $C_{1-4}$haloalkyl or $C_{1-4}$haloalkoxy; and $R^{1a}$, and $R^{1e}$ are H;

(b) $R^{1b}$ is halogen; $R^{1d}$ is halogen, CN, $C_{1-4}$haloalkyl or $C_{1-4}$haloalkoxy; $R^{1d}$ is halogen; and $R^{1a}$ and $R^{1e}$ are H;

(c) $R^{1b}$ is $C_{1-4}$alkyl; $R^{1d}$ is $C_{1-4}$alkyl, $C_{1-4}$haloalkoxy or CN; $R^{1a}$, $R^{1c}$ and $R^{1e}$ are H;

(d) $R^{1b}$ is CN; $R^{1d}$ is $C_{1-4}$ haloalkyl or $C_{1-4}$haloalkoxy; and $R^{1a}$, $R^{1c}$ and $R^{1e}$ are H;

(e) $R^{1b}$ is $C_{1-4}$haloalkyl or $C_{1-4}$haloalkoxy; and $R^{1a}$, $R^{1c}$ and $R^{1e}$ are H; and $R^{1d}$ is H or CN;

(f) $R^{1a}$ is halogen; $R^{1c}$ is halogen, CN, $C_{1-4}$haloalkyl or $C_{1-4}$haloalkoxy; and $R^{1b}$, $R^{1d}$ and $R^{1e}$ are H;

(g) $R^{1c}$ is halogen, CN, $C_{1-4}$haloalkyl or $C_{1-4}$haloalkoxy; and $R^{1d}$, $R^{1b}$ and $R^{1e}$ are H; and $R^{1d}$ is halogen, CN, $C_{1-4}$haloalkoxy, or H;

$R^2$ is selected from H, $C_{1-4}$alkyl and halogen;

$R^{2a}, R^{2b}, R^{2c}, R^3, R^{4a}, R^{4b}, R^{4c}, R^{4d}, R^{5a}, R^{5b}, R^{5c}, R^{6a}, R^{6b}, R^{6c}, R^{6d}, R^{6e}, R^{6f}, R^{6g}, R^{6h}, R^{6i}, R^{6j}, R^{6k}$ and $R^{6l}$ are independently selected from H and $C_{1-4}$alkyl; and wherein when L is

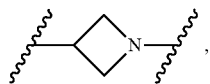

n is not 1.

In an embodiment 1.2 of the invention, there is provided a compound of formula (I)

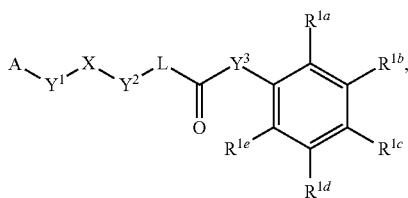

or a pharmaceutically acceptable salt thereof, wherein

A is selected from

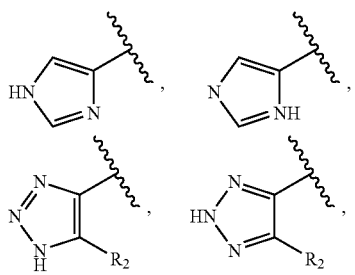

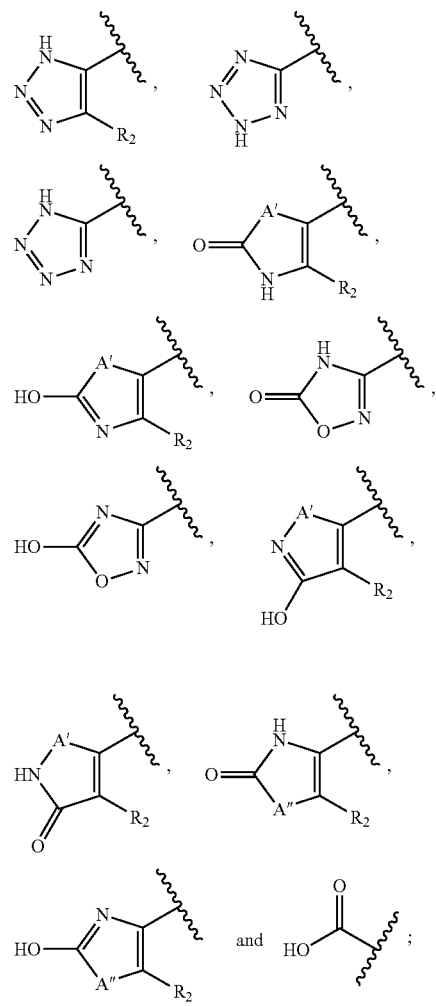

A' is selected from O, S and $NR^{2a}$;

A" is selected from O and S;

$Y^1$ is $-(CR^{2b}R^{2c})_m-$ or $-CH=CH-$;

X is selected from $-C(=O)-$, $-N(R^3)-C(=O)-$ and $-C(=O)-N(R^3)-$;

$Y^2$ is $-(CR^{4a}R^{4b})_n-$;

m is selected from 0, 1, 2, 3, 4 and 5;

n is selected from 0, 1, 2, 3, 4 and 5;

wherein when $Y^1$ is $-(CR^{2b}R^{2c})_m-$ the sum of m and n is not less than 2 and no more than 5;

or $A-Y^1-X-$ is

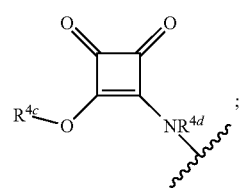

L is selected from

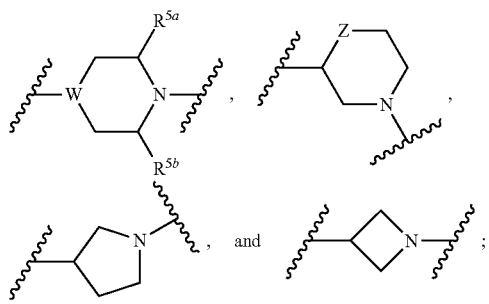

W is CH or N;
Z is selected from CH$_2$, O and NR$^{5c}$;
Y$^3$ is selected from —O—(CR$^{6a}$R$^{6b}$)—, —(CR$^{6c}$R$^{6d}$)—O—, —CH=CH— and —CR$^{6e}$R$^{6f}$—CR$^{6g}$R$^{6h}$—; R$^{1a}$, R$^{1b}$, R$^{1c}$, R$^{1d}$ and R$^{1e}$ are defined according to any one of
(a) R$^{1b}$ and R$^{1d}$ is halogen, and R$^{1a}$, R$^{1c}$ and R$^{1e}$ is H;
(b) R$^{1a}$ and R$^{1c}$ is halogen, and R$^{1b}$, R$^{1d}$ and R$^{1e}$ is H;
(c) R$^{1c}$ is C$_{1-4}$ haloalkyl, in particular CF$_3$, or C$_{1-4}$haloalkoxy, and R$^{1a}$, R$^{1b}$ and R$^{1e}$ are H, and R$^{1d}$ is halogen, C$_{1-4}$ alkyl, particularly methyl, or H;
(d) R$^{1b}$ is C$_{1-4}$haloalkyl, in particular CF$_3$, or C$_{1-4}$haloalkoxy, and R$^{1a}$, R$^{1c}$ and R$^{1e}$ are H, and R$^{1d}$ is halogen, C$_{1-4}$ alkyl, particularly methyl, or H;
(e) R$^{1b}$ is C$_{1-4}$alkyl, R$^{1d}$ is halogen, and R$^{1a}$, R$^{1c}$ and R$^{1e}$ is H; and
(f) R$^{1b}$ is CN, R$^{1d}$ is halogen, and R$^{1a}$, R$^{1c}$ and R$^{1e}$ is H;
R$^2$ is selected from H, C$_{1-4}$alkyl and halogen;
R$^{2a}$, R$^{2b}$, R$^{2c}$, R$^3$, R$^{4a}$, R$^{4b}$, R$^{4c}$, R$^{4d}$, R$^{5a}$, R$^{5b}$, R$^{5c}$, R$^{6a}$, R$^{6b}$, R$^{6c}$, R$^{6d}$, R$^{6e}$, R$^{6f}$, R$^{6g}$ and R$^{6h}$ are independently selected from H and C$_{1-4}$alkyl.

In an embodiment 2 of the invention, there is provided a compound of formula (I)

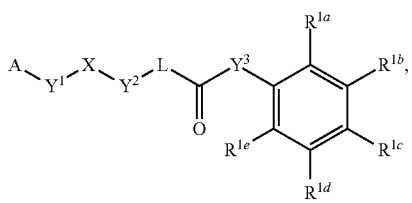

(I)

or a pharmaceutically acceptable salt thereof, wherein
A is selected from

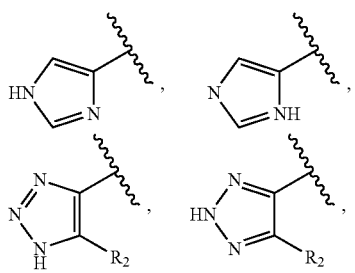

-continued

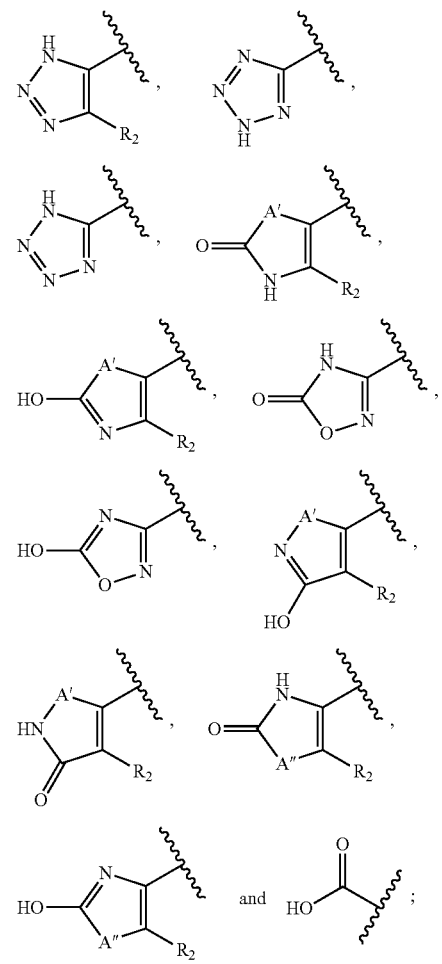

A' is selected from O, S and NR$^{2a}$;
A" is selected from O and S;
Y$^1$ is —(CR$^{2b}$R$^{2c}$)$_m$— or —CH=CH—;
X is selected from —C(=O)—, —N(R$^3$)—C(=O)— and —C(=O)—N(R$^3$)—;
Y$^2$ is —(CR$^{4a}$R$^{4b}$)$_n$—,
m is selected from 0, 1, 2, 3, 4 and 5;
n is selected from 0, 1, 2, 3, 4 and 5;
wherein when Y$^1$ is —(CR$^{2b}$R$^{2c}$)$_m$— the sum of m and n is not less than 2 and no more than 5;

or
A-Y$^1$—X— is

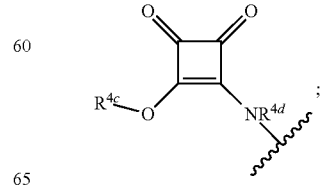

L is selected from

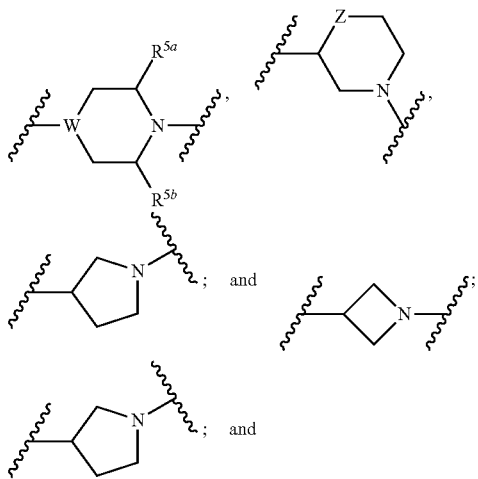

W is CH or N;
Z is selected from CH$_2$, O and NR$^{5c}$;
Y$^3$ is selected from —O—(CR$^{6a}$R$^{6b}$)—, —(CR$^{6c}$R$^{6d}$)—O—, —CH=CH— and —CR$^{6e}$R$^{6f}$—CR$^{6g}$R$^{6h}$—; R$^{1a}$, R$^{1b}$, R$^{1c}$, R$^{1d}$ and R$^{1e}$ are defined according to any one of
(a) R$^{1b}$ and R$^{1d}$ is halogen, and R$^{1a}$, R$^{1c}$ and R$^{1e}$ is H;
(b) R$^{1c}$ is C$_{1-4}$haloalkyl, in particular CF$_3$, and R$^{1d}$, R$^{1b}$, R$^{1d}$ and R$^{1e}$ are H;
(c) R$^{1b}$ is C$_{1-4}$alkyl, R$^{1d}$ is halogen, and R$^{1a}$, R$^{1c}$ and R$^{1e}$ is H;
(d) R$^{1b}$ is CN, R$^{1d}$ is halogen, and R$^{1a}$, R$^{1c}$ and R$^{1e}$ is H; and
(e) R$^{1a}$ and R$^{1c}$ is halogen, and R$^{1b}$, R$^{1d}$ and R$^{1e}$ is H;
R$^2$ is selected from H, C$_{1-4}$alkyl and halogen;
R$^{2a}$, R$^{2b}$, R$^{2c}$, R$^3$, R$^{4a}$, R$^{4b}$, R$^{4c}$, R$^{4d}$, R$^{5a}$, R$^{5b}$, R$^{5c}$, R$^{6a}$, R$^{6b}$, R$^{6c}$, R$^{6d}$, R$^{6e}$, R$^{6f}$, R$^{6g}$ and R$^{6h}$ are independently selected from H and C$_{1-4}$alkyl.

DEFINITIONS

"Halo" or "halogen", as used herein, may be fluoro, chloro, bromo or iodo.

"C$_{1-4}$ alkyl", as used herein, denotes straight chain or branched alkyl having 1-4 carbon atoms. If a different number of carbon atoms is specified, such as C$_6$ or C$_3$, then the definition is to be amended accordingly, such as "C$_1$-C$_4$ alkyl" will represent methyl, ethyl, propyl, isopropyl, butyl, isobutyl, sec-butyl and tert-butyl.

"C$_{1-4}$ haloalkyl", as used herein, denotes straight chain or branched alkyl having 1-4 carbon atoms with at least one hydrogen substituted with a halogen. If a different number of carbon atoms is specified, such as C$_6$ or C$_3$, then the definition is to be amended accordingly, such as "C$_1$-C$_4$-Haloalkyl" will represent methyl, ethyl, propyl, isopropyl, butyl, isobutyl, sec-butyl and tert-butyl that have at least one hydrogen substituted with halogen, such as where the halogen is fluorine: CF$_3$CF$_2$—, (CF$_3$)$_2$CH—, CH$_3$—CF$_2$—, CF$_3$CF$_2$—, CF$_3$, CF$_2$H—, CF$_3$CF$_2$CHCF$_3$ or CF$_3$CF$_2$CF$_2$CF$_2$—.

"C$_{1-4}$ haloalkoxy" as used herein refers to an —O—C$_{1-4}$ alkyl group wherein C$_{1-4}$ alkyl is as defined herein and substituted with one or more halogen groups, e.g. —O—CF$_3$.

The term "a," "an," "the" and similar terms used in the context of the present invention (especially in the context of the claims) are to be construed to cover both the singular and plural unless otherwise indicated herein or clearly contradicted by the context.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, when one embodiment refers to several other embodiments by using the term "according to any one of", for example "according to any one of embodiments 1 to 5", then said embodiment refers not only to embodiments indicated by the integers such as 1 and 2 but also to embodiments indicated by numbers with a decimal component such as 1.1, 1.2 or 2.1, 2.2, 2.3. For example, "according to any one of embodiments 1 to 3" means according to any one of embodiments 1, 1.1, 2, 3, 3.1, 3.2, 3.3, 3.4, 3.5, 3.6, 3.7.

Various embodiments of the invention are described herein. It will be recognized that features specified in each embodiment may be combined with other specified features to provide further embodiments.

In an embodiment 3 of the invention, there is provided a compound or salt according to any one of embodiments 1 to 2, wherein
R$^{1a}$, R$^{1b}$, R$^{1c}$, R$^{1d}$ and R$^{1e}$ are defined according to any one of
(a) R$^{1b}$ is halogen, R$^{1d}$ is halogen, CN, C$_{1-4}$haloalkyl or C$_{1-4}$haloalkoxy, and R$^{1a}$, R$^{1c}$ and R$^{1e}$ is H;
(b) R$^{1b}$ is halogen, R$^{1d}$ is halogen, CN, C$_{1-4}$haloalkyl or C$_{1-4}$haloalkoxy, R$^{1c}$ is halogen, and R$^{1a}$ and R$^{1e}$ is H;
(c) R$^{1b}$ is C$_{1-4}$alkyl, R$^{1d}$ is C$_{1-4}$alkyl, C$_{1-4}$haloalkoxy or CN, R$^{1a}$, R$^{1c}$ and R$^{1e}$ is H;
(d) R$^{1b}$ is CN, R$^{1d}$ is C$_{1-4}$ haloalkyl or C$_{1-4}$haloalkoxy, and R$^{1a}$, R$^{1c}$ and R$^{1e}$ is H;
(f) R$^{1a}$ is halogen, R$^{1c}$ is halogen, CN, C$_{1-4}$haloalkyl or C$_{1-4}$haloalkoxy, and R$^{1b}$, R$^{1d}$ and R$^{1e}$ is H; and
(g) R$^{1c}$ is halogen, CN, C$_{1-4}$haloalkyl or C$_{1-4}$haloalkoxy, and R$^{1a}$, R$^{1b}$ and R$^{1e}$ are H, and R$^{1d}$ is halogen, CN, C$_{1-4}$haloalkyl or C$_{1-4}$haloalkoxy, or H.

In an embodiment 3.1 of the invention, there is provided a compound or salt according to any one of embodiments 1 to 2, wherein
R$^{1a}$, R$^{1b}$, R$^{1c}$, R$^{1d}$ and R$^{1e}$ are defined according to any one of
(a) R$^{1b}$ is halogen, R$^{1d}$ is halogen, CN, C$_{1-4}$haloalkyl or C$_{1-4}$haloalkoxy, and R$^{1a}$, R$^{1c}$ and R$^{1e}$ is H;
(c) R$^{1b}$ is C$_{1-4}$alkyl, R$^{1d}$ is C$_{1-4}$alkyl, C$_{1-4}$haloalkoxy or CN, R$^{1a}$, R$^{1c}$ and R$^{1e}$ is H;

(f) $R^{1a}$ is halogen, $R^{1c}$ is halogen, CN, $C_{1-4}$haloalkyl or $C_{1-4}$haloalkoxy, and $R^{1b}$, Rid and $R^{1e}$ is H; and (g) $R^{1c}$ is halogen, CN, $C_{1-4}$haloalkyl or $C_{1-4}$haloalkoxy, and $R^{1a}$, $R^{1b}$ and $R^{1e}$ are H, and $R^{1d}$ is halogen, CN, $C_{1-4}$haloalkyl or $C_{1-4}$haloalkoxy, or H.

In an embodiment 3.2 of the invention, there is provided a compound or salt according to any one of embodiments 1 to 2, wherein $R^{1a}$, $R^{1b}$, $R^{1c}$, $R^{1d}$ and $R^{1e}$ are defined according to any one of (a) $R^{1b}$ is fluoro, chloro or bromo; $R^{1d}$ is fluoro, chloro, bromo, CN, methyl, trifluoromethyl or trifluoromethoxy; and $R^{1a}$, $R^{1c}$ and $R^{1e}$ are H;

(c) $R^{1b}$ is methyl; $R^{1d}$ is methyl, trfluoromethyl, trifluoromethoxy or CN; $R^{1a}$, $R^{1c}$ and $R^{1e}$ are H;

(f) $R^{1a}$ is fluoro, chloro or bromo; $R^{1c}$ is fluoro, chloro, bromo, CN, methyl, trifluoromethyl or trifluoromethoxy; and $R^{1b}$, $R^{1d}$ and $R^{1e}$ are H; and (g) $R^{1c}$ is fluoro, chloro, bromo, CN, methyl, trifluoromethyl or trifluoromethoxy; and $R^{1a}$, $R^{1b}$ and $R^{1e}$ are H; and $R^{1d}$ is fluoro, chloro, bromo, CN, methyl, trifluoromethyl, trifluoromethoxy, or H.

In an embodiment 3.3 of the invention, there is provided a compound or salt according to any one of embodiments 1 to 2, wherein $R^{1b}$ is fluoro, chloro or bromo; $R^{1d}$ is fluoro, chloro, bromo, CN, methyl, trifluoromethyl or trifluoromethoxy; and $R^{1a}$, $R^{1c}$ and $R^{1e}$ are H.

In an embodiment 3.4 of the invention, there is provided a compound or salt according to any one of embodiments 1 to 2, wherein $R^{1b}$ is methyl; $R^{1d}$ is methyl, trfluoromethyl, trifluoromethoxy or CN; $R^{1a}$, $R^{1c}$ and $R^{1e}$ are H.

In an embodiment 3.5 of the invention, there is provided a compound or salt according to any one of embodiments 1 to 2, wherein $R^{1a}$ is fluoro, chloro or bromo; $R^{1c}$ is fluoro, chloro, bromo, CN, methyl, trifluoromethyl or trifluoromethoxy; and $R^{1b}$, $R^{1d}$ and $R^{1e}$ are H.

In an embodiment 3.6 of the invention, there is provided a compound or salt according to any one of embodiments 1 to 2, wherein $R^{1c}$ is fluoro, chloro, bromo, CN, methyl, trifluoromethyl or trifluoromethoxy; $R^{1a}$, $R^{1b}$ and $R^{1e}$ are H; and $R^{1d}$ is fluoro, chloro, bromo, CN, methyl, trifluoromethyl, trifluoromethoxy, or H.

In an embodiment 3.7 of the invention, there is provided a compound or salt according to any one of embodiments 1 to 2, wherein $R^{1b}$ and $R^{1d}$ is halogen and $R^{1a}$, $R^{1c}$ and $R^{1e}$ is H.

In an embodiment 4 of the invention, there is provided a compound or salt according to embodiment 3.7, wherein $R^{1b}$ and $R^{1d}$ is chloro and $R^{1a}$, $R^{1c}$ and $R^{1e}$ is H.

In an embodiment 4.1 of the invention, there is provided a compound or salt according to any one of embodiments 1 to 3, wherein $R^b$ is CN, $R^d$ is methyl, and $R^a$, $R^c$ and $R^e$ are H.

In an embodiment 4.2 of the invention, there is provided a compound or salt according to any one of embodiments 1 to 3, wherein $R^b$ is fluoro, $R^d$ is chloro, and $R^a$, $R^c$ and $R^e$ are H.

In an embodiment 4.3 of the invention, there is provided a compound or salt according to any one of embodiments 1 to 3, wherein $R^b$ is chloro, $R^c$ is chloro, and $R^a$, $R^d$ and $R^e$ are H.

In an embodiment 4.4 of the invention, there is provided a compound or salt according to any one of embodiments 1 to 3, wherein $R^b$ is CN, $R^d$ is chloro, and $R^a$, $R^c$ and $R^e$ are H.

In an embodiment 4.5 of the invention, there is provided a compound or salt according to any one of embodiments 1 to 3, wherein $R^b$ is methyl, $R^d$ is methyl, and $R^a$, $R^c$ and $R^e$ are H.

In an embodiment 4.6 of the invention, there is provided a compound or salt according to any one of embodiments 1 to 3, wherein $R^c$ is $CF_3$, and $R^a$, $R^b$, $R^d$ and $R^e$ are H.

In an embodiment 4.7 of the invention, there is provided a compound or salt according to any one of embodiments 1 to 3, wherein $R^b$ is methyl, $R^d$ is chloro, and $R^a$, $R^c$ and $R^e$ are H.

In an embodiment 4.8 of the invention, there is provided a compound or salt according to any one of embodiments 1 to 3, wherein $R^b$ is methyl, $R^d$ is $CF_3$, and $R^a$, $R^c$ and $R^e$ are H.

In an embodiment 4.9 of the invention, there is provided a compound or salt according to any one of embodiments 1 to 3, wherein $R^b$ is bromo, $R^d$ is $CF_3$, and $R^a$, $R^c$ and $R^e$ are H.

In an embodiment 4.10 of the invention, there is provided a compound or salt according to any one of embodiments 1 to 3, wherein $R^b$ is CN, $R^d$ is $CF_3$, and $R^a$, $R^c$ and $R^e$ are H.

In an embodiment 4.11 of the invention, there is provided a compound or salt according to any one of embodiments 1 to 3, wherein $R^b$ is trifluoromethoxy, $R^d$ is chloro, and $R^a$, $R^c$ and $R^e$ are H.

In an embodiment 4.12 of the invention, there is provided a compound or salt according to any one of embodiments 1 to 3, wherein $R^b$ is chloro, $R^c$ is fluoro, $R^d$ is CN and $R^a$ and $R^e$ are H.

In an embodiment 5 of the invention, there is provided a compound or salt according to any one of embodiments 1 to 4, wherein $Y^3$ is selected from —O—$(CH_2)$—, —$(CH_2)$—O—, —CH=CH—, —$CH_2$—$CH_2$—, and —O—$(CH_2$—$CH_2)$—.

In an embodiment 5.1 of the invention, there is provided a compound or salt according to any one of embodiments 1 to 4, wherein $Y^3$ is —O—$(CR^{6a}R^{6b})$— or —$(CR^{6c}R^{6d})$—O—, particularly —O—$(CR^{6a}R^{6b})$—.

In an embodiment 6 of the invention, there is provided a compound or salt according to any one of embodiments 1 to 5, wherein X is selected from —N($R^3$)—C(=O)— and —C(=O)—N($R^3$)—, in particular —N(H)—C(=O)— and —C(=O)—N(H)—

In an embodiment 6.1 of the invention, there is provided a compound or salt according to any one of embodiments 1 to 5, wherein X is selected from —C(=O)—, —N(H)—C(=O)—, —C(=O)—N(H)— and —C(=O)—N($CH_3$)—.

In an embodiment 7 of the invention, there is provided a compound or salt according to any one of embodiments 1 to 6, wherein L is selected from

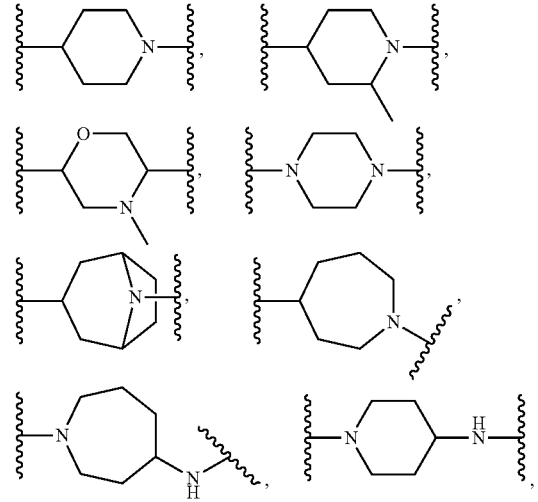

-continued

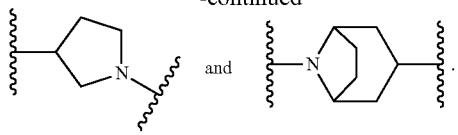 and

In an embodiment 7.1 of the invention, there is provided a compound or salt according to any one of embodiments 1 to 6, wherein L is selected from

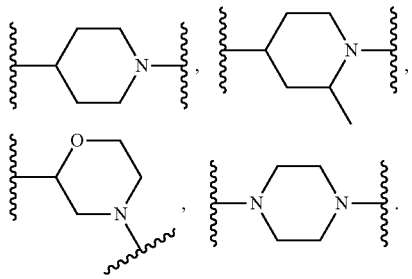

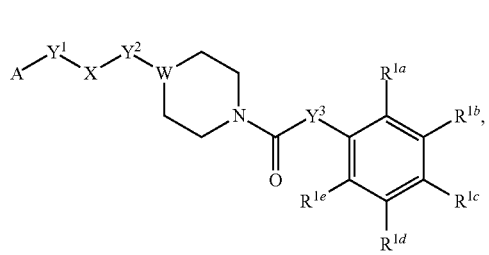

In an embodiment 8 of the invention, there is provided a compound or salt according to any one of embodiments 1 to 7 with formula (II)

$$A-Y^1-X-Y^2-W\begin{pmatrix}\\ \\N\end{pmatrix}N-\underset{O}{\overset{\|}{C}}-Y^3-\begin{pmatrix}R^{1a}\\ R^{1b}\\ R^{1c}\\ R^{1d}\end{pmatrix}R^{1e}$$ (II)

or a pharmaceutically acceptable salt thereof.

In an embodiment 8.1 of the invention, there is provided a compound or salt according to any one of embodiments 1 to 7, wherein
$Y^1$ is —$(CR^{2b}R^{2c})_m$— and $Y^2$ is —$(CR^{4a}R^{4b})_n$—;
m is selected from 0, 1, 2, 3, 4 and 5;
n is selected from 0, 1, 2 and 3; and wherein
the sum of m and n is not less than 2 and no more than 5.

In an embodiment 9 of the invention, there is provided a compound or salt according to embodiment 8, wherein
m is selected from 2, 3 and 4, and n is selected from 0 and 1; or
m is selected from 0 and 1, and n is selected from 2 and 3.

In an embodiment 10 of the invention, there is provided a compound or salt according to embodiment 9, wherein
m is selected from 2, 3 and 4, and n is 0.

In an embodiment 11 of the invention, there is provided a compound or salt according to embodiment 10, wherein
m is 3 or 4, and n is 0.

In an embodiment 12 of the invention, there is provided a compound or salt according to any one of embodiments 1 to 11, wherein
X is —C(=O)—N($R^3$)—.

In an embodiment 12.1 of the invention, there is provided a compound or salt according to any one of embodiments 1 to 7, wherein —$Y^1$—X—$Y^2$— is selected from

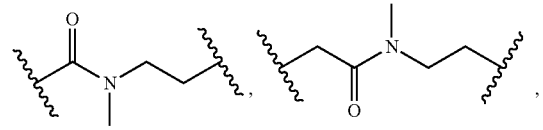

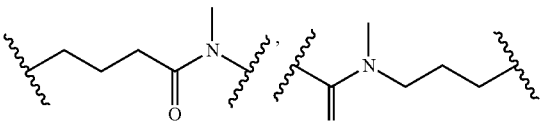

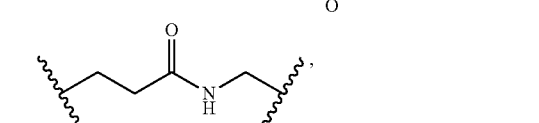

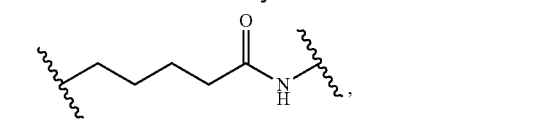

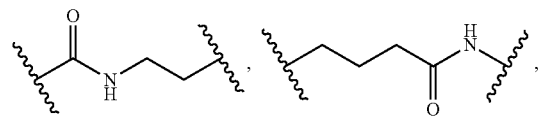

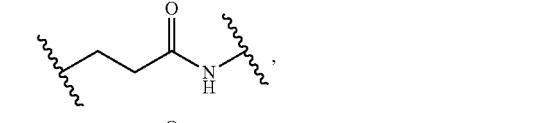

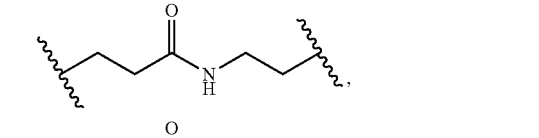

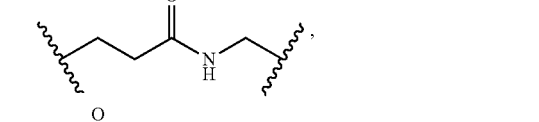

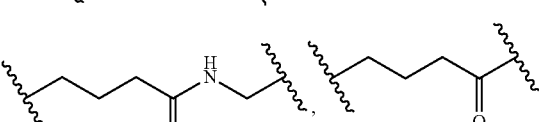

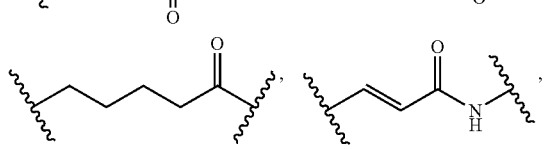

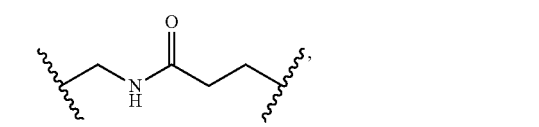

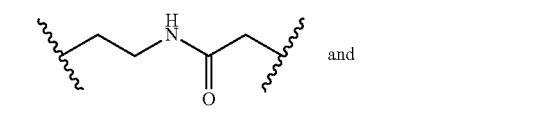 and

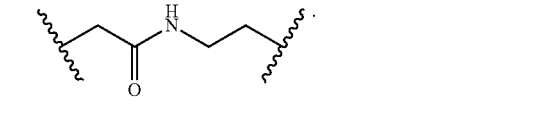

In an embodiment 12.2 of the invention, there is provided a compound or salt according to any one of embodiments 1 to 7, wherein —$Y^1$—X—$Y^2$— is selected from

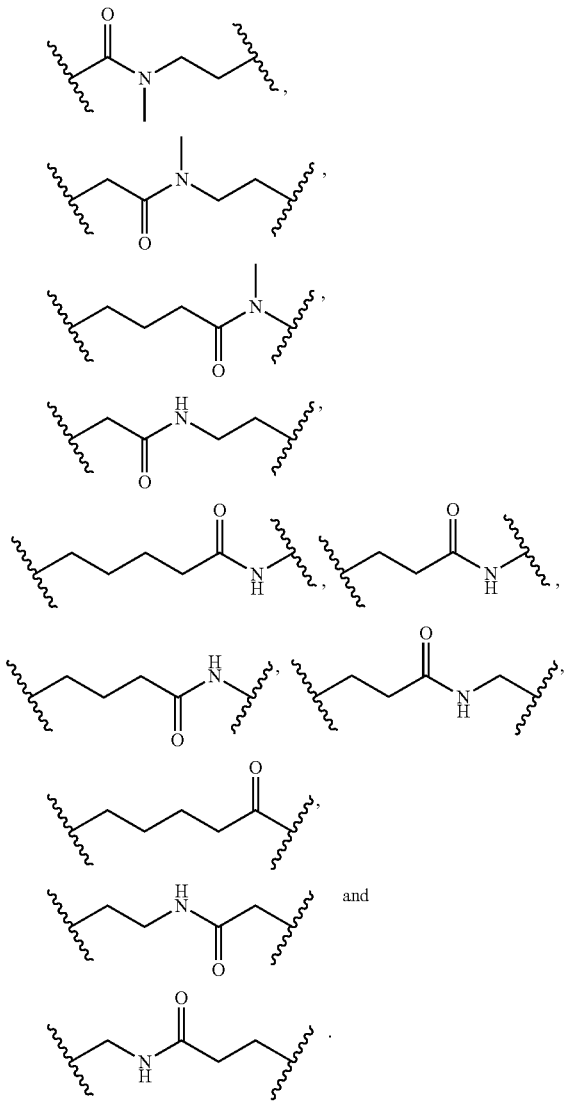

In an embodiment 12.3 of the invention, there is provided a compound or salt according to any one of embodiments 1 to 7, wherein —$Y^1$—X—$Y^2$— is selected from

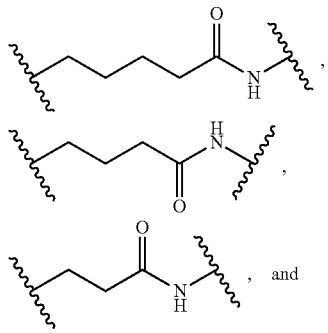

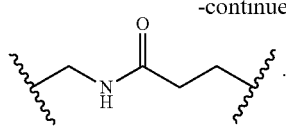

In an embodiment 13 of the invention, there is provided a compound or salt according to any one of embodiments 1 to 12, wherein
A is selected from

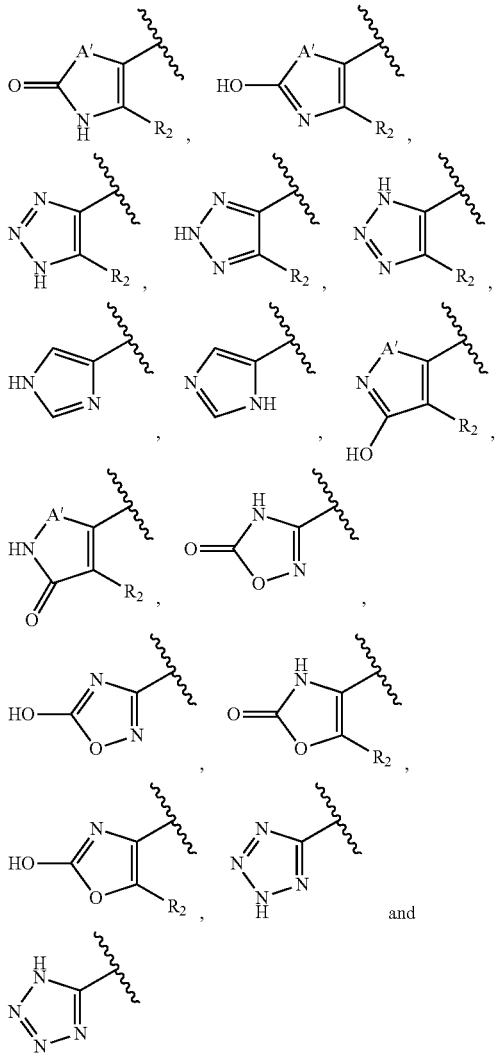

In an embodiment 14 of the invention, there is provided a compound or salt according to embodiment 13, wherein
A is selected from

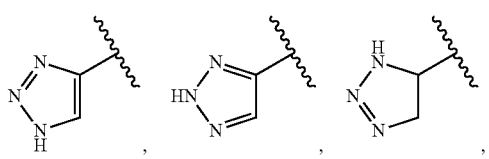

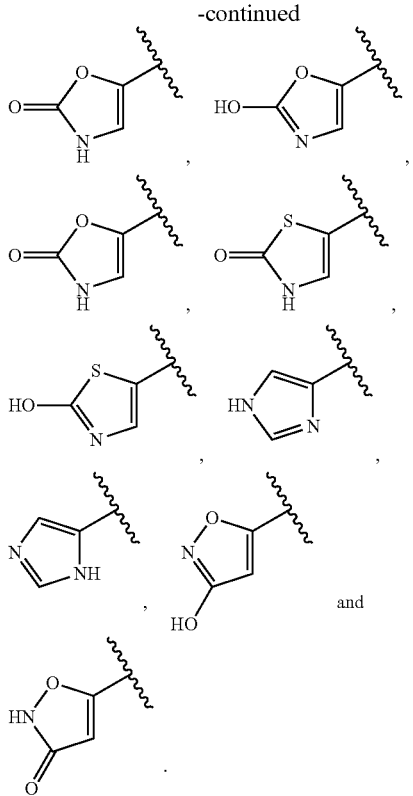
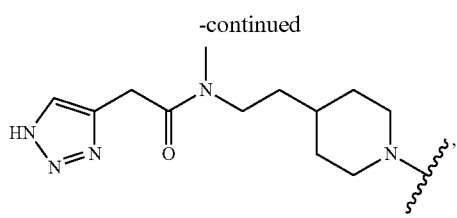
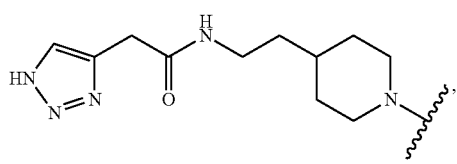
In an embodiment 15 of the invention, there is provided a compound or salt according to embodiment 14, wherein A is
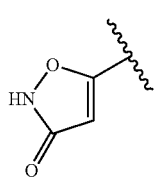
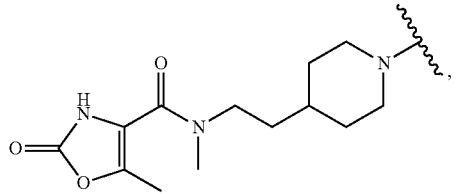
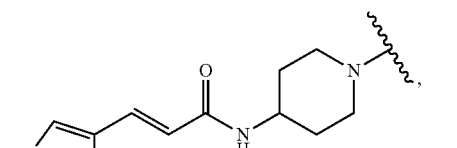
In an embodiment 16 of the invention, there is provided a compound or salt according to any one of embodiments 1 to 5, wherein A-Y¹—X—Y²-L- is selected from
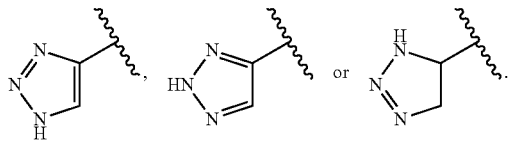 [SMILES: *c1c[nH]nn1 ; *c1cn[nH]n1 ; *C1CN=NN1]
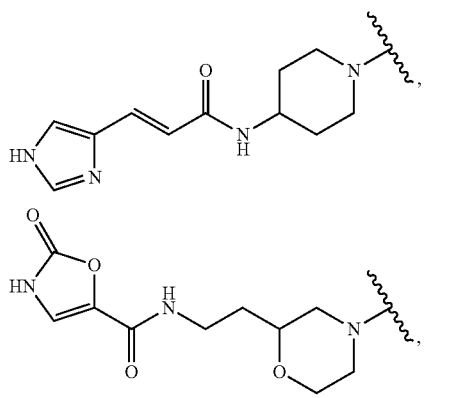
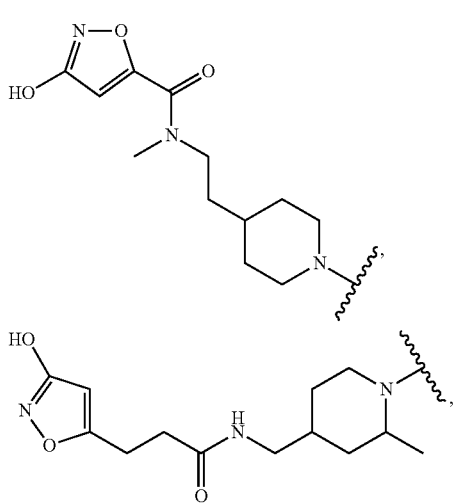
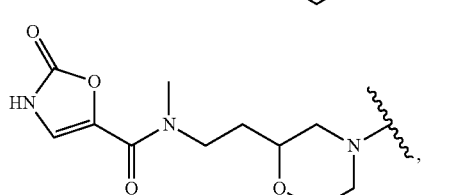
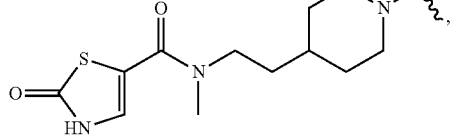
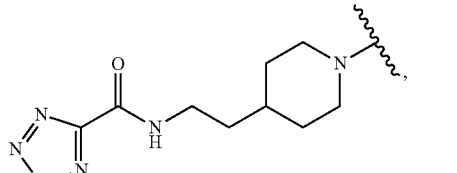
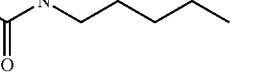
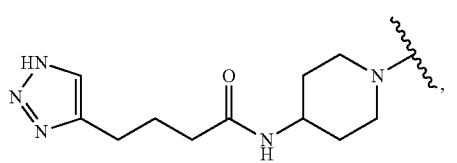

21
-continued
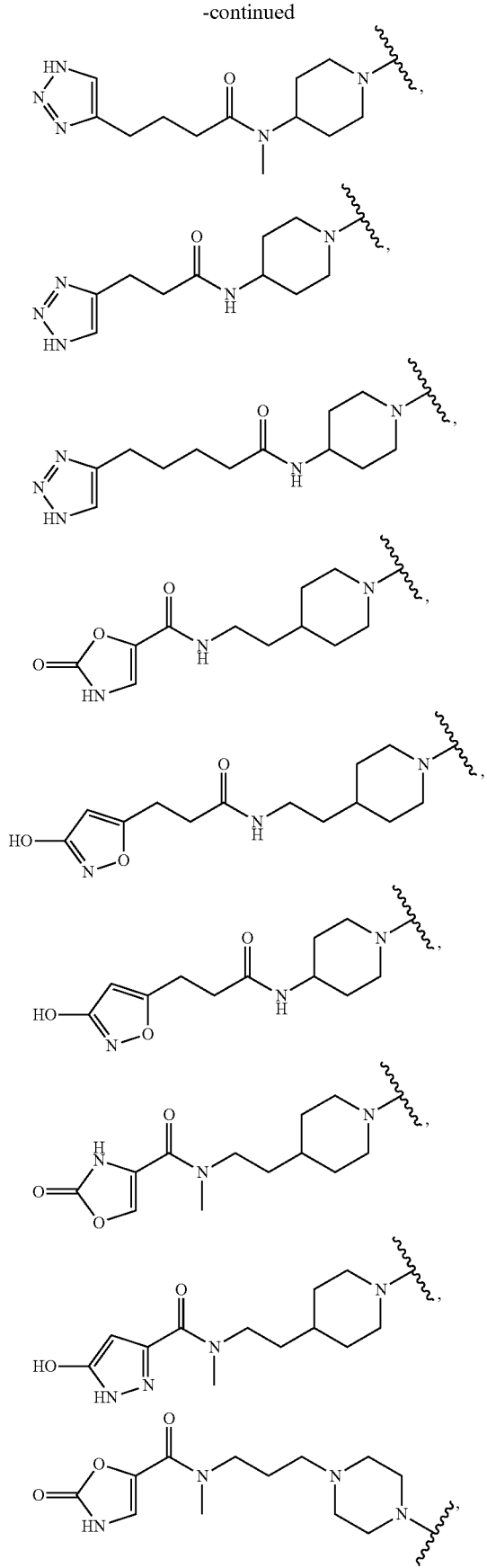
22
-continued
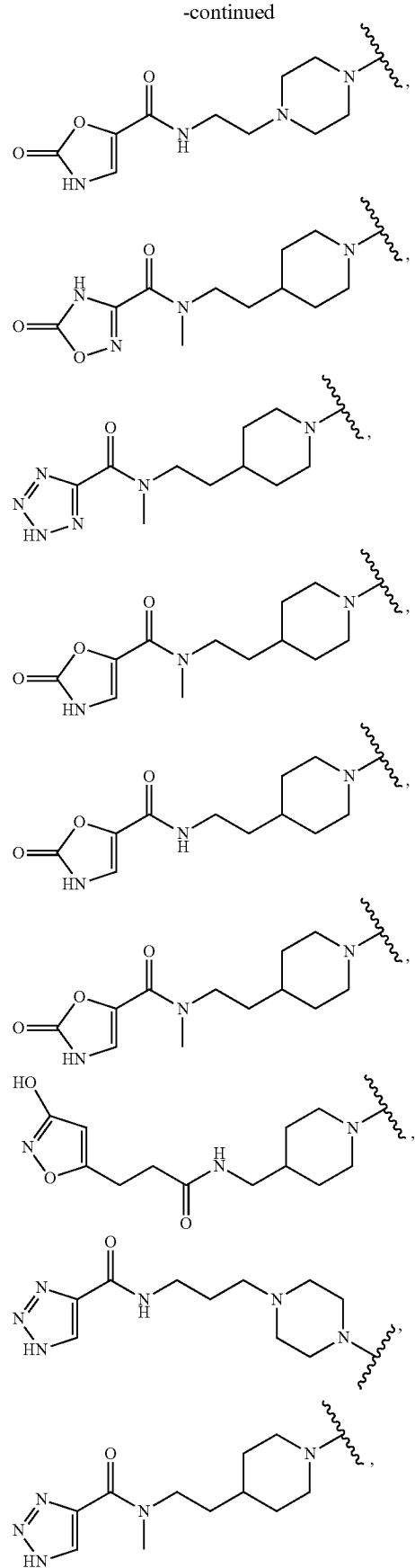

23
-continued
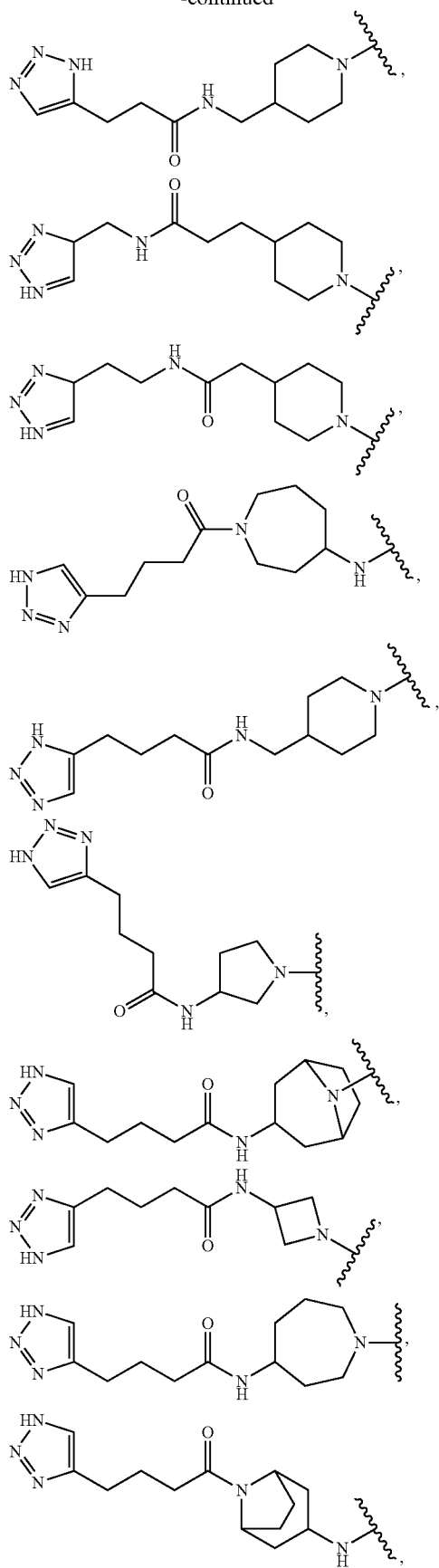
24
-continued
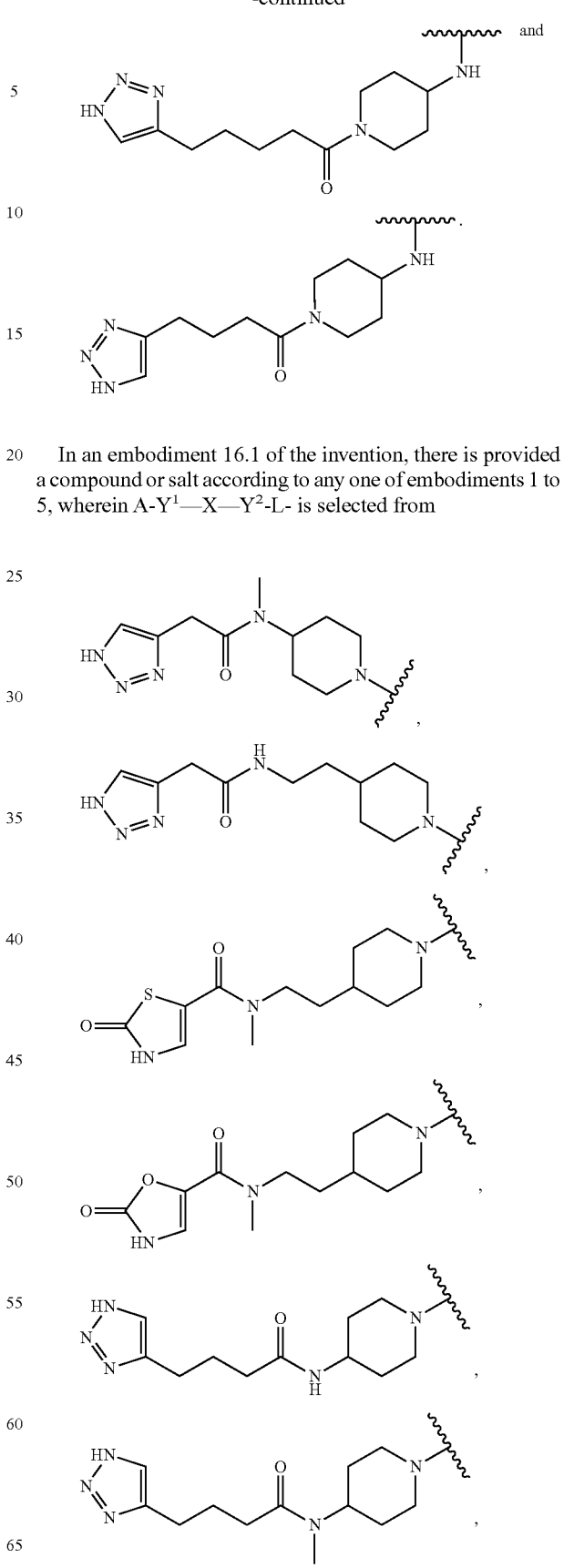
In an embodiment 16.1 of the invention, there is provided a compound or salt according to any one of embodiments 1 to 5, wherein A-$Y^1$—X—$Y^2$-L- is selected from -continued

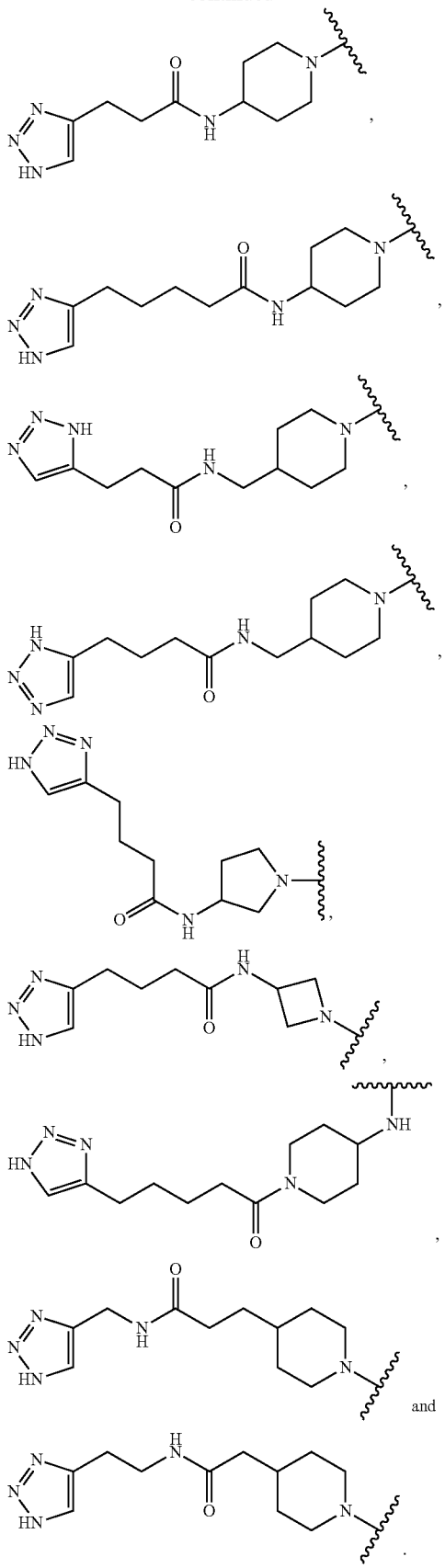

In an embodiment 16.2 of the invention, there is provided a compound or salt according to any one of embodiments 1 to 5, wherein A-Y$^1$—X—Y$^2$-L- is selected from

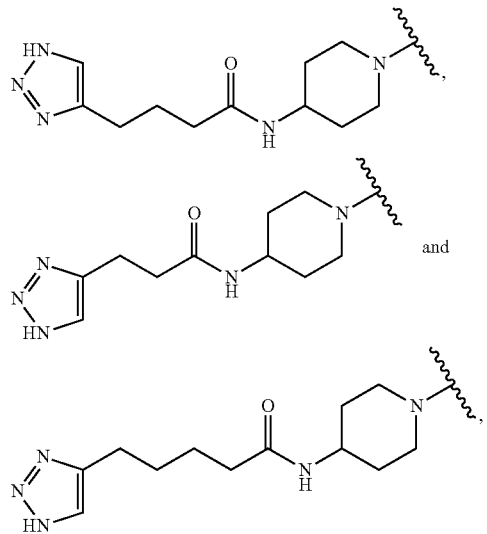

In an embodiment 17 of the invention, there is provided a compound or salt according to any one of embodiments 1 to 6, wherein W is CH.

In an embodiment 18 of the invention, there is provided a compound or salt according to any one of embodiments 1 to 7, of formula (III)

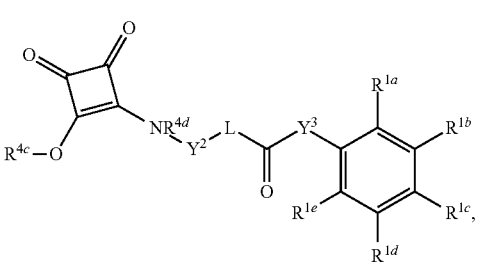

(III)

or a pharmaceutically acceptable salt thereof.

In an embodiment 19 of the invention, there is provided a compound or salt according to embodiment 18, wherein L is selected from

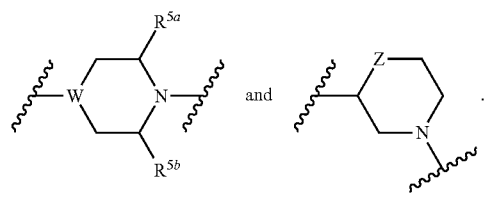

In an embodiment 20 of the invention, there is provided a compound or salt according to embodiment 18 or 19, wherein Y$^2$ is —(CR$^{4a}$R$^{4b}$)$_n$— and n is 1 or 2, particularly 2.

In an embodiment 21 of the invention, there is provided a compound or salt according to any one of embodiments 18 to 20, wherein $R^{4c}$ is methyl or ethyl and $R^{4d}$ is methyl or H.

In an embodiment 22 of the invention, there is provided a compound according to embodiment 1 or 2 selected from the group consisting of 3,5-dichlorobenzyl 4-(2-(3-hydroxy-N-methylisoxazole-5-carboxamido)ethyl)piperidine-1-carboxylate;

3,5-dichlorobenzyl 4-(2-((2-methoxy-3,4-dioxocyclobut-1-en-1-yl)(methyl)amino)ethyl)piperidine-1-carboxylate;

3,5-dichlorobenzyl 4-(2-((2-ethoxy-3,4-dioxocyclobut-1-en-1-yl)amino)ethyl)piperidine-1-carboxylate;

3,5-dichlorobenzyl 4-(2-((2-hydroxy-3,4-dioxocyclobut-1-en-1-yl)amino)ethyl)piperidine-1-carboxylate;

3,5-dichlorobenzyl 4-((3-(3-hydroxyisoxazol-5-yl)propanamido)methyl)-2-methylpiperidine-1-carboxylate;

3,5-dichlorobenzyl 4-(2-(N-methyl-2-(1H-1,2,3-triazol-4-yl)acetamido)ethyl)piperidine-1-carboxylate;

3,5-dichlorobenzyl 4-(2-(2-(1H-1,2,3-triazol-4-yl)acetamido)ethyl)piperidine-1-carboxylate;

3,5-dichlorobenzyl 4-(2-(N,5-dimethyl-2-oxo-2,3-dihydrooxazole-4-carboxamido)ethyl)piperidine-1-carboxylate;

(E)-3,5-dichlorobenzyl 4-(3-(1H-imidazol-4-yl)acrylamido)piperidine-1-carboxylate;

6-((1-(((3,5-Dichlorobenzyl)oxy)carbonyl)piperidin-4-yl)amino)-6-oxohexanoic acid;

3,5-dichlorobenzyl 2-(2-((2-ethoxy-3,4-dioxocyclobut-1-en-1-yl)amino)ethyl)morpholine-4-carboxylate;

3,5-dichlorobenzyl 2-(2-(2-oxo-2,3-dihydrooxazole-5-carboxamido)ethyl)morpholine-4-carboxylate;

3,5-dichlorobenzyl 2-(2-(N-methyl-2-oxo-2,3-dihydrooxazole-5-carboxamido)ethyl)morpholine-4-carboxylate;

3,5-dichlorobenzyl 2-(2-((2-ethoxy-3,4-dioxocyclobut-1-en-1-yl)(methyl)amino)ethyl)morpholine-4-carboxylate;

3,5-dichlorobenzyl 4-(2-(N-methyl-2-oxo-2,3-dihydrothiazole-5-carboxamido)ethyl)piperidine-1-carboxylate;

3,5-dichlorobenzyl 4-(2-(2H-tetrazole-5-carboxamido)ethyl)piperidine-1-carboxylate;

3,5-dichlorobenzyl 4-(4-(1H-1,2,3-triazol-4-yl)butanamido)piperidine-1-carboxylate;

3,5-dichlorobenzyl 4-(N-methyl-4-(1H-1,2,3-triazol-4-yl)butanamido)piperidine-1-carboxylate;

3,5-dichlorobenzyl 4-(3-(1H-1,2,3-triazol-4-yl)propanamido)piperidine-1-carboxylate;

3,5-dichlorobenzyl 4-(5-(1H-1,2,3-triazol-4-yl)pentanamido)piperidine-1-carboxylate;

3,5-dichlorobenzyl 4-(2-(2-oxo-2,3-dihydrooxazole-5-carboxamido)ethyl)piperidine-1-carboxylate;

3,5-dichlorobenzyl 4-(2-(3-(3-hydroxyisoxazol-5-yl)propanamido)ethyl)piperidine-1-carboxylate;

3,5-dichlorobenzyl 4-(3-(3-hydroxyisoxazol-5-yl)propanamido)piperidine-1-carboxylate;

3,5-dichlorobenzyl 4-(2-(N-methyl-2-oxo-2,3-dihydrooxazole-4-carboxamido)ethyl)piperidine-1-carboxylate;

3,5-dichlorobenzyl 4-(2-(5-hydroxy-N-methyl-1H-pyrazole-3-carboxamido)ethyl)piperidine-1-carboxylate;

3,5-dichlorobenzyl 4-(3-(N-methyl-2-oxo-2,3-dihydrooxazole-5-carboxamido)propyl)piperazine-1-carboxylate;

3,5-dichlorobenzyl 4-(2-(2-oxo-2,3-dihydrooxazole-5-carboxamido)ethyl)piperazine-1-carboxylate;

3,5-dichlorobenzyl 4-(2-(N-methyl-5-oxo-4,5-dihydro-1,2,4-oxadiazole-3-carboxamido)ethyl)piperidine-1-carboxylate;

3,5-dichlorobenzyl 4-(2-(N-methyl-2H-tetrazole-5-carboxamido)ethyl)piperidine-1-carboxylate;

(E)-N-(2-(1-(3-(3,5-dichlorophenyl)acryloyl)piperidin-4-yl)ethyl)-N-methyl-2-oxo-2,3-dihydrooxazole-5-carboxamide;

(E)-N-(2-(1-(3-(3,5-dichlorophenyl)acryloyl)piperidin-4-yl)ethyl)-2-oxo-2,3-dihydrooxazole-5-carboxamide;

3,5-dichlorobenzyl 4-(2-(N-methyl-2-oxo-2,3-dihydrooxazole-5-carboxamido)ethyl)piperidine-1-carboxylate;

3,5-dichlorobenzyl 4-((3-(3-hydroxyisoxazol-5-yl)propanamido)methyl)piperidine-1-carboxylate;

3,5-dichlorobenzyl 4-(3-(1H-1,2,3-triazole-4-carboxamido)propyl)piperazine-1-carboxylate;

3,5-dichlorobenzyl 4-(2-(N-methyl-1H-1,2,3-triazole-4-carboxamido)ethyl)piperidine-1-carboxylate; and 3-Chloro-5-cyanobenzyl 4-(2-(N-methyl-1H-1,2,3-triazole-4-carboxamido)ethyl)piperidine-1-carboxylate;

3-Chloro-5-fluorobenzyl 4-(4-(1H-1,2,3-triazol-4-yl)butanamido)piperidine-1-carboxylate;

(E)-N-(1-(3-(3,5-Dichlorophenyl)acryloyl)piperidin-4-yl)-4-(1H-1,2,3-triazol-4-yl)butanamide;

(E)-N-(1-(3-(2,4-Dichlorophenyl)acryloyl)piperidin-4-yl)-4-(1H-1,2,3-triazol-4-yl)butanamide;

8-((1-(((3,5-Dichlorobenzyl)oxy)carbonyl)piperidin-4-yl)amino)-8-oxooctanoic acid;

3,5-Dichlorobenzyl 4-((4-(1H-1,2,3-triazol-5-yl)butanamido)methyl)piperidine-1-carboxylate;

N-(1-(3-(3,5-Dichlorophenyl)propanoyl)piperidin-4-yl)-4-(1H-1,2,3-triazol-4-yl)butanamide;

N-(1-(3-(2,4-Dichlorophenyl)propanoyl)piperidin-4-yl)-4-(1H-1,2,3-triazol-4-yl)butanamide;

3-Chloro-5-cyanobenzyl 4-(4-(1H-1,2,3-triazol-4-yl)butanamido)piperidine-1-carboxylate;

3,5-Dichlorobenzyl 3-(4-(1H-1,2,3-triazol-4-yl)butanamido)-8-azabicyclo[3.2.1]octane-8-carboxylate;

3,5-Dichlorobenzyl 4-(4-(1H-1,2,3-triazol-4-yl)butanamido)azepane-1-carboxylate;

3,5-Dichlorobenzyl(8-(4-(1H-1,2,3-triazol-4-yl)butanoyl)-8-azabicyclo[3.2.1]octan-3-yl)carbamate;

3,5-Dichlorobenzyl(1-(4-(1H-1,2,3-triazol-4-yl)butanoyl)azepan-4-yl)carbamate;

3,5-dichlorobenzyl 3-(4-(1H-1,2,3-triazol-4-yl)butanamido)pyrrolidine-1-carboxylate;

(S)-3,5-Dichlorobenzyl 3-(4-(1H-1,2,3-triazol-4-yl)butanamido)pyrrolidine-1-carboxylate;

(R)-3,5-Dichlorobenzyl 3-(4-(1H-1,2,3-triazol-4-yl)butanamido)pyrrolidine-1-carboxylate;

3,5-Dichlorobenzyl 3-(4-(1H-1,2,3-triazol-4-yl)butanamido)azetidine-1-carboxylate;

3,5-Dimethylbenzyl 4-(4-(1H-1,2,3-triazol-4-yl)butanamido)piperidine-1-carboxylate;

3,5-Dichlorobenzyl(1-(5-(1H-1,2,3-triazol-4-yl)pentanoyl)piperidin-4-yl)carbamate;

4-(Trifluoromethyl)benzyl 4-(4-(1H-1,2,3-triazol-4-yl)butanamido)piperidine-1-carboxylate;

4-(1H-1,2,3-Triazol-4-yl)-N-(1-(3-(4-(trifluoromethyl)phenyl)propanoyl)piperidin-4-yl)butanamide;

N-(1-(2-(3,5-Dichlorophenoxy)acetyl)piperidin-4-yl)-4-(1H-1,2,3-triazol-4-yl)butanamide;

3-Chloro-5-methylbenzyl 4-(4-(1H-1,2,3-triazol-4-yl)butanamido)piperidine-1-carboxylate;

3,5-Dichlorobenzyl 4-((3-(1H-1,2,3-triazol-5-yl)propanamido)methyl)piperidine-1-carboxylate;

2,4-Dichlorobenzyl 4-(4-(1H-1,2,3-triazol-4-yl)butanamido)piperidine-1-carboxylate;

3,5-Dichlorophenethyl 4-(4-(1H-1,2,3-triazol-4-yl)butanamido)piperidine-1-carboxylate;

3,5-dichlorobenzyl 4-(3-(((1H-1,2,3-triazol-4-yl)methyl)amino)-3-oxopropyl)piperidine-1-carboxylate;

3,5-dichlorobenzyl 4-(2-((2-(1H-1,2,3-triazol-4-yl)ethyl)amino)-2-oxoethyl)piperidine-1-carboxylate;

3-methyl-5-(trifluoromethyl)benzyl 4-(4-(1H-1,2,3-triazol-4-yl)butanamido)piperidine-1-carboxylate;
3-bromo-5-(trifluoromethyl)benzyl 4-(4-(1H-1,2,3-triazol-4-yl)butanamido)piperidine-1-carboxylate;
3-chloro-5-cyanobenzyl 4-(5-(1H-1,2,3-triazol-4-yl)pentanamido)piperidine-1-carboxylate;
3-chloro-5-cyanobenzyl 4-(3-(1H-1,2,3-triazol-4-yl)propanamido)piperidine-1-carboxylate;
3-chloro-5-cyanobenzyl 4-(5-(1H-1,2,3-triazol-4-yl)pentanamido)piperidine-1-carboxylate;
3-chloro-5-cyanobenzyl 4-(3-(1H-1,2,3-triazol-4-yl)propanamido)piperidine-1-carboxylate;
3-cyano-5-(trifluoromethyl)benzyl 4-(4-(1H-1,2,3-triazol-4-yl)butanamido)piperidine-1-carboxylate;
3,5-dichlorobenzyl 4-(6-(1H-1,2,3-triazol-4-yl)hexanamido)piperidine-1-carboxylate;
or a pharmaceutically acceptable salt thereof.

In an embodiment 22.1 of the invention, there is provided a compound according to embodiment 1 or 2 selected from the group consisting of
3,5-dichlorobenzyl 4-(2-(3-hydroxy-N-methylisoxazole-5-carboxamido)ethyl)piperidine-1-carboxylate;
3,5-dichlorobenzyl 4-(2-((2-methoxy-3,4-dioxocyclobut-1-en-1-yl)(methyl)amino)ethyl)piperidine-1-carboxylate;
3,5-dichlorobenzyl 4-(2-((2-ethoxy-3,4-dioxocyclobut-1-en-1-yl)amino)ethyl)piperidine-1-carboxylate;
3,5-dichlorobenzyl 4-(2-((2-hydroxy-3,4-dioxocyclobut-1-en-1-yl)amino)ethyl)piperidine-1-carboxylate;
3,5-dichlorobenzyl 4-((3-(3-hydroxyisoxazol-5-yl)propanamido)methyl)-2-methylpiperidine-1-carboxylate;
3,5-dichlorobenzyl 4-(2-(N-methyl-2-(1H-1,2,3-triazol-4-yl)acetamido)ethyl)piperidine-1-carboxylate;
3,5-dichlorobenzyl 4-(2-(2-(1H-1,2,3-triazol-4-yl)acetamido)ethyl)piperidine-1-carboxylate;
3,5-dichlorobenzyl 4-(2-(N,5-dimethyl-2-oxo-2,3-dihydrooxazole-4-carboxamido)ethyl)piperidine-1-carboxylate;
(E)-3,5-dichlorobenzyl 4-(3-(1H-imidazol-4-yl)acrylamido)piperidine-1-carboxylate;
6-((1-(((3,5-Dichlorobenzyl)oxy)carbonyl)piperidin-4-yl)amino)-6-oxohexanoic acid;
3,5-dichlorobenzyl 2-(2-((2-ethoxy-3,4-dioxocyclobut-1-en-1-yl)amino)ethyl)morpholine-4-carboxylate;
3,5-dichlorobenzyl 2-(2-(2-oxo-2,3-dihydrooxazole-5-carboxamido)ethyl)morpholine-4-carboxylate;
3,5-dichlorobenzyl 2-(2-(N-methyl-2-oxo-2,3-dihydrooxazole-5-carboxamido)ethyl)morpholine-4-carboxylate;
3,5-dichlorobenzyl 2-(2-((2-ethoxy-3,4-dioxocyclobut-1-en-1-yl)(methyl)amino)ethyl)morpholine-4-carboxylate;
3,5-dichlorobenzyl 4-(2-(N-methyl-2-oxo-2,3-dihydrothiazole-5-carboxamido)ethyl)piperidine-1-carboxylate;
3,5-dichlorobenzyl 4-(2-(2H-tetrazole-5-carboxamido)ethyl)piperidine-1-carboxylate;
3,5-dichlorobenzyl 4-(4-(1H-1,2,3-triazol-4-yl)butanamido)piperidine-1-carboxylate;
3,5-dichlorobenzyl 4-(N-methyl-4-(1H-1,2,3-triazol-4-yl)butanamido)piperidine-1-carboxylate;
3,5-dichlorobenzyl 4-(3-(1H-1,2,3-triazol-4-yl)propanamido)piperidine-1-carboxylate;
3,5-dichlorobenzyl 4-(5-(1H-1,2,3-triazol-4-yl)pentanamido)piperidine-1-carboxylate;
3,5-dichlorobenzyl 4-(2-(2-oxo-2,3-dihydrooxazole-5-carboxamido)ethyl)piperidine-1-carboxylate;
3,5-dichlorobenzyl 4-(2-(3-(3-hydroxyisoxazol-5-yl)propanamido)ethyl)piperidine-1-carboxylate;
3,5-dichlorobenzyl 4-(3-(3-hydroxyisoxazol-5-yl)propanamido)piperidine-1-carboxylate;
3,5-dichlorobenzyl 4-(2-(N-methyl-2-oxo-2,3-dihydrooxazole-4-carboxamido)ethyl)piperidine-1-carboxylate;
3,5-dichlorobenzyl 4-(2-(5-hydroxy-N-methyl-1H-pyrazole-3-carboxamido)ethyl)piperidine-1-carboxylate;
3,5-dichlorobenzyl 4-(3-(N-methyl-2-oxo-2,3-dihydrooxazole-5-carboxamido)propyl)piperazine-1-carboxylate;
3,5-dichlorobenzyl 4-(2-(2-oxo-2,3-dihydrooxazole-5-carboxamido)ethyl)piperazine-1-carboxylate;
3,5-dichlorobenzyl 4-(2-(N-methyl-5-oxo-4,5-dihydro-1,2,4-oxadiazole-3-carboxamido)ethyl)piperidine-1-carboxylate;
3,5-dichlorobenzyl 4-(2-(N-methyl-2H-tetrazole-5-carboxamido)ethyl)piperidine-1-carboxylate;
(E)-N-(2-(1-(3-(3,5-dichlorophenyl)acryloyl)piperidin-4-yl)ethyl)-N-methyl-2-oxo-2,3-dihydrooxazole-5-carboxamide;
(E)-N-(2-(1-(3-(3,5-dichlorophenyl)acryloyl)piperidin-4-yl)ethyl)-2-oxo-2,3-dihydrooxazole-5-carboxamide;
3,5-dichlorobenzyl 4-(2-(N-methyl-2-oxo-2,3-dihydrooxazole-5-carboxamido)ethyl)piperidine-1-carboxylate;
3,5-dichlorobenzyl 4-((3-(3-hydroxyisoxazol-5-yl)propanamido)methyl)piperidine-1-carboxylate;
3,5-dichlorobenzyl 4-(3-(1H-1,2,3-triazole-4-carboxamido)propyl)piperazine-1-carboxylate;
3,5-dichlorobenzyl 4-(2-(N-methyl-1H-1,2,3-triazole-4-carboxamido)ethyl)piperidine-1-carboxylate; and
3-Chloro-5-cyanobenzyl 4-(2-(N-methyl-1H-1,2,3-triazole-4-carboxamido)ethyl)piperidine-1-carboxylate;
or a pharmaceutically acceptable salt thereof.

In an embodiment 22.2 of the invention, there is provided a compound according to embodiment 1 or 2 selected from the group consisting of
3-Chloro-5-fluorobenzyl 4-(4-(1H-1,2,3-triazol-4-yl)butanamido)piperidine-1-carboxylate;
(E)-N-(1-(3-(3,5-Dichlorophenyl)acryloyl)piperidin-4-yl)-4-(1H-1,2,3-triazol-4-yl)butanamide;
(E)-N-(1-(3-(2,4-Dichlorophenyl)acryloyl)piperidin-4-yl)-4-(1H-1,2,3-triazol-4-yl)butanamide;
8-((1-(((3,5-Dichlorobenzyl)oxy)carbonyl)piperidin-4-yl)amino)-8-oxooctanoic acid;
3,5-Dichlorobenzyl 4-((4-(1H-1,2,3-triazol-5-yl)butanamido)methyl)piperidine-1-carboxylate;
N-(1-(3-(3,5-Dichlorophenyl)propanoyl)piperidin-4-yl)-4-(1H-1,2,3-triazol-4-yl)butanamide;
N-(1-(3-(2,4-Dichlorophenyl)propanoyl)piperidin-4-yl)-4-(1H-1,2,3-triazol-4-yl)butanamide;
3-Chloro-5-cyanobenzyl 4-(4-(1H-1,2,3-triazol-4-yl)butanamido)piperidine-1-carboxylate;
3,5-Dichlorobenzyl 3-(4-(1H-1,2,3-triazol-4-yl)butanamido)-8-azabicyclo[3.2.1]octane-8-carboxylate;
3,5-Dichlorobenzyl 4-(4-(1H-1,2,3-triazol-4-yl)butanamido)azepane-1-carboxylate;
3,5-Dichlorobenzyl(8-(4-(1H-1,2,3-triazol-4-yl)butanoyl)-8-azabicyclo[3.2.1]octan-3-yl)carbamate;
3,5-Dichlorobenzyl(1-(4-(1H-1,2,3-triazol-4-yl)butanoyl)azepan-4-yl)carbamate;
3,5-dichlorobenzyl 3-(4-(1H-1,2,3-triazol-4-yl)butanamido)pyrrolidine-1-carboxylate;
(S)-3,5-Dichlorobenzyl 3-(4-(1H-1,2,3-triazol-4-yl)butanamido)pyrrolidine-1-carboxylate;
(R)-3,5-Dichlorobenzyl 3-(4-(1H-1,2,3-triazol-4-yl)butanamido)pyrrolidine-1-carboxylate;
3,5-Dichlorobenzyl 3-(4-(1H-1,2,3-triazol-4-yl)butanamido)azetidine-1-carboxylate;
3,5-Dimethylbenzyl 4-(4-(1H-1,2,3-triazol-4-yl)butanamido)piperidine-1-carboxylate;

3,5-Dichlorobenzyl(1-(5-(1H-1,2,3-triazol-4-yl)pentanoyl) piperidin-4-yl)carbamate;
4-(Trifluoromethyl)benzyl 4-(4-(1H-1,2,3-triazol-4-yl)butanamido)piperidine-1-carboxylate;
4-(1H-1,2,3-Triazol-4-yl)-N-(1-(3-(4-(trifluoromethyl)phenyl)propanoyl)piperidin-4-yl)butanamide;
N-(1-(2-(3,5-Dichlorophenoxy)acetyl)piperidin-4-yl)-4-(1H-1,2,3-triazol-4-yl)butanamide;
3-Chloro-5-methylbenzyl 4-(4-(1H-1,2,3-triazol-4-yl)butanamido)piperidine-1-carboxylate;
3,5-Dichlorobenzyl 4-((3-(1H-1,2,3-triazol-5-yl)propanamido)methyl)piperidine-1-carboxylate;
2,4-Dichlorobenzyl 4-(4-(1H-1,2,3-triazol-4-yl)butanamido)piperidine-1-carboxylate;
3,5-Dichlorophenethyl 4-(4-(1H-1,2,3-triazol-4-yl)butanamido)piperidine-1-carboxylate;
3,5-dichlorobenzyl 4-(3-(((1H-1,2,3-triazol-4-yl)methyl)amino)-3-oxopropyl)piperidine-1-carboxylate;
3,5-dichlorobenzyl 4-(2-((2-(1H-1,2,3-triazol-4-yl)ethyl)amino)-2-oxoethyl)piperidine-1-carboxylate;
3-methyl-5-(trifluoromethyl)benzyl 4-(4-(1H-1,2,3-triazol-4-yl)butanamido)piperidine-1-carboxylate;
3-bromo-5-(trifluoromethyl)benzyl 4-(4-(1H-1,2,3-triazol-4-yl)butanamido)piperidine-1-carboxylate;
3-chloro-5-cyanobenzyl 4-(5-(1H-1,2,3-triazol-4-yl)pentanamido)piperidine-1-carboxylate;
3-chloro-5-cyanobenzyl 4-(3-(1H-1,2,3-triazol-4-yl)propanamido)piperidine-1-carboxylate;
3-cyano-5-(trifluoromethyl)benzyl 4-(4-(1H-1,2,3-triazol-4-yl)butanamido)piperidine-1-carboxylate;
3,5-dichlorobenzyl 4-(6-(1H-1,2,3-triazol-4-yl)hexanamido)piperidine-1-carboxylate;
or a pharmaceutically acceptable salt thereof.

In an embodiment 23 of the invention, there is provided a compound according to embodiment 1 or 2 selected from the group consisting of
3,5-dichlorobenzyl 4-(2-(3-hydroxy-N-methylisoxazole-5-carboxamido)ethyl)piperidine-1-carboxylate;
3,5-dichlorobenzyl 4-((3-(3-hydroxyisoxazol-5-yl)propanamido)methyl)-2-methylpiperidine-1-carboxylate;
3,5-dichlorobenzyl 4-(2-(N-methyl-2-(1H-1,2,3-triazol-4-yl)acetamido)ethyl)piperidine-1-carboxylate;
3,5-dichlorobenzyl 4-(2-(2-(1H-1,2,3-triazol-4-yl)acetamido)ethyl)piperidine-1-carboxylate;
3,5-dichlorobenzyl 4-(2-(N,5-dimethyl-2-oxo-2,3-dihydrooxazole-4-carboxamido)ethyl)piperidine-1-carboxylate;
(E)-3,5-dichlorobenzyl 4-(3-(1H-imidazol-4-yl)acrylamido)piperidine-1-carboxylate;
6-((1-(((3,5-Dichlorobenzyl)oxy)carbonyl)piperidin-4-yl)amino)-6-oxohexanoic acid;
3,5-dichlorobenzyl 2-(2-(2-oxo-2,3-dihydrooxazole-5-carboxamido)ethyl)morpholine-4-carboxylate;
3,5-dichlorobenzyl 2-(2-(N-methyl-2-oxo-2,3-dihydrooxazole-5-carboxamido)ethyl)morpholine-4-carboxylate;
3,5-dichlorobenzyl 4-(2-(N-methyl-2-oxo-2,3-dihydrothiazole-5-carboxamido)ethyl)piperidine-1-carboxylate;
3,5-dichlorobenzyl 4-(2-(2H-tetrazole-5-carboxamido)ethyl)piperidine-1-carboxylate;
3,5-dichlorobenzyl 4-(4-(1H-1,2,3-triazol-4-yl)butanamido)piperidine-1-carboxylate;
3,5-dichlorobenzyl 4-(N-methyl-4-(1H-1,2,3-triazol-4-yl)butanamido)piperidine-1-carboxylate;
3,5-dichlorobenzyl 4-(3-(1H-1,2,3-triazol-4-yl)propanamido)piperidine-1-carboxylate;
3,5-dichlorobenzyl 4-(5-(1H-1,2,3-triazol-4-yl)pentanamido)piperidine-1-carboxylate;
3,5-dichlorobenzyl 4-(2-(2-oxo-2,3-dihydrooxazole-5-carboxamido)ethyl)piperidine-1-carboxylate;
3,5-dichlorobenzyl 4-(2-(3-(3-hydroxyisoxazol-5-yl)propanamido)ethyl)piperidine-1-carboxylate;
3,5-dichlorobenzyl 4-(3-(3-hydroxyisoxazol-5-yl)propanamido)piperidine-1-carboxylate;
3,5-dichlorobenzyl 4-(2-(N-methyl-2-oxo-2,3-dihydrooxazole-4-carboxamido)ethyl)piperidine-1-carboxylate;
3,5-dichlorobenzyl 4-(2-(5-hydroxy-N-methyl-1H-pyrazole-3-carboxamido)ethyl)piperidine-1-carboxylate;
3,5-dichlorobenzyl 4-(3-(N-methyl-2-oxo-2,3-dihydrooxazole-5-carboxamido)propyl)piperazine-1-carboxylate;
3,5-dichlorobenzyl 4-(2-(2-oxo-2,3-dihydrooxazole-5-carboxamido)ethyl)piperazine-1-carboxylate;
3,5-dichlorobenzyl 4-(2-(N-methyl-5-oxo-4,5-dihydro-1,2,4-oxadiazole-3-carboxamido)ethyl)piperidine-1-carboxylate;
3,5-dichlorobenzyl 4-(2-(N-methyl-2H-tetrazole-5-carboxamido)ethyl)piperidine-1-carboxylate;
(E)-N-(2-(1-(3-(3,5-dichlorophenyl)acryloyl)piperidin-4-yl)ethyl)-N-methyl-2-oxo-2,3-dihydrooxazole-5-carboxamide;
(E)-N-(2-(1-(3-(3,5-dichlorophenyl)acryloyl)piperidin-4-yl)ethyl)-2-oxo-2,3-dihydrooxazole-5-carboxamide;
3,5-dichlorobenzyl 4-(2-(N-methyl-2-oxo-2,3-dihydrooxazole-5-carboxamido)ethyl)piperidine-1-carboxylate;
3,5-dichlorobenzyl 4-((3-(3-hydroxyisoxazol-5-yl)propanamido)methyl)piperidine-1-carboxylate;
3,5-dichlorobenzyl 4-(3-(1H-1,2,3-triazole-4-carboxamido)propyl)piperazine-1-carboxylate;
3,5-dichlorobenzyl 4-(2-(N-methyl-1H-1,2,3-triazole-4-carboxamido)ethyl)piperidine-1-carboxylate; and and
3-Chloro-5-cyanobenzyl 4-(2-(N-methyl-1H-1,2,3-triazole-4-carboxamido)ethyl)piperidine-1-carboxylate;
or a pharmaceutically acceptable salt thereof.

In an embodiment 24 of the invention, there is provided a compound according to embodiment 1 or 2 selected from the group consisting of
3,5-dichlorobenzyl 4-(2-((2-methoxy-3,4-dioxocyclobut-1-en-1-yl)(methyl)amino)ethyl)piperidine-1-carboxylate;
3,5-dichlorobenzyl 4-(4-(1H-1,2,3-triazol-4-yl)butanamido)piperidine-1-carboxylate;
3,5-dichlorobenzyl 4-(2-((2-ethoxy-3,4-dioxocyclobut-1-en-1-yl)amino)ethyl)piperidine-1-carboxylate;
3,5-dichlorobenzyl 4-(2-((2-hydroxy-3,4-dioxocyclobut-1-en-1-yl)amino)ethyl)piperidine-1-carboxylate;
3,5-dichlorobenzyl 2-(2-((2-ethoxy-3,4-dioxocyclobut-1-en-1-yl)amino)ethyl)morpholine-4-carboxylate; and
3,5-dichlorobenzyl 2-(2-((2-ethoxy-3,4-dioxocyclobut-1-en-1-yl)(methyl)amino)ethyl)morpholine-4-carboxylate;
(E)-N-(1-(3-(3,5-Dichlorophenyl)acryloyl)piperidin-4-yl)-4-(1H-1,2,3-triazol-4-yl)butanamide;
3-Chloro-5-cyanobenzyl 4-(4-(1H-1,2,3-triazol-4-yl)butanamido)piperidine-1-carboxylate;
3,5-Dichlorobenzyl 4-((4-(1H-1,2,3-triazol-5-yl)butanamido)methyl)piperidine-1-carboxylate;
3,5-dichlorobenzyl 3-(4-(1H-1,2,3-triazol-4-yl)butanamido)pyrrolidine-1-carboxylate;
3,5-Dichlorobenzyl 3-(4-(1H-1,2,3-triazol-4-yl)butanamido)azetidine-1-carboxylate;
3,5-Dimethylbenzyl 4-(4-(1H-1,2,3-triazol-4-yl)butanamido)piperidine-1-carboxylate;
4-(Trifluoromethyl)benzyl 4-(4-(1H-1,2,3-triazol-4-yl)butanamido)piperidine-1-carboxylate;
3-Chloro-5-methylbenzyl 4-(4-(1H-1,2,3-triazol-4-yl)butanamido)piperidine-1-carboxylate;

3,5-Dichlorophenethyl 4-(4-(1H-1,2,3-triazol-4-yl)butanamido)piperidine-1-carboxylate;
3-chloro-5-cyanobenzyl 4-(5-(1H-1,2,3-triazol-4-yl)pentanamido)piperidine-1-carboxylate;
3-chloro-5-cyanobenzyl 4-(3-(1H-1,2,3-triazol-4-yl)propanamido)piperidine-1-carboxylate;
3,5-dichlorobenzyl 4-(3-(((1H-1,2,3-triazol-4-yl)methyl)amino)-3-oxopropyl)piperidine-1-carboxylate;
3,5-dichlorobenzyl 4-(2-((2-(1H-1,2,3-triazol-4-yl)ethyl)amino)-2-oxoethyl)piperidine-1-carboxylate;
3-methyl-5-(trifluoromethyl)benzyl 4-(4-(1H-1,2,3-triazol-4-yl)butanamido)piperidine-1-carboxylate; and
3-bromo-5-(trifluoromethyl)benzyl 4-(4-(1H-1,2,3-triazol-4-yl)butanamido)piperidine-1-carboxylate;
or a pharmaceutically acceptable salt thereof.

In an embodiment 24.1 of the invention, there is provided a compound according to embodiment 1 or 2 selected from the group consisting of
3,5-dichlorobenzyl 4-(2-((2-methoxy-3,4-dioxocyclobut-1-en-1-yl)(methyl)amino)ethyl)piperidine-1-carboxylate;
3,5-dichlorobenzyl 4-(4-(1H-1,2,3-triazol-4-yl)butanamido)piperidine-1-carboxylate;
3,5-dichlorobenzyl 4-(2-((2-ethoxy-3,4-dioxocyclobut-1-en-1-yl)amino)ethyl)piperidine-1-carboxylate;
3,5-dichlorobenzyl 4-(2-((2-hydroxy-3,4-dioxocyclobut-1-en-1-yl)amino)ethyl)piperidine-1-carboxylate;
3,5-dichlorobenzyl 2-(2-((2-ethoxy-3,4-dioxocyclobut-1-en-1-yl)amino)ethyl)morpholine-4-carboxylate; and
3,5-dichlorobenzyl 2-(2-((2-ethoxy-3,4-dioxocyclobut-1-en-1-yl)(methyl)amino)ethyl)morpholine-4-carboxylate;
or a pharmaceutically acceptable salt thereof.

In an embodiment 25 of the invention, there is provided a compound according to embodiment 1 which is
3,5-dichlorobenzyl 4-(2-(3-hydroxy-N-methylisoxazole-5-carboxamido)ethyl)piperidine-1-carboxylate, or pharmaceutically acceptable salt thereof.

In an embodiment 26 of the invention, there is provided a compound according to embodiment 1 which is
3,5-dichlorobenzyl 4-(2-((2-methoxy-3,4-dioxocyclobut-1-en-1-yl)(methyl)amino)ethyl)piperidine-1-carboxylate; or a pharmaceutically acceptable salt thereof.

In an embodiment 27 of the invention, there is provided a compound according to embodiment 1 which is
3,5-dichlorobenzyl 4-(2-((2-ethoxy-3,4-dioxocyclobut-1-en-1-yl)amino)ethyl)piperidine-1-carboxylate, or a pharmaceutically acceptable salt thereof.

In an embodiment 28 of the invention, there is provided a compound according to embodiment 1 which is
3,5-dichlorobenzyl 4-(2-((2-hydroxy-3,4-dioxocyclobut-1-en-1-yl)amino)ethyl)piperidine-1-carboxylate, or a pharmaceutically acceptable salt thereof.

In an embodiment 29 of the invention, there is provided a compound according to embodiment 1 which is
3,5-dichlorobenzyl 4-((3-(3-hydroxyisoxazol-5-yl)propanamido)methyl)-2-methylpiperidine-1-carboxylate, or a pharmaceutically acceptable salt thereof.

In an embodiment 30 of the invention, there is provided a compound according to embodiment 1 which is
3,5-dichlorobenzyl 4-(2-(N-methyl-2-(1H-1,2,3-triazol-4-yl)acetamido)ethyl)piperidine-1-carboxylate, or a pharmaceutically acceptable salt thereof.

In an embodiment 31 of the invention, there is provided a compound according to embodiment 1 which is
3,5-dichlorobenzyl 4-(2-(2-(1H-1,2,3-triazol-4-yl)acetamido)ethyl)piperidine-1-carboxylate, or a pharmaceutically acceptable salt thereof.

In an embodiment 32 of the invention, there is provided a compound according to embodiment 1 which is
3,5-dichlorobenzyl 4-(2-(N,5-dimethyl-2-oxo-2,3-dihydrooxazole-4-carboxamido)ethyl)piperidine-1-carboxylate, or a pharmaceutically acceptable salt thereof.

In an embodiment 33 of the invention, there is provided a compound according to embodiment 1 which is
(E)-3,5-dichlorobenzyl 4-(3-(1H-imidazol-4-yl)acrylamido)piperidine-1-carboxylate, or a pharmaceutically acceptable salt thereof.

In an embodiment 34 of the invention, there is provided a compound according to embodiment 1 which is
6-((1-(((3,5-Dichlorobenzyl)oxy)carbonyl)piperidin-4-yl)amino)-6-oxohexanoic acid, or a pharmaceutically acceptable salt thereof.

In an embodiment 35 of the invention, there is provided a compound according to embodiment 1 which is
3,5-dichlorobenzyl 2-(2-((2-ethoxy-3,4-dioxocyclobut-1-en-1-yl)amino)ethyl)morpholine-4-carboxylate, or a pharmaceutically acceptable salt thereof.

In an embodiment 36 of the invention, there is provided a compound according to embodiment 1 which is
3,5-dichlorobenzyl 2-(2-(2-oxo-2,3-dihydrooxazole-5-carboxamido)ethyl)morpholine-4-carboxylate, or a pharmaceutically acceptable salt thereof.

In an embodiment 37 of the invention, there is provided a compound according to embodiment 1 which is
3,5-dichlorobenzyl 2-(2-(N-methyl-2-oxo-2,3-dihydrooxazole-5-carboxamido)ethyl)morpholine-4-carboxylate, or a pharmaceutically acceptable salt thereof.

In an embodiment 38 of the invention, there is provided a compound according to embodiment 1 which is
3,5-dichlorobenzyl 2-(2-((2-ethoxy-3,4-dioxocyclobut-1-en-1-yl)(methyl)amino)ethyl)morpholine-4-carboxylate, or a pharmaceutically acceptable salt thereof.

In an embodiment 39 of the invention, there is provided a compound according to embodiment 1 which is
3,5-dichlorobenzyl 4-(2-(N-methyl-2-oxo-2,3-dihydrothiazole-5-carboxamido)ethyl)piperidine-1-carboxylate, or a pharmaceutically acceptable salt thereof.

In an embodiment 40 of the invention, there is provided a compound according to embodiment 1 which is
3,5-dichlorobenzyl 4-(2-(2H-tetrazole-5-carboxamido)ethyl)piperidine-1-carboxylate, or a pharmaceutically acceptable salt thereof.

In an embodiment 41 of the invention, there is provided a compound according to embodiment 1 which is
3,5-dichlorobenzyl 4-(4-(1H-1,2,3-triazol-4-yl)butanamido)piperidine-1-carboxylate, or a pharmaceutically acceptable salt thereof.

In an embodiment 42 of the invention, there is provided a compound according to embodiment 1 which is
3,5-dichlorobenzyl 4-(N-methyl-4-(1H-1,2,3-triazol-4-yl)butanamido)piperidine-1-carboxylate, or a pharmaceutically acceptable salt thereof.

In an embodiment 43 of the invention, there is provided a compound according to embodiment 1 which is
3,5-dichlorobenzyl 4-(3-(1H-1,2,3-triazol-4-yl)propanamido)piperidine-1-carboxylate, or a pharmaceutically acceptable salt thereof.

In an embodiment 44 of the invention, there is provided a compound according to embodiment 1 which is
3,5-dichlorobenzyl 4-(5-(1H-1,2,3-triazol-4-yl)pentanamido)piperidine-1-carboxylate, or a pharmaceutically acceptable salt thereof.

In an embodiment 45 of the invention, there is provided a compound according to embodiment 1 which is 3,5-dichlorobenzyl 4-(2-(2-oxo-2,3-dihydrooxazole-5-carboxamido)ethyl)piperidine-1-carboxylate, or a pharmaceutically acceptable salt thereof.

In an embodiment 46 of the invention, there is provided a compound according to embodiment 1 which is
3,5-dichlorobenzyl 4-(2-(3-(3-hydroxyisoxazol-5-yl)propanamido)ethyl)piperidine-1-carboxylate, or a pharmaceutically acceptable salt thereof.

In an embodiment 47 of the invention, there is provided a compound according to embodiment 1 which is
3,5-dichlorobenzyl 4-(3-(3-hydroxyisoxazol-5-yl)propanamido)piperidine-1-carboxylate, or a pharmaceutically acceptable salt thereof.

In an embodiment 48 of the invention, there is provided a compound according to embodiment 1 which is
3,5-dichlorobenzyl 4-(2-(N-methyl-2-oxo-2,3-dihydrooxazole-4-carboxamido)ethyl)piperidine-1-carboxylate, or a pharmaceutically acceptable salt thereof.

In an embodiment 49 of the invention, there is provided a compound according to embodiment 1 which is
3,5-dichlorobenzyl 4-(2-(5-hydroxy-N-methyl-1H-pyrazole-3-carboxamido)ethyl)piperidine-1-carboxylate, or a pharmaceutically acceptable salt thereof.

In an embodiment 50 of the invention, there is provided a compound according to embodiment 1 which is
3,5-dichlorobenzyl 4-(3-(N-methyl-2-oxo-2,3-dihydrooxazole-5-carboxamido)propyl)piperazine-1-carboxylate, or a pharmaceutically acceptable salt thereof.

In an embodiment 51 of the invention, there is provided a compound according to embodiment 1 which is
3,5-dichlorobenzyl 4-(2-(2-oxo-2,3-dihydrooxazole-5-carboxamido)ethyl)piperazine-1-carboxylate, or a pharmaceutically acceptable salt thereof.

In an embodiment 52 of the invention, there is provided a compound according to embodiment 1 which is
3,5-dichlorobenzyl 4-(2-(N-methyl-5-oxo-4,5-dihydro-1,2,4-oxadiazole-3-carboxamido)ethyl)piperidine-1-carboxylate, or a pharmaceutically acceptable salt thereof.

In an embodiment 53 of the invention, there is provided a compound according to embodiment 1 which is
3,5-dichlorobenzyl 4-(2-(N-methyl-2H-tetrazole-5-carboxamido)ethyl)piperidine-1-carboxylate, or a pharmaceutically acceptable salt thereof.

In an embodiment 54 of the invention, there is provided a compound according to embodiment 1 which is
(E)-N-(2-(1-(3-(3,5-dichlorophenyl)acryloyl)piperidin-4-yl)ethyl)-N-methyl-2-oxo-2,3-dihydrooxazole-5-carboxamide, or a pharmaceutically acceptable salt thereof.

In an embodiment 55 of the invention, there is provided a compound according to embodiment 1 which is
(E)-N-(2-(1-(3-(3,5-dichlorophenyl)acryloyl)piperidin-4-yl)ethyl)-2-oxo-2,3-dihydrooxazole-5-carboxamide, or a pharmaceutically acceptable salt thereof.

In an embodiment 56 of the invention, there is provided a compound according to embodiment 1 which is
3,5-dichlorobenzyl 4-(2-(N-methyl-2-oxo-2,3-dihydrooxazole-5-carboxamido)ethyl)piperidine-1-carboxylate, or a pharmaceutically acceptable salt thereof.

In an embodiment 57 of the invention, there is provided a compound according to embodiment 1 which is
3,5-dichlorobenzyl 4-((3-(3-hydroxyisoxazol-5-yl)propanamido)methyl)piperidine-1-carboxylate, or a pharmaceutically acceptable salt thereof.

In an embodiment 58 of the invention, there is provided a compound according to embodiment 1 which is
3,5-dichlorobenzyl 4-(3-(1H-1,2,3-triazole-4-carboxamido)propyl)piperazine-1-carboxylate, or a pharmaceutically acceptable salt thereof.

In an embodiment 59 of the invention, there is provided a compound according to embodiment 1 which is
3,5-dichlorobenzyl 4-(2-(N-methyl-1H-1,2,3-triazole-4-carboxamido)ethyl)piperidine-1-carboxylate, or a pharmaceutically acceptable salt thereof.

In an embodiment 60 of the invention, there is provided a compound according to embodiment 1 which is
3-Chloro-5-cyanobenzyl 4-(2-(N-methyl-1H-1,2,3-triazole-4-carboxamido)ethyl)piperidine-1-carboxylate, or a pharmaceutically acceptable salt thereof.

In an embodiment 60.1 of the invention, there is provided a compound according to embodiment 1 which is
3-Chloro-5-fluorobenzyl 4-(4-(1H-1,2,3-triazol-4-yl)butanamido)piperidine-1-carboxylate; or a pharmaceutically acceptable salt thereof.

In an embodiment 60.2 of the invention, there is provided a compound according to embodiment 1 which is
(E)-N-(1-(3-(3,5-Dichlorophenyl)acryloyl)piperidin-4-yl)-4-(1H-1,2,3-triazol-4-yl)butanamide; or a pharmaceutically acceptable salt thereof.

In an embodiment 60.3 of the invention, there is provided a compound according to embodiment 1 which is
(E)-N-(1-(3-(2,4-Dichlorophenyl)acryloyl)piperidin-4-yl)-4-(1H-1,2,3-triazol-4-yl)butanamide; or a pharmaceutically acceptable salt thereof.

In an embodiment 60.4 of the invention, there is provided a compound according to embodiment 1 which is
8-((1-(((3,5-Dichlorobenzyl)oxy)carbonyl)piperidin-4-yl)amino)-8-oxooctanoic acid; or a pharmaceutically acceptable salt thereof.

In an embodiment 60.5 of the invention, there is provided a compound according to embodiment 1 which is
3,5-Dichlorobenzyl 4-((4-(1H-1,2,3-triazol-5-yl)butanamido)methyl)piperidine-1-carboxylate; or a pharmaceutically acceptable salt thereof.

In an embodiment 60.6 of the invention, there is provided a compound according to embodiment 1 which is
N-(1-(3-(3,5-Dichlorophenyl)propanoyl)piperidin-4-yl)-4-(1H-1,2,3-triazol-4-yl)butanamide; or a pharmaceutically acceptable salt thereof.

In an embodiment 60.7 of the invention, there is provided a compound according to embodiment 1 which is
N-(1-(3-(2,4-Dichlorophenyl)propanoyl)piperidin-4-yl)-4-(1H-1,2,3-triazol-4-yl)butanamide; or a pharmaceutically acceptable salt thereof.

In an embodiment 60.8 of the invention, there is provided a compound according to embodiment 1 which is
3-Chloro-5-cyanobenzyl 4-(4-(1H-1,2,3-triazol-4-yl)butanamido)piperidine-1-carboxylate; or a pharmaceutically acceptable salt thereof.

In an embodiment 60.9 of the invention, there is provided a compound according to embodiment 1 which is
3,5-Dichlorobenzyl 3-(4-(1H-1,2,3-triazol-4-yl)butanamido)-8-azabicyclo[3.2.1]octane-8-carboxylate; or a pharmaceutically acceptable salt thereof.

In an embodiment 60.10 of the invention, there is provided a compound according to embodiment 1 which is
3,5-Dichlorobenzyl 4-(4-(1H-1,2,3-triazol-4-yl)butanamido)azepane-1-carboxylate; or a pharmaceutically acceptable salt thereof.

In an embodiment 60.11 of the invention, there is provided a compound according to embodiment 1 which is 3,5-Dichlorobenzyl(8-(4-(1H-1,2,3-triazol-4-yl)butanoyl)-8-azabicyclo[3.2.1]octan-3-yl)carbamate; or a pharmaceutically acceptable salt thereof.

In an embodiment 60.12 of the invention, there is provided a compound according to embodiment 1 which is
3,5-Dichlorobenzyl(1-(4-(1H-1,2,3-triazol-4-yl)butanoyl)azepan-4-yl)carbamate; or a pharmaceutically acceptable salt thereof.

In an embodiment 60.13 of the invention, there is provided a compound according to embodiment 1 which is
3,5-dichlorobenzyl 3-(4-(1H-1,2,3-triazol-4-yl)butanamido)pyrrolidine-1-carboxylate; or a pharmaceutically acceptable salt thereof.

In an embodiment 60.14 of the invention, there is provided a compound according to embodiment 1 which is
(S)-3,5-Dichlorobenzyl 3-(4-(1H-1,2,3-triazol-4-yl)butanamido)pyrrolidine-1-carboxylate; or a pharmaceutically acceptable salt thereof.

In an embodiment 60.15 of the invention, there is provided a compound according to embodiment 1 which is
(R)-3,5-Dichlorobenzyl 3-(4-(1H-1,2,3-triazol-4-yl)butanamido)pyrrolidine-1-carboxylate; or a pharmaceutically acceptable salt thereof.

In an embodiment 60.16 of the invention, there is provided a compound according to embodiment 1 which is
3,5-Dichlorobenzyl 3-(4-(1H-1,2,3-triazol-4-yl)butanamido)azetidine-1-carboxylate; or a pharmaceutically acceptable salt thereof.

In an embodiment 60.17 of the invention, there is provided a compound according to embodiment 1 which is
3,5-Dimethylbenzyl 4-(4-(1H-1,2,3-triazol-4-yl)butanamido)piperidine-1-carboxylate; or a pharmaceutically acceptable salt thereof.

In an embodiment 60.18 of the invention, there is provided a compound according to embodiment 1 which is
3,5-Dichlorobenzyl(1-(5-(1H-1,2,3-triazol-4-yl)pentanoyl)piperidin-4-yl)carbamate; or a pharmaceutically acceptable salt thereof.

In an embodiment 60.19 of the invention, there is provided a compound according to embodiment 1 which is
4-(Trifluoromethyl)benzyl 4-(4-(1H-1,2,3-triazol-4-yl)butanamido)piperidine-1-carboxylate; or
a pharmaceutically acceptable salt thereof.

In an embodiment 60.20 of the invention, there is provided a compound according to embodiment 1 which is
4-(1H-1,2,3-Triazol-4-yl)-N-(1-(3-(4-(trifluoromethyl)phenyl)propanoyl)piperidin-4-yl)butanamide; or a pharmaceutically acceptable salt thereof.

In an embodiment 60.21 of the invention, there is provided a compound according to embodiment 1 which is
N-(1-(2-(3,5-Dichlorophenoxy)acetyl)piperidin-4-yl)-4-(1H-1,2,3-triazol-4-yl)butanamide; or a pharmaceutically acceptable salt thereof.

In an embodiment 60.22 of the invention, there is provided a compound according to embodiment 1 which is
3-Chloro-5-methylbenzyl 4-(4-(1H-1,2,3-triazol-4-yl)butanamido)piperidine-1-carboxylate; or
a pharmaceutically acceptable salt thereof.

In an embodiment 60.23 of the invention, there is provided a compound according to embodiment 1 which is
3,5-Dichlorobenzyl 4-((3-(1H-1,2,3-triazol-5-yl)propanamido)methyl)piperidine-1-carboxylate;
or a pharmaceutically acceptable salt thereof.

In an embodiment 60.24 of the invention, there is provided a compound according to embodiment 1 which is
2,4-Dichlorobenzyl 4-(4-(1H-1,2,3-triazol-4-yl)butanamido)piperidine-1-carboxylate; or a pharmaceutically acceptable salt thereof.

In an embodiment 60.25 of the invention, there is provided a compound according to embodiment 1 which is
3,5-Dichlorophenethyl 4-(4-(1H-1,2,3-triazol-4-yl)butanamido)piperidine-1-carboxylate; or a pharmaceutically acceptable salt thereof.

In an embodiment 60.26 of the invention, there is provided a compound according to embodiment 1 which is
3,5-dichlorobenzyl 4-(3-(((1H-1,2,3-triazol-4-yl)methyl)amino)-3-oxopropyl)piperidine-1-carboxylate; or a pharmaceutically acceptable salt thereof.

In an embodiment 60.27 of the invention, there is provided a compound according to embodiment 1 which is
3,5-dichlorobenzyl 4-(2-((2-(1H-1,2,3-triazol-4-yl)ethyl)amino)-2-oxoethyl)piperidine-1-carboxylate; or a pharmaceutically acceptable salt thereof.

In an embodiment 60.28 of the invention, there is provided a compound according to embodiment 1 which is
3-methyl-5-(trifluoromethyl)benzyl 4-(4-(1H-1,2,3-triazol-4-yl)butanamido)piperidine-1-carboxylate; or a pharmaceutically acceptable salt thereof.

In an embodiment 60.29 of the invention, there is provided a compound according to embodiment 1 which is
3-bromo-5-(trifluoromethyl)benzyl 4-(4-(1H-1,2,3-triazol-4-yl)butanamido)piperidine-1-carboxylate; or a pharmaceutically acceptable salt thereof.

In an embodiment 60.30 of the invention, there is provided a compound according to embodiment 1 which is
3-chloro-5-cyanobenzyl 4-(5-(1H-1,2,3-triazol-4-yl)pentanamido)piperidine-1-carboxylate; or
a pharmaceutically acceptable salt thereof.

In an embodiment 60.31 of the invention, there is provided a compound according to embodiment 1 which is
3-chloro-5-cyanobenzyl 4-(3-(1H-1,2,3-triazol-4-yl)propanamido)piperidine-1-carboxylate; or
a pharmaceutically acceptable salt thereof.

In an embodiment 60.32 of the invention, there is provided a compound according to embodiment 1 which is
3-cyano-5-(trifluoromethyl)benzyl 4-(4-(1H-1,2,3-triazol-4-yl)butanamido)piperidine-1-carboxylate, or a pharmaceutically acceptable salt thereof.

In an embodiment 60.33 of the invention, there is provided a compound according to embodiment 1 which is
3,5-dichlorobenzyl 4-(6-(1H-1,2,3-triazol-4-yl)hexanamido)piperidine-1-carboxylate, or a pharmaceutically acceptable salt thereof.

The reason for the disclaimer in embodiment 1.1 "when L is

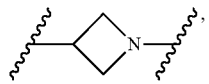 [SMILES: *C1CN(*)C1]

n is not 1" is that a compound where L is X is

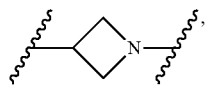

—C(=O)—N(R³)— and n is 1 was observed not to be stable.

The term "compounds of the (present) invention" or "a compound of the (present) invention" refers to a compound as defined in any one of embodiments 1 to 60.

The compounds of the present invention may be prepared by the routes described in the following Schemes or the Examples.

Compound of the present invention where X is —C(=O)—N($R^3$)— may be prepared according to Scheme 1 or 2.

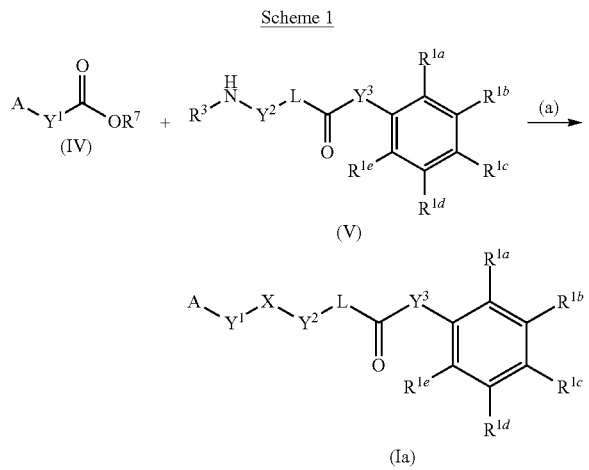

where A, L, $R^{1a}$, $R^{1b}$, $R^{1c}$, $R^{1d}$, $R^{1e}$, $R^3$, $Y^1$, $Y^2$, $Y^3$ are as defined in embodiment 1, X is —C(=O)—N($R^3$)—.

When $R^7$ is H, then step (a) involves reacting the compounds shown in scheme 1 in a suitable solvent such as DMF in the presence of a suitable amide coupling reagent, for example ®T3P or HATU, and a suitable base such as DIPEA at a suitable temperature such as room temperature.

When $R^7$ is an alkyl group, such as methyl or ethyl, then step (a) involves reacting the compounds shown in scheme 1 in a suitable solvent such as acetonitrile or methanol in the presence of a suitable base such as 2,3,4,6,7,8-hexahydro-1H-pyrimido[1,2-a]pyrimidine or sodium methoxide at a suitable temperature such as room temperature.

where A, L, $R^{1a}$, $R^{1b}$, $R^{1c}$, $R^{1d}$, $R^{1e}$, $R^3$, $Y^1$, $Y^2$, $Y^3$ are as defined in embodiment 1, X is —C(=O)—N($R^3$)—, $R^7$ is H and P represents a suitable protection group, for example a BOC (tert-butoxy carbonyl) group.

Step (a) involves reaction of a mono protected amine with an acid in a suitable solvent such as DMF with a suitable base such as diisopropylethylamine with a suitable amide coupling reagent such as T3P© or HATU at a suitable temperature such as room temperature.

Step (b) involves the removal of a suitable protection group P which is well known in the art. For example, when P is BOC, a compound is treated in a suitable solvent, for example DCM, under acidic conditions, for example by the addition of TFA, at a suitable temperature such as room temperature.

Step (c) involves reaction of an amine with a chloroformate in a suitable solvent such as DCM with a suitable base such as aqueous sodium hydroxide at a suitable temperature such as room temperature; alternatively reaction of an amine with an acid chloride in a suitable solvent such as DCM with a suitable base such as triethylamine at a suitable temperature such as room temperature.

Compounds of the present invention where X is —N($R^3$)—C(=O)— may be prepared according to Scheme 3.

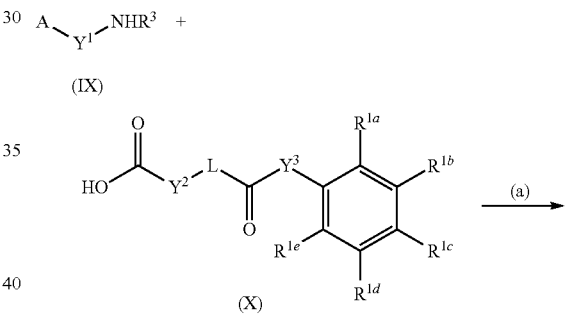

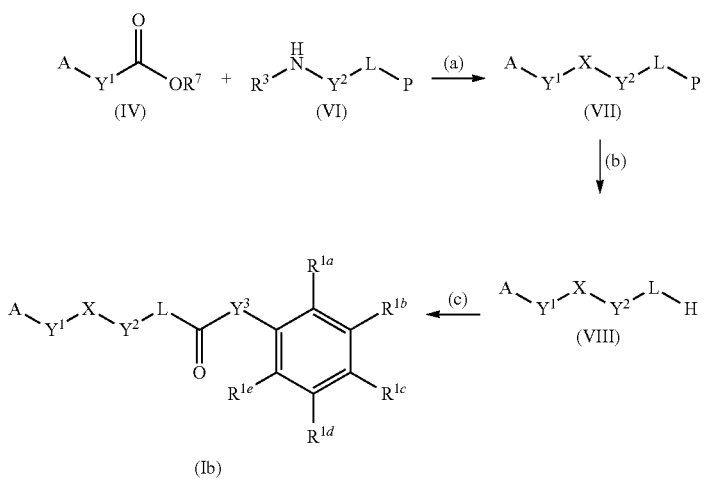

41

-continued

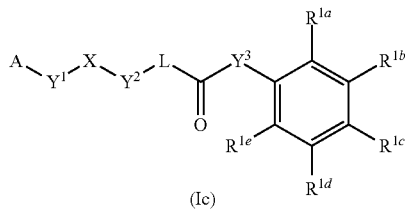

(Ic)

where A, L, $R^{1a}$, $R^{1b}$, $R^{1c}$, $R^{1d}$, $R^{1e}$, $R^3$, $Y^1$, $Y^2$, $Y^3$ are as defined in embodiment 1, X is —N($R^3$)—C(=O)—.

Step (a) involves reaction of a mono protected amine with an acid in a suitable solvent such as DMF with a suitable base such as diisopropylethylamine with a suitable amide coupling reagent such as T3P© or HATU at a suitable temperature such as room temperature.

Compounds of the present invention where A-$Y^1$—X— is dioxocyclobutenyl may be prepared according to Scheme 4.

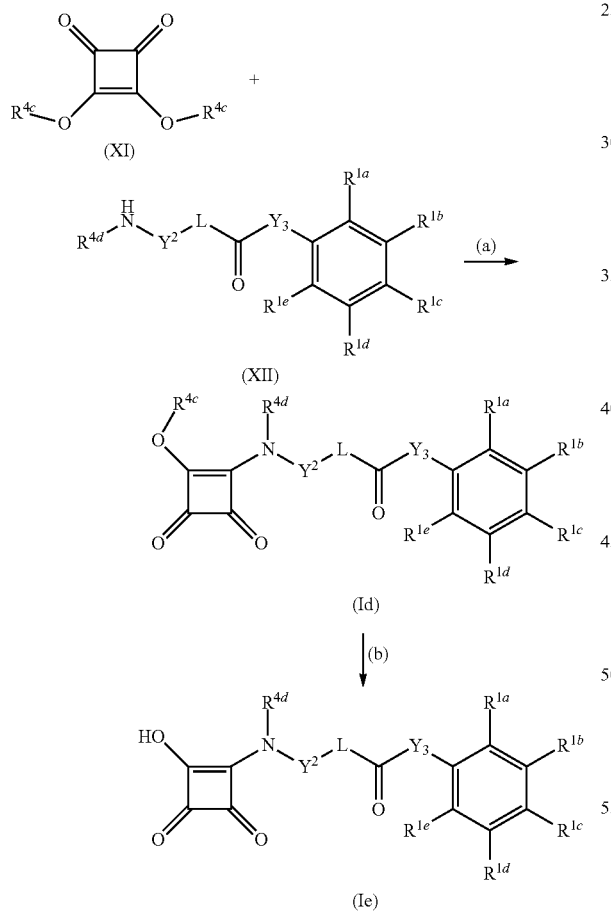

where A, L, $R^{1a}$, $R^{1b}$, $R^{1c}$, $R^{1d}$, $R^{1e}$, $R^3$, $R^{4c}$, $R^{4d}$, $Y^1$, $Y^2$, $Y^3$ are as defined in embodiment 1.

Step (a) involves reacting a suitable dialkoxycyclobutene-1,2-dione with the amine (XII) in a suitable solvent such as methanol with a suitable base such as triethylamine at a suitable temperature such as room temperature.

42

Step (b) involves hydrolysis of the squarate ester in a suitable solvent such as tetrahydrofuran with a suitable acid such as hydrochloric acid at a suitable temperature such as room temperature.

Compounds (IV) are either commercially available or may be prepared according to Scheme 5 and 6.

Scheme 5

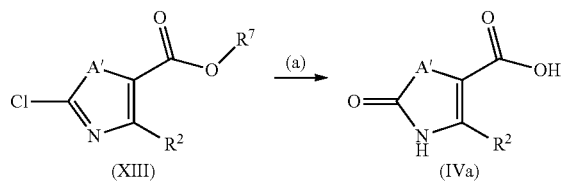

where $R^7$ is an alkyl group, such as methyl or ethyl, and $R^2$ is as defined in embodiment 1.

Step (a) involves reacting a compound (XIII) in a suitable solvent such as acetonitrile and methanol in the presence of a suitable base such as sodium methoxide and sodium hydroxide at a suitable temperature such as 80° C. or reflux.

Scheme 6

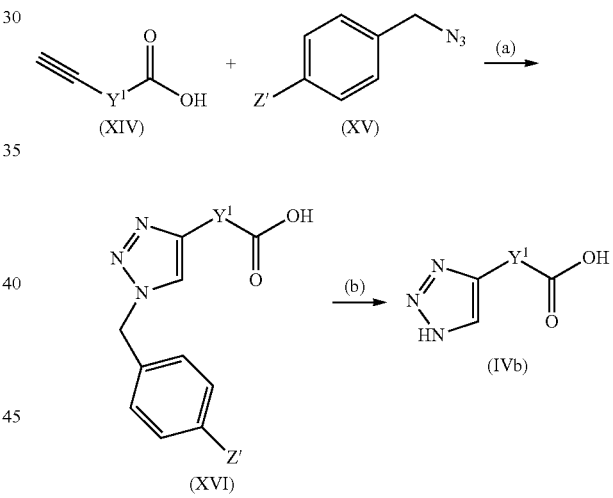

where Z' is H or OMe and $Y^1$ is as defined in embodiment 1.

Step (a) involves reacting the acetylene (XIV) with a suitable azide (XV) such as benzyl or 4-methoxybenzyl in suitable solvents such as tert-butanol and water in the presence of a suitable catalyst such as that formed in-situ from copper acetate and sodium ascorbate at a suitable temperature such as room temperature.

Step (b) involves removal of the benzyl group in a suitable solvent such as acetonitrile with a suitable oxidising agent such as ceric ammonium nitrate at a suitable temperature such as room temperature; or alternatively in a suitable solvent such as ethanol, with a suitable catalyst such as palladium on carbon, at a suitable temperature such as 70° C., and a suitable pressure of hydrogen such as 30 bar.

Compounds (X) may either be commercially available or may be prepared according to Scheme 7.

Scheme 7

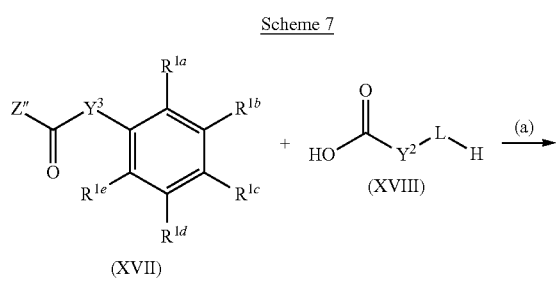

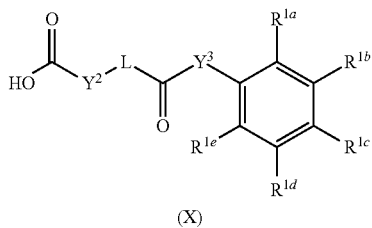

where Z" is Cl or O-succinyl and L, $R^{1a}$, $R^{1b}$, $R^{1c}$, $Y^2$, $Y^3$ are as defined in embodiment 1.

Step (a) is carried out in a suitable solvent such as DCM with a suitable base such as aqueous sodium hydroxide at a suitable temperature such as room temperature.

Compounds (IX) may either be commercially available or may be prepared according to Scheme 8.

where P represents a suitable protection group, for example p-methoxybenzyl (PMB) or pivaloyloxymethyl (POM), $R^7$ is an alkyl group, such as ethyl, and A, $Y^1$, $R^3$ are defined as in embodiment 1.

Step (a) involves reaction of an acid (IXX) with a suitable chloroformate such as ethyl chloroformate in a suitable solvent such as acetone and water with a suitable base such as triethylamine at a suitable temperature such as 0° C.

Step (b) involves reaction with sodium azide in a suitable solvent such as acetone at a suitable temperature such as 0° C.

Step (c) involves heating of compound (XXI) in a suitable solvent such as toluene at a suitable temperature such as 110° C., followed by acid hydrolysis of the resulting isocyanate in a suitable acid, such as hydrochloric acid, at a suitable temperature such as 100° C.

Step (d) involves reductive alkylation of the amine (XXII) with a suitable aldehyde such as formaldehyde in a suitable solvent such as DCM with a suitable reducing agent such as sodium triacetoxyborohydride at a suitable temperature such as room temperature.

Step (e) involves the removal of a suitable protection group P which is well known in the art. For example, when P is POM, a compound is treated in a suitable solvent, for example MeOH, under basic conditions, for example by the addition of sodium hydroxide, at a suitable temperature such as room temperature. Alternatively, when P is PMB, a compound is treated in a suitable solvent, for example acetonitrile, with a suitable oxidising agent such as ceric ammonium nitrate, at a suitable temperature such as room temperature.

Compounds (IX) where A is triazole may also be prepared according to the following Scheme 8a.

Scheme 8

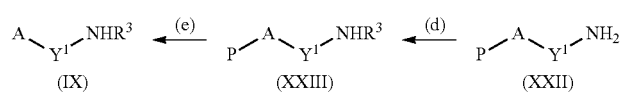

Scheme 8a

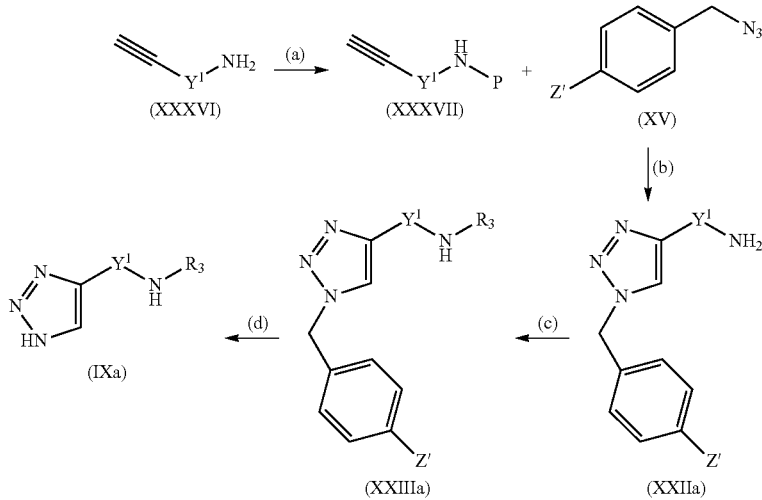

where P represents a suitable protection group, for example tert-butylcarbamate (BOC), Z' is H or OMe, and $Y^1$ and $R^3$ are defined as in embodiment 1.

Step (a) involves protection of an acetylene amine (XXXVI) with a suitable protecting group such as BOC in a suitable solvent such as THF with a suitable base such as triethylamine at a suitable temperature such as RT.

Step (b) involves reacting the acetylene (XXXVII) with a suitable azide (XV) such as benzyl or 4-methoxybenzyl in suitable solvents such as tert-butanol and water in the presence of a suitable catalyst such as that formed in-situ from copper acetate and sodium ascorbate at a suitable temperature such as room temperature, with in-situ deprotection of the amine by a suitable method such as an acid wash.

Step (c) involves reductive alkylation of the amine (XXIIa) with a suitable aldehyde such as formaldehyde in a suitable solvent such as DCM with a suitable reducing agent such as sodium triacetoxyborohydride at a suitable temperature such as room temperature.

Step (d) involves the removal of a benzyl protecting group which is well known in the art. For example, when Z' is OMe, the compound is treated in a suitable solvent, for example acetonitrile, with a suitable oxidising agent such as ceric ammonium nitrate, at a suitable temperature such as room temperature. When Z' is H, the compound is treated in a suitable solvent, for example, ethanol, with a suitable catalyst, such as palladium on carbon, under a suitable pressure of hydrogen, such as 30 bar, at a suitable temperature, such as 70° C.

Compounds (V) may either be commercially available or may be prepared according to Scheme 9.

Scheme 9

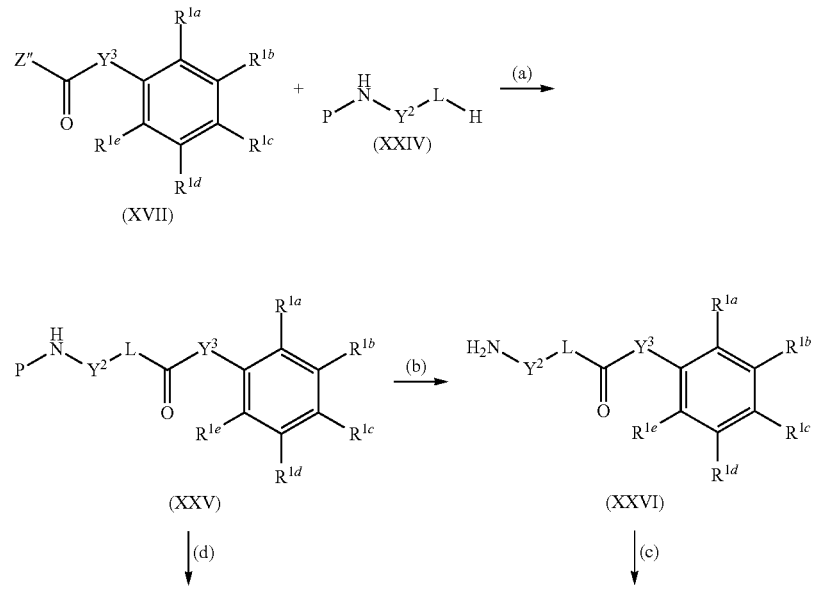

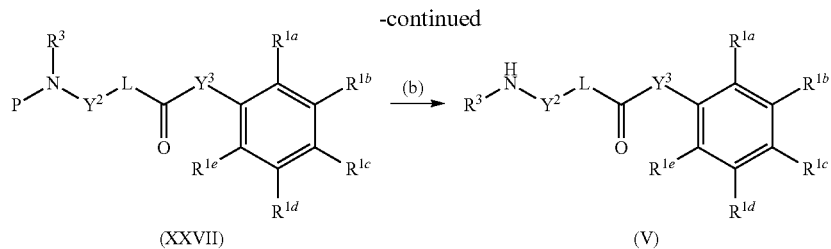

(XXVII) → (V)

where Z" is Cl or O-succinyl, P represents a suitable protection group, for example a BOC (tert-butoxy carbonyl) group and L, $R^{1a}$, $R^{1b}$, $R^{1c}$, $R^{1d}$, $R^{1e}$, $R^3$, $Y^2$, $Y^3$ are as defined in embodiment 1.

Step (a) involves reaction of a mono protected diamine (XXIV) with a chloroformate or O-succinyl ester (XVII) in a suitable solvent such as dichloromethane with a suitable base such as aqueous sodium hydroxide at a suitable temperature such as room temperature; alternatively reaction of an amine with an acid chloride in a suitable solvent such as DCM with a suitable base such as triethylamine at a suitable temperature such as room temperature.

Step (b) involves the removal of a suitable protection group P which is well known in the art. For example, when P is BOC, a compound is treated in a suitable solvent, for example DCM, under acidic conditions, for example by the addition of TFA, at a suitable temperature such as room temperature.

Step (c) involves reductive alkylation of an amine (XXVI) with a suitable aldehyde such as formaldehyde in a suitable solvent such as dichloromethane with a suitable reducing agent such as sodium triacetoxyborohydride at a suitable temperature such as room temperature.

Step (d) involves deprotonation of a carbamate with a suitable base such as sodium hydride in a suitable solvent such as N,N'-dimethylformamide at a suitable temperature such as 0° C., followed by alkylation with a suitable alkylating agent such as iodomethane at a suitable temperature such as room temperature.

Compounds (XVII) may either be commercially available or may be prepared according to Scheme 10.

Scheme 10

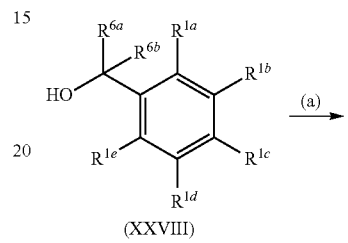

(XXVIII)

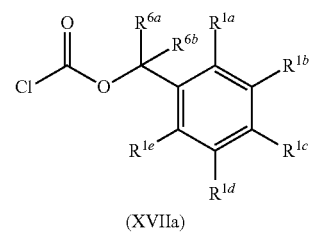

(XVIIa)

where $R^{1a}$, $R^{1b}$, $R^{1c}$, $R^{1d}$, $R^{1e}$, $R^{6a}$, $R^{6b}$ are as defined in embodiment 1.

Step (a) involves reaction of a benzyl alcohol (XXVIII) dissolved in a suitable solvent such as tetrahydrofuran with phosgene in a suitable solvent such as toluene at a suitable temperature such as 10° C.

Compounds (XXVII) where $Y^3$ is —CH═CH— or —$CR^{6e}R^{6f}CR^{6g}R^{6h}$— may either be commercially available or may be prepared according to Scheme 11.

Scheme 11

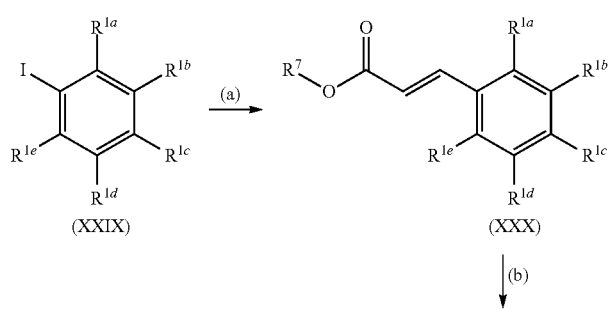

(XXIX) (XXX)

↓(b)

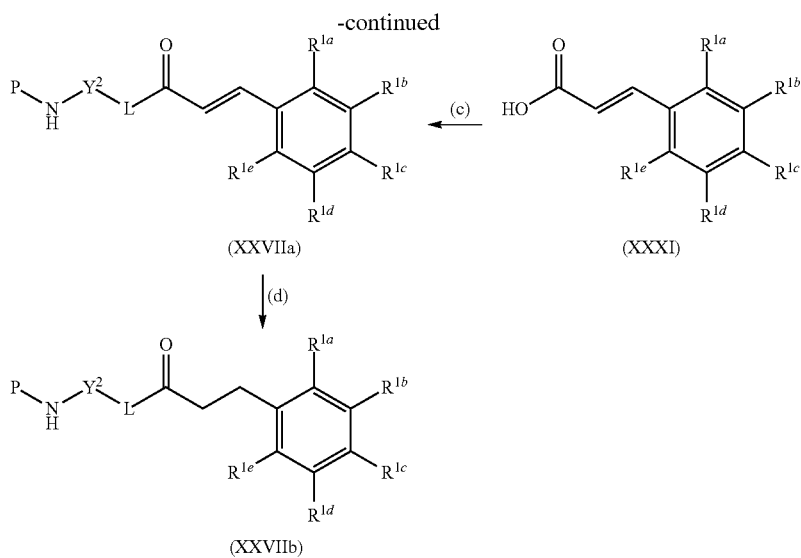

where $R^7$ is an alkyl group, such as methyl or ethyl, P represents a suitable protection group, for example a BOC (tert-butoxy carbonyl) group, L, $R^{1a}$, $R^{1b}$, $R^{1c}$, $R^{1d}$, $R^{1e}$, $Y^2$ are as defined in embodiment 1.

Step (a) involves reaction of an iodobenzene (XXIX) with an acrylate ester in a suitable solvent such as N,N'-dimethylformamide with a suitable base such as triethylamine and a suitable catalyst such as palladium bis(tritert-butylphosphine) at a suitable temperature such as 80° C.

Step (b) involves hydrolysis of the ester in a suitable solvent such as tetrahydrofuran with a suitable base such as sodium hydroxide at a suitable temperature such as room temperature.

Step (c) involves reaction of a monoprotected diamine (XXIV) with an acid (XXXI) in a suitable solvent such as DMF in the presence of a suitable amide coupling reagent, for example ®T3P or HATU, and a suitable base such as DIPEA at a suitable temperature such as room temperature.

Step (d) involves reduction of a cinnamide in a suitable solvent such as ethanol in the presence of a suitable catalyst such as platinum on carbon under a suitable pressure of hydrogen such as at a suitable temperature such as room temperature.

Compounds (XXVII) where L is piperazine (XXXII) is either commercially available or may also be prepared according to Scheme 12.

Scheme 12

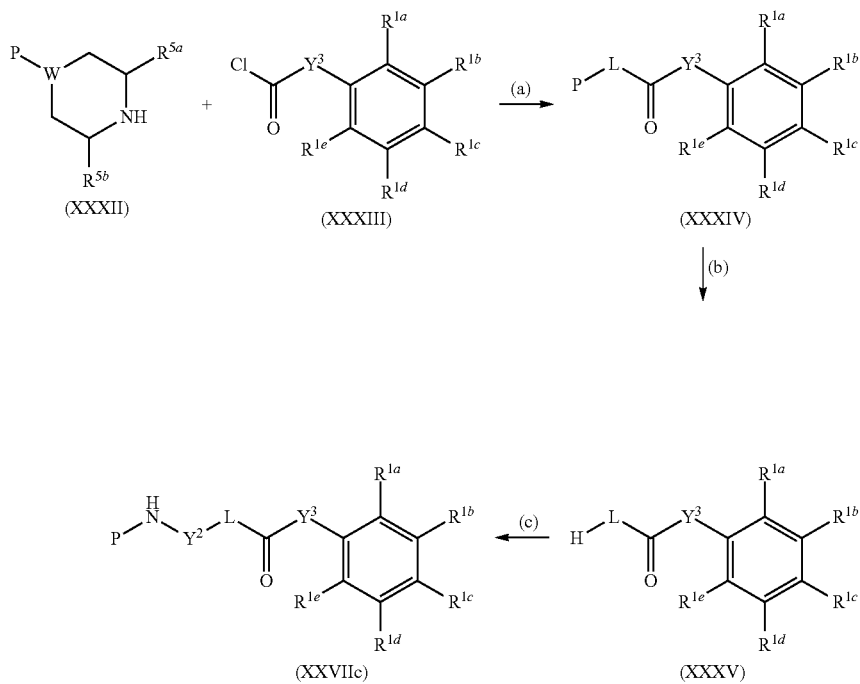

where W is specifically N, P represents a suitable protection group, for example a BOC (tert-butoxy carbonyl) group, $R^{1a}$, $R^{1b}$, $R^{1c}$, $R^{1d}$, $R^{1e}$, $Y^2$, $Y^3$ are as defined in embodiment 1 and L is specifically

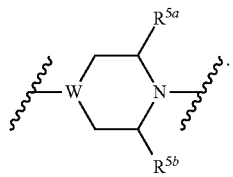

Step (a) involves reaction of an amine (XXXII) with a chloroformate (XXXIII) in a suitable solvent such as DCM with a suitable base such as aqueous sodium hydroxide at a suitable temperature such as room temperature; alternatively reaction of an amine with an acid chloride in a suitable solvent such as DCM with a suitable base such as triethylamine at a suitable temperature such as room temperature.

Step (b) involves the removal of a suitable protection group P which is well known in the art. For example, when P is BOC, a compound is treated in a suitable solvent, for example DCM, under acidic conditions, for example by the addition of TFA, at a suitable temperature such as room temperature.

Step (c) involves reaction of an amine (XXXV) with a suitable aldehyde such as tert-butyl methyl(3-oxopropyl)carbamate in suitable solvent such as dichloromethane in the presence of a suitable reducing agent such as sodium triacetoxyborohydride at a suitable temperature such as room temperature.

Compounds (VI), (XI), (XIII), (XIV), (XV), (XVII), (XVIII), (IXX), (XVII), (XXVIII), (XXIX), (XXXII) and (XXXIII) are either commercially available or may be prepared according to known methods.

Compounds of the present invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter. All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compounds of the present invention. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds of the present invention described herein may contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds of the present invention may be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound of the present invention contains a double bond, the substituent may be E or Z configuration. If the compound of the present invention contains a disubstituted cycloalkyl, the cycloalkyl substituent may have a cis- or trans-configuration. All tautomeric forms, for example for group A in embodiment 1, are also intended to be included.

As used herein, the terms "salt" or "salts" refers to an acid addition or base addition salt of a compound of the present invention. "Salts" include in particular "pharmaceutical acceptable salts". The term "pharmaceutically acceptable salts" refers to salts that retain the biological effectiveness and properties of the compounds of the present invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Thus, in an embodiment 61, there is provided a pharmaceutically acceptable salt of a compound according to any one of embodiments 25 to 60, wherein the salt is selected from acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salt.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Thus, in an embodiment 62, there is provided a pharmaceutically acceptable salt of a compound according to any one of embodiments 25 to 60, wherein the salt is selected from ammonium, potassium, sodium, calcium and magnesium salt.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

Thus, in an embodiment 63, there is provided a pharmaceutically acceptable salt of a compound according to any one of embodiments 25 to 60, wherein the salt is selected from isopropylamine, benzathine, cholinate, diethanolamine, diethylamine, lysine, meglumine, piperazine and tromethamine salt.

The pharmaceutically acceptable salts of the compounds of the present invention can be synthesized from a basic or acidic moiety, by conventional chemical methods. Generally, such salts can be prepared by reacting free acid forms of the compounds of the present invention with a stoichiometric amount of the appropriate base (such as Na, Ca, Mg, or K hydroxide, carbonate, bicarbonate or the like), or by reacting free base forms of the compounds of the present invention with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds of the present invention have structures depicted by the formulas given herein except that one or more atoms are replaced by an atom having a selected atomic mass or mass number. Examples of isotopes that can be incorporated into compounds of the present invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}F$, $^{35}S$, $^{36}Cl$, $^{125}I$ respectively. The invention includes various isotopically labeled compounds of the present invention, for example those into which radioactive isotopes, such as $^{3}H$ and $^{14}C$, or those into which non-radioactive isotopes, such as $^{2}H$ and $^{13}C$ are present. Such isotopically labelled compounds of the present invention are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound of the present invention may be particularly desirable for PET or SPECT studies. Isotopically-labeled compounds of the present invention can generally be prepared by conventional techniques known to those skilled in the art or by processes analogous to those described in the accompanying Generic Schemes, Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of the present invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The compounds of the present invention in free form or in salt form, exhibit valuable pharmacological properties, e.g. as indicated in in vitro tests as provided herein, and are therefore indicated for therapy or for use as research chemicals, e.g. as tool compounds.

Thus, in an embodiment 64, there is provided a compound according to any one of embodiments 1 to 60 for use in medicine.

The compounds according to any one of embodiments 1 to 60 are potent inhibitors of ATX (see $IC_{50}$ data disclosed herein). The compound of the present invention are hence useful in the treatment of an ATX-dependent or ATX-mediated disease or condition.

Thus, in an embodiment 65, there is provided a compound according to any one of embodiments 1 to 60 for use in the treatment of an ATX-dependent or ATX-mediated disease or condition. In an embodiment 66, there is provided the use of a compound according to any one of embodiments 1 to 60 in the treatment of an ATX-dependent or ATX-mediated disease or condition. In an embodiment 67, there is provided the use of a compound according to any one of embodiments 1 to 60 in the manufacture of a medicament for the treatment of an ATX-dependent or ATX-mediated disease or condition. In an embodiment 68, there is provided a method of treating an ATX-dependent or ATX-mediated disease or condition comprising administering to the subject a therapeutically effective amount of a compound according to any one of embodiments 1 to 60.

Hence, in a further embodiment 69, the compounds of the invention are useful for the treatment of a disease or condition according to embodiments 65, 66, 67 and 68, wherein the disease or condition is selected from fibrosis, pruritus, cirrhosis, cancer, diabetes, kidney diseases and pain.

In an embodiment 70, the compounds of the invention are useful for the treatment of a disease or condition according to embodiment 69, wherein the disease or condition is selected from pulmonary fibrosis, idiopathic pulmonary fibrosis, a diffuse parenchymal interstitial lung disease including iatrogenic drug-induced fibrosis, occupational and/or environmental induced fibrosis (Farmer lung), radiation induced fibrosis, bleomycin induced pulmonary fibrosis, asbestos induced pulmonary fibrosis, acute respiratory distress syndrome (ARDS), kidney fibrosis, tubulointerstitium fibrosis, gut fibrosis, liver fibrosis, alcohol induced liver fibrosis, toxic/drug induced liver fibrosis, infection induced liver fibrosis, viral induced liver fibrosis, cutaneous fibrosis, spinal cord injury/fibrosis, myelofibrosis, renal fibrosis, skin fibrosis, ocular fibrosis, post-transplant fibrosis, hepatic fibrosis with or without cirrhosis, cardiac fibrosis, neuropathic pruritus, neurogenic pruritus, psychogenic pruritus, cholestatic pruritus, primary biliary cirrhosis, liver cirrhosis, breast cancer, pancreatic cancer, ovarian cancer, prostate cancer, glioblastoma, bone cancer, colon cancer, bowel cancer, head and neck cancer, diabetes, polycystic kidney disease, acute kidney injury, chronic kidney disease, neuropathic pain and cancer pain.

In an embodiment 71, the compounds of the invention are useful for the treatment of a disease or condition according to embodiment 70, wherein the disease or condition is selected from idiopathic pulmonary fibrosis, breast cancer, pancreatic cancer, prostate cancer, cholestatic pruritus, primary biliary cirrhosis and polycystic kidney disease, particularly idiopathic pulmonary fibrosis.

The compounds of the invention will be typically formulated as pharmaceutical compositions.

Thus, in an embodiment 72 of the invention, the present invention provides a pharmaceutical composition comprising a compound according to any one of embodiments 1 to 60, or a pharmaceutically acceptable salt thereof, and a pharmaceutically acceptable carrier.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the present invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042 (including the BREEZHALER™ device), WO 97/20589 (including the CERTIHALER™ device), WO 97/30743 (including the TWISTHALER™ device), WO 05/37353 (including the GYROHALER™ device), U.S. Pat. No. 6,536,427 (including the DISKUS™ device), WO 97/25086 (including the DISKHALER™ device), WO 95/14089 (including the GEMINI™ device), WO 03/77979 (including the PROHALER™ device), and also the devices disclosed in WO 08/51621, WO 09/117112 and US 2005/0183724.

Hence, the invention also includes (A) a compound of the present invention, or a pharmaceutically acceptable salt thereof, in inhalable form; (B) an inhalable medicament comprising a compound of the present invention in inhalable form together with a pharmaceutically acceptable carrier in inhalable form; (C) a pharmaceutical product comprising a compound of the present invention in inhalable form in association with an inhalation device; and (D) an inhalation device containing a compound of the present invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of the present invention and at least one other therapeutic agent as a combined preparation for simultaneous, separate or sequential use in therapy. In one embodiment, the therapy is the treatment of a disease or condition mediated by blockade of the epithelial sodium channel. Products provided as a combined preparation include a composition comprising the compound of the present invention and the other therapeutic agent(s) together in the same pharmaceutical composition, or the compound of the present invention and the other therapeutic agent(s) in separate form, e.g. in the form of a kit.

Thus, in an embodiment 73, the invention provides a pharmaceutical composition comprising a compound according to any one of embodiments 1 to 60 and one or more therapeutically active co-agent. Optionally, the pharmaceutical composition may comprise a pharmaceutically acceptable excipient, as described above.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In an embodiment 74 of the invention, there is provided a pharmaceutical combination, comprising:
a therapeutically effective amount of the compound according to any one of embodiments 1 to 60, or a pharmaceutically acceptable salt thereof, and one or more therapeutically active co-agent.

In an embodiment 75 of the invention, there is provided a pharmaceutical combination according to embodiment 74, wherein the therapeutically active co-agent is selected from immunosuppressants, analgesics, anti-cancer agent, anti-inflammatories, chemokine receptor antagonists, bronchodilators, leukotriene receptor antagonists, leukotriene formation inhibitors, monoacylglycerol kinase inhibitors, phospholipase A1 inhibitors, phospholipase A2 inhibitors, lysophospholipase D (lysoPLD) inhibitors, decongestants, antihistamines, mucolytics, anticholinergics, antitussives, expectorants, and β-2 agonists.

Suitable anti-inflammatory drugs include steroids, for example corticosteroids. Suitable steroids include budesonide, beclamethasone (e.g. dipropionate), butixocort (e.g. propionate), CHF5188, ciclesonide, dexamethasone, flunisolide, fluticasone (e.g. propionate or furoate), GSK-685698, GSK-870086, LAS40369, methyl prednisolone, mometasone (e.g. furoate), prednisolone, rofleponide, and triamcinolone (e.g. acetonide). In certain preferred embodiments the steroid is long-acting corticosteroids such as budesonide, ciclesonide, fluticasone propionate, fluticasone furoate or mometasone furoate.

Suitable $β_2$-agonists include arformoterol (e.g. tartrate), albuterol/salbutamol (e.g. racemate or single enantiomer such as the R-enantiomer, or salt thereof especially sulfate), AZD3199, bambuterol, BI-171800, bitolterol (e.g. mesylate), carmoterol, clenbuterol, etanterol, fenoterol (e.g. racemate or single enantiomer such as the R-enantiomer, or salt thereof especially hydrobromide), flerbuterol, formoterol (e.g. racemate or single diastereomer such as the R,R-diastereomer, or salt thereof especially fumarate or fumarate dihydrate), GSK-159802, GSK-597901, GSK-678007, indacaterol (e.g. racemate or single enantiomer such as the R-enantiomer, or salt thereof especially maleate, acetate or xinafoate), LAS100977, metaproterenol, milveterol (e.g. hydrochloride), naminterol, olodaterol (e.g. racemate or single enantiomer such as the R-enantiomer, or salt thereof especially hydrochloride), PF-610355, pirbuterol (e.g. acetate), procaterol, reproterol, salmefamol, salmeterol (e.g. racemate or single enantiomer such as the R-enantiomer, or salt thereof especially xinafoate), terbutaline (e.g. sulphate) and vilanterol (or a salt thereof especially trifenatate. In certain preferred embodiments the $β_2$-agonist is an ultra-long-acting $β_2$-agonist such as indacaterol, or potentially carmoterol, LAS-100977, milveterol, olodaterol, PF-610355 or vilanterol. A preferred embodiment one of the second active ingredients is indacaterol (i.e. (R)-5-[2-(5,6-diethyl-indan-2-ylamino)-1-hydroxyethyl]-8-hydroxy-1H-quinolin-2-one) or a salt thereof. This is a $β_2$-adrenoceptor agonist that has an especially long duration of action (i.e. over 24 hours) and a short onset of action (i.e. about 10 minutes). This compound is prepared by the processes described in international patent applications WO 2000/75114 and WO 2005/123684. It is capable of forming acid addition salts, particularly pharmaceutically acceptable acid addition salts. A preferred salt of (R)-5-[2-(5,6-diethyl-indan-2-ylamino)-1-hydroxyethyl]-8-hydroxy-1H-quinolin-2-one is the maleate salt. Another preferred salt is (R)-5-[2-(5,6-diethyl-indan-2-ylamino)-1-hydroxyethyl]-8-hydroxy-1H-quinolin-2-one acetate. Another preferred salt is (R)-5-[2-(5,6-diethyl-indan-2-ylamino)-1-hydroxyethyl]-8-hydroxy-1H-quinolin-2-one xinafoate.

Suitable bronchodilatory drugs include anticholinergic or antimuscarinic agents, such as aclidinium (e.g. bromide), BEA-2108 (e.g. bromide), BEA-2180 (e.g. bromide), CHF-5407, darifenacin (e.g. bromide), darotropium (e.g. bromide), glycopyrrolate (e.g. racemate or single enantiomer, or salt thereof especially bromide), dexpirronium (e.g. bromide), iGSK-202405, GSK-203423, GSK-573719, GSK-656398, ipratropium (e.g. bromide), LAS35201, LAS186368, otilonium (e.g. bromide), oxitropium (e.g. bromide), oxybutynin, PF-3715455, PF-3635659, pirenzepine, revatropate (e.g. hydrobromide), solifenacin (e.g. succinate), SVT-40776, TD-4208, terodiline, tiotropium (e.g. bromide), tolterodine (e.g. tartrate), and trospium (e.g. chloride). In certain preferred embodiments the muscarinic antagonists is long-acting muscarinic antagonist such as darotropium bromide, glycopyrrolate or tiotropium bromide.

Suitable dual anti-inflammatory and bronchodilatory drugs include dual beta-2 adrenoceptor agonist/muscarinic antagonists such as GSK-961081 (e.g. succinate). and those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

EXPERIMENTAL

Examples

The following examples are intended to illustrate the invention and are not to be construed as being limitations thereon.

General Conditions:

Mass spectra were acquired on LC-MS, SFC-MS, or GC-MS systems using electrospray, chemical and electron impact ionization methods from a range of instruments of the following configurations: Agilent 1100 HPLC systems with an Agilent 6110 Mass Spectrometer, or Micromass Platform Mass Spectrometer or Thermo LTQ Mass Spectrometer; a Waters Acquity UPLC system with SQD Mass Spectrometer, a Waters FractionLynx HPLC system with 3100 Mass Spectrometer, a Waters UPC2 system with TQD Mass Spectrometer or a Waters Prep100 SFC-MS system with SQD2 Mass Spectrometer. [M+H]+ refers to protonated molecular ion of the chemical species.

NMR spectra were run on Bruker AVANCE 400 MHz or 500 MHz NMR spectrometers using ICON-NMR, under TopSpin program control. Spectra were measured at 298K, unless indicated otherwise, and were referenced relative to the solvent resonance.

Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

ABBREVIATIONS anh anhydrous
aq aqueous
BOC tert-butoxy carbonyl
br broad
BSA bovine serum albumin
CDI 1,1'-carbonyldiimidazole
d doublet
dd doublet of doublets
DCM dichloromethane
DIPEA diisopropylethylamine
DMF N,N-dimethylformamide
DMSO dimethylsulfoxide
EDC N-(3-dimethylaminopropyl)-N'-ethylcarbodiimide
EtOAc ethyl acetate
EtOH ethanol
H or hrs hour(s)
HATU (O-(7-azabenzotriazol-1-yl)-N,N,N',N'-tetramethyluronium hexafluorophosphate)
HBSS Hanks' balanced salt solution
HPLC high pressure liquid chromatography
HRP Horseradish peroxidase
Int. intermediate
LCMS liquid chromatography and mass spectrometry
MeOH methanol
Me methyl
MS mass spectrometry
m multiplet
min minutes
ml milliliter(s)
m/z mass to charge ratio
NMR nuclear magnetic resonance
NMM N-methylmorpholine
O/N overnight
PS polymer supported
PE-AX PE-anion exchange (e.g. Isolute® PE-AX columns from Biotage)
T3P® Propylphosphonic anhydride
RT room temperature
Rt retention time
s singlet
SCX-2 strong cation exchange (e.g. Isolute® SCX-2 columns from Biotage)
sol solution
triplet
TEA triethylamine
TFA trifluoroacetic acid
THF tetrahydrofuran Referring to the examples that follow, compounds of the Examples were synthesized using the methods described herein, or other methods, which are known in the art.

The various starting materials, intermediates, and compounds of the Examples may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the compounds of the Examples encompasses any tautomeric form of the drawn structure.

If not indicated otherwise, the analytical HPLC conditions are as follows:
Method 2minLowpHv02:

| Column: | Waters Acquity CSH 1.7 µm, 2.1 × 50 mm |
|---|---|
| Temperature: | 50° C. |
| Mobile Phase: | A: Water + 0.1% TFA B: Acetonitrile + 0.1% TFA |

| | |
|---|---|
| Flow rate: | 1.0 mL/min |
| Gradient: | 0.0 min 5% B, 0.2-1.55 min 5-98% B, 1.55-1.75 min 98% B, 1.75-1.8 min 98-5% B |

Method 2minLowpHv01:

| | |
|---|---|
| Column: | Waters Acquity CSH 1.7 μm, 2.1 × 50 mm |
| Temperature: | 50° C. |
| Mobile Phase: | A: Water + 0.1% Formic Acid B: Acetonitrile + 0.1% Formic Acid |
| Flow rate: | 1.0 mL/min |
| Gradient: | 0.0 min 5% B, 0.2-1.55 min 5-98% B, 1.55-1.75 min 98% B, 1.75-1.8 min 98-5% B |

Method 2minLowpFlv03:

| | |
|---|---|
| Column: | Waters Acquity CSH 1.7 μm, 2.1 × 50 mm |
| Temperature: | 50° C. |
| Mobile Phase: | A: Water + 0.1% Formic Acid B: Acetonitrile + 0.1% Formic Acid |
| Flow rate: | 1.0 mL/min |
| Gradient: | 0.0 min 5% B, 0.2-1.8 min 5-98% B, 1.8-2.1 min 98% B, 2.1-2.3 min 98% B |

Method 2minLC_v001

| | |
|---|---|
| Column | Waters BEH C18 100 × 2.1 mm, 1.7 μm |
| Column Temperature | 50° C. |
| Eluents | A: $H_2O$, B: acetonitrile, both containing 0.1% TFA |
| Flow Rate | 0.7 mL/min |
| Gradient | 0.25 min 5% B; 5% to 95% B in 1.00 min, 0.25 min 95% B |

8minLowpHv01:

| | |
|---|---|
| Column: | Waters Acquity CSH 1.7 μm, 2.1 × 100 mm |
| Temperature: | 50° C. |
| Mobile Phase: | A: Water + 0.1% Formic Acid B: Acetonitrile + 0.1% Formic Acid |
| Flow rate: | 0.7 mL/min |
| Gradient: | 0.0 min 2% B, 0.3-6.5 min 2-98% B, 6.5-7.5 min 98% B, 7.5-8.0 min 5-98% B |

Method 10minLowpHv01:

| | |
|---|---|
| Column: | Waters Acquity CSH 1.7 μm, 2.1 × 100 mm |
| Temperature: | 50° C. |
| Mobile Phase: | A: Water + 0.1% Formic Acid B: Acetonitrile + 0.1% Formic Acid |
| Flow rate: | 0.7 mL/min |
| Gradient: | 0.0 min 2% B, 0.5-8.0 min 2-98% B, 8.0-9.0 min 98% B, 9.0-9.1 min 98-2% B |

Example 1

3,5-Dichlorobenzyl 4-(2-(3-hydroxy-N-methyl isoxazole-5-carboxamido)ethyl)piperidine-1-carboxylate

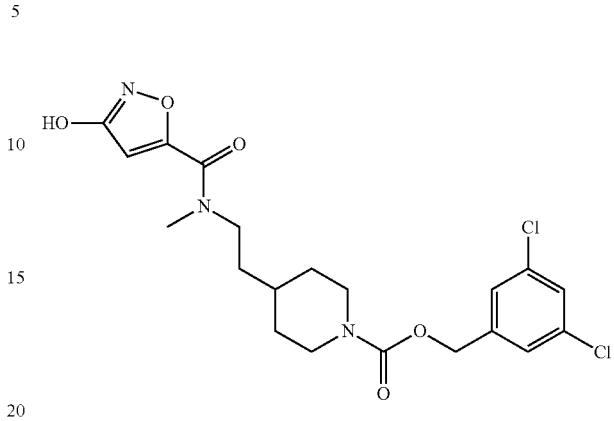

Step 1: 3,5-Dichlorobenzyl 4-(2-((tert-butoxycarbonyl)amino)ethyl)piperidine-1-carboxylate A mixture comprising of tert-butyl(2-(piperidin-4-yl) ethyl)carbamate (1.85 g, 8.10 mmol) in DCM (80 ml), sat. aqueous sodium bicarbonate solution (20 ml, 8.10 mmol) and 3,5-dichlorobenzyl carbonochloridate (prepared according to Bioorganic & Medicinal Chemistry Letters, 21(21), 6608-6612; 2011, Intermediate 33) (1.940 g, 8.10 mmol) was stirred at room temperature for 3 hours. The resulting mixture was treated with 2M NaOH soln. (50 ml). The organics were separated, dried ($MgSO_4$) and concentrated under reduced pressure to afford the title compound;

1H NMR (400 MHz, $CDCl_3$) 7.3 (1H, s), 7.2 (2H, s), 5.1 (2H, s), 4.5 (1H, s), 4.2 (2H, s), 3.2 (2H, bs), 2.8 (2H, bs), 1.75 (2H, d), 1.5 (11H, m), 1.15 (2H, m)

Step 2: 3,5-Dichlorobenzyl 4-(2-((tert-butoxycarbonyl)(methyl)amino)ethyl)piperidine-1-carboxylate A solution of 3,5-dichlorobenzyl 4-(2-((tert-butoxycarbonyl)amino)ethyl)piperidine-1-carboxylate (step 1) (3.5 g, 8.11 mmol) in DMF (40 ml) was cooled to 0° C. 60% sodium hydride/oil (0.487 g, 12.17 mmol) was added. The solution was stirred at 0° C. for 15 mins and then was warmed to RT. Iodomethane (0.761 ml, 12.17 mmol) was added and the resulting mixture was stirred at room temperature for 5 hours. The reaction was quenched with ammonium chloride (20 ml). The mixture was diluted with water (200 ml) and extracted with EtOAc (2×200 ml). The organic portion was dried using $MgSO_4$, filtered and concentrated under reduced pressure. The residue was applied to an 80 g silica cartridge in DCM and eluted with 0-100% EtOAc in iso-hexane to afford the title compound;

LCMS: Rt=1.58 mins; MS m/z 345.2 and 347.2 [M-BOC+H]+; Method 2minLowpHv02

1H NMR (400 MHz, $CDCl_3$) 7.3 (1H, s), 7.2 (2H, s), 5.1 (2H, s), 4.2 (1H, bs), 3.3 (2H, t), 3.2 (2H, bs), 2.85 (3H, s), 2.8 (2H, bs), 1.8 (2H, d), 1.5 (11H, s), 1.15 (2H, m),

Step 3: 3,5-Dichlorobenzyl 4-(2-(methylamino)ethyl)piperidine-1-carboxylate

To a solution of 3,5-dichlorobenzyl 4-(2-((tert-butoxycarbonyl)(methyl)amino)ethyl)piperidine-1-carboxylate (step 2) (2.73 g, 6.13 mmol) in DCM (20 mL) was added trifluoroacetic acid (19 ml, 247 mmol). The reaction mixture was stirred at room temperature for 1 hour. The mixture was concentrated under pressure and the residue was suspended in sat. sodium bicarbonate solution (100 ml). The resultant mixture was extracted with EtOAc (2×100 ml). The organic portion was dried using $MgSO_4$, filtered and concentrated under reduced pressure. The oil was applied to a 40 g silica cartridge in DCM and eluted with 0-20% MeOH/DCM containing 1% aqueous ammonia to afford the title compound;

LCMS; Rt=0.83 mins; MS m/z 354.3 and 347.3 [M+H]+; Method 2minLowpHv01

1H NMR (400 MHz, MeOD) 7.45 (1H, s), 7.4 (2H, s), 5.1 (2H, s), 4.2 (2H, d), 2.8 (4H, M), 2.6 (3H, s), 1.8 (2H, d), 1.6 (3H, m), 1.2 (2H, m).

Step 4: 3,5-Dichlorobenzyl 4-(2-(3-hydroxy-N-methylisoxazole-5-carboxamido)ethyl)piperidine-1-carboxylate A solution comprising of methyl 3-hydroxyisoxazole-5-carboxylate (20.72 mg, 0.145 mmol), 3,5-dichlorobenzyl 4-(2-(methylamino)ethyl)piperidine-1-carboxylate (step 3) (50 mg, 0.145 mmol) and 2,3,4,6,7,8-hexahydro-1H-pyrimido[1,2-a]pyrimidine (20.16 mg, 0.145 mmol) in DMF (483 µl) was refluxed for 18 hours. The reaction mixture was diluted with EtOAc and washed with water. The organic portion was separated, dried over $MgSO_4$, filtered and concentrated under reduced pressure to afford the title compound;

1H NMR (400 MHz, MeOD) 7.4 (1H, s), 7.3 (2H, s), 6.35 (1H, d), 5.1 (2H, s), 4.15 (2H, bs), 3.6 (2H, q), 3.2 (3H, d), 2.9 (2H, bs), 1.9 (1H, d), 1.6 (4H, m), 1.1 (2H, m),

LC-MS: Rt 5.24 mins; MS m/z 456 [M+H]+; Method 10minLowpHv01

Example 2

3,5-Dichlorobenzyl 4-(2-((2-methoxy-3,4-dioxocyclobut-1-en-1-yl)(methyl)amino)ethyl)piperidine-1-carboxylate

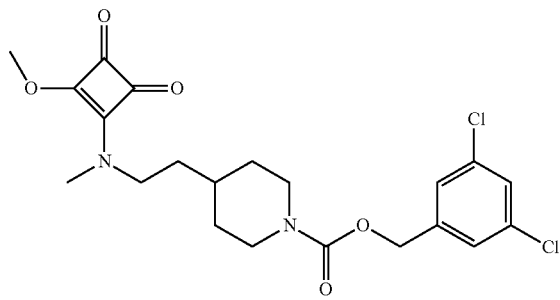 [SMILES: COc1c(N(C)CCC2CCN(C(=O)OCc3cc(Cl)cc(Cl)c3)CC2)c(=O)c1=O]

A solution of 3,4-dimethoxycyclobut-3-ene-1,2-dione (20.58 mg, 0.145 mmol) and triethylamine (81 µl, 0.579 mmol) in MeOH (483 µl) was warmed to 45° C. for 30 mins. 3,5-Dichlorobenzyl 4-(2-(methylamino)ethyl)piperidine-1-carboxylate (Example 1, step 3) (50 mg, 0.145 mmol) was added drop wise and the reaction mixture was stirred at room temperature for 18 hours. The resulting mixture was concentrated under reduced pressure and the crude oily product was dissolved in water and extracted with EtOAc. The organic portion was dried over MgSO4, filtered and solvent concentrated under reduced pressure. The crude product was suspended in MeOH and sonicated. The resulting white solid was filtered and dried to afford the title compound;

1H NMR (400 MHz, DMSO-d6) 7.6 (1H, s), 7.45 (2H, s) 5.1 (2H, s), 4.3 (3H, s), 4 (2H, d), 3.65 (1H, t), 3.2 (1H, s), 3.05 (1H, s), 2.8 (1H, bs), 1.7 (2H, bs), 1.55 (2H, bs), 1.5 (1H, bs), 1 (1H, m),

LC-MS: Rt 5.51 mins; MS m/z 455.6 [M+H]+; Method 10minLowpH

Example 3

3,5-Dichlorobenzyl 4-(2-((2-ethoxy-3,4-dioxocyclobut-1-en-1-yl)amino)ethyl)piperidine-1-carboxylate

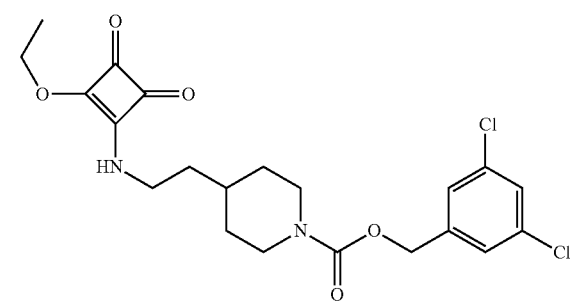 [SMILES: CCOc1c(NCCC2CCN(C(=O)OCc3cc(Cl)cc(Cl)c3)CC2)c(=O)c1=O]

Step 1: 3,5-Dichlorobenzyl 4-(2-aminoethyl)piperidine-1-carboxylate

The title compound was prepared from 3,5-dichlorobenzyl 4-(2-(tert-butoxycarbonylamino)ethyl)piperidine-1-carboxylate (Example 1, step 1) analogously to Example 1, step 3;

LCMS: Rt=0.94 mins; MS m/z 331.1 [M+H]+; Method 2minLowpHv02

Step 2: 3,5-Dichlorobenzyl 4-(2-((2-ethoxy-3,4-dioxocyclobut-1-en-1-yl)amino)ethyl)piperidine-1-carboxylate The title compound was prepared from 3,4-diethoxycyclobut-3-ene-1,2-dione and 3,5-dichlorobenzyl 4-(2-aminoethyl)piperidine-1-carboxylate (step 1) analogously to Example 2;

1H NMR (400 MHz, DMSO-d6) 7.6 (1H, s), 7.4 (2H, s), 5.1 (2H, s), 4.65 (2H, d), 4 (2H, d), 3.55 (1H, bs), 2.8 (2H, bs), 1.7 (2H, d), 1.5 (3H, m), 1.35 (4H, M), 1 (2H, m)

LC-MS: Rt 5.38 mins; MS m/z 455 [M+H]+; Method 10minLowpHv01

Example 4

3,5-Dichlorobenzyl 4-(2-((2-hydroxy-3,4-dioxocyclobut-1-en-1-yl)amino)ethyl)piperidine-1-carboxylate

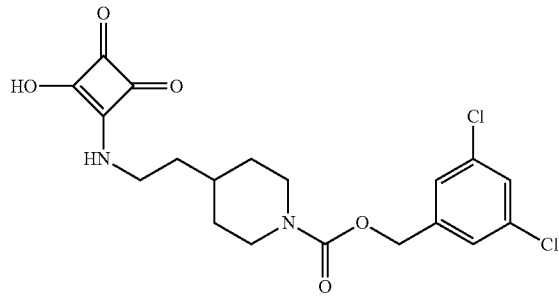 [SMILES: O=C(OCc1cc(Cl)cc(Cl)c1)N1CCC(CCNc2c(O)c(=O)c2=O)CC1]

A mixture comprising 3,5-dichlorobenzyl 4-(2-((2-ethoxy-3,4-dioxocyclobut-1-en-1-yl)amino)ethyl)piperidine-1-carboxylate (Example 3) (35 mg, 0.077 mmol) and 6M HCl (aq) (38.4 µl, 0.077 mmol) in THF (256 µl) was stirred overnight at room temperature. The reaction mixture was concentrated under pressure to give an aqueous suspension. The suspension was filtered, air dried and partitioned between EtOAc and water. The organic portion was separated, dried over MgSO$_4$, filtered and concentrated under reduced pressure. Further purification was carried out using preparative LC-MS. The resulting product fractions were concentrated under reduced pressure to give an aqueous solution and then extracted with EtOAc. The organic extracts were dried over MgSO$_4$, filtered and concentrated under reduced pressure to afford the title compound.

1H NMR (400 MHz, MeOD) 7.4 (1H, s), 7.35 (2H, s), 5.1 (2H, s), 4.15 (2H, d), 3.65 (2H, t), 2.9 (2H, bs), 1.85 (2H, d), 1.6 (2H, m), 1.3 (1H, s), 1.15 (2H, m)

LC-MS: Rt 1.39 mins; MS m/z 425 [M+H]+; Method 10minLowpH

Example 5

3,5-Dichlorobenzyl 4-((3-(3-hydroxyisoxazol-5-yl)propanamido)methyl)-2-methylpiperidine-1-carboxylate

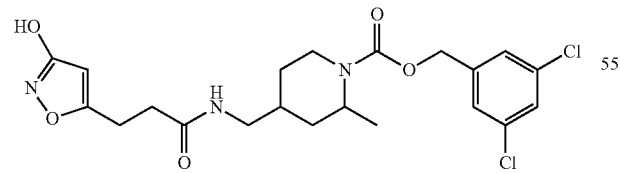

Step 1: (2-Methylpiperidin-4-yl)methanamine

A mixture comprising tert-butyl 4-(aminomethyl)-2-methylpiperidine-1-carboxylate (2 g, 8.76 mmol) and trifluoroacetic acid (10 ml, 130 mmol) in DCM (29.2 ml) was stirred at room temperature for 1 hour. The resulting mixture was loaded on to an Isolute® SCX-2 10 g cartridge and washed with DCM. The product was eluted with 7M ammonia in MeOH and concentrated under reduced pressure. The crude material was suspended in EtOH and filtered. The filtrate was concentrated under pressure to afford the title compound which was used in the next step without further purification;

Step 2: Tert-butyl((2-methylpiperidin-4-yl)methyl) carbamate

A mixture comprising (2-methylpiperidin-4-yl)methanamine (step 1) (1.123 g 8.76 mmol), di-t-butyl dicarbonate (2.237 ml, 9.63 mmol) and 4-dimethylaminopyridine (0.535 g, 4.38 mmol) in DCM (29.2 ml) was stirred at room temperature for 18 hours. The resulting mixture was diluted with DCM and washed with a minimal volume of water. The organic portion was dried over MgSO$_4$, filtered and concentrated under reduced pressure to afford the title compound;

LC-MS: Rt 0.45 mins; MS m/z 227 [M+H]+; Method 2minLowpHv01

Step 3: 3,5-Dichlorobenzyl 4-(((tert-butoxycarbonyl)amino)methyl)-2-methylpiperidine-1-carboxylate A mixture comprising tert-butyl((2-methylpiperidin-4-yl)methyl)carbamate (step 2) (1.15 g, 5.04 mmol) and 3,5-dichlorobenzyl carbonochloridate (1.327 g, 5.54 mmol) in DCM (15 ml) was treated with aq. saturated sodium bicarbonate (0.504 ml, 5.04 mmol) and stirred at room temperature for 18 hours. The organic portion was separated and the aqueous phase extracted with DCM (2×10 ml). The combined organic extracts were dried over MgSO$_4$, filtered and concentrated under reduced pressure. Further purification by chromatography on silica, eluting in 0-20% 2M ammonia in MeOH in DCM afforded the title compound;

LC-MS: Rt 1.38 mins; MS m/z 429 [M+H]+; Method 2minLowpH_v01

Step 4: 3,5-Dichlorobenzyl 4-(aminomethyl)-2-methylpiperidine-1-carboxylate

A mixture comprising of 3,5-dichlorobenzyl 4-(((tert-butoxycarbonyl)amino)methyl)-2-methylpiperidine-1-carboxylate (step 3) (970 mg, 2.249 mmol) and trifluoroacetic acid (173 µl, 2.249 mmol) in DCM (7.5 ml) was left stirring at room temperature 18 hours. The resulting mixture was loaded on to a 10 g Isolute® SCX-2 cartridge and washed with MeOH. The product was eluted with 2M ammonia in MeOH and the product fractions were concentrated under reduced pressure to afford the title compound;

LC-MS: Rt 0.84 mins; MS m/z 331 [M+H]+; Method 2minLowpH_v01

Step 5: 3,5-Dichlorobenzyl 4-((3-(3-hydroxyisoxazol-5-yl)propanamido)methyl)-2-methylpiperidine-1-carboxylate A mixture comprising of 3-(3-hydroxyisoxazol-5-yl)propanoic acid (40.2 mg, 0.256 mmol), 3,5-dichlorobenzyl 4-(aminomethyl)-2-methylpiperidine-1-carboxylate (step 4) (84.7 mg, 0.128 mmol), Huenig's base (89 µl, 0.511 mmol) and T3P® (50% solution in DMF)(149 µl, 0.256 mmol) in DMF (426 µl) was left stirring at room temperature 18 hours. The resulting mixture was concentrated under pressure and diluted with water. The aqueous solution was extracted with EtOAc and the combined organic extracts were dried over MgSO$_4$, filtered and concentrated under reduced pressure.

Further purification was carried out using preparative LC-MS. The resulting product fractions were concentrated under reduced pressure to give an aqueous solution and then extracted with EtOAc. The organic extracts were dried over MgSO$_4$, filtered and concentrated under reduced pressure to afford the title compound.

1H NMR (400 MHz, MeOD) 7.45 (1H, s), 7.35 (2H, s), 5.1 (2H, t), 4 (1H, m), 3.75 (1H, m), 3.2 (2H, m), 3.1 (1H, m), 3 (2H, t), 2.6 (2H, t), 1.85 (1H, m), 1.75 (2H, m), 1.3 (4H, m),

LC-MS: Rt 4.65 mins; MS m/z 470 [M+H]+; Method 10minLowpH

Example 6

3,5-Dichlorobenzyl 4-(2-(N-methyl-2-(1H-1,2,3-triazol-4-yl)acetamido)ethyl)piperidine-1-carboxylate

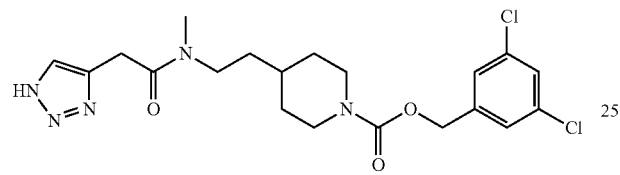

A mixture comprising of 3,5-dichlorobenzyl 4-(2-(methylamino)ethyl)piperidine-1-carboxylate (Example 1, step 3) (100 mg, 0.290 mmol), 2-(1H-1,2,3-triazol-4-yl)acetic acid (55.2 mg, 0.434 mmol), T3P® (50% solution in DMF) (338 µl, 0.579 mmol) and Huenig's base (101 µl, 0.579 mmol) in DMF was stirred at room temperature for 18 hours. The resulting mixture was concentrated under pressure. The crude residue was diluted with water and extracted with EtOAc. The organic portion was dried over MgSO$_4$, filtered and solvent concentrated under reduced pressure. Further purification was carried out using preparative LC-MS. The resulting product fractions were concentrated under reduced pressure to give an aqueous solution and then extracted with EtOAc. The organic extracts were dried over MgSO$_4$, filtered and concentrated under reduced pressure to afford the title compound.

1H NMR (400 MHz, MeOD) 7.75 (1H, bs), 7.5 (1H, s), 7.35 (2H, s), 5.1 (2H, s), 4.15 (2H, bs), 3.9 (2H, s), 3.5 (2H, m), 3.15 (2H, s), 3 (1H, s), 2.9 (2H, bs), 1.8 (2H, d), 1.5 (3H, m), 1.15 (2H, m)

LC-MS: Rt 4.78 mins; MS m/z 454 [M+H]+; Method 10minLowpH

Example 7

3,5-Dichlorobenzyl 4-(2-(2-(1H-1,2,3-triazol-4-yl)acetamido)ethyl)piperidine-1-carboxylate

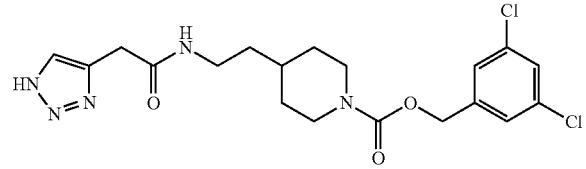 [SMILES: O=C(Cc1c[nH]nn1)NCCC1CCN(C(=O)OCc2cc(Cl)cc(Cl)c2)CC1]

A mixture comprising of 3,5-dichlorobenzyl 4-(2-aminoethyl)piperidine-1-carboxylate (Example 3, step 1) (100 mg, 0.302 mmol), 2-(1H-1,2,3-triazol-4-yl)acetic acid (57.6 mg, 0.453 mmol), 1-propanephosphonic anhydride solution (0.353 mL, 0.604 mmol) and Huenig's Base (0.105 mL, 0.604 mmol) in DMF (1 mL) was stirred at room temperature for 18 hours, and then concentrated under reduced pressure. The mixture was diluted with water and extracted with EtOAc. The organic portion was dried over MgSO$_4$, filtered and the solvent concentrated under pressure. Further purification was carried out using preparative LC-MS. The resulting product fractions were concentrated under reduced pressure to give an aqueous solution and then extracted with EtOAc. The organic extracts were dried over MgSO$_4$, filtered and concentrated under reduced pressure to afford the title compound;

1H NMR (400 MHz, MeOD) 7.7 (1H, bs), 7.45 (1H, s), 7.35 (2H, s), 5.1 (2H, s), 4.15 (2H, d), 3.7 (2H, s), 3.25 (2H, t), 2.85 (2H, bs), 1.75 (2H, d), 1.5 (3H, m), 1.1 (2H, m)

LC-MS: Rt 4.58 mins; MS m/z 440 [M+H]+; Method 10minLowpH

Example 8

3,5-Dichlorobenzyl 4-(2-(N,5-dimethyl-2-oxo-2,3-dihydrooxazole-4-carboxamido)ethyl)piperidine-1-carboxylate

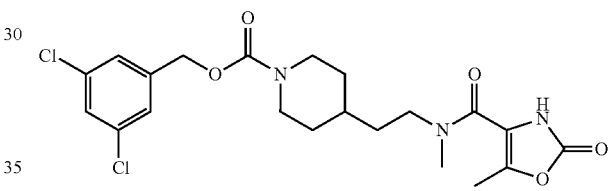

The title compound was prepared from 3,5-dichlorobenzyl 4-(2-methylamino)ethyl)piperidine-1-carboxylate (Example 1, step 3) and 5-methyl-2-oxo-2,3-dihydrooxazole-4-carboxylic acid analogously to Example 6;

LC-MS: Rt 1.22 mins; MS m/z 470.4 and 472.4 (M+H)+; Method 2minLowpHv01.

Example 9

(E)-3,5-Dichlorobenzyl 4-(3-(1H-imidazol-4-yl)acrylamido)piperidine-1-carboxylate

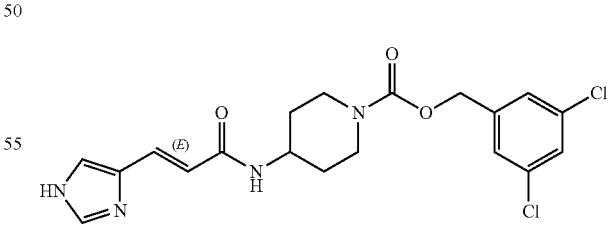

Step 1: 3,5-Dichlorobenzyl 4-(tert-butoxycarbonylamino)piperidine-1-carboxylate

A mixture comprising tert-butyl piperidin-4-ylcarbamate (5 g, 24.97 mmol), 3,5-dichlorobenzyl alcohol (4.42 g, 24.97 mmol) and carbonyldiimidazole (4.05 g, 24.97 mmol) in DMF (83 ml) was heated at 50° C. with stirring for 3 days. The resulting mixture was concentrated under reduced pressure. The crude material was redissolved in EtOAc and washed with 1M HCl, a saturated solution of sodium bicarbonate and brine. The organic phase was dried over MgSO$_4$, filtered and concentrated under reduced pressure. The mixture was purified by chromatography on silica eluting with 50-100% EtOAc in iso-hexane and then 1-10% MeOH in EtOAc to afford the title product;

LC-MS: Rt 1.26 mins; MS m/z 303.2 [M-BOC+H]+; Method 2minLowpH

Step 2: 3,5-Dichlorobenzyl 4-aminopiperidine-1-carboxylate

To a solution of 3,5-dichlorobenzyl 4-(tert-butoxycarbonylamino)piperidine-1-carboxylate (step 1)(5.3098 g, 13.17 mmol) in DCM (20 ml) was added 4M HCl in dioxane (33 ml, 132 mmol) and the mixture was stirred at RT for 2 hrs. The reaction mixture was concentrated under reduced pressure to afford the title product as hydrochloride salt;

LC-MS: Rt 0.70 mins; MS m/z 303.2 and 305.2 [M+H]+; Method 2minLowpH

Step 3: (E)-3,5-Dichlorobenzyl 4-(3-(1H-imidazol-4-yl)acrylamido)piperidine-1-carboxylate To a solution of urocanic acid (122 mg, 0.883 mmol) and 3,5-dichlorobenzyl 4-amino piperidine-1-carboxylate HCl salt (step 2) (300 mg, 0.883 mmol) in DCM (2 mL) was added 1-ethyl-3-(3-dimethylaminopropyl)carbodiimide hydrochloride (169 mg, 0.883 mmol) and N-methylmorpholine (0.291 mL, 2.65 mmol) and the mixture was stirred at RT for 3 h. The resulting mixture was diluted with EtOAc, washed with a saturated solution of sodium bicarbonate and brine. The organic portion was dried over MgSO$_4$, filtered and concentrated under reduced pressure. The resulting mixture was dissolved in MeOH and purified on an Isolute® SCX-2 cartridge eluting with MeOH followed by 2N ammonia in MeOH. Further purification was carried out using 0-100% EtOAc in iso-hexane and then 0-15% MeOH in EtOAc to afford the title product as a solid;

LC-MS: Rt 0.84 mins; MS m/z 423.3 and 425.3 [M+H]+; Method 2minLowpHv01

1H NMR (400 MHz, d$_6$-DMSO) δ 12.15-11.90 (1H, br s), 7.67-7.60 (2H, m), 7.48 (1H, s), 7.40-7.37 (2H, m), 7.32-7.28 (2H, m), 6.52-6.47 (1H, br d), 5.10 (2H, s), 3.94-3.85 (3H, m), 3.09-2.97 (2H, m), 1.85-1.78 (2H, m), 1.44-1.35 (2H, m) (acquired at 363K)

Example 10

6-((1-(((3,5-Dichlorobenzyl)oxy)carbonyl)piperidin-4-yl)amino)-6-oxohexanoic acid

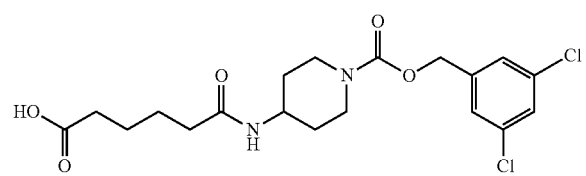 [SMILES: O=C(O)CCCCC(=O)NC1CCN(C(=O)OCc2cc(Cl)cc(Cl)c2)CC1]

Step 1: 3,5-Dichlorobenzyl 4-(6-ethoxy-6-oxohexanamido)pipendine-1-carboxylate

To a suspension of adipic acid mono ethyl ester (154 mg, 0.883 mmol) and 3,5-dichlorobenzyl 4-aminopiperidine-1-carboxylate HCl salt (Example 9, step 2)(300 mg, 0.883 mmol) in DMF (2 mL) was added Huenig's base (0.771 mL, 4.42 mmol) and T3P® (50% in DMF) (1.031 mL, 1.767 mmol) and the mixture was stirred at RT for 4 hrs. The resulting mixture was diluted with EtOAc and washed with a saturated solution of sodium bicarbonate.

The organic portion was dried over MgSO$_4$, filtered and concentrated under reduced pressure. Purification was carried out by chromatography on silica using 0-100% EtOAc in iso-hexane to afford the title product;

LC-MS; Rt 1.24 mins; MS m/z 459.1 and 461.1 [M+H]+; Method 2minLowpHv01

Step 2: 6-((1-(((3,5-Dichlorobenzyl)oxy)carbonyl) piperidin-4-yl)amino)-6-oxohexanoic acid To a suspension of 3,5-dichlorobenzyl 4-(6-ethoxy-6-oxohexanamido)piperidine-1-carboxylate (step 1) (130 mg, 0.283 mmol) in THF (3 mL)/water (1 mL) was added LiOH.H$_2$O (26.1 mg, 0.623 mmol) and the reaction mixture stirred at RT for 3 hrs. The resulting mixture was diluted with water and EtOAc and the aqueous portion acidified with 0.1 M HCl solution (pH 5-6). The resulting precipitate was collected by filtration and washed with water to afford the title product;

LC-MS: Rt 4.35 mins; MS m/z 431.1, 433.1 [M+H]+; Method 10minLowpHv01

1H NMR (400 MHz, d$_6$DMSO) δ12.0 (1H, s), 7.78-7.76 (1H, d), 7.58 (1H, s), 7.42 (2H, s), 5.08 (2H, s), 3.92-3.89 (2H, br d), 3.80-3.70 (1H, m), 3.10-2.87 (2H, br m), 2.2-2.18 (2H, t), 2.07-2.03 (2H, t), 1.77-1.7 (2H, m), 1.54-1.42 (4H, m), 1.32-1.20 (2H, m)

Example 11

3,5-Dichlorobenzyl 2-(2-((2-ethoxy-3,4-dioxocyclobut-1-en-1-yl)amino)ethyl)morpholine-4-carboxylate

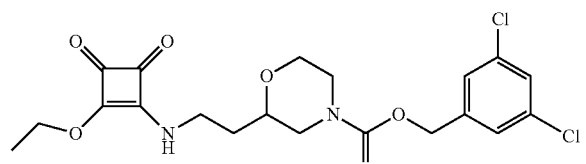

Step 1: 3,5-Dichlorobenzyl 2-(2-((tert-butoxycarbonyl)amino)ethyl)morpholine-4-carboxylate To a mixture comprising of t-butyl(2-morpholin-2-ylethyl) carbamate (3 g, 13.03 mmol) in DCM (100 ml), was added saturated aqueous sodium bicarbonate solution (100 ml, 13.03 mmol), followed by 3,5-dichlorobenzyl carbonochloridate (3.43 g, 14.33 mmol). The biphasic mixture was stirred at room temperature for 2 hours. The resulting mixture was treated with 2M NaOH solution (50 ml). The reaction mixture was separated and the organic portion was dried over MgSO$_4$ and concentrated under reduced pressure to afford the title compound.

LCMS Rt=1.36 mins; MS m/z 433.4 [M+H]+; Method 2minLowpHv01.

Step 2: 3,5-Dichlorobenzyl 2-(2-aminoethyl)morpholine-4-carboxylate

A mixture comprising of 3,5-dichlorobenzyl 2-(2-((tert-butoxycarbonyl)amino)ethyl)morpholine-4-carboxylate (step 1)(500 mg, 1.154 mmol) and trifluoroacetic acid (3556 µl, 46.2 mmol) in DCM (3.8 ml) was stirred for 1 hour at room temperature. The resulting mixture was concentrated under reduced pressure and the crude product was diluted with EtOAc. The mixture was washed with sat. NaHCO$_3$ and the organic portion was separated, dried over MgSO$_4$, filtered and concentrated under reduced pressure to afford the title compound;

LC-MS: Rt: 0.72 mins; MS m/z 333 [M+H]$^+$; Method 2minLowpH_v01.

Step 3: 3,5-Dichlorobenzyl 2-(2-((2-ethoxy-3,4-dioxocyclobut-1-en-1-yl)amino)ethyl)morpholine-4-carboxylate A mixture comprising of 3,4-diethoxycyclobut-3-ene-1,2-dione (77 mg, 0.453 mmol) and triethylamine (253 µl, 1.813 mmol) in EtOH (1511 µl) was stirred at 40° C. for 20 minutes under nitrogen. After cooling to room temperature, 3,5-dichlorobenzyl 2-(2-aminoethyl)morpholine-4-carboxylate (step 2) (151 mg, 0.453 mmol) was added dropwise and the reaction mixture was allowed to stir at room temperature for a further 30 minutes. The resulting reaction mixture was concentrated under reduced pressure and diluted with EtOAc. The organic portion was washed with water, dried over MgSO$_4$, filtered and concentrated under reduced pressure. The crude material was dried loaded using silica onto an ISCO 4 g column, eluting with 0-100% EtOAc in iso-hexane. The product fractions were concentrated under reduced pressure to afford the title compound;

LC-MS: Rt: 1.18 mins; MS m/z 457.0 [M+H]+; Method 2minLowpH_v01

1H NMR (400 MHz, CDCl3). δ 7.35 (1H, d), 7.25 (2H, d), 6.45 (1H, d), 5.10 (2H, s), 4.80 (2H, s), 4.00 (3H, d), 3.70 (1H, s), 3.55 (3H, s), 3.10 (1H, s), 2.75 (1H, s), 1.80 (5H, s).

Example 12

3,5-Dichlorobenzyl 2-(2-(2-oxo-2,3-dihydrooxazole-5-carboxamido)ethyl)morpholine-4-carboxylate

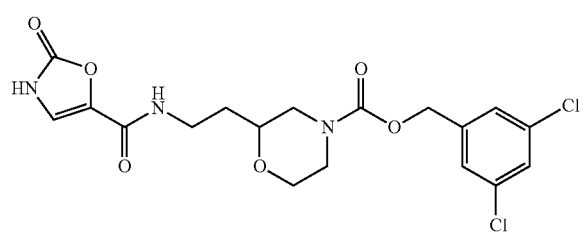 [SMILES: O=C(NCCC1CN(C(=O)OCc2cc(Cl)cc(Cl)c2)CCO1)c1c[nH]c(=O)o1]

A mixture comprising of 3,5-dichlorobenzyl 2-(2-aminoethyl)morpholine-4-carboxylate (Example 11, step 2) (178 mg, 0.534 mmol), 2-oxo-2,3-dihydrooxazole-5-carboxylic acid (Example 21, step 1) (68.9 mg, 0.534 mmol), T3P® (50% in DMF) (510 mg, 0.801 mmol), Huenig's base (466 µl, 2.67 mmol) in DMF (1781 µl) was stirred at room temperature. Another 1 equivalent of 2-oxo-2,3-dihydrooxazole-5-carboxylic acid was added and the reaction mixture was left stirring at room temperature overnight. The resulting reaction mixture was concentrated under reduced pressure and the crude product was diluted with EtOAc. The organic portion was dried with MgSO$_4$, filtered and concentrated under reduced pressure. The crude material was dried loaded using silica onto an ISCO 4 g column eluting with 0-100% EtOAc (1% acetic acid) in iso-hexane. The product fractions were concentrated under reduced pressure to afford the title compound;

1H NMR (400 MHz, MeOD) δ 7.42 (2H, d), 7.43 (2H, s), 5.15 (2H, s), 3.95 (3H, d), 3.45 (4H, m), 3.08 (1H, s), 1.70 (3H, m), 1.40 (1H, q).

Example 13

3,5-Dichlorobenzyl 2-(2-(N-methyl-2-oxo-2,3-dihydrooxazole-5-carboxamido)ethyl)morpholine-4-carboxylate

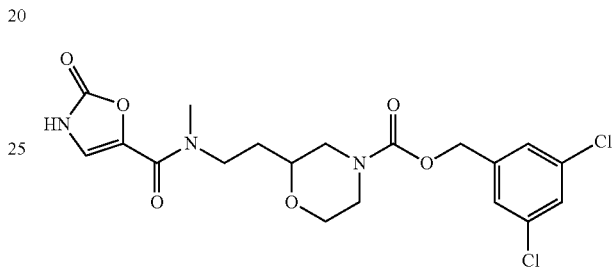

Step 1: 3,5-Dichlorobenzyl 2-(2-((tert-butoxycarbonyl)(methyl)amino)ethyl)morpholine-4-carboxylate A mixture comprising of 3,5-dichlorobenzyl 2-(2-((tert-butoxycarbonyl)amino)ethyl)morpholine-4-carboxylate (Example 11, step 1) (1 g, 2.308 mmol) and sodium hydride (60% in oil) (0.111 g, 2.77 mmol) in DMF (20 mL) was stirred at 0° C. for 15 minutes. Iodomethane (0.216 mL, 3.46 mmol) was added and the mixture was left to stir at room temperature for 16 hours. The reaction was quenched with water (10 ml) to form a suspension. The suspension was diluted with H$_2$O (100 ml) and extracted with EtOAc (200 ml). The organic portion was separated and washed with H$_2$O (100 ml), dried over MgSO$_4$, filtered and concentrated under reduced pressure to afford the title compound;

1H NMR (400 MHz, CDCl3) δ 7.35 (1H, s), 7.25 (2H, s), 5.15 (2H, s), 3.50 (1H, d), 2.85 (2H, s), 2.75 (2H, s), 1.70 (9H, s), 1.35 (6H, t), 0.85 (3H, d).

Step 2: 3,5-Dichlorobenzyl 2-(2-(methylamino)ethyl)morpholine-4-carboxylate

A mixture comprising of 3,5-dichlorobenzyl 2-(2-((tert-butoxycarbonyl)(methyl)amino)ethyl)morpholine-4-carboxylate (step 1) (0.9984 g, 2.232 mmol) and triflouroacetic acid (6.88 ml, 89 mmol) in DCM (7.44 ml) was stirred at room temperature for 1 hour. The reaction mixture was diluted with DCM (7.44 ml) and washed with water followed by sat NaHCO$_3$. The organic portion was separated, dried over MgSO$_4$, filtered and concentrated under reduced pressure to afford the title compound.

1H NMR (400 MHz, CDCl3) δ 7.35 (1H, d), 7.25 (2H, s), 5.10 (2H, s), 3.95 (3H, s), 3.60 (2H, t), 3.20 (3H, t), 2.75 (3H, s), 1.90 (2H, d), 1.65 (1H, t), 1.30 (1H, s).

Step 3: 3,5-Dichlorobenzyl 2-(2-(N-methyl-2-oxo-2, 3-dihydrooxazole-5-carboxamido)ethyl)morpholine-4-carboxylate A mixture comprising of 3,5-dichlorobenzyl 2-(2-(methylamino)ethyl)morpholine-4-carboxylate (step 2)(169 mg, 0.487 mmol), 2-oxo-2,3-dihydrooxazole-5-carboxylic acid ((Example 21, step 1)) (161 mg, 0.487 mmol), T3P® (50% in DMF) (426 µl, 0.730 mmol) and Huenig's base (425 µl, 2.433 mmol) in DMF (1622 µl) was stirred at room temperature for 20 hours. The resulting mixture was diluted with EtOAc and washed with water. The organic portion was dried with MgSO$_4$, filtered and concentrated under reduced pressure. The crude material was dry loaded with silica onto an ISCO 4 g column eluting with 0-100% EtOAc (1% acetic acid) in iso-hexane. The product fractions were concentrated under reduced pressure to afford the title compound;

LC-MS: Rt: 0.48 mins; MS m/z 458 [M+H]+; Method 2minLowpH_v01.

1H NMR (400 MHz, MeOD) δ 7.40 (1H, s). 7.35 (2H, d), 5.15 (2H, s), 3.95 (3H, s), 3.70 (1H, s), 3.55 (1H, m), 3.40 (2H, m), 3.10 (4H, m), 2.85 (1H, m), 1.80 (2H, d), 1.35 (1H, d).

Example 14

3,5-Dichlorobenzyl 2-(2-((2-ethoxy-3,4-dioxocyclobut-1-en-1-yl)(methyl)amino)ethyl)morpholine-4-carboxylate

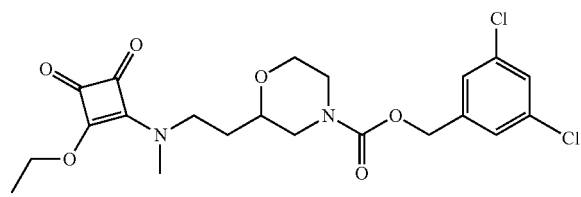 [SMILES: CCOc1c(N(C)CCC2CN(C(=O)OCc3cc(Cl)cc(Cl)c3)CCO2)c(=O)c1=O]

A mixture comprising of 3,4-diethoxycyclobut-3-ene-1,2-dione (29.0 µl, 0.196 mmol) and triethylamine (1093 µl, 7.84 mmol) in EtOH (654 µl) was stirred at 40° C. for 20 minutes. The reaction was allowed to cool back to room temperature and 3,5-dichlorobenzyl 2-(2-(methylamino)ethyl)morpholine-4-carboxylate (Example 13, step 2) (68.1 mg, 0.196 mmol) was added. The reaction mixture was allowed to stir at room temperature for 16 hours. The resulting reaction mixture was concentrated under reduced pressure and purification was carried our using preparative LC-MS. The resulting product fractions were concentrated under reduced pressure to give an aqueous solution and then extracted with EtOAc. The organic extracts were dried over MgSO$_4$, filtered and concentrated under reduced pressure to afford the title compound;

1H NMR (400 MHz, CDCl3) δ 7.45 (1H, s), 7.25 (2H, s), 5.10 (2H, s), 4.40 (3H, s), 3.90 (4H, s), 3.5 (3H, s), 3.35 (1H, s), 3.15 (1H, s), 3.05 (1H, s), 2.70 (1H, s), 1.25 (4H, s), 0.90 (1H, s).

Example 15

3,5-Dichlorobenzyl 4-(2-(N-methyl-2-oxo-2,3-dihydrothiazole-5-carboxamido)ethyl)piperidine-1-carboxylate

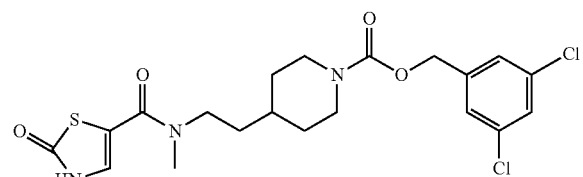

Step 1: 2-Methoxythiazole-5-carboxylic acid

To a solution of tert-butyl 2-chlorothiazole-5-carboxylate (100 mg, 0.455 mmol) in MeCN (880 µl) and MeOH (880 ul) was added 5.4M NaOMe in MeOH (337 µl, 1.821 mmol) followed by 2M NaOH (881 µl, 1.762 mmol). The reaction mixture was heated to 80° C. overnight and, after cooling to RT, the mixture was evaporated under reduced pressure. The residue was acidified with a minimal volume of 6M aqueous hydrochloric acid. The resulting precipitate was filtered, washed with water and dried in a high vacuum oven overnight to afford the title compound;

LCMS: Rt 0.68 mins MS m/z 160.3 [M+H]+Method 2minLowpHv01

Step 2: 2-Oxo-2,3-dihydrothiazole-5-carboxylic acid

2-Methoxythiazole-5-carboxylic acid (step 1) (45.5 mg, 0.286 mmol) was solubilised in MeOH (2 ml) and treated with 5.4M NaOMe in MeOH (212 µl, 1.143 mmol) followed by 2M NaOH (572 µl, 1.143 mmol). The reaction mixture was refluxed overnight and after cooling to RT, the solvent was evaporated under reduced pressure. The residue was acidified with 6M aqueous hydrochloric acid and aqueous layer extracted with EtOAc. The organics were combined and dried over MgSO$_4$ (anh) filtered and evaporated under reduced pressure resulting in a pale yellow solid.

LCMS: Rt 0.33 mins MS m/z 146.1 [M+H]+Method 2minLowpHv01

Step 3: 3,5-Dichlorobenzyl 4-(2-(N-methyl-2-oxo-2, 3-dihydrothiazole-5-carboxamido)ethyl)piperidine-1-carboxylate 2-Oxo-2,3-dihydrothiazole-5-carboxylic acid (33 mg, 0.227 mmol) and 3,5-dichlorobenzyl 4-(2-(methylamino) ethyl)piperidine-1-carboxylate (Example 1, step 3) (79 mg, 0.227 mmol) was dissolved in DMF (1 ml) and treated with DIPEA (159 µl, 0.909 mmol). The reaction mixture was stirred for 5 mins at RT and then treated with 50% T3P® solution in DMF (265 µl, 0.455 mmol) and stirring continued at RT overnight. The reaction mixture was evaporated under reduced pressure and the residue was dissolved in EtOAc and washed with 10% citric acid. The organic layer was dried over MgSO$_4$ (anh), filtered and evaporated under reduced pressure. The resultant crude material was solubilised in minimal DCM and loaded on to a 1 g Isolute® SCX/PEAX cartridge pre-wetted with DCM and eluted with MeOH and the product fractions were evaporated under reduced pressure. Further purification was carried out using preparative LC-MS to afford the title compound together with a small amount of TFA. To remove the TFA, the mixture was dissolved in EtOAc and washed with water, dried over MgSO4 (anh), filtered and evaporated to yield an oil. The oil was dried in the high vacuum oven overnight to afford the title compound;

LCMS: Rt 1.26 mins MS m/z 472.1 [M+H]+Method 2min-LowpHv01

NMR: 1H NMR (400 MHz, CDCl3) δ 9.01 (1H, s), 7.33 (1H, s), 7.28 (2H, s), 5.09 (2H, s), 4.18 (2H, m), 3.54 (2H, t), 3.17 (3H, s), 2.83 (2H, br m), 1.76 (2H, d), 1.60 (2H, m), 1.50 (1H, m), 1.22 (2H, m).

Example 16

3,5-Dichlorobenzyl 4-(2-(2H-tetrazole-5-carboxamido)ethyl)piperidine-1-carboxylate

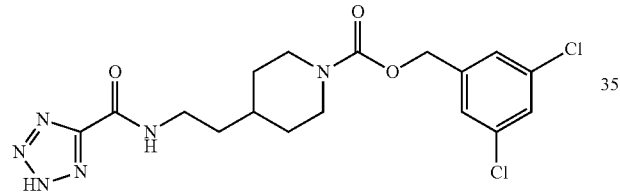

Under nitrogen, oxalyl chloride (58 μl, 0.657 mmol) was dissolved in MeCN (0.5 ml) and cooled to −20° C. DMF (25 μl, 0.329 mmol) was added and the reaction mixture was stirred for 15 minutes. Potassium 5-carboxytetrazol-1-ide (50 mg, 0.329 mmol) was added and the reaction mixture was stirred for a further 20 minutes. A suspension of 3,5-dichlorobenzyl 4-(2-aminoethyl)piperidine-1-carboxylate (Example 3, step 1) (109 mg, 0.329 mmol) and pyridine (32 μl, 0.394 mmol) in MeCN (2 ml) was added and after warming to RT, the reaction mixture was heated at reflux for 1 hr then was allowed to cool. The mixture was evaporated under reduced pressure and the crude product was purified by preparative LC-MS. The product fractions were evaporated under reduced pressure and the residue was partitioned between EtOAc and water. The organic layer was separated, dried over MgSO4 (anh), filtered and evaporated under reduced pressure to afford the title product.

LCMS: Rt 1.30 mins MS m/z 427.6 [M+H]+Method 2min-LowpHv01

NMR: 1H NMR (400 MHz, CDCl3) δ 7.70 (1H, s), 7.32 (1H, t), 7.27 (2H, s), 5.09 (2H, s), 4.21 (2H, br s), 3.64 (2H, q), 2.83 (2H, br s), 1.81 (2H, d), 1.71-1.55 (3H, m), 1.30-1.20 (4H, m-2 extra protons seen from impurity in sample).

Example 17

3,5-Dichlorobenzyl 4-(4-(1H-1,2,3-triazol-4-yl)butanamido)piperidine-1-carboxylate

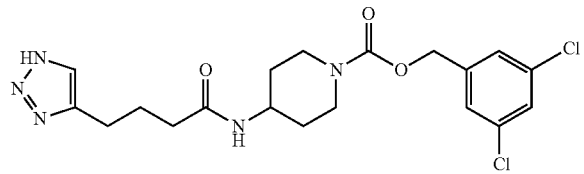 [SMILES: O=C(CCCc1c[nH]nn1)NC1CCN(C(=O)OCc2cc(Cl)cc(Cl)c2)CC1]

Step 1: 3,5-Dichlorobenzyl 4-((tert-butoxycarbonyl)amino)piperidine-1-carboxylate A solution of tert-butyl piperidin-4-ylcarbamate (2.0 g, 9.99 mmol) in DCM (40 ml) was treated with sodium bicarbonate solution (50 ml, 9.99 mmol) followed by a solution of 3,5-dichlorobenzyl carbonochloridate (2.392 g, 9.99 mmol) in DCM (10 ml). The reaction mixture was stirred vigorously at RT until gas evolution ceased. The organic layer was separated, dried over MgSO4 (anh), filtered and evaporated under reduced pressure, yielding the title compound as colourless oil that solidified on standing;

LCMS: Rt 1.38 mins MS m/z 303.2 [M+H-Boc]+Method 2minLowpHv01

Step 2: 3,5-Dichlorobenzyl 4-aminopiperidine-1-carboxylate 3,5-Dichlorobenzyl 4-((tert-butoxycarbonyl)amino)piperidine-1-carboxylate (step 1) (3.53 g, 8.75 mmol) was dissolved in DCM (20 ml). 4M HCl in dioxane (22 ml, 88 mmol) was added which resulted in the formation of a white solid. After gas evolution ceased, DCM (20 ml) was added and the reaction mixture was stirred vigorously for 4 hrs. The resulting mixture was filtered and the white solid was dried in a vacuum oven under reduced pressure to afford the title compound as a hydrochloride salt;

LCMS: Rt 0.75 mins MS m/z 303.1 [M+H]+Method 2min-LowpHv01

Step 3: 4-(1-Benzyl-1H-1,2,3-triazol-4-yl)butanoic acid

Benzyl azide (2.82 ml, 21.18 mmol) was dissolved in tert-butanol (212 ml) and water (212 ml). Hex-5-ynoic acid (2.337 ml, 21.18 mmol) was added followed by copper (II) acetate (385 mg, 2.118 mmol) and sodium L-ascorbate (837 mg, 4.24 mmol) and the reaction mixture was stirred vigorously for 72 hrs. Sodium chloride (solid) was added to the reaction mixture followed by EtOAc (100 ml). The phases separated and the aqueous layer was further extracted with EtOAc. The organics phases were combined, dried over MgSO4 (anh), filtered and evaporated under reduced pressure to afford the title compound;

LCMS: Rt 0.81 mins MS m/z 246.5 [M+H]+Method 2min-lowpHv01

Step 4: 4-(1H-1,2,3-Triazol-4-yl)butanoic acid 4-(1-Benzyl-1H-1,2,3-triazol-4-yl)butanoic acid (step 3) (5.34 g, 21.77 mmol) was dissolved in EtOH (435 ml) and re-circulated through a 75 mm 10% Pd/C catalyst cartridge and hydrogenated using the H-Cube continuous flow hydrogenation at 60° C., 30 bar pressure for 72 hr. The reaction mixture was evaporated under reduced pressure to afford the title compound;

LCMS: Rt 0.33 mins MS m/z 156.2 [M+H]+Method 2min-LowpHv01

Step 5: 3,5-Dichlorobenzyl 4-(4-(1H-1,2,3-triazol-4-yl)butanamido)piperidine-1-carboxylate 4-(1H-1,2,3-Triazol-4-yl)butanoic acid (step 4) (882 mg, 4.95 mmol) and 3,5-dichlorobenzyl 4-aminopiperidine-1-carboxylate hydrochloride (step 2) (1.5 g, 4.95 mmol) were suspended in DMF (20 ml). DIPEA (4.32 ml, 24.74 mmol) was added and the reaction mixture stirred until all components were in solution. 50% T3P® solution in DMF (5.78 ml, 9.89 mmol) was added and the reaction mixture was stirred at RT for 48 hrs. The reaction mixture was diluted with EtOAc and washed twice with 10% citric acid. The aqueous citric acid wash was extracted with DCM (3×) and the combined extracted were dried over MgSO$_4$, filtered and concentrated under reduced pressure. The residue was purified by flash chromatography, using a gradient solvent system of 0-10% MeOH in EtOAc. The resulting product was further purified by stirring in diethyl ether over 72 hours. The mixture was filtered and the solid was dried in a vacuum oven to afford the title compound;

LCMS: Rt 1.06 mins MS m/z 440.2 [M+H]+Method 2min-LowpHv01.

NMR: 1H NMR (400 MHz, DMSO-d6) δ 15.09-14.21 (1H, br s), 7.77 (1H, d), 7.58 (1H, br s), 7.56 (1H, d), 7.41 (2H, d), 5.06 (2H, s), 3.89 (2H, m), 3.76 (1H, m), 2.96 (2H, m), 2.61 (2H, t), 2.08 (2H, t), 1.84 (2H, m), 1.72 (2H, m), 1.24 (2H, m).

Example 18

3,5-Dichlorobenzyl 4-(N-methyl-4-(1H-1,2,3-triazol-4-yl)butanamido)piperidine-1-carboxylate

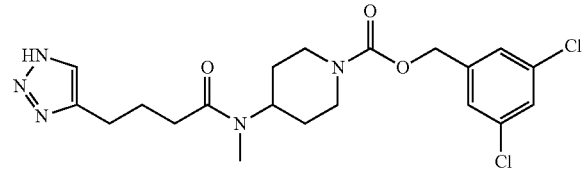 [SMILES: CN(C(=O)CCCc1c[nH]nn1)C1CCN(C(=O)OCc2cc(Cl)cc(Cl)c2)CC1]

Step 1: 3,5-Dichlorobenzyl 4-((tert-butoxycarbonyl)(methyl)amino)piperidine-1-carboxylate A solution of tert-butyl methyl(piperidin-4-yl)carbamate (1.25 g, 5.83 mmol), 3,5-dichlorobenzyl carbonochloridate (1.537 g, 6.42 mmol) and sat. sodium bicarbonate (0.583 ml, 5.83 mmol) in DCM (15 ml) was stirred at RT for 72 hrs. The resulting mixture was extracted with DCM and the combined organic extracts were dried over MgSO$_4$, filtered and concentrated under pressure to afford the title compound which was used without further purification.

Step 2: 3,5-Dichlorobenzyl 4-(methylamino)piperidine-1-carboxylate 3,5-Dichlorobenzyl 4-((tert-butoxycarbonyl)(methyl)amino)piperidine-1-carboxylate (2.4 g, 5.75 mmol) in DCM (13 ml) was treated with and 4M HCl in dioxane (14.38 ml, 57.5 mmol) to give a colourless solution. The mixture was stirred for 3.5 hours at room temperature and then concentrated under reduced pressure to afford the title compound which was used without further purification;

LC-MS: Rt 0.73 mins; MS m/z 315 [M+H]+; Method 2minLowpH_v01

Step 3: 3,5-Dichlorobenzyl 4-(N-methyl-4-(1H-1,2,3-triazol-4-yl)butanamido)piperidine-1-carboxylate 4-(1H-1,2,3-Triazol-4-yl)butanoic acid (Example 17, step 4) (200 mg, 1.289 mmol) and 3,5-dichlorobenzyl 4-(methylamino)piperidine-1-carboxylate (Step 2) (456 mg, 1.289 mmol) were dissolved in DMF (6 ml) and treated with DIPEA (1.126 ml, 6.45 mmol) followed by 50% T3P® in DMF (1.505 ml, 2.58 mmol). After stirring at RT for 9 days, the mixture was evaporated under reduced pressure. The crude product was solubilised in DCM and washed with 10% citric acid. The organic portion was passed through a phase separating cartridge and the filtrate was evaporated under reduced pressure. The crude residue was purified by chromatography on silica eluting with 0-10% MeOH in EtOAc to afford the title compound;

LCMS: Rt 1.18 mins MS m/z 454.2 [M+H]+Method 2min-LowpHv01

NMR 1H (400 MHz, DMSO-d6) δ 7.52 (1H, s), 7.48 (1H, s), 7.39 (2H, d), 5.09 (2H, s), 4.10 (2H, d), 2.90 (2H, t), 2.74 (3H, s), 2.69 (2H, t), 2.37 (2H, t), 1.88 (2H, m), 1.56 (5H, m) (carried out at 363K)

Example 19

3,5-Dichlorobenzyl 4-(3-(1H-1,2,3-triazol-4-yl)propanamido)piperidine-1-carboxylate

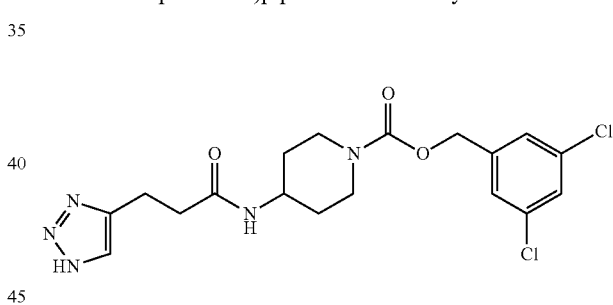

Step 1: 3-(1-Benzyl-1H-1,2,3-triazol-4-yl)propanoic acid

Benzyl azide (2.82 ml, 21.18 mmol) was dissolved in tert-butanol (212 ml) and water (212 ml). Pent-4-ynoic acid (2.078 g, 21.18 mmol) was added followed by copper (II) acetate (385 mg, 2.118 mmol) and sodium L-ascorbate (837 mg, 4.24 mmol) and the reaction mixture was stirred vigorously overnight. Sodium chloride (solid) was added to the reaction mixture followed by EtOAc. The phases separated and the aqueous layer was further extracted with EtOAc. The organic phases were combined, dried over MgSO$_4$ (anh), filtered and evaporated under reduced pressure and dried in a vacuum oven to afford the title compound;

LCMS:Rt 0.76 mins MS m/z 232.2 [M+H]+Method 2min-LowpHv01

Step 2: 3-(1H-1,2,3-Triazol-4-yl)propanoic acid 3-(1-Benzyl-1H-1,2,3-triazol-4-yl)propanoic acid (step 1) (4.37 g, 18.90 mmol) was dissolved in EtOH and stirred for 10 mins with activated charcoal (1.13 g) and of Celite® (filter material). The reaction mixture was filtered and transferred into a 400 mL Duran Bottle. The colorless solution was set on a continuous cycle at 30 bar pressure and 70° C. through the H-Cube (continuous flow hydrogenation) for 24 hrs. The resulting material was concentrated under reduced pressure and the crude product was suspended in ether and filtered to afford the title compound;

Step 3: 3,5-Dichlorobenzyl 4-(3-(1H-1,2,3-triazol-4-yl)propanamido)piperidine-1-carboxylate 3-(1H-1,2,3-Triazol-4-yl)propanoic acid (step 2) (42 mg, 0.294 mmol) and 3,5-dichlorobenzyl 4-aminopiperidine-1-carboxylate hydrochloride (Example 17, step 2) (100 mg, 0.294 mmol) were dissolved in DMF (1 ml) and treated with DIPEA (257 µl, 1.472 mmol) followed by 50% T3P® solution in DMF (344 µl, 0.589 mmol). The reaction mixture was stirred at RT for 2 days and then concentrated under reduced pressure. The crude product was dissolved in DCM and washed with 10% citric acid. The organic portion was separated, dried over MgSO4 (anh), filtered and evaporated under reduced pressure. Purification by chromatography on silica eluting with 0-10% MeOH in EtOAc afforded the title compound;
LCMS: Rt 1.05 mins MS m/z 426.1 [M+H]+Method 2min-LowpHv01
1H NMR (400 MHz, MeOD-d4) δ 8.00 (1H, d), 7.67-7.49 (1H, br m), 7.40 (1H, t), 7.34 (2H, d), 5.10 (2H, s), 4.07 (2H, d), 3.91-3.81 (1H, m), 3.04 (4H, m), 2.56 (2H, t), 1.84 (2H, dd), 1.34 (2H, m).

Example 20

3,5-Dichlorobenzyl 4-(5-(1H-1,2,3-triazol-4-yl)pentanamido)piperidine-1-carboxylate

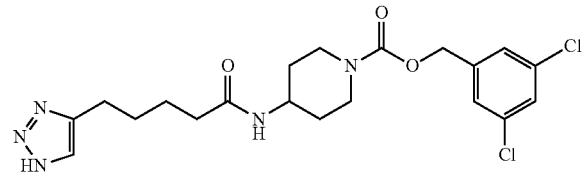 [SMILES: O=C(CCCCc1c[nH]nn1)NC1CCN(C(=O)OCc2cc(Cl)cc(Cl)c2)CC1]

Step 1: 1-(Azidomethyl)-4-methoxybenzene

To 4-methoxybenzyl chloride (8.52 mL, 62.8 mmol) in DMF (40 ml) was added sodium azide (4.08 g, 62.8 mmol). The suspension formed was stirred at RT for 24 hrs. The reaction mixture was diluted with ether (400 ml) and washed with water (2×200 mL) and brine (20 ml). The organic layers were dried (MgSO4) and concentrated (water bath temp 20° C.) under reduced pressure to afford the title compound;

Step 2: 5-(1-(4-Methoxybenzyl)-1H-1,2,3-triazol-4-yl)pentanoic acid 1-(Azidomethyl)-4-methoxybenzene (259 mg, 1.585 mmol) was solubilised in t-BuOH (15.9 ml). Hept-6-ynoic acid (201 µl, 1.585 mmol) was added followed by water (15.9 ml) copper acetate (28.2 mg, 0.159 mmol) and sodium L-ascorbate (63 mg, 0.317 mmol). The reaction mixture was stirred at RT for 72 hrs. Sodium chloride was added and the mixture was stirred vigorously. EtOAc was added and the phases were separated. The aqueous layer was re-extracted with EtOAc and the combined organics were treated with charcoal & MgSO4 (anh), stirring for 5 minutes. The resulting mixture was filtered and the filtrate was evaporated under reduced pressure to afford the title compound;
LCMS: Rt 0.87 mins MS m/z 290.3 [M+H]+Method 2min-LowpHv01

Step 3: 5-(1H-1,2,3-Triazol-4-yl)pentanoic acid 5-(1-(4-Methoxybenzyl)-1H-1,2,3-triazol-4-yl)entanoic acid (464 mg, 1.604 mmol) was solubilised in EtOH (32.1 ml) and hydrogenated at 30 bar, 70° C. using a H-Cube apparatus, with a 10% Pd/C catcart cartridge (small). The reaction mixture was recirculated overnight and then concentrated under reduced pressure to afford the title compound;
LCMS:Rt 0.54 mins MS m/z 170.1 [M+H]+170.1 Method 2minLowpHv01

Step 4: 3,5-Dichlorobenzyl 4-(5-(1H-1,2,3-triazol-4-yl)pentanamido)piperidine-1-carboxylate 5-(1H-1,2,3-Triazol-4-yl)entanoic acid (step 3) (50 mg, 0.294 mmol) and 3,5-dichlorobenzyl 4-aminopiperidine-1-carboxylate hydrochloride (Example 17, step 2) (100 mg, 0.294 mmol) were dissolved in DMF (1 ml). DIPEA (257 µl, 1.472 mmol) was added followed by 50% T3P® solution in DMF (344 µl, 0.589 mmol). The reaction mixture was stirred at RT for 96 hrs and concentrated under reduced pressure. The crude product was dissolved in DCM and washed with 10% citric acid. The organic portion was separated, dried over MgSO4 (anh), filtered and evaporated under reduced pressure. Purification by preparative HPLC afforded product fractions that were concentrated to afford a residue. The residue was dissolved in DCM and washed with a minimal volume of water, dried over MgSO4 (anh) filtered and evaporated under reduced pressure to afford the title compound;
LCMS Rt 1.10 mins MS m/z 454.2 [M+H]+Method 2min-LowpHv01
1H NMR (400 MHz, MeOD-d4) δ 8.09 (¼H, s), 7.99 (½H, d), (due to exchange) 7.56 (1H, s) 7.41 (1H, t), 7.34 (2H, d), 5.11 (2H, s), 4.10 (2H, d), 3.86 (1H, m), 3.110-02.89 (2H, br m), 2.76 (2H, t), 2.22 (2H, t), 1.87 (2H, m), 1.68 (4H, m), 1.38 (2H, m).

Example 21

3,5-Dichlorobenzyl 4-(2-(2-oxo-2,3-dihydrooxazole-5-carboxamido)ethyl)piperidine-1-carboxylate

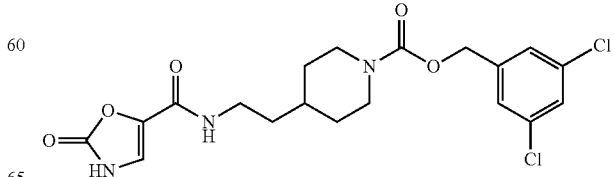

Step 1: 2-Oxo-2,3-dihydrooxazole-5-carboxylic acid

Ethyl 2-chlorooxazole-5-carboxylate (1.816 g, 10.34 mmol) was solubilised in MeCN (20 ml) and MeOH (20 ml). Sodium methoxide (9 ml, 25% solution in MeOH, 41.4 mmol) was added and the reaction mixture was heated at reflux overnight. The solvent was removed under reduced pressure and the crude product was dissolved in MeOH (20 ml) and 2M NaOH(aq) (20 ml) and stirred at RT overnight. The resulting mixture was acidified with 1M HCl and evaporated under reduced pressure. The residue was triturated with a minimal volume of 5M HCl and filtered. The solid was slurried with ice chips (approx. 10 ml), filtered, washed with water and dried under high vacuum to afford the title compound;

LCMS: Rt 0.26 mins MS m/z 127.8 [M−H]− Method 2minLowpHv01

Step 2: Tert-butyl 4-(2-(2-oxo-2,3-dihydrooxazole-5-carboxamido)ethyl)piperidine-1-carboxylate The title compound was prepared from 2-oxo-2,3-dihydrooxazole-5-carboxylic acid (step 1) and tert-butyl 4-(2-aminoethyl)piperidine-1-carboxylate analogously to Example 20 step 4;

LCMS: Rt 0.95 mins MS m/z 338.4 [M−H]− Method 2minLowpHv01

Step 3: 2-oxo-N-(2-(piperidin-4-yl)ethyl)-2,3-dihydrooxazole-5-carboxamide

Tert-butyl 4-(2-(2-oxo-2,3-dihydrooxazole-5-carboxamido)ethyl)piperidine-1-carboxylate (step 2) (257.8 mg, 0.760 mmol) was solubilised in DCM (1.5 ml). 4M HCl in dioxane (1.9 ml, 7.60 mmol) was added and the reaction mixture stirred at RT. After all gas had ceased to be evolved, the reaction mixture was solubilised with in MeOH and evaporated under reduced pressure to afford the title compound;

Step 4: 3,5-Dichlorobenzyl 4-(2-(2-oxo-2,3-dihydrooxazole-5-carboxamido)ethyl)piperidine-1-carboxylate 2-oxo-N-(2-(piperidin-4-yl)ethyl)-2,3-dihydrooxazole-5-carboxamide (step 3) (210 mg, 0.76 mmol) was suspended in DCM (2 ml). DIPEA (265 µl, 1.52 mmol) was added and the reaction mixture sonicated to aid dissolution. 3,5-dichlorobenzyl carbonochloridate (182 mg, 0.76 mmol) in DCM (2 ml) was added and the mixture was left stirring vigorously at RT overnight. The resulting mixture was diluted with DCM and washed with citric acid (emulsion formed). Brine was added and organics were separated, dried over MgSO4 (anh), filtered and evaporated under reduced pressure. The crude product was purified by chromatography on silica eluting with 75-100% EtOAc in iso-hexane to afford the title compound;

LCMS: Rt 1.17 mins MS m/z 442.4 [M+H]+ Method 2min-LowpHv001

1H NMR (400 MHz, MeOD-d4) δ 7.41 (2H, s), 7.34 (2H, d), 5.11 (2H, s), 4.20-4.08 (2H, br m), 3.38 (2H, t), 2.96-2.76 (2H, br m), 1.80 (2H, d), 1.55 (3H, m), 1.15 (2H, m).

Example 22

3,5-Dichlorobenzyl 4-(2-(3-(3-hydroxyisoxazol-5-yl)propanamido)ethyl)piperidine-1-carboxylate

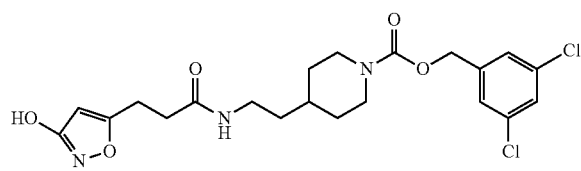 [SMILES: O=C(CCc1cc(O)no1)NCCC1CCN(C(=O)OCc2cc(Cl)cc(Cl)c2)CC1]

Step 1: tert-Butyl 4-(2-(3-(3-hydroxyisoxazol-5-yl)propanamido)ethyl)piperidine-1-carboxylate The title compound was prepared from commercially available 3-(3-hydroxyisoxazol-5-yl)propanoic acid and tert-butyl 4-(2-aminoethyl)piperidine-1-carboxylate analogously to Example 21 (step 2);

LCMS: Rt 0.98 mins MS m/z 368.5 [M+H]+ Method 2min-LowpHv001

Step 2: 3-(3-Hydroxyisoxazol-5-yl)-N-(2-(piperidin-4-yl)ethyl)propanamide

The title compound was prepared from tert-butyl 4-(2-(3-(3-hydroxyisoxazol-5-yl)propanamido)ethyl)piperidine-1-carboxylate (step 1) analogously to Example 21 step 3;

Step 3: 3,5-Dichlorobenzyl 4-(2-(3-(3-hydroxyisoxazol-5-yl)propanamido)ethyl)piperidine-1-carboxylate 3-(3-Hydroxyisoxazol-5-yl)-N-(2-(piperidin-4-yl)ethyl)propanamide (step 2) (201 mg, 0.662 mmol) was suspended in DCM (2 ml). 2M NaOH (1 ml, 2.00 mmol) was added and the reaction mixture stirred. To the mixture was added a solution of 3,5-dichlorobenzyl carbonochloridate (158 mg, 0.662 mmol) in DCM (1 ml) and the reaction mixture was stirred vigorously overnight. The resulting mixture was diluted with DCM and washed with citric acid. The organics were separated and evaporated under reduced pressure. The crude residue was dissolved in DMSO and purified by preparative HPLC. The product fractions were concentrated under reduced pressure and partitioned between EtOAc and water. The organics were separated, dried over MgSO4 (anh) filtered and evaporated under reduced pressure and dried in a high vacuum oven to afford the title compound;

LCMS: Rt 1.17 mins MS m/z 470.1 [M+H]+ Method 2min-LowpHv01

1H NMR (400 MHz, MeOD-d4) δ 8.04 (¼H, s), (due to exchange) 7.41 (1H, t), 7.34 (2H, d), 5.72 (1H, s), 5.10 (2H, s), 4.13 (2H, m), 3.24 (1H, t), 2.87 (4H, m), 2.54 (2H, t), 1.74 (2H, d), 1.44 (3H, m), 1.11 (2H, m) (1H under solvent peak).

Example 23

3,5-Dichlorobenzyl 4-(3-(3-hydroxyisoxazol-5-yl)propanamido)piperidine-1-carboxylate

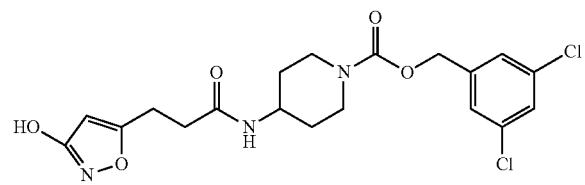 [SMILES: O=C(CCc1cc(O)no1)NC1CCN(C(=O)OCc2cc(Cl)cc(Cl)c2)CC1]

The title compound was prepared from commercially available hydroxyisoxazol-5-yl)propanoic acid and 3,5-dichlorobenzyl 4-aminopiperidine-1-carboxylate hydrochloride (Ex 17, step 2) analogously to Example 21 (step 4);

LCMS: Rt 1.10 mins MS m/z 442.1 [M+H]+ or 440.2 [M−H]− Method 2minLowpHv01

Example 24

3,5-Dichlorobenzyl 4-(2-(N-methyl-2-oxo-2,3-dihydrooxazole-4-carboxamido)ethyl)piperidine-1-carboxylate

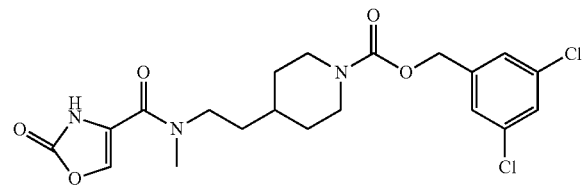 [SMILES: CN(CCC1CCN(C(=O)OCc2cc(Cl)cc(Cl)c2)CC1)C(=O)c1coc(=O)[nH]1]

Step 1: 2-Oxo-2,3-dihydrooxazole-4-carboxylic acid

The title compound was prepared from ethyl 2-oxo-2,3-dihydrooxazole-4-carboxylate analogously to Example 30 step 6;

LC-MS: Rt 0.32 mins; MS m/z 130.4 (M+H)+; Method 2minLowpHv01

Step 2: 3,5-Dichlorobenzyl 4-(2-(N-methyl-2-oxo-2,3-dihydrooxazole-4-carboxamido)ethyl)piperidine-1-carboxylate The title compound was prepared from 2-oxo-2,3-dihydrooxazole-4-carboxylic acid (step 1) and 3,5-dichlorobenzyl 4-(2-(methylamino)ethyl)piperidine-1-carboxylate (Example 1, step 3) analogously to Example 15 step 3;

LCMS: Rt 1.21 mins MS m/z 454.4 [M−H]− Method 2minLowpHv01

Example 25

3,5-Dichlorobenzyl 4-(2-(5-hydroxy-N-methyl-1H-pyrazole-3-carboxamido)ethyl)piperidine-1-carboxylate

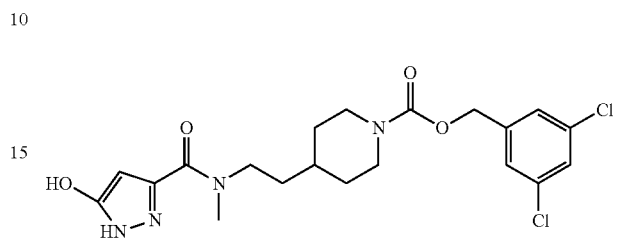

The title compound was prepared from commercially available 5-hydroxy-1H-pyrazole-3-carboxylic acid and 3,5-dichlorobenzyl 4-(2-(methylamino)ethyl)piperidine-1-carboxylate (Example 1, step 3) analogously to Example 15 step 3;

LCMS Rt 1.17 mins MS m/z 455.5 [M+H]+Method 2minLowpHv01

Example 26

3,5-Dichlorobenzyl 4-(3-(N-methyl-2-oxo-2,3-dihydrooxazole-5-carboxamido)propyl)piperazine-1-carboxylate

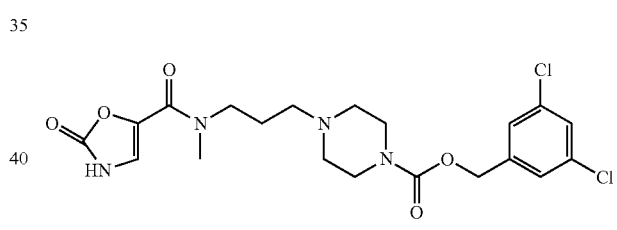

Step 1: 1-tert-Butyl 4-(3,5-dichlorobenzyl)piperazine-1,4-dicarboxylate

A solution of 1-Boc-piperazine (2.0 g, 10.74 mmol) in DCM (30 ml) was treated with 2M NaOH (aq.) (10.74 ml, 21.48 mmol) and stirred at RT. A solution of 3,5-dichlorobenzyl carbonochloridate (2.57 g, 10.74 mmol) in DCM (10 ml) was added and stirring continued at RT for 2.5 hrs. The resulting mixture was separated and the organic portion was dried over MgSO4, filtered and concentrated under reduced pressure to afford the title compound as a white solid;

LCMS: Rt 1.42 mins MS M/z 291.4 [M+H-Boc]+Method 2minLowpHv01

Step 2: 3,5-Dichlorobenzyl piperazine-1-carboxylate 1-tert-Butyl 4-(3,5-dichlorobenzyl)piperazine-1,4-dicarboxylate (step 1) (4.093 g, 10.51 mmol) was solubilised in DCM (20 ml). 4M HCl in dioxane (26 ml, 105 mmol) was added and the reaction mixture stirred until gas evolution ceased. The resulting mixture was concentrated under reduced pressure and treated with NaOH (aq.) to pH14. The organic portion was separated, dried over MgSO₄ (anh), filtered and evaporated under reduced pressure to afford the title compound;

LCMS:Rt 0.69 mins MS m/z 289.3 [M+H]+Method 2min-LowpHv01

Step 3: Tert-butyl methyl(3-oxopropyl)carbamate

Commercially available tert-butyl(3-hydroxypropyl)(methyl)carbamate (1.858 g, 9.82 mmol) was solubilised in DCM (40 ml) and treated with sodium bicarbonate (4.12 g, 49.1 mmol) followed by Dess-Martin reagent (5.21 g, 12.28 mmol). The reaction mixture was stirred at RT for 2 hrs and then partitioned between DCM and sodium bicarbonate solution. Sodium thiosulphate was added and the organic portion was separated. The aqueous layer was extracted with DCM (×2) and the combined organic extracts were dried over MgSO₄ (anh), filtered and evaporated under reduced pressure to afford the title compound without further purification;

Step 4: 3,5-Dichlorobenzyl 4-(3-((tert-butoxycarbonyl)(methyl)amino)propyl)piperazine-1-carboxylate Tert-butyl methyl(3-oxopropyl)carbamate (step 3) (1.528 g, 8.16 mmol) was solubilised in DCM (50 ml) and added to 3,5-dichlorobenzyl piperazine-1-carboxylate (step 2) (3.09 g, 9.82 mmol). The resulting mixture was treated with acetic acid (56 µl, 0.982 mmol) and after stirring for 1 hr at RT, sodium triacetoxyborohydride (4.16 g, 19.64 mmol) was added. The reaction mixture was stirred at RT overnight and then quenched by addition of 2M NaOH (aq.). The aqueous layer was basified to pH 14 with conc NaOH solution. The organic layer was separated and the aqueous layer was extracted with more DCM. The organic portions were combined, dried over MgSO₄ (anh), filtered and evaporated under reduced pressure, yielding a yellow oil. The crude product was purified by chromatography on silica eluting with 0-10% MeOH (with ammonia) in DCM to afford the title compound;

LCMS:Rt 0.94 mins MS m/z 462.6 [M+H]+Method 2min-LowpHv01

Step 5: 3,5-Dichlorobenzyl 4-(3-(methylamino)propyl)piperazine-1-carboxylate

The title compound was prepared by acid hydrolysis of 3,5-dichlorobenzyl 4-(3-((tert-butoxycarbonyl)(methyl)amino)propyl)piperazine-1-carboxylate (step 4) analogously to step 2;

LCMS: Rt 0.56 mins MS m/z 360.4 Method 2minLowpHv01

Step 6: 3,5-Dichlorobenzyl 4-(3-(N-methyl-2-oxo-2,3-dihydrooxazole-5-carboxamido)propyl)piperazine-1-carboxylate The title compound was prepared from 2-oxo-2,3-dihydrooxazole-5-carboxylic acid (Example 21 step 1) and 3,5-dichlorobenzyl 4-(3-(methylamino)propyl)piperazine-1-carboxylate (step 5) analogously to Example 15 step 3;

LCMS: Rt 0.75 mins MS m/z 471.2 [M+H]+Method 2min-LowpHv01

Example 27

3,5-Dichlorobenzyl 4-(2-(2-oxo-2,3-dihydrooxazole-5-carboxamido)ethyl)piperazine-1-carboxylate

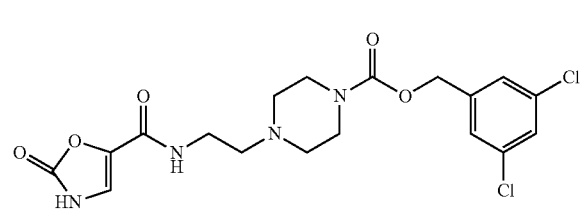 [SMILES: O=C(NCCN1CCN(C(=O)OCc2cc(Cl)cc(Cl)c2)CC1)c1c[nH]c(=O)o1]

Step 1: 3,5-Dichlorobenzyl 4-(2-((tert-butoxycarbonyl)amino)ethyl)piperazine-1-carboxylate 3,5-Dichlorobenzyl piperazine-1-carboxylate (Example 26, step 2) (3.466 mg, 11.99 mmol), potassium carbonate (4.97 g, 36 mmol) and triethlyamine (5.01 ml, 36 mmol) were suspended in MeCN (60 ml). tert-Butyl(2-bromoethyl)carbamate (3.49 g, 15.58 mmol) was added and the reaction mixture was refluxed for 18 hrs at 80° C. A further portion of tert-butyl(2-bromoethyl)carbamate (1.05 g, 4.69 mmol) was added and heating continued at 80° C. for 3 hrs. After cooling to RT, the reaction mixture was diluted with EtOAc and filtered. The organic portion was evaporated under reduced pressure. The crude product was solubilised in EtOAc and washed with 2M NaOH. The organic portion was dried over MgSO₄ (anh) filtered and evaporated under reduced pressure. Purification by chromatography on silica using a gradient solvent system of DCM to 10% MeOH with ammonia in DCM afforded product fractions that were concentrated to give the title compound;

LCMS: Rt 0.90 mins MS m/z 434.6 [M+H]+Method 2min-lowpHv01

Step 2: 3,5-Dichlorobenzyl 4-(2-aminoethyl)piperazine-1-carboxylate

The title compound was prepared from 3,5-dichlorobenzyl 4-(2-((tert-butoxycarbonyl)amino)ethyl)piperazine-1-carboxylate (step 1) analogously to 3,5-dichlorobenzyl 4-(3-(methylamino)propyl)piperazine-1-carboxylate (Ex 26 step 5);

LCMS: Rt 0.69 mins MS m/z 332.5 [M+H]+Method 2min-LowpHv01

Step 3: 3,5-Dichlorobenzyl 4-(2-(2-oxo-2,3-dihydrooxazole-5-carboxamido)ethyl)piperazine-1-carboxylate The title compound was prepared from 2-oxo-2,3-dihydrooxazole-5-carboxylic acid (Example 21 step 1) and 3,5-dichlorobenzyl 4-(2-aminoethyl)piperazine-1-carboxylate (step 2) analogously to Example 15 step 3;

LCMS: Rt 0.75 mins MS m/z 443.4 [M+H]+Method 2min-LowpHv01

Example 28

3,5-Dichlorobenzyl 4-(2-(N-methyl-5-oxo-4,5-dihydro-1,2,4-oxadiazole-3-carboxamido)ethyl)piperidine-1-carboxylate

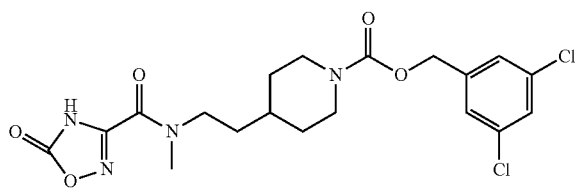 [SMILES: CN(CCC1CCN(C(=O)OCc2cc(Cl)cc(Cl)c2)CC1)C(=O)c1noc(=O)[nH]1]

The title compound was prepared from commercially available 5-oxo-4,5-dihydro-1,2,4-oxadiazole-3-carboxylic acid and 3,5-dichlorobenzyl 4-(2-(methylamino)ethyl)piperidine-1-carboxylate (Example 1, step 3) analogously to Example 15 step 3;
LCMS: Rt 1.29 mins MS m/z 459.2 [M+H]+Method 2min-LowpHv01

Example 29

3,5-Dichlorobenzyl 4-(2-(N-methyl-2H-tetrazole-5-carboxamido)ethyl)piperidine-1-carboxylate

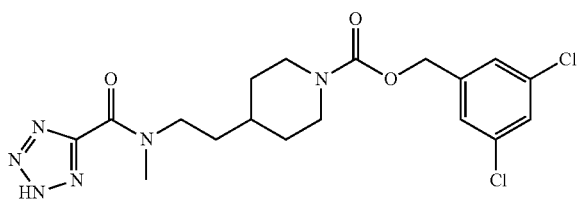 [SMILES: CN(CCC1CCN(C(=O)OCc2cc(Cl)cc(Cl)c2)CC1)C(=O)c1nn[nH]n1]

The title compound was prepared from potassium 5-carboxytetrazol-1-ide and 3,5-dichlorobenzyl 4-(2-(methylamino)ethyl)piperidine-1-carboxylate (Example 1 step 3) analogously to Example 16;
LCMS: Rt 1.30 mins MS m/z 441.6 [M+H]+Method 2min-LowpHv01

Example 30

(E)-N-(2-(1-(3-(3,5-Dichlorophenyl)acryloyl)piperidin-4-yl)ethyl)-N-methyl-2-oxo-2,3-dihydrooxazole-5-carboxamide

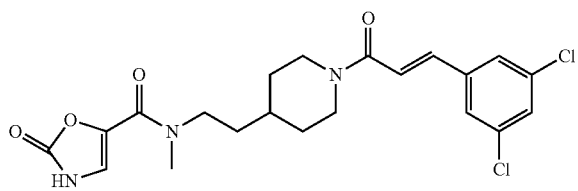 [SMILES: CN(CCC1CCN(C(=O)/C=C/c2cc(Cl)cc(Cl)c2)CC1)C(=O)c1c[nH]c(=O)o1]

Step 1: (E)-Methyl 3-(3,5-dichlorophenyl)acrylate

To 1,3-dichloro-5-iodobenzene (300 mg, 1.099 mmol) and methyl acrylate (0.099 ml, 1.099 mmol) in DMF (10 ml) under nitrogen was added [Pd(t-BuP)]$_2$ (56.1 mg, 0.110 mmol) and triethylamine (0.306 ml, 2.199 mmol). The reaction mixture was heated to 80° C. for 2 h. The reaction mixture was diluted with EtOAc and filtered through a silica cartridge (2 g). The organic solution was washed with water, saturated sodium bicarbonate solution, water and brine. The organic portion was dried using a phase separating column and the solvent was removed under reduced pressure to afford the title compound;
LC-MS Rt=1.34 mins; MS m/z=no mass ion; Method 2minLowpHv01.
1H NMR (400 MHz, DMSO-d6): δ 7.87 (2H, d), 7.65 (1H, d), 7.64 (1H, d), 6.85 (1H, d), 3.74 (3H, s).

Step 2: (E)-3-(3,5-Dichlorophenyl)acrylic acid

To (E)-methyl 3-(3,5-dichlorophenyl)acrylate (step 1) (2 g, 8.66 mmol) in THF (35 ml) was added 2M NaOH (12.98 ml, 26.0 mmol) and the reaction mixture was stirred at RT overnight. The solvent was removed under reduced pressure and the residue was dissolved in water and washed with EtOAc. The aqueous portion was acidified to pH 4 using 1M HCl and extracted with DCM. The organic portion was dried using a phase separating column and the solvent removed under reduced pressure to afford the title compound as a white solid;
LC-MS: Rt=1.17 mins; MS m/z=217.0 [M+H]+; Method 2minLowpHv01.
1H NMR (400 MHz, DMSO-d6): δ 12.60 (1H, broad), 7.83 (2H, d), 7.64 (1H, s), 7.55 (1H, d), 6.72 (1H, d).

Step 3: (E)-tert-Butyl(2-(1-(3-(3,5-dichlorophenyl)acryloyl)piperidin-4-yl)ethyl)carbamate To (E)-3-(3,5-dichlorophenyl)acrylic acid (step 2) (1.365 g, 6.29 mmol) in NMP (12 ml) was added HATU (2.87 g, 7.55 mmol) and the mixture was stirred for 5 minutes at RT. tert-Butyl(2-(piperidin-4-yl)ethyl)carbamate (1.436 g, 6.29 mmol) was added followed by DIPEA (3.30 ml, 18.87 mmol) and stirring continued at RT overnight. The reaction mixture was poured into water and extracted with EtOAc. The organic portion was washed with water, saturated sodium bicarbonate solution, water, brine and dried using a phase separating column and the solvent removed under reduced pressure. The crude material was purified by chromatography on silica eluting with 0-100% EtOAc in iso-hexane to afford the title compound;
LC-MS: Rt=1.42 mins; MS m/z=427.2 [M+H]+; Method 2minLowpHv01.
1H NMR, (400 MHz, DMSO-d6): δ 7.88 (1H, s), 7.87 (1H, s), 7.58 (1H, s), 7.43 (2H, d), 6.79 (1H, t), 4.45 (1H, d), 4.31 (1H, d), 3.06-2.92 (2H, m), 2.62 (1H, m), 1.73 (2H, m), 1.55 (1H, m), 1.42-1.28 (12H, m), 1.01 (2H, m)

Step 4: (E)-1-(4-(2-Aminoethyl)piperidin-1-yl)-3-(3,5-dichlorophenyl)prop-2-en-1-one To (E)-tert-butyl(2-(1-(3-(3,5-dichlorophenyl)acryloyl)piperidin-4-yl)ethyl)carbamate (step 3) (400 mg, 0.936 mmol) in DCM (5 ml) was added TFA (0.865 ml, 11.23 mmol) and the mixture was stirred at RT for 1 h. The solvent was removed under reduced pressure and the crude material was dissolved in MeOH and loaded on to an Isolute® SCX-2 cartridge (10 g). The cartridge was washed with excess MeOH. The product was eluted using 2.0 M ammonia in MeOH and the solvent removed under reduced pressure to afford the title compound as a white solid;

LC-MS: Rt=0.83 mins; MS m/z=327.2 [M+H]+; Method 2minLowpHv01.

1H NMR, (400 MHz, DMSO-d6): δ 7.87 (2H, m), 7.58 (1H, s), 7.48-7.37 (2H, m), 4.45 (1H, d), 4.30 (1H, d), 3.29 (2H, broad), 3.04 (2H, t), 2.73-2.55 (3H, m), 1.81-1.46 (4H, m), 1.01 (2H, m).

Step 5: (E)-3-(3,5-Dichlorophenyl)-1-(4-(2-(methylamino)ethyl)piperidin-1-yl)prop-2-en-1-one (E)-1-(4-(2-Aminoethyl)piperidin-1-yl)-3-(3,5-dichlorophenyl)prop-2-en-1-one (step 4) (150 mg, 0.458 mmol) was dissolved in DCM (1.528 ml). Formaldehyde (37% in water, 0.034 ml, 0.458 mmol) was added followed by acetic acid (2.62 µl, 0.046 mmol) and the mixture was stirred at RT for 5 mins. Sodium triacetoxyborohydride (194 mg, 0.917 mmol) was added and stirring continued at RT overnight. 2M NaOH was added and the mixture was stirred for 10 minutes. The organic portion was separated, diluted with DCM and dried using a phase separating column. The solvent was removed under reduced pressure to afford a colourless oil. The oil was loaded onto an Isolute® SCX-2 cartridge (1 g) and washed with excess MeOH. The product was eluted using 2.0M ammonia in MeOH and the solvent removed under reduced pressure to afford the title compound as a mixture with (E)-1-(4-(2-aminoethyl)piperidin-1-yl)-3-(3,5-dichlorophenyl)prop-2-en-1-one and (E)-3-(3,5-dichlorophenyl)-1-(4-(2-(dimethylamino)ethyl)piperidin-1-yl)prop-2-en-1-one as a clear film.

Step 6: 2-Oxo-2,3-dihydrooxazole-5-carboxylic acid

To a solution of ethyl 2-oxo-2,3-dihydrooxazole-5-carboxylate (300 mg, 1.909 mmol) in THF (5 ml) was added LiOH.H₂O (352 mg, 8.4 mmol) as a solution in water (5 ml). The mixture was stirred at room temperature overnight. The solvent was removed under reduced pressure. To the residue was added 4M HCl in dioxane (6 ml, 24.0 mmol) and the solid was sonicated for ~1 minute. The solvent was removed under reduced pressure to afford a yellow solid. The solid was redissolved in MeOH and concentrated under reduced pressure. The solid was dried in the vacuum oven to afford the title compound;

LC-MS: Rt 0.26 mins; MS m/z 128.4 M−; Method 2minLowpHv01

1H NMR (400 MHz, DMSO-d6) δ 11.46 (1H, broad), 7.53 (1H, s)

Step 7: (E)-N-(2-(1-(3-(3,5-Dichlorophenyl)acryloyl) piperidin-4-yl)ethyl)-N-methyl-2-oxo-2,3-dihydrooxazole-5-carboxamide To the mixture containing (E)-3-(3,5-dichlorophenyl)-1-(4-(2-(methylamino)ethyl)piperidin-1-yl)prop-2-en-1-one (step 5) (118 mg, 0.346 mmol) and 2-oxo-2,3-dihydrooxazole-5-carboxylic acid (step 7) (2.59 ml, 0.2M solution in DMF, 0.519 mmol) and DIPEA (0.483 ml, 2.77 mmol) in DMF (3.458 ml) was added T3P® (50% solution in EtOAc) (2.421 ml, 4.149 mmol). The reaction mixture was stirred at RT for 1 h. Water was added to quench the excess T3P® and the solvent was removed under reduced pressure. The residue was passed through an Isolute SCX-2 cartridge (10 g) and washed with excess MeOH. The solvent was removed under reduced pressure to afford a yellow oil which was dried using a high vacuum oven. The crude material was purified using preparative HPLC with water (+0.1% TFA) and acetonitrile (+0.1% TFA) and the product fractions were concentrated under high vacuum to afford the title compound as a clear film;

LC-MS: Rt=4.65 mins; MS m/z=452.2 [M+H]+; Method 10minLowpHv01.

1H NMR, (400 MHz, DMSO-d6): δ 11.27 (1H, s), 7.91-7.83 (2H, m), 7.58 (1H, t), 7.56 (1H, d), 7.48-7.37 (2H, m), 5.76 (1H, s), 4.43 (1H, d), 4.30 (1H, d), 3.45 (1H, m), 3.03 (4H, m), 2.63 (1H, m), 1.75 (2H, m), 1.50 (3H, m), 1.07 (2H, m).

Example 31

(E)-N-(2-(1-(3-(3,5-Dichlorophenyl)acryloyl)piperidin-4-yl)ethyl)-2-oxo-2,3-dihydrooxazole-5-carboxamide

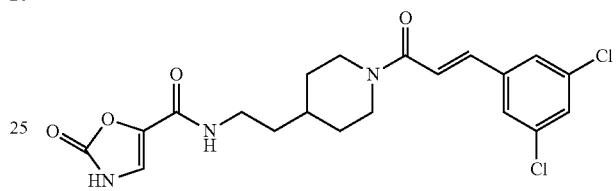

To (E)-1-(4-(2-aminoethyl)piperidin-1-yl)-3-(3,5-dichlorophenyl)prop-2-en-1-one (Example 30, step 4) (110 mg, 0.336 mmol) and 2-oxo-2,3-dihydrooxazole-5-carboxylic acid (Example 21, step 1) (167 mg, 0.504 mmol) in DMF (2 ml) was added DIPEA (0.470 mL, 2.69 mmol) and T3P® (50% in EtOAc, 1.571 ml, 2.69 mmol). The reaction mixture was stirred at RT overnight.

The reaction was quenched with water and the mixture was partitioned between water and EtOAc. The organic portion was separated and concentrated under reduced pressure to afford a yellow oil. Purification by preparative HPLC eluting with water (+0.1% TFA) and acetonitrile (+0.1% TFA) afforded product fractions which were concentrated under reduced pressure to afford the title compound as a white solid;

LC-MS: Rt=1.10 mins; MS m/z=438.5 [M+H]+; Method 2minLowpHv01.

1H NMR, (400 MHz, DMSO-d6): δ 11.24 (1H, s), 8.21 (1H, t), 7.91-7.83 (2H, m), 7.62-7.50 (2H, m), 7.49-7.32 (2H, m), 4.45 (1H, d), 4.31 (1H, d), 3.22 (2H, m), 3.03 (1H, m), 2.63 (1H, m), 1.84-1.68 (2H, m), 1.64-1.50 (1H, m), 1.49-1.38 (2H, m), 1.02 (2H, m).

Example 32

3,5-Dichlorobenzyl 4-(2-(N-methyl-2-oxo-2,3-dihydrooxazole-5-carboxamido)ethyl)piperidine-1-carboxylate

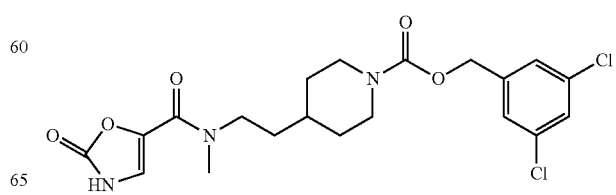

To 2-oxo-2,3-dihydrooxazole-5-carboxylic acid (Example 21, step 1) (317 mg, 1.471 mmol) and 3,5-dichlorobenzyl 4-(2-(methylamino)ethyl)piperidine-1-carboxylate (Example 1, step 3)(508 mg, 1.471 mmol) in DMF (10 ml) was added DIPEA (0.257 ml, 1.471 mmol) and HATU (559 mg, 1.471 mmol). The orange suspension formed was stirred at RT for 16 hrs. The mixture was concentrated under reduced pressure and the residue was dissolved in EtOAc (100 ml). The mixture was filtered and the filtrate was dry loaded in MeOH onto silica (~5 g). Purification was carried out by chromatography on silica (12 g silica cartridge) eluting with 0-100% EtOAc/iso-hexane. The product fractions were combined and concentrated to give a gum. This was dissolved in minimum volume of EtOAc and applied to a combined 10 g Isolute® PEAX/SCX-2 cartridge. The column was washed with MeOH and the fractions combined and concentrated under reduced pressure. The resultant solid was dissolved in DMSO (500 µl), MeCN (2 ml) and water and applied to a 13 g C18 cartridge which was eluted with 0-100% MeCN/water. The product fractions were combined and concentrated to give an aqueous suspension which was extracted with EtOAc (50 ml). The extracts were dried (MgSO$_4$) and concentrated to give 3,5-dichlorobenzyl 4-(2-(N-methyl-2-oxo-2,3-dihydrooxazole-5-carboxamido)ethyl)piperidine-1-carboxylate as a white solid.

LCMS: Rt=1.19 mins; MS m/z 456.1 and 458.1 [M+H]+; Method 2minLowpHv01

$^1$H NMR (500 MHz, d6-DMSO, 333K) δ 11.08 (1H, br s), 7.51 (1H, dd), 7.46 (1H, s), 7.39 (2H, d), 5.08 (2H, s), 3.97 (2H, m), 3.46 (2H, m), 3.02 (3H, br s), 2.83 (2H, m), 1.70 (2H, m), 1.41-1.54 (3H, m), 1.09 (2H, m).

Example 33

3,5-Dichlorobenzyl 4-((3-(3-hydroxyisoxazol-5-yl)propanamido)methyl)piperidine-1-carboxylate

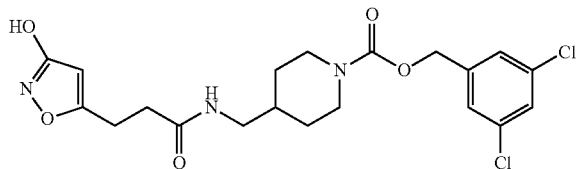 [SMILES: O=C(CCc1cc(O)no1)NCC1CCN(C(=O)OCc2cc(Cl)cc(Cl)c2)CC1]

Step 1: Tert-butyl 4-((3-(3-hydroxyisoxazol-5-yl)propanamido)methyl)piperidine-1-carboxylate To 3-(3-hydroxyisoxazol-5-yl)propanoic acid (300 mg, 1.909 mmol) in DMF (7 mL) was added DIPEA (0.667 mL, 3.82 mmol) followed by 1-[(1-(cyano-2-ethoxy-2-oxoethylideneaminooxy)dimethylaminomorpholino)]uronium hexafluorophosphate (COMU) (981 mg, 2.291 mmol). The resulting brown solution was stirred at RT for 5 mins and then treated with 1-BOC-4-(aminomethyl)piperidine (409 mg, 1.909 mmol). After stirring at RT for 2 hrs, the solution was concentrated under reduced pressure and the residue suspended in 0.2M aqueous HCl (200 ml). The mixture was extracted with EtOAc (2×100 ml) and the combined extracts were dried (MgSO$_4$) and concentrated under reduced pressure. The crude residue was dissolved in DCM (100 ml) and treated with 2M NaOH (50 ml). The mixture was stirred vigorously at ambient temperature for 16 hrs. The mixture was then acidified with citric acid and the organics removed, dried (MgSO$_4$) and concentrated under reduced pressure. The residue was applied to a 24 g silica cartridge and eluted with 0-100% EtOAc/iso-hexane. The product fractions were combined and concentrated to give a tert-butyl 4-((3-(3-hydroxyisoxazol-5-yl)propanamido)methyl)piperidine-1-carboxylate as a gum.

LCMS; Rt=0.91 mins; MS m/z 354.5 [M+H]+; Method 2minLowpHv01

Step 2: 3-(3-Hydroxyisoxazol-5-yl)-N-(piperidin-4-ylmethyl)propanamide

To tert-butyl 4-((3-(3-hydroxyisoxazol-5-yl)propanamido)methyl)piperidine-1-carboxylate (step 1) (539 mg, 1.525 mmol) in EtOAc (15 mL) was added 4N HCl in dioxane (15 ml, 60.0 mmol). The suspension was stirred at RT for 2 hrs and then concentrated under reduced pressure to give 3-(3-hydroxyisoxazol-5-yl)-N-(piperidin-4-ylmethyl)propanamide as a gum.

LCMS: Rt=0.58 mins; MS m/z 254.5 [M+H]+; Method 2minLowpHv01

Step 3: 3,5-Dichlorobenzyl 4-((3-(3-hydroxyisoxazol-5-yl)propanamido)methyl)piperidine-1-carboxylate To 3,5-dichlorobenzyl carbonochloridate (331 mg, 1.380 mmol) and 3-(3-hydroxyisoxazol-5-yl)-N-(piperidin-4-ylmethyl)propanamide (step 2) (200 mg, 0.690 mmol) in DCM (7 ml) was added 2M NaOH solution (6.90 ml, 13.80 mmol) and the mixture stirred vigorously at RT for 16 hrs. The mixture was diluted with EtOAc (50 ml) and acidified with 2M HCl. The organics were dried (MgSO$_4$) and concentrated under reduced pressure. The residue was dissolved in MeOH/EtOAc and dry loaded onto silica (10 g). This was applied to a 12 g silica cartridge, eluting with 1% AcOH/EtOAc. The product fractions were combined and concentrated under reduced pressure and the residue was triturated with diethyl ether to afford 3,5-dichlorobenzyl 4-((3-(3-hydroxyisoxazol-5-yl)propanamido)methyl)piperidine-1-carboxylate as a white solid.

LCMS solid; Rt=1.16 mins; MS m/z 456.2 and 458.2 [M+H]+ for Cl isotopes; Method 2minLowpHv01

$^1$H NMR (400 MHz, d6-DMSO) δ 10.99 (1H, s), 7.94 (1H, t), 7.56 (1H, t), 7.40 (2H, d), 5.71 (1H, s), 5.06 (2H, s), 3.97 (2H, m), 2.93 (2H, t), 2.81 (2H, t), 2.75 (2H, m), 2.41 (2H, t), 1.56-1.60 (3H, m), 0.98 (2H, m).

Example 34

3,5-Dichlorobenzyl 4-(3-(1H-1,2,3-triazole-4-carboxamido)propyl)piperazine-1-carboxylate

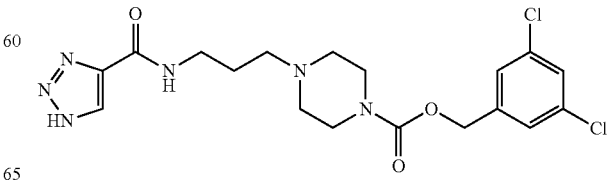

Step 1: 3,5-Dichlorobenzyl 4-(3-(tert-butoxycarbonylamino)propyl)piperazine-1-carboxylate To tert-butyl 3-oxopropylcarbamate (213 mg, 1.231 mmol) and 3,5-dichlorobenzyl piperazine-1-carboxylate (Example 26, step 2) (356 mg, 1.231 mmol) in DCM (10 ml) was added sodium triacetoxyborohydride (522 mg, 2.462 mmol) and the suspension stirred for 2 hrs.

Further tert-butyl 3-oxopropylcarbamate (50 mg) was added and the mixture stirred at ambient temperature for 16 hrs. The reaction mixture was diluted with DCM (100 ml) and quenched with saturated sodium bicarbonate solution (50 ml). The organic phase was separated, dried (MgSO$_4$) and concentrated under reduced pressure. The residue was applied to a 12 g silica cartridge and eluted with 0-100% EtOAc/iso-hexane. The product fractions were combined and concentrated to give 3,5-dichlorobenzyl 4-(3-(tert-butoxycarbonylamino)piperazine-1-carboxylate as a gum.

LCMS: Rt=0.88 mins, MS m/z 446.5 and 448.5 [M+H]+ for Cl isotopes; Method 2minLowpHv01

Step 2: 3,5-Dichlorobenzyl 4-(3-aminopropyl)piperazine-1-carboxylate

To 3,5-dichlorobenzyl 4-(3-(tert-butoxycarbonylamino) propyl)piperazine-1-carboxylate (step 1) (438 mg, 0.981 mmol) in DCM (6 ml) was added TFA (3 ml, 38.9 mmol). The resulting solution was stirred for 1 hr and then concentrated under reduced pressure. The residue was basified with saturated sodium bicarbonate solution (50 ml) and extracted with EtOAc (2×100 ml). The combined extracts were dried (MgSO$_4$) and concentrated to give 3,5-dichlorobenzyl 4-(3-aminopropyl)piperazine-1-carboxylate as a tan crystalline solid;

LCMS: Rt=0.54 mins; MS m/z 346.2 and 348.2 [M+H]+ for Cl isotopes; Method 2minLowpHv01

Step 3: 3,5-Dichlorobenzyl 4-(3-(1H-1,2,3-triazole-4-carboxamido)propyl)piperazine-1-carboxylate To 1H-1,2,3-triazole-4-carboxylic acid (32.7 mg, 0.289 mmol) in DMF (2 ml) was added HATU (110 mg, 0.289 mmol) and DIPEA (0.050 ml, 0.289 mmol). The resulting yellow solution was stirred for 10 mins and treated with 3,5-dichlorobenzyl 4-(3-amino propyl)piperazine-1-carboxylate (step 2) (100 mg, 0.289 mmol). After stirring at ambient temperature for 4 hrs, the mixture was diluted with EtOAc (50 ml) and washed with water (2×10 ml). The organic extracts were dried (MgSO$_4$) and concentrated under reduced pressure. The residue was dissolved in DCM and applied to a 20 g silica cartridge eluting with 10% MeOH/DCM containing 1% aqueous 880 ammonia. The product fractions were concentrated to give 3,5-dichlorobenzyl 4-(3-(1H-1,2,3-triazole-4-carboxamido)propyl)piperazine-1-carboxylate as a white foam;

LCMS: Rt=0.74 mins; MS m/z 439.2 and 441.2 [M−H] for chlorine isotopes; Method 2minLowpHv01

Example 35

3,5-Dichlorobenzyl 4-(2-(N-methyl-1H-1,2,3-triazole-4-carboxamido)ethyl)piperidine-1-carboxylate

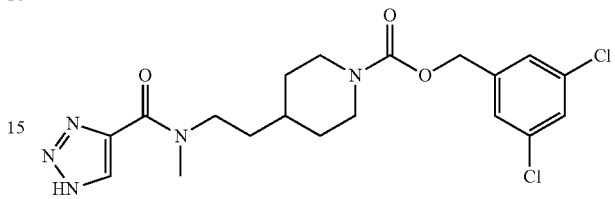

The title compound was prepared analogously to Example 34, step 3 from 1H-1,2,3-triazole-4-carboxylic acid and 3,5-dichlorobenzyl 4-(2-(methylamino)ethyl)piperidine-1-carboxylate (Example 1, step 3) (200 mg, 0.579 mmol);

LCMS: Rt=1.23 mins; MS m/z 440.5 and 442.5 [M+H]+ for Cl isotopes; Method 2minLowpHv01

Example 36

3-Chloro-5-cyanobenzyl 4-(2-(N-methyl-1H-1,2,3-triazole-4-carboxamido)ethyl)piperidine-1-carboxylate

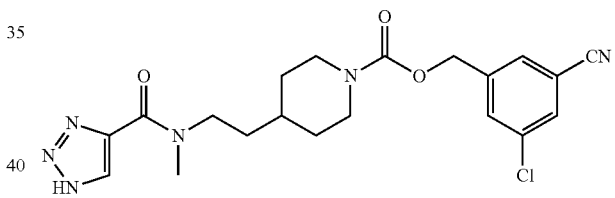

Step 1: Tert-butyl 4-(2-(methylamino)ethyl)piperidine-1-carboxylate

Tert-butyl 4-(2-aminoethyl)piperidine-1-carboxylate (1.0 g, 4.38 mmol) was dissolved in DCM (40 ml) and treated with 36.5% formaldehyde solution (326 µl, 4.38 mmol) followed by acetic acid (1 drop). The reaction mixture was stirred for 20 mins and treated with sodium triacetoxyborohydride (93 mg, 0.438 mmol). The resulting mixture was stirred at ambient temperature for 16 hrs and quenched with 2M NaOH (40 ml). The mixture was extracted with DCM (2×100 ml) and the combined organic extracts were dried (MgSO$_4$) and concentrated under reduced pressure to give tert-butyl 4-(2-(methylamino)ethyl)piperidine-1-carboxylate as an oil;

LCMS: Rt=0.64 mins; MS m/z 242.0 [M]+; Method 2minLowpHv01

Step 2: Tert-butyl 4-(2-(N-methyl-1H-1,2,3-triazole-4-carboxamido)ethyl)piperidine-1-carboxylate To 1H-1,2,3-triazole-4-carboxylic acid (150 mg, 1.327 mmol) and tert-butyl 4-(2-(methylamino)ethyl)piperidine-1-carboxylate (step 1) (322 mg, 1.327 mmol) in DMF (6 ml) was added DIPEA (0.695 ml, 3.98 mmol) and 50% T3P® in DMF (1.549 ml, 2.65 mmol). The resulting orange solution was stirred for 4 hrs. The mixture was diluted with EtOAc (200 ml) and washed with 1M HCl (2×50 ml). The organics were dried (MgSO4) and concentrated under reduced pressure. The crude residue in was dissolved in DCM and applied to a 12 g silica cartridge eluting with 0-100% EtOAc/iso-hexane. The product fractions were concentrated to give tert-butyl 4-(2-(N-methyl-1H-1,2,3-triazole-4-carboxamido)ethyl)piperidine-1-carboxylate as a gum.

LCMS: Rt=1.01 mins; MS m/z 338.5 [M+H]+; Method 2minLowpHv01

Step 3: N-Methyl-N-(2-(piperidin-4-yl)ethyl)-1H-1,2,3-triazole-4-carboxamide

To tert-butyl 4-(2-(N-methyl-1H-1,2,3-triazole-4-carboxamido)ethyl)piperidine-1-carboxylate (step 2) (190 mg, 0.563 mmol) in EtOAc (5 ml) was added 4N HCl in dioxane (5 ml, 20.00 mmol). The mixture was stirred for 30 mins and concentrated under reduced pressure to give crude N-methyl-N-(2-(piperidin-4-yl)ethyl)-1H-1,2,3-triazole-4-carboxamide as a gum. This was used in the next step without further purification.

Step 4: 3-Chloro-5-cyanobenzyl carbonochloridate

3-Chloro-5-(hydroxymethyl)benzonitrile (25 g, 145 mmol) was dissolved in THF (200 mL). The resulting yellow solution was cooled to 10° C. in an ice bath and treated dropwise with phosgene in toluene (152 mL, 289 mmol). The reaction mixture was stirred at ambient temperature for 16 hrs. The mixture was concentrated under reduced pressure and the crude material was diluted with toluene (200 ml) and re-concentrated under reduced pressure. The residue was purified by chromatography on silica (Redisep 340 g column on a Biotage system), eluting with EtOAc/iso-hexane to give 3-chloro-5-cyanobenzyl carbonochloridate as an oil.

$^1$H NMR (600 MHz, CDCl$_3$) δ 7.70 (1H, s), 7.66 (1H, s), 7.62 (1H, s), 5.32 (2H, s).

Step 5: 3-Chloro-5-cyanobenzyl 4-(2-(N-methyl-1H-1,2,3-triazole-4-carboxamido)ethyl)piperidine-1-carboxylate To 3-chloro-5-cyanobenzyl carbonochloridate (step 4) (65.5 mg, 0.285 mmol) and N-methyl-N-(2-(piperidin-4-yl)ethyl)-1H-1,2,3-triazole-4-carboxamide (step 3) (78 mg, 0.285 mmol) in DCM (5 mL) was added saturated aqueous sodium bicarbonate solution (5 mL, 0.285 mmol), and the mixture stirred vigorously for 16 hrs. The resulting mixture was acidified with 10% citric acid solution and the organic portion was separated, dried (MgSO4) and concentrated under reduced pressure. The residue was dissolved in DCM and applied to a 12 g silica cartridge eluting with 0-100% EtOAc/iso-hexane. The product fractions were combined and concentrated to give a gum. This was further purified by UV triggered HPLC, to give 3-chloro-5-cyanobenzyl 4-(2-(N-methyl-1H-1,2,3-triazole-4-carboxamido)ethyl)piperidine-1-carboxylate as a gum;

LCMS: Rt=1.07 mins; MS m/z 431.5 and 433.6 [M+H]+ for Cl isotopes; Method 2minLowpHv01

Example 37

3-Chloro-5-fluorobenzyl 4-(4-(1H-1,2,3-triazol-4-yl)butanamido)piperidine-1-carboxylate

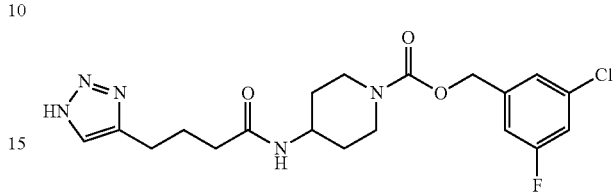

Step 1: 3-Chloro-5-fluorobenzyl 2,5-dioxopyrrolidin-1-yl carbonate

To a stirred suspension of N,N'-disuccinimidyl carbonate [CAS 74124-79-1] (7.08 g, 27.6 mmol) in 2-Me-THF (20 ml) and triethylamine (10.44 ml, 75 mmol) at 5° C. was added dropwise 3-chloro-5-fluorophenyl)methanol [CAS 79944-64-2] (3 ml, 25.1 mmol). After 10 minutes the white suspension was allowed to slowly warm to RT and stirred at RT for 24 hrs. The white solid was filtered off, washed with iso-hexane and the filtrate and washings were combined, diluted with EtOAc, washed with water and a saturated solution of brine. The organic portion was dried over MgSO4, filtered and concentrated under reduced pressure to yield a pale yellow oily solid. Purification was carried out by chromatography on silica using 0-100% iso-hexane in TBME to afford the title product as a white solid;

LC-MS: Rt 1.09 min; MS m/z 319.2 [M+H2O]+; Method 2minLowpHv01

Step 2: Azidomethyl Pivalate

To a stirred suspension of chloromethyl pivalate (21.2 g, 141 mmol) in water (25 ml) was added sodium azide (13.7 g, 211 mmol) and the mixture was stirred vigorously at 90° C. for 24 hrs. On cooling the reaction mixture was diluted with H2O and the organic portion was filtered through a pad of MgSO4 to afford the title compound as a clear liquid;

1H NMR (400 MHz, CDCl3) δ 5.15 (s, 2H), 1.26 (s, 9H).

Step 3: 4-(1-((Pivaloyloxy)methyl-1H-1,2,3-triazol-4-yl)butanoic acid

To a stirred suspension of 5-hexynoic acid (1.375 g, 12.26 mmol) in tBuOH (120 ml) and water (120 ml) was added azidomethyl pivalate (1.927 g, 12.26 mmol) and copper (II) acetate (0.223 g, 1.226 mmol). Sodium L-ascorbate (0.486 g, 2.452 mmol) was added and the suspension was stirred at RT for 24 hours. The resulting suspension was acidified with conc.HCl, saturated with NaCl and extracted with EtOAc. The organic portions were combined, dried over MgSO4, filtered and concentrated under reduced pressure. Purification was carried out on a Isolute® PEAX cartridge eluting with EtOAc, MeCN and then 10% AcOH/EtOAc to afford the title product;

LC-MS: Rt 0.88 mins; MS m/z 270.2 [M+H]+; Method 2minLowpHv01

Step 4: Tert-butyl 4-(4-(1-((pivaloyloxy)methyl)-1H-1,2,3-triazol-4-yl)butanamido)piperidine-1-carboxylate To a stirred solution of 4-(1-((pivaloyloxy)methyl)-1H-1,2,3-triazol-4-yl)butanoic acid (1.63 g, 6.05 mmol) and tert-butyl 4-aminopiperidine-1-carboxylate (1.212 g, 6.05 mmol) in DMF (10 mL) was added Huenig's Base (3.17 mL, 18.16 mmol) followed by T3P® 50% in DMF (7.07 mL, 12.11 mmol) at RT. The reaction mixture was allowed to stir at RT for 20 hours. The DMF was removed under reduced pressure and the residue dissolved in EtOAc and washed with a saturated solution of sodium bicarbonate, a saturated solution of brine, dried over MgSO$_4$, filtered and concentrated under reduced pressure to afford the title product;

LC-MS: Rt 1.22 mins; MS m/z 452.4 [M+H]+; Method 2minLowpHv03

Step 5: (4-(4-oxo-4-(piperidin-4-ylamino)butyl)-1H-1,2,3-triazol-1-yl)methyl pivalate To a stirred solution of tert-butyl 4-(4-(1-((pivaloyloxy)methyl)-1H-1,2,3-triazol-4-yl)butanamido)piperidine-1-carboxylate (2.73 g, 6.05 mmol) in EtOAc (20 ml) was added dropwise 4M HCl in dioxane (15.11 ml, 60.5 mmol) and the reaction mixture stirred at RT for 4 hrs. The resulting oily solution was concentrated under reduced pressure, triturated with ether and concentrated under reduced pressure to afford the title compound as the HCl salt;

LC-MS: Rt 0.61 mins; MS m/z 352.4 [M+H]+; Method 2minLowpHv03

Step 6: 3-Chloro-5-fluorobenzyl 4-(4-(1-((pivaloyloxy)methyl)-1H-1,2,3-triazol-4-yl)butanamido)piperidine-1-carboxylate To a stirred suspension of (4-(4-oxo-4-(piperidin-4-ylamino)butyl)-1H-1,2,3-triazol-1-yl)methyl pivalate (step 5) (150 mg, 0.387 mmol) and 3-chloro-5-fluorobenzyl 2,5-dioxopyrrolidin-1-yl carbonate (117 mg, 0.387 mmol) in DCM (5 mL) was added NaOH (1.547 mL, 1.547 mmol) with stirring at RT and the mixture was stirred at RT for 18 hrs. A further 5 ml DCM was added followed by 1M NaOH (1 ml). The reaction mixture was diluted with DCM (30 ml) and the organic portion was dried over MgSO$_4$, filtered and concentrated under reduced pressure to afford the title product;

LC-MS:Rt 1.35 mins; MS m/z 538.5, 540.53 [M+H]+; Method 2minLowpHv03

Step 7: 3-Chloro-5-fluorobenzyl 4-(4-(1H-1,2,3-triazol-4-yl)butanamido)piperidine-1-carboxylate To a stirred solution of 3-chloro-5-fluorobenzyl 4-(4-(1-((pivaloyloxy)methyl)-1H-1,2,3-triazol-4-yl)butanamido)piperidine-1-carboxylate (200 mg, 0.372 mmol) in MeOH (1 mL) was added 1M NaOH (0.818 mL, 0.818 mmol). The reaction mixture was allowed to stir at RT for 1 hour. An equivalent of 1M HCl (0.8 ml) was added to neutralise the reaction mixture and the MeOH was removed under reduced pressure. The mixture was diluted with water and extracted with EtOAc. The organic portion was dried over MgSO$_4$, filtered and concentrated under reduced pressure. Purification was carried out by chromatography on silica using 0-100% EtOAc in hexanes and then 0-10% MeOH in EtOAc to afford the title product;

LC-MS: Rt 1.10 mins; MS m/z 424.3, 426.3 [M+H]+; Method 2minLowpHv03

Example 38

(E)-N-(1-(3-(3,5-Dichlorophenyl)acryloyl)piperidin-4-yl)-4-(1H-1,2,3-triazol-4-yl)butanamide

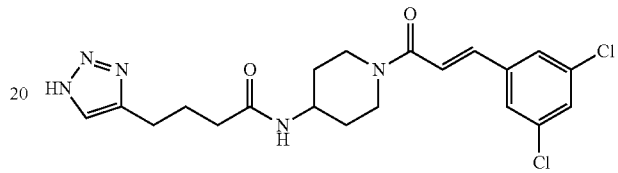

Step 1: (E)-(4-(4-((1-(3-(3,5-Dichlorophenyl)acryloyl)piperidin-4-yl)amino)-4-oxobutyl)-1H-1,2,3-triazol-1-yl)methyl pivalate To a stirred suspension of (4-(4-oxo-4-(piperidin-4-ylamino)butyl)-1H-1,2,3-triazol-1-yl)methyl pivalate (Example 37, step 5)(200 mg, 0.516 mmol) and (E)-3-(3,5-dichlorophenyl)acrylic acid (Example 30, step 2) (112 mg, 0.516 mmol) in DMF (2 mL) at RT was added Huenig's base (0.450 mL, 2.58 mmol) followed by T3P® 50% in DMF (0.602 mL, 1.031 mmol) after a few minutes. The reaction mixture was stirred at RT for 20 hours. The reaction mixture was diluted with EtOAc and washed with a saturated solution of brine, organics dried over MgSO$_4$, filtered, and concentrated under reduced pressure to afford the title crude product;

LCMS:Rt 1.35 mins; 550.5, 552.6 [M+H]+; Method 2minLowpHv03

Step 2: (E)-N-(1-(3-(3,5-Dichlorophenyl)acryloyl)piperidin-4-yl)-4-(1H-1,2,3-triazol-4-yl)butanamide To a stirred solution of (E)-(4-(4-((1-(3-(3,5-dichlorophenyl)acryloyl)piperidin-4-yl)amino)-4-oxobutyl)-1H-1,2,3-triazol-1-yl)methyl pivalate (284 mg, 0.516 mmol) in MeOH (1 mL) was added 1M NaOH (1.135 mL, 1.135 mmol) and the mixture allowed to stir at RT for 1.5 hrs. An equivalent of 1M HCl (1.1 ml) was added to neutralise the reaction mixture and the MeOH was removed under reduced pressure. The reaction mixture was diluted with EtOAc and washed with water. The organic portion was dried over MgSO4, filtered and concentrated under reduced pressure. Purification was carried out by chromatography on silica using 0-10% MeOH in DCM to afford the title product;

LC-MS: Rt 1.12 mins; MS m/z 436.4, 438.4 [M+H]+; Method 2minLowpHv03

Example 39

(E)-N-(1-(3-(2,4-Dichlorophenyl)acryloyl)piperidin-4-yl)-4-(1H-1,2,3-triazol-4-yl)butanamide

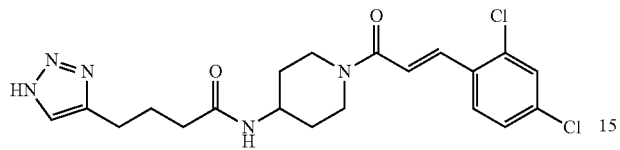

Step 1: (E)-3-(2,4-Dichlorophenyl)acrylic acid

To a stirred solution of (E)-methyl 3-(2,4-dichlorophenyl)acrylate (5052 mg, 21.86 mmol) in THF (109.00 mL) at RT was added 2M NaOH (32.8 mL, 65.6 mmol) and the mixture allowed to stir for 24 hrs. The THF was removed under reduced pressure and on cooling HCl (37%) was added dropwise to the aqueous solution. A solid precipitated out of solution which was filtered and dried to afford the title product;
LC-MS: Rt 1.14 mins; MS m/z 216.9 [M+H]+; Method 2minLowpHv01

Step 2: (E)-(4-(4-((1-(3-(2,4-Dichlorophenyl)acryloyl)piperidin-4-yl)amino)-4-oxobutyl)-1H-1,2,3-triazol-1-yl)methyl pivalate The title compound was prepared from (4-(4-oxo-4-(piperidin-4-ylamino)butyl)-1H-1,2,3-triazol-1-yl)methyl pivalate (Example 37, step 5) (200 mg, 0.516 mmol) and (E)-3-(2,4-dichlorophenyl)acrylic acid (step 1) analogously to Example 38 step 1.
LCMS: Rt 1.33 mins; MS m/z 550.5, 552.6 [M+H]+; Method 2minLowpHv03

Step 3: (E)-N-(1-(3-(2,4-Dichlorophenyl)acryloyl)piperidin-4-yl)-4-(1H-1,2,3-triazol-4-yl)butanamide The title compound was prepared from (E)-(4-(4-((1-(3-(2,4-dichlorophenyl)acryloyl)piperidin-4-yl)amino)-4-oxobutyl)-1H-1,2,3-triazol-1-yl)methyl pivalate analogously to Example 38 step 2;
LC-MS: Rt 1.10 mins; MS m/z 436.4, 438.4 [M+H]+; Method 2minLowpHv03

Example 40

8-((1-(((3,5-Dichlorobenzyl)oxy)carbonyl)piperidin-4-yl)amino)-8-oxooctanoic acid

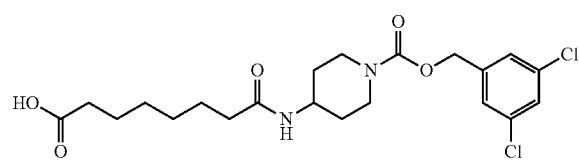 [SMILES: O=C(O)CCCCCCC(=O)NC1CCN(C(=O)OCc2cc(Cl)cc(Cl)c2)CC1]

The title compound was prepared from 3,5-dichlorobenzyl 4-aminopiperidine-1-carboxylate (Example 9, step 2) analogously to Example 10;
LC-MS: Rt 1.28 mins; MS m/z 459.4, 461.4 [M+H]+; Method 2minLowpHv03

Example 41

3,5-Dichlorobenzyl 4-((4-(1H-1,2,3-triazol-5-yl)butanamido)methyl)piperidine-1-carboxylate

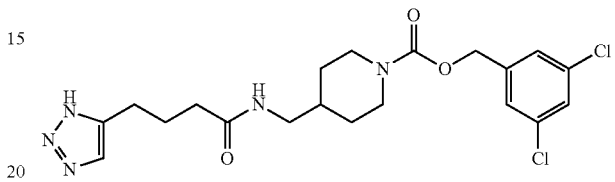

Step 1: 3,5-Dichlorobenzyl 4-(((tert-butoxycarbonyl)amino)methyl)piperidine-1-carboxylate A reaction mixture comprising tert-butyl(piperidin-4-ylmethyl)carbamate (1 g, 4.67 mmol), 3,5-dichlorobenzyl carbonochloridate, (1.117 g, 4.67 mmol) and sodium bicarbonate (15 mL, 4.67 mmol) in DCM (15.55 mL) was stirred at room temperature for 18 hours. The reaction mixture was separated and the organic portion was dried over MgSO$_4$, filtered and solvent concentrated under reduced pressure to give the title compound as a yellow oil;
1H NMR (400 MHz, DMSO-d6) 7.6 (1H, s) 7.4 (2H, s), 6.9 (1H, bt), 5.1 (2H, s), 4 (2H, d), 2.8 (3H, m), 1.6 (2H, m), 1.4 (9H, s), 1 (2H, d)

Step 2: 3,5-Dichlorobenzyl 4-(aminomethyl)piperidine-1-carboxylate hydrochloride A reaction mixture comprising of 3,5-dichlorobenzyl 4-(((tert-butoxycarbonyl)amino)methyl)piperidine-1-carboxylate (947 mg, 2.269 mmol) and 4M HCl in dioxane (2.84 mL, 11.35 mmol) in DCM (5 mL) was stirred at room temperature for 3 hours. The reaction mixture was concentrated under reduced pressure to give the title compound as the hydrochloride salt;
LCMS; Rt=0.71 mins; MS m/z 317.3 and 319.3; Method 2minLowpHv01

Step 3: 3,5-Dichlorobenzyl 4-((4-(1H-1,2,3-triazol-5-yl)butanamido)methyl)piperidine-1-carboxylate A mixture comprising of 4-(1H-1,2,3-triazol-4-yl)butanoic acid (Example 17, step 4) (65.8 mg, 0.424 mmol), 3,5-dichlorobenzyl 4-(aminomethyl)piperidine-1-carboxylate hydrochloride (step 2) (100 mg, 0.283 mmol), HATU (215 mg, 0.565 mmol) and TEA (197 µl, 1.414 mmol) in DMF (942 µl) was stirred at room temperature for 3 hours. Purification was carried out using preparative LC-MS under low pH conditions. The resulting product fractions were concentrated under reduced pressure to give aqueous solutions which were extracted with ethyl acetate. The organic extracts were dried over MgSO$_4$, filtered and concentrated under reduced pressure to afford the title compound;

LC-MS; Rt 3.75 mins; MS m/z 454 [M+H]+; Method 8minLowpHv01

1H NMR (400 Hz, MeOD), 8 (1H, bs), 7.6 (1H, s), 7.4 (1H, s), 7.45 (2H, s), 5.6 (2H, s), 4.15 (2H, d), 3.1 (2H, d), 2.8 (3H, m), 2.4 (2H, t), 2 (2H, m), 1.7 (3H, m), 1.35 (1H, m), 1.2 (1H, m),

Example 42

N-(1-(3-(3,5-Dichlorophenyl)propanoyl)piperidin-4-yl)-4-(1H-1,2,3-triazol-4-yl)butanamide

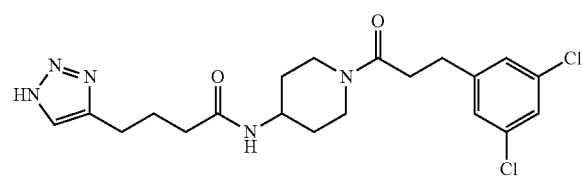

A solution of (E)-N-(1-(3-(3,5-dichlorophenyl)acryloyl)piperidin-4-yl)-4-(1H-1,2,3-triazol-4-yl)butanamide (Example 38) (70 mg, 0.160 mmol) in EtOH (6 ml) was allowed to pass through the H cube fitted with a 10% Pt/C catalytic cartridge for 3 hours. The reaction mixture was concentrated under reduced pressure to afford the title product;

LC-MS: Rt 1.10 mins; MS m/z 438.4, 440.4 [M+H]+; Method 2minLowpHv03

Example 43

N-(1-(3-(2,4-Dichlorophenyl)propanoyl)piperidin-4-yl)-4-(1H-1,2,3-triazol-4-yl)butanamide

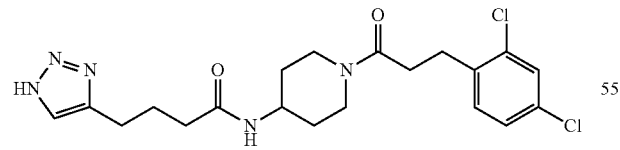

The title compound was prepared from (4-(4-oxo-4-(piperidin-4-ylamino)butyl)-1H-1,2,3-triazol-1-yl)methyl pivalate (Example 37, step 5) (200 mg, 0.516 mmol) and commercially available 3-(2,4-dichlorophenyl)propanoic acid (Fisher) (113 mg, 0.516 mmol) analogously to Example 38, steps 1 and 2;

LC-MS: Rt 1.08 mins; MS m/z 438.3, 440.3 [M+H]+; Method 2minLowpHv03

Example 44

3-Chloro-5-cyanobenzyl 4-(4-(1H-1,2,3-triazol-4-yl)butanamido)piperidine-1-carboxylate

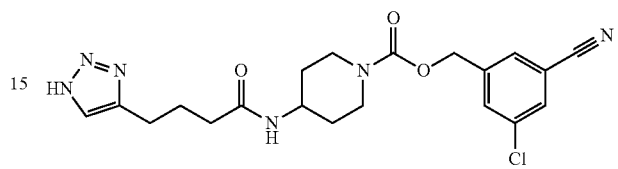

Step 1: 3-Chloro-5-cyanobenzyl carbonochloridate

To a stirred yellow solution of 3-chloro-5-(hydroxymethyl)benzonitrile (25 g, 145 mmol) in THF (200 mL) at 10° C. was added dropwise phosgene in toluene (152 mL, 289 mmol) over 45 mins and the reaction mixture was allowed to warm to RT over 24 hrs. The resulting mixture was concentrated under reduced pressure and azeotroped with toluene. Purification was carried out by chromatography on silica to afford the title product;

Step 2: 3-Chloro-5-cyanobenzyl 4-(4-(1-((piyaloyloxy)methyl)-1H-1,2,3-triazol-4-yl)butanamido)piperidine-1-carboxylate To a stirred suspension of (4-(4-oxo-4-(piperidin-4-ylamino)butyl)-1H-1,2,3-triazol-1-yl)methyl pivalate (Example 37, step 5) (550 mg, 1.418 mmol) and 3-chloro-5-cyanobenzyl carbonochloridate (359 mg, 1.560 mmol) in DCM (10 mL) was added a saturated solution of sodium bicarbonate (1.418 mL, 14.18 mmol). The reaction mixture was allowed to stir at RT for 2 hours and then diluted with DCM. The organic portion was dried over MgSO₄, filtered and concentrated under reduced pressure. Purification was carried out on silica eluting with 1-10% MeOH in DCM to afford the title product;

LC-MS: Rt 1.28 mins; MS m/z 545.4, 547.4 [M−H-1]+; Method 2minLowpHv03.

Step 3: 3-Chloro-5-cyanobenzyl 4-(4-(1H-1,2,3-triazol-4-yl)butanamido)piperidine-1-carboxylate To a stirred solution of 3-chloro-5-cyanobenzyl 4-(4-(1-((piyaloyloxy)methyl)-1H-1,2,3-triazol-4-yl)butanamido)piperidine-1-carboxylate (150 mg, 0.275 mmol) in MeOH (1 mL) at RT was added 1M NaOH (0.165 mL, 0.165 mmol). The reaction mixture was allowed to stir at RT for 30 mins. An equivalent of 1M HCl (0.165 ml) was added to neutralise the mixture and EtOAc and water were added. The organic portion was dried over MgSO₄, filtered and concentrated under reduced pressure. Purification was carried out on silica eluting with 0-10% MeOH in DCM to afford the title product;

LC-MS: Rt 1.04 mins; MS m/z 431.3, 433.3 [M+H]+; Method 2minLowpHv03

Example 45

3,5-Dichlorobenzyl 3-(4-(1H-1,2,3-triazol-4-yl)butanamido)-8-azabicyclo[3.2.1]octane-8-carboxylate

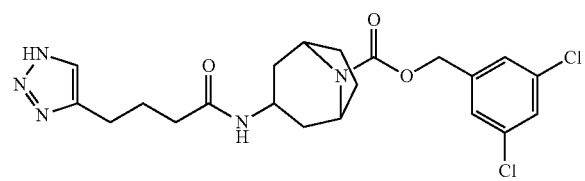 [SMILES: O=C(CCCc1c[nH]nn1)NC1CC2CCC(C1)N2C(=O)OCc1cc(Cl)cc(Cl)c1]

Step 1: Tert-butyl 3-(4-(1H-1,2,3-triazol-4-yl)butanamido)-8-azabicyclo[3.2.1]octane-8-carboxylate A reaction mixture comprising of tert-butyl 3-amino-8-azabicyclo[3.2.1]octane-8-carboxylate (250 mg, 1.105 mmol), 4-(1H-1,2,3-triazol-4-yl)butanoic acid (Example 17, step 4) (171 mg, 1.105 mmol), T3P® 50% DMF (1.29 ml, 2.209 mmol) and TEA (462 μl, 3.31 mmol) in DMF (3.6 ml) was stirred for 4 hours. The reaction mixture was concentrated under reduced pressure. The resulting oil was diluted with DCM and washed with water. The organic portion was dried over MgSO₄, filtered and concentrated under reduced pressure. The material was taken crude to the next step.

LCMS; Rt 0.89 mins MS m/z 364.5, 365.5 Method 2minLowpHv03

Step 2: N-(8-Azabicyclo[3.2.1]octan-3-yl)-4-(1H-1,2,3-triazol-4-yl)butanamide

A reaction mixture comprising of tert-butyl 3-(4-(1H-1,2,3-triazol-4-yl)butanamido)-8-azabicyclo[3.2.1]octane-8-carboxylate (401 mg, 1.103 mmol) in dioxane (5 ml) was treated with 4M HCl in dioxane (0.827 ml, 3.31 mmol) and stirred at room temperature for 3 hours. The reaction mixture was concentrated under reduced pressure to afford the title compound. The material was taken on to the next step without further purification.

LC-MS: Rt 0.59 mins; MS m/z 263 [M+H]+; Method 2minLowpHv01

Step 3: 3,5-Dichlorobenzyl 3-(4-(1H-1,2,3-triazol-4-yl)butanamido)-8-azabicyclo[3.2.1]octane-8-carboxylate A reaction mixture comprising of N-(8-azabicyclo[3.2.1]octan-3-yl)-4-(1H-1,2,3-triazol-4-yl)butanamide (294 mg, 1.116 mmol), 3,5-dichlorobenzyl carbonochloridate (267 mg, 1.116 mmol) and sodium hydroxide (5.58 ml, 112 mmol) in DCM (3.7 ml) was stirred at room temperature for 18 hours. The reaction mixture was separated and the organic portion was dried over MgSO₄, filtered and concentrated under reduced pressure. Further purification was carried out using preparative LC-MS and the resulting product fractions were concentrated under reduced pressure to give aqueous solutions which were extracted with ethyl acetate. The organic extracts were dried over MgSO₄, filtered and concentrated under reduced pressure to afford the title compound.

LC-MS: Rt 1.31 mins; MS m/z 466.5 and 468.5 [M+H]+; Method 2minLowpHv01

Example 46

3,5-Dichlorobenzyl 4-(4-(1H-1,2,3-triazol-4-yl)butanamido)azepane-1-carboxylate

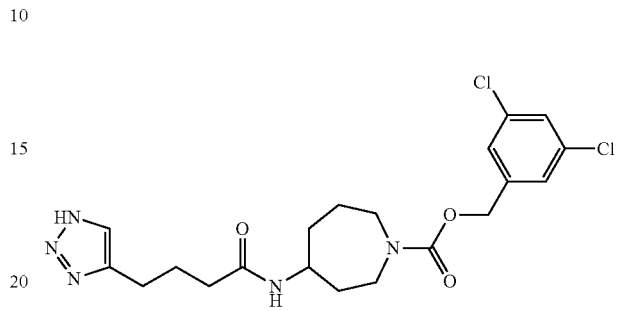

The title compound was prepared from 4-(1H-1,2,3-triazol-4-yl)butanoic acid (Example 17, step 4) and tert-butyl 4-aminoazepane-1-carboxylate analogously to Example 45 step 3;

LC-MS: Rt 1.20 mins; MS m/z 454.4 and 456.4 [M+H]+; Method 2minLowpHv01

Example 47

3,5-Dichlorobenzyl(8-(4-(1H-1,2,3-triazol-4-yl)butanoyl)-8-azabicyclo[3.2.1]octan-3-yl)carbamate

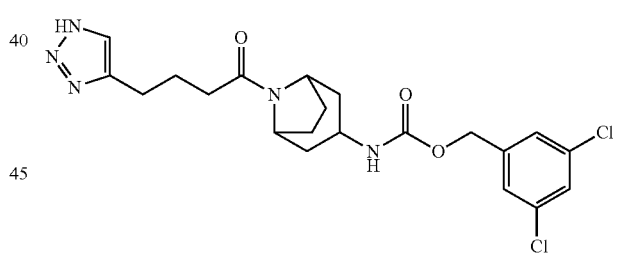

Step 1: Tert-butyl 3-((((3,5-dichlorobenzyl)oxy)carbonyl)amino)-8-azabicyclo[3.2.1]octane-8-carboxylate A reaction mixture comprising of tert-butyl 3-amino-8-azabicyclo[3.2.1]octane-8-carboxylate (210 mg, 0.928 mmol), 3,5-dichlorobenzyl carbonochloridate (222 mg, 0.928 mmol), and sodium hydroxide (4.64 ml, 93 mmol) in DCM (3.1 ml) was stirred at room temperature for 4 hours. The reaction mixture separated and the organic portion dried over MgSO₄, filtered and concentrated under reduced pressure. No further purification was carried out and the material was taken on crude to the next step.

LC-MS: Rt 1.63 mins; MS m/z 329 [M+H]+; Method 2minLowpHv01

Step 2: 3,5-Dichlorobenzyl 8-azabicyclo[3.2.1]octan-3-ylcarbamate hydrochloride A reaction mixture comprising of tert-butyl 3-((((3,5-dichlorobenzyl)oxy)carbonyl)amino)-8-azabicyclo[3.2.1]octane-8-carboxylate (388.3 mg, 0.904 mmol) in dioxane (5 mL) was treated with 4M HCl in dioxane (0.678 mL, 2.71 mmol) and stirred at room temperature for 3 hours. The resulting mixture concentrated under reduced pressure. No further purification was carried out and the material was taken on crude to the next step.

LC-MS: Rt 0.79 mins; MS m/z 329 [M+H]+; Method 2minLowpHv01

Step 3: 3,5-Dichlorobenzyl(8-(4-(1H-1,2,3-triazol-4-yl)butanoyl)-8-azabicyclo[3.2.1]octan-3-yl)carbamate A reaction mixture comprising 3,5-dichlorobenzyl 8-azabicyclo[3.2.1]octan-3-ylcarbamate hydrochloride (118 mg, 0.322 mmol), 4-(1H-1,2,3-triazol-4-yl)butanoic acid (Example 17, step 4) (50 mg, 0.322 mmol), TEA (135 µl, 0.967 mmol) and T3P® (376 µl, 0.645 mmol) in DMF (1.0 ml) was stirred at room temperature overnight. The reaction mixture was diluted with water and extracted with DCM. The organic portion was concentrated under reduced pressure. Purification was carried out using preparative LC-MS method (Prep Run 30-70% Gradient low pH 9.5 min). The resulting product fractions were concentrated under reduced pressure to give aqueous solutions which were extracted with ethyl acetate. The organic extracts were dried over MgSO4, filtered and concentrated under reduced pressure to afford the title compound.

LC-MS; Rt 3.96 mins; MS m/z 466.0 and 469.6 [M+H]+; Method 8minLowpHv01

Example 48

3,5-Dichlorobenzyl(1-(4-(1H-1,2,3-triazol-4-yl)butanoyl)azepan-4-yl)carbamate

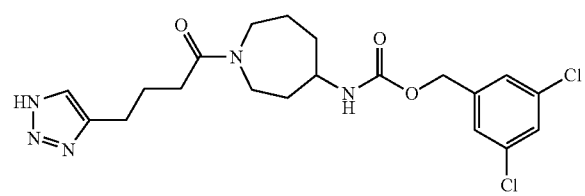 [SMILES: O=C(NC1CCCN(C(=O)CCCc2c[nH]nn2)CC1)OCc1cc(Cl)cc(Cl)c1]

The title compound was prepared from tert-butyl 4-aminoazepane-1-carboxylate and 3,5-dichlorobenzyl carbonochloridate analogously to Example 47 steps 1-3;

LC-MS: Rt 1.22 mins; MS m/z 454 [M+H]+; Method 2minLowpHv01

Example 49

Racemic 3,5-dichlorobenzyl 3-(4-(1H-1,2,3-triazol-4-yl)butanamido)pyrrolidine-1-carboxylate

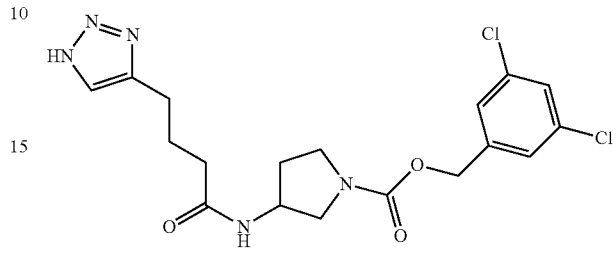

Step 1: 3,5-Dichlorobenzyl 3-((tert-butoxycarbonyl)amino)pyrrolidine-1-carboxylate A mixture comprising of 3-(boc-amino)pyrrolidine (1 g, 5.37 mmol) and saturated sodium bicarbonate (9 mL, 5.37 mmol) in DCM (17.90 mL) was stirred at room temperature for 5 minutes. The resulting mixture was treated with 3,5-dichlorobenzyl carbonochloridate (1.286 g, 5.37 mmol) and stirred at room temperature for one hour. The reaction mixture was concentrated under reduced pressure, diluted with water and extracted with DCM. The organic portion was separated and dried over MgSO4, filtered and concentrated under reduced pressure to afford the title compound;

LC-MS: Rt: 1.49 mins; MS m/z 389 [M+H]+; Method 2minLowpHv01.

Step 2: 3,5-Dichlorobenzyl 3-aminopyrrolidine-1-carboxylate

A mixture comprising of 3,5-dichlorobenzyl 3-((tert-butoxycarbonyl)amino)pyrrolidine-1-carboxylate (1.8143 g, 4.66 mmol) and trifluoroacetic acid (14.36 ml, 186 mmol) in DCM (15.54 ml) was stirred at RT for 2 hours. The reaction mixture was concentrated under reduced pressure, diluted with DCM and washed with water. The organic portion was separated, dried over MgSO4, filtered and concentrated under reduced pressure to form an orange oil which was used in the next step without further purification;

LC-MS: Rt: 0.72 mins; MS m/z 289 [M+H]+; Method 2minLowpHv01.

Step 3: Racemic 3,5-Dichlorobenzyl 3-(4-(1H-1,2,3-triazol-4-yl)butanamido)pyrrolidine-1-carboxylate A mixture comprising of 3,5-dichlorobenzyl 3-aminopyrrolidine-1-carboxylate (1 equiv), 4-(1H-1,2,3-triazol-4-yl) butanoic acid (1 equiv.), HATU (1.5 equiv.) and triethylamine (5 equiv.) in dimethylformamide was stirred at RT for 18 hours. Another 1 equivalent of 4-(1H-1,2,3-triazol-4-yl)butanoic acid was added to the reaction mixture and stirring continued for a further 2 hours. The reaction mixture was concentrated under reduced pressure, diluted with water and extracted with DCM. The organic portion was separated, dried over MgSO4, filtered and concentrated under reduced pressure. The crude product was dry loaded using silica onto a 12 g ISCO column, eluting with 0-15% MeOH in DCM. The product fractions were combined and concentrated under reduced pressure. Further purification was carried our using preparative LC-MS. The product fractions were concentrated under reduced pressure to give an aqueous solution and extracted with EtOAc to afford the title compound;

1H NMR (400 MHz, CDCl3) δ 7.50 (1H, d), 7.15 (3H, t), 6.25 (1H, s), 5.00 (2H, d), 4.45 (1H, s), 3.60 (1H, d), 3.45 (2H, s), 3.30 (1H, s), 2.75 (2H, s), 2.15 (3H, d), 1.95 (2H, s), 1.20 (1H, t).

LC-MS: Rt: 1.14 mins; MS m/z 426 [M+H]+; Method 2minLowpHv01

Example 49a (S)- or (R)-3,5-Dichlorobenzyl 3-(4-(1H-1,2,3-triazol-4-yl)butanamido)pyrrolidine-1-carboxylate and Example 49b: (S)- or (R)-3,5-Dichlorobenzyl 3-(4-(1H-1,2,3-triazol-4-yl)butanamido)pyrrolidine-1-carboxylate

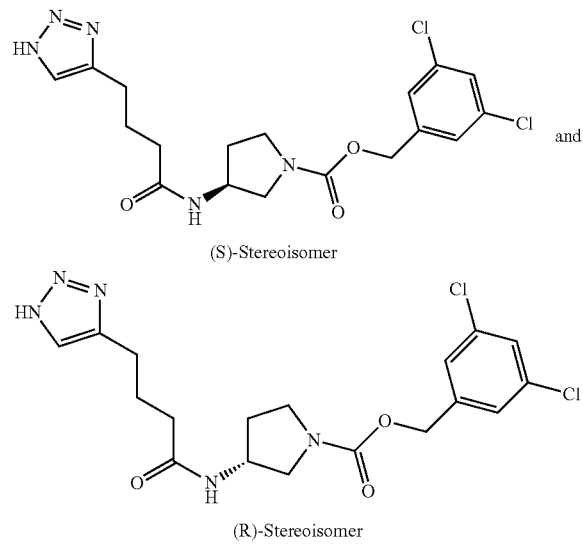

(S)-Stereoisomer (R)-Stereoisomer

Chiral separation of 3,5-dichlorobenzyl 3-(4-(1H-1,2,3-triazol-4-yl)butanamido)pyrrolidine-1-carboxylate (racemate; Example 49) using Supercritical Fluid Chromatography afforded the individual enantiomers (Example 49a and 49b).
Method Details:
Column: Phenomenex LUX-A2, 250×10 mm, 5 μm
Mobile phase: 50% isopropanol/50% CO2
Flow: 10 ml/min
Detection: UV @ 220 nm
System: Berger Minigram SFC1

Example 49a

First eluted peak: (S)-3,5-Dichlorobenzyl 3-(4-(1H-1,2,3-triazol-4-yl)butanamido)pyrrolidine-1-carboxylate or (R)-3,5-Dichlorobenzyl 3-(4-(1H-1,2,3-triazol-4-yl)butanamido)pyrrolidine-1-carboxylate SFC Retention Time=2.720 min.
1H NMR (400 MHz, MeOD). δ 7.50 (1H, d), 7.15 (3H, t), 6.25 (1H, s), 5.00 (2H, d), 4.45 (1H, s), 3.60 (1H, d), 3.45 (2H, s), 3.30 (1H, s), 2.75 (2H, s), 2.15 (3H, d), 1.95 (2H, s), 1.20 (1H, t).

Example 49b

Second eluted peak: (S)-3,5-Dichlorobenzyl 3-(4-(1H-1,2,3-triazol-4-yl)butanamido)pyrrolidine-1-carboxylate or (R)-3,5-Dichlorobenzyl 3-(4-(1H-1,2,3-triazol-4-yl)butanamido)pyrrolidine-1-carboxylate SFC Retention Time=4.163 min.
1H NMR (400 MHz, MeOD). δ 7.50 (1H, d), 7.15 (3H, t), 6.25 (1H, s), 5.00 (2H, d), 4.45 (1H, s), 3.60 (1H, d), 3.45 (2H, s), 3.30 (1H, s), 2.75 (2H, s), 2.15 (3H, d), 1.95 (2H, s), 1.20 (1H, t).

Example 50

3,5-Dichlorobenzyl 3-(4-(1H-1,2,3-triazol-4-yl)butanamido)azetidine-1-carboxylate

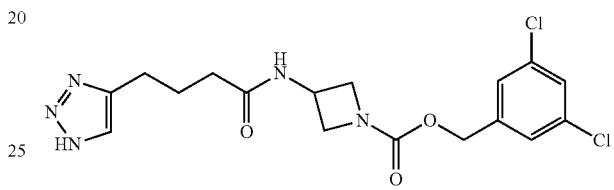

The title compound was prepared from commercially available 3-N-Boc-amino-azetidine and 3,5-dichlorobenzyl carbonochloridate (prepared according to Bioorganic & Medicinal Chemistry Letters, 21(21), 6608-6612; 2011, Intermediate 33) analogously to Example 49 steps 1-3;

LC-MS: Rt: 1.12 mins; MS m/z 412 [M+H]+; Method 2minLowpHv01

Example 51

3,5-Dimethylbenzyl 4-(4-(1H-1,2,3-triazol-4-yl)butanamido)piperidine-1-carboxylate

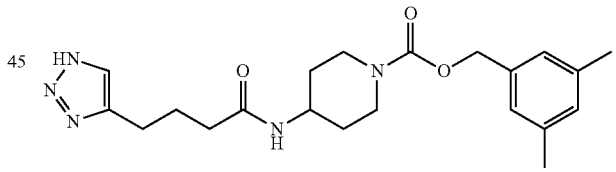

Step 1: 4-(1H-1,2,3-Triazol-4-yl)butanoyl chloride

To a stirred solution/suspension of 4-(1H-1,2,3-triazol-4-yl)butanoic acid (150 mg, 0.967 mmol) in dry DCM (10 mL) was added thionyl chloride (0.847 mL, 11.60 mmol) at RT. After 30 mins some solid still remained so a further 0.4 ml thionyl chloride was added and the reaction mixture allowed to stir at RT for 2 hrs. The reaction mixture was concentrated under reduced pressure to afford the title product which was used in the next step without further purification.

Step 2: 3,5-Dimethylbenzyl 4-((tert-butoxycarbonyl)amino)piperidine-1-carboxylate To a stirred solution of (3,5-dimethylphenyl)methanol (1.020 g, 7.49 mmol) in DMF (5 mL) at RT was added CU (1.214 g, 7.49 mmol). The reaction mixture was heated at 50° C. for 20 hrs. Tert-butyl piperidin-4-ylcarbamate (1.5 g, 7.49 mmol) was added and the reaction mixture stirred at 50° C. for 4 hrs. The mixture was diluted with EtOAc and washed with a saturated solution of sodium bicarbonate, brine, dried over $MgSO_4$, filtered and concentrated under reduced pressure. Purification was carried out by chromatography on silica using 0-100% EtOAc in hexanes as eluent to afford the title product.

LC-M: Rt 1.47 mins; MS m/z 263.3, 264.2; [M-Boc]+; Method 2minLowpHv03

Step 3: 3,5-Dimethylbenzyl 4-aminopiperidine-1-carboxylate

To a solution of 3,5-dimethylbenzyl 4-((tert-butoxycarbonyl)amino)piperidine-1-carboxylate (1.1 g, 3.03 mmol) in DCM (5 ml) at RT was added 4M HCl in dioxane (7.59 ml, 30.3 mmol). The reaction mixture was allowed to stir for 2 hrs, concentrated under reduced pressure redissolved in DCM and concentrated under reduced pressure to afford the crude title compound as the HCl salt;

LC-MS: Rt 0.74 mins; MS m/z 263.2, 264.2; [M+H]+; Method 2minLowpHv03

Step 4: 3,5-Dimethylbenzyl 4-(4-(1H-1,2,3-triazol-4-yl)butanamido)piperidine-1-carboxylate To a stirred solution of 4-(1H-1,2,3-triazol-4-yl)butanoic acid chloride in DCM (5 ml) at RT (168 mg, 0.967 mmol) was added 3,5-dimethylbenzyl 4-aminopiperidine-1-carboxylate (318 mg, 1.064 mmol) and Huenig's Base (0.338 mL, 1.934 mmol) and the reaction mixture was allowed to stir for 3 hrs. The reaction mixture was diluted with DCM and washed with a saturated solution of brine. The layers were separated and the organic portion dried over $MgSO_4$, filtered and concentrated under reduced pressure. Purification was carried out by chromatography on silica using 0-10% MeOH in DCM as eluent to afford the title product;

LC-MS: Rt 1.12 mins; MS m/z 400.4, 401.4 [M+H]+; Method 2minLowpHv03

Example 52

3,5-Dichlorobenzyl(1-(5-(1H-1,2,3-triazol-4-yl)pentanoyl)piperidin-4-yl)carbamate

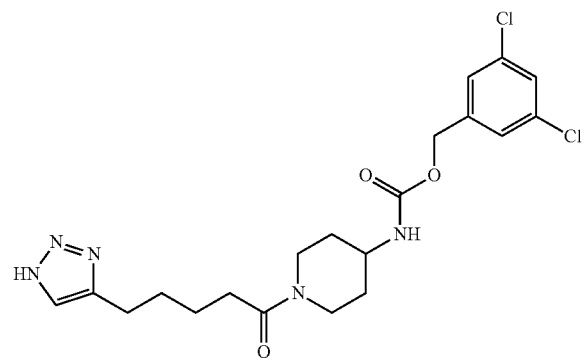 [SMILES: O=C(NC1CCN(C(=O)CCCCc2c[nH]nn2)CC1)OCc1cc(Cl)cc(Cl)c1]

Step 1: Tert-butyl 4-((((3,5-dichlorobenzyl)oxy)carbonyl)amino)piperidine-1-carboxylate A reaction mixture comprising tert-butyl 4-aminopiperidine-1-carboxylate (1 g, 4.99 mmol), 3,5-dichlorobenzyl carbonochloridate (1.196 g, 4.99 mmol) and sodium hydroxide (250 ml, 499 mmol) in DCM (16.64 ml) was stirred at room temperature for 18 hours. The reaction mixture separated and the organic portion dried over $MgSO_4$, filtered and concentrated under reduced pressure. No further purification was carried out and the material was taken crude to the next step.

LC-MS; Rt 1.63 mins; MS m/z 329 [M+H]+; Method 2minLowpHv01

Step 2: 3,5-Dichlorobenzyl piperidin-4-ylcarbamate

A reaction mixture comprising tert-butyl 4-((((3,5-dichlorobenzyl)oxy)carbonyl)amino)piperidine-1-carboxylate (2.01 g, 4.98 mmol) and 4M HCl in dioxane (1.246 ml, 4.98 mmol) in dioxane (16.61 ml) was stirred at room temperature for 1 hour. The resulting mixture was concentrated under reduced pressure. No further purification under taken and the material was dried and taken on to the next step.

LC-MS; Rt 1.63 mins; MS m/z 329 [M+H]+; Method 2minLowpHv01

Step 3: 5-(1-Benzyl-1H-1,2,3-triazol-4-yl)entanoic acid

A reaction mixture comprising (azidomethyl)benzene (950 mg, 7.13 mmol) in tert-BuOH (100 mL) and Water (100 mL), hept-6-ynoic acid (900 mg, 7.13 mmol) copper (II) acetate (130 mg, 0.713 mmol) and sodium L-ascorbate (283 mg, 1.427 mmol) was stirred at room temperature for 18 hours. The reaction mixture was acidified using 6M HCl to pH1. The mixture was saturated with NaCl and concentrated under pressure to a give a green slurry. The mixture was then diluted with ethyl acetate. The organics were separated and dried over $MgSO_4$, filtered and solvent concentrated under reduced pressure to give the title compound;

LC-MS; Rt 0.94 mins; MS m/z 259 [M+H]+; Method 2minLowpHv01

Step 4: 5-(1H-1,2,3-Triazol-4-yl)pentanoic acid

A reaction mixture comprising 5-(1-benzyl-1H-1,2,3-triazol-4-yl)entanoic acid (1 g, 3.86 mmol) in ethanol (77 ml) to give a green solution. The reaction solution was passed through a continuous flow H cube system for 3 hours at 30 bar pressure and 70° C. The reaction mixture was concentrated under reduced pressure to afford the title compound;

LC-MS: Rt 0.55 mins; MS m/z 168 [M+H]+; Method 2minLowpHv01

Step 5: 3,5-Dichlorobenzyl(1-(5-(1H-1,2,3-triazol-4-yl)pentanoyl)piperidin-4-yl)carbamate A reaction mixture comprising 5-(1H-1,2,3-triazol-4-yl)entanoic acid (55.8 mg, 0.330 mmol), 3,5-dichlorobenzyl piperidin-4-ylcarbamate (100 mg, 0.330 mmol), TEA (138 µl, 0.989 mmol) and T3P® (385 µl, 0.660 mmol) in DMF (1.1 ml) was stirred at room temperature for 18 hours. The reaction mixture was concentrated under reduced pressure. Purification was carried out using preparative LC-MS (low pH over 9.5 mins). The resulting product fractions were concentrated under reduced pressure to give aqueous solutions which were extracted with ethyl acetate. The organic extracts were dried over $MgSO_4$, filtered and concentrated under reduced pressure to afford the title compound;

LC-MS: Rt 3.49 mins; MS m/z 455 [M+H]+; Method 8minHighpHv01

Example 53

4-(Trifluoromethyl)benzyl 4-(4-(1H-1,2,3-triazol-4-yl)butanamido)piperidine-1-carboxylate

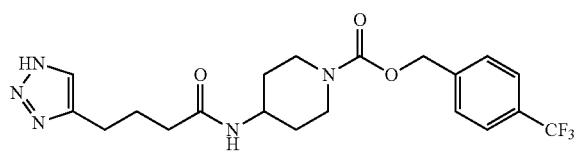 [SMILES: O=C(CCCc1c[nH]nn1)NC1CCN(C(=O)OCc2ccc(C(F)(F)F)cc2)CC1]

The title compound was prepared from commercially available (4-(trifluoromethyl)phenyl)methanol and tert-butyl piperidin-4-ylcarbamate analogously to Example 51 steps 2-4;

LC-MS: Rt 1.12 mins; MS m/z 440.4 [M+H]+; Method 2minLowpHv03

Example 54

4-(1H-1,2,3-Triazol-4-yl)-N-(1-(3-(4-(trifluoromethyl)phenyl)propanoyl)piperidin-4-yl)butanamide

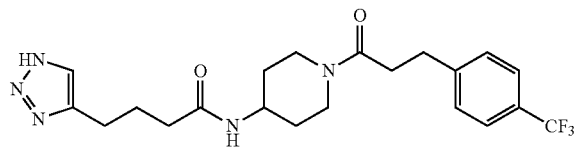 [SMILES: O=C(CCCc1c[nH]nn1)NC1CCN(C(=O)CCc2ccc(C(F)(F)F)cc2)CC1]

Step 1: 3-(4-(Trifluoromethyl)phenyl)propanoyl chloride

A stirred solution of 3-(4-(trifluoromethyl)phenyl)propanoic acid (500 mg, 2.292 mmol) in thionyl chloride was allowed to reflux for 2 hours and concentrated under reduced pressure to afford the crude title product.

Step 2: 4-(1H-1,2,3-Triazol-4-yl)-N-(1-(3-(4-(trifluoromethyl)phenyl)propanoyl)piperidin-4-yl)butanamide The title compound was prepared from 3-(4-(trifluoromethyl)phenyl)propanoyl chloride (step 1) and commercially available tert-butyl piperidin-4-ylcarbamate analogously to Example 51;

LC-MS: Rt 1.05 mins; MS m/z 438.4 [M+H]+; Method 2minLowpHv03

Example 55

N-(1-(2-(3,5-Dichlorophenoxy)acetyl)piperidin-4-yl)-4-(1H-1,2,3-triazol-4-yl)butanamide

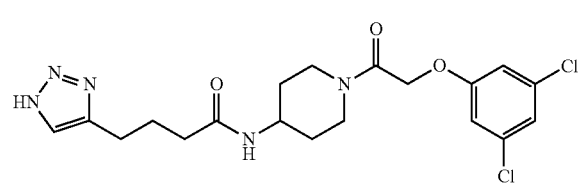 [SMILES: O=C(CCCc1c[nH]nn1)NC1CCN(C(=O)COc2cc(Cl)cc(Cl)c2)CC1]

Step 1: Tert-butyl(1-(2-(3,5-dichlorophenoxy)acetyl)piperidin-4-yl)carbamate

To a stirred solution of tert-butyl piperidin-4-ylcarbamate (300 mg, 1.498 mmol) and 2-(3,5-dichlorophenoxy)acetic acid 331 mg, 1.498 mmol) in DMF (5 mL) at RT was added NMM (0.329 mL, 3.00 mmol) and EDC.HCl (287 mg, 1.498 mmol). The reaction mixture was stirred for 5 hours, diluted with DCM and washed with a saturated solution of sodium bicarbonate, brine, dried over MgSO₄, filtered and concentrated under reduced pressure. Purification was carried out by chromatography on silica using 0-50% EtOAc in hexanes to afford the title product.

LC-MS: Rt: 1.44 mins; MS m/z 347.3, 349.3 [M-tBu]+; Method 2minLowpHv03

Step 2: N-(1-(2-(3,5-Dichlorophenoxy)acetyl)piperidin-4-yl)-4-(1H-1,2,3-triazol-4-yl)butanamide The title compound was prepared from tert-butyl(1-(2-(3,5-dichlorophenoxy)acetyl)piperidin-4-yl)carbamate (step 1) analogously to Example 51 steps 3 and 4;

LC-MS: Rt 1.10 mins; MS m/z 440.3, 442.3 [M+H]+; Method 2minLowpHv03

Example 56

3-Chloro-5-methylbenzyl 4-(4-(1H-1,2,3-triazol-4-yl)butanamido)piperidine-1-carboxylate

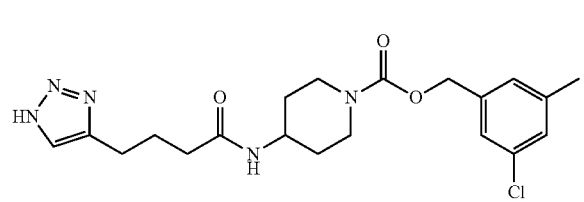 [SMILES: Cc1cc(Cl)cc(COC(=O)N2CCC(NC(=O)CCCc3c[nH]nn3)CC2)c1]

Step 1: (3-Chloro-5-methylphenyl)methanol

To a stirred solution/suspension of 3-chloro-5-methylbenzoic acid (800 mg, 4.69 mmol) in THF (5 ml) at 0° C. under nitrogen was added dropwise borane tetrahydrofuran complex (1 M in THF, 23.45 ml, 23.45 mmol) over 30 mins maintaining the temperature around 0° C. The reaction mixture was then allowed to warm to RT over 20 hrs. On cooling in an ice/water bath the reaction mixture was quenched dropwise with water and after a few minutes the THF was removed under reduced pressure. Water was added to the residue and on cooling a few drops of 1M HCl were added until effervescence ceased. The mixture was diluted with water and extracted into EtOAc, the organic portion dried over MgSO₄, filtered and concentrated under reduced pressure. Purification was carried out by chromatography on silica using 0-50% EtOAc in hexanes as eluent and azeotroping with toluene to afford the title product.

Step 2: 3-Chloro-5-methylbenzyl 4-(4-(1H-1,2,3-triazol-4-yl)butanamido)piperidine-1-carboxylate The title compound was prepared from commercially available tert-butyl piperidin-4-ylcarbamate and (3-chloro-5-methylphenyl)methanol (step 1) analogously to Example 51 steps 2-4;

LC-MS: Rt 1.15 mins; MS m/z 420.3, 422.3 [M+H]+; Method 2minLowpHv03

Example 57

3,5-Dichlorobenzyl 4-((3-(1H-1,2,3-triazol-5-yl)propanamido)methyl)piperidine-1-carboxylate

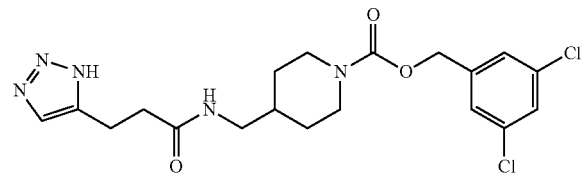 [SMILES: O=C(CCc1cnn[nH]1)NCC1CCN(C(=O)OCc2cc(Cl)cc(Cl)c2)CC1]

Step 1: 3-(1H-1,2,3-Triazol-4-yl)propanoic acid

The title compound was prepared from (azidomethyl)benzene and pent-4-ynoic acid analogously to Example 17, steps 3 and 4;

1H NMR (400 MHz, MeOD) 14.8 (1H, s), 12.2 (1H, s), 7.6 (1H, s), 2.9 (2H, t), 2.6 (2H, t),

Step 2: 3,5-Dichlorobenzyl 4-((3-(1H-1,2,3-triazol-5-yl)propanamido)methyl)piperidine-1-carboxylate The title compound was prepared from 3,5-dichlorobenzyl 4-(aminomethyl)piperidine-1-carboxylate hydrochloride (Example 41, step 2) and 3-(1H-1,2,3-triazol-4-yl)propanoic acid (step 1) analogously to Example 41 step 3;

LC-MS; Rt 0.86 mins; MS m/z 440 [M+H]+; Method 2minLowpHv01

Example 58

2,4-Dichlorobenzyl 4-(4-(1H-1,2,3-triazol-4-yl)butanamido)piperidine-1-carboxylate

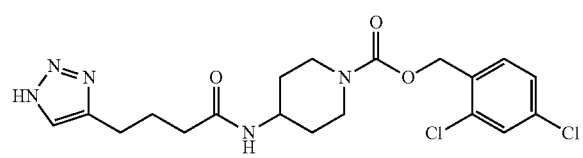 [SMILES: O=C(CCCc1c[nH]nn1)NC1CCN(C(=O)OCc2ccc(Cl)cc2Cl)CC1]

Step 1: 2,4-Dichlorobenzyl 4-(4-(1-((pivaloyloxy)methyl)-1H-1,2,3-triazol-4-yl)butanamido)piperidine-1-carboxylate To a stirred solution of commercially available (2,4-dichlorophenyl)methanol (137 mg, 0.774 mmol) in DMF (2 mL) at RT was added CU (125 mg, 0.774 mmol). The reaction mixture was allowed to heat at 50° C. for 20 hrs. (4-(4-oxo-4-(piperidin-4-ylamino)butyl)-1H-1,2,3-triazol-1-yl)methyl pivalate (Example 37, step 5)(272 mg, 0.774 mmol) was added and the reaction mixture was stirred at 50° C. for 10 hrs. The reaction mixture was diluted with EtOAc and washed with a saturated solution of sodium bicarbonate and brine, dried over MgSO₄, filtered and concentrated under reduced pressure. Purification was carried out by chromatography on silica eluting with 0-100% EtOAc in iso-hexane to afford the title product;

LC-MS: Rt 1.41 mins; MS m/z 554.6, 556.6 [M+H]+; Method 2minLowpHv03.

Step 2: 2,4-Dichlorobenzyl 4-(4-(1H-1,2,3-triazol-4-yl)butanamido)piperidine-1-carboxylate To a stirred solution of 2,4-dichlorobenzyl 4-(4-(1-((pivaloyloxy)methyl)-1H-1,2,3-triazol-4-yl)butanamido)piperidine-1-carboxylate (100 mg, 0.180 mmol) in MeOH (1 mL) at RT was added 1M NaOH (0.397 mL, 0.397 mmol). The reaction mixture was allowed to stir for 1 hr. An equivalent of 1M HCl (0.4 ml) was added to neutralise the reaction mixture and the MeOH removed under reduced pressure. The reaction mixture was diluted with EtOAc and water and the organic portion was separated, dried over MgSO₄, filtered and concentrated under reduced pressure. Trituration with diethyl ether afforded the title product;

LC-MS: Rt 1.17 mins; MS m/z 440.3, 442.3 [M+H]+; Method 2minLowpHv03

Example 59

3,5-Dichlorophenethyl 4-(4-(1H-1,2,3-triazol-4-yl)butanamido)piperidine-1-carboxylate

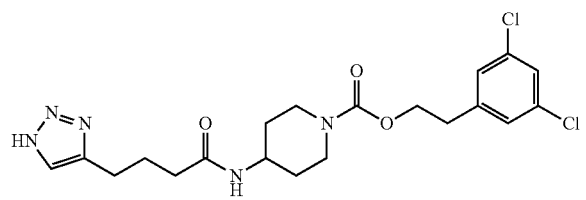 [SMILES: O=C(CCCc1c[nH]nn1)NC1CCN(C(=O)OCCc2cc(Cl)cc(Cl)c2)CC1]

The title compound was prepared from commercially available tert-butyl piperidin-4-ylcarbamate and 2-(3,5-dichlorophenyl)ethanol analogously to Example 51 steps 2-4;
LC-MS: Rt 1.24 mins; MS m/z 454.3, 456.3 [M+H]+; Method 2minLowpHv03

Example 60

3,5-dichlorobenzyl 4-(3-(((1H-1,2,3-triazol-4-yl)methyl)amino)-3-oxopropyl)piperidine-1-carboxylate

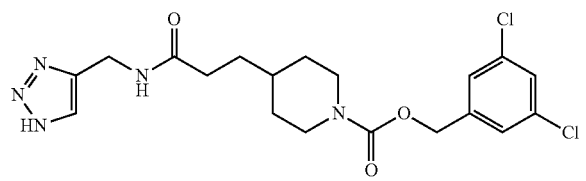 [SMILES: O=C(CCC1CCN(C(=O)OCc2cc(Cl)cc(Cl)c2)CC1)NCc1c[nH]nn1]

Step 1: Tert-butyl prop-2-yn-1-ylcarbamate

A reaction mixture comprising of prop-2-yn-1-amine (100 mg, 1.816 mmol), di-tert-butyl dicarbonate (396 mg, 1.816 mmol), and triethylamine (380 μl, 2.72 mmol) in THF (6.1 ml was stirred at room temperature for 18 hours. The reaction mixture was diluted with a small amount of water and the solvent removed in vacuo. The water was then extracted with ethyl acetate. The organics were dried over MgSO4, filtered and concentrated under reduced pressure to afford the title compound.
LC-MS: Rt 1.01 mins; MS m/z 170 [M+H]+; Method 2minLowpH_v01

Step 2: (1-benzyl-1H-1,2,3-triazol-4-yl)methanamine

A reaction mixture comprising of tert-butyl prop-2-yn-1-ylcarbamate (219 mg, 1.411 mmol), (azidomethyl)benzene (188 mg, 1.411 mmol), copper (II) acetate (25.6 mg, 0.141 mmol) and sodium L-ascorbate (55.9 mg, 0.282 mmol) in tert-butanol (20 ml)/water (20 ml) was stirred for 18 hours at room temperature. The reaction mixture was acidified to pH1 using 6M HCl, then saturated with solid NaCl. The reaction mixture was concentrated under pressure to yield a green aqueous solution. The mixture was diluted with ethyl acetate and the organics were removed and dried (MgSO4). Concentration under reduced pressure afforded an orange oil. The oil was loaded on to a 10 g SCX2 cartridge, and this was washed with water and methanol. The product was then eluted with 2M ammonia in methanol. The solution was then concentrated to afford the title compound.
LC-MS: Rt 1.10 mins; MS m/z 189 [M+H]+; Method 2minLowpH_v01

Step 3: 3-(1-(((3,5-dichlorobenzyl)oxy)carbonyl)piperidin-4-yl)propanoic acid

To 3-piperidin-4-yl-propionic acid (1 g, 6.36 mmol) in DCM (20 ml) was added 2M NaOH (9.54 ml, 19.08 mmol) to give a colorless biphasic solution. 3,5-Dichlorobenzyl carbono-chloridate (1.523 g, 6.36 mmol) was added to the reaction mixture and this was stirred at RT for 2 hrs. The mixture was extracted with DCM (2×50 ml), and the organics were dried (MgSO4) and concentrated to give the product as a white solid.
LC-MS: Rt: 1.39 mins; MS m/z 360 [M+H]+; Method 2minLowpH_v01

Step 4: 3,5-dichlorobenzyl 4-(3-(((1-benzyl-1H-1,2,3-triazol-4-yl)methyl)amino)-3-oxopropyl)piperidine-1-carboxylate A reaction mixture comprising of (1-benzyl-1H-1,2,3-triazol-4-yl)methanamine (46.2 mg, 0.245 mmol), 3-(1-(((3,5-dichlorobenzyl)oxy)carbonyl)piperidin-4-yl)propanoic acid (88 mg, 0.245 mmol), HATU (187 mg, 0.491 mmol) and TEA (103 μl, 0.736 mmol) in DMF (0.8 ml) was stirred for 2 hours at room temperature. The reaction mixture was diluted with water and ethyl acetate. The organic layer was separated and dried over MgSO4, filtered and concentrated under reduced pressure. Further purification was carried out using preparative LC-MS. The resulting product fractions were concentrated under reduced pressure to give aqueous solutions which were extracted with ethyl acetate. The organic extracts were dried over MgSO4, filtered and concentrated under reduced pressure to afford the title compound.
LC-MS: Rt 1.36 mins; MS m/z 530 [M+H]+; Method 2minLowpH_v01

Step 5: 3,5-dichlorobenzyl 4-(3-(((1H-1,2,3-triazol-4-yl)methyl)amino)-3-oxopropyl)piperidine-1-carboxylate 3,5-dichlorobenzyl 4-(3-(((1-benzyl-1H-1,2,3-triazol-4-yl)methyl)amino)-3-oxopropyl)piperidine-1-carboxylate (51 mg, 0.096 mmol) was dissolved in ethanol (4 ml). The solution was then submitted to continuous flow hydrogenation using H-cube hydrogenation apparatus, at 70° C. and 30 bar hydrogen pressure. After 90 mins the solution was concentrated and the residue purified using preparative LC-MS. Product fractions were collected, concentrated under reduced pressure, diluted with ethyl acetate, and extracted with water. The organics were separated, dried over MgSO4, filtered, and concentrated under reduced pressure to give the title compound.

1H NMR (400 MHz, MeOD) δ 7.65 (1H, s), 7.40 (1H, s), 7.35 (2H, s), 5.10 (2H, s), 3.45 (2H, s), 4.10 (2H, d), 2.80 (2H, m), 2.25 (2H, m), 1.75 (2H, m), 1.60 (2H, m), 1.45 (1H, m), 1.10 (2H, m).

LC-MS: Rt: 3.87 mins; MS m/z 440 [M+H]+; Method 8minLowpHv01

Example 61

3,5-dichlorobenzyl 4-(2-((2-(1H-1,2,3-triazol-4-yl)ethyl)amino)-2-oxoethyl)piperidine-1-carboxylate

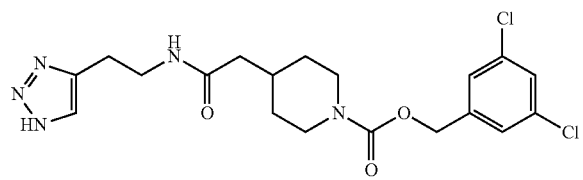 [SMILES: O=C(CC1CCN(C(=O)OCc2cc(Cl)cc(Cl)c2)CC1)NCCc1c[nH]nn1]

Step 1: Tert-butyl but-3-yn-1-ylcarbamate

A reaction mixture comprising of but-3-yn-1-amine (130 mg, 1.881 mmol), di-tert-butyl dicarbonate (411 mg, 1.881 mmol), and triethylamine (393 µl, 2.82 mmol) in THF (6.2 ml) was stirred for 18 hours at room temperature. A small amount of water was added to the reaction mixture and the resultant mixture was concentrated under reduced pressure. The aqueous solution was extracted with ethyl acetate. The organics were dried over MgSO4, filtered and concentrated under reduced pressure to afford the title compound.

1H NMR (400 MHz, DMSO-d6) δ 6.9 (1H, s), 3 (2H, q), 2.25 (2H, q), 1.4 (9H, s)

Step 2: 2-(1-benzyl-1H-1,2,3-triazol-4-yl)ethanamine

A reaction mixture comprising tert-butyl but-3-yn-1-ylcarbamate (306 mg, 1.808 mmol), (azidomethyl)benzene (241 mg, 1.808 mmol), copper (II) acetate (32.8 mg, 0.181 mmol) and Sodium L-ascorbate (71.6 mg, 0.362 mmol) in tert-butanol (25 ml)/water (25 ml) was stirred for 18 hours at room temperature. The reaction mixture was acidified to pH1 using 6M HCl and then saturated with solid NaCl. The reaction mixture was concentrated under reduced pressure. The remaining mixture was diluted with ethyl acetate. The organics were separated and dried over MgSO4, filtered, and the solvent concentrated under reduced pressure to afford an orange oil. The oil was loaded on to a 10 g SCX2 cartridge. The cartridge was washed with water and methanol. Product was then eluted with 2M ammonia in methanol. The solution was then concentrated under pressure to afford the title compound.

LC-MS: Rt 1.11 mins; MS m/z 203 [M+H]+; Method 2minLowpH_v01

Step 3: 2-(1-(((3,5-dichlorobenzyl)oxy)carbonyl)piperidin-4-yl)acetic acid

To 2-(piperidin-4-yl)acetic acid (1 g, 6.98 mmol) in DCM (23 ml) was added 2M NaOH (10.48 ml, 20.95 mmol) and 3,5-dichlorobenzyl carbono-chloridate (1.673 g, 6.98 mmol) to give a white biphasic mixture. After vigorous stirring at RT for 1 hr the reaction mixture was acidified with HCl (6M, 3.49 ml) and then extracted with DCM. The organics were dried with MgSO4, filtered and concentrated under pressure to give the title compound as a colourless oil.

LC-MS: Rt: 1.34 mins; MS m/z 346 [M+H]+; Method 2minLowpH_v01

Step 4: 3,5-dichlorobenzyl 4-(2-((2-(1-benzyl-1H-1,2,3-triazol-4-yl)ethyl)amino)-2-oxoethyl)piperidine-1-carboxylate A reaction mixture comprising of 2-(1-benzyl-1H-1,2,3-triazol-4-yl)ethanamine (59.1 mg, 0.292 mmol), 2-(1-(((3,5-dichlorobenzyl)oxy)carbonyl)piperidin-4-yl)acetic acid (101 mg, 0.292 mmol), HATU (222 mg, 0.584 mmol) and TEA (122 µl, 0.877 mmol) in DMF (0.97 ml) was stirred for 3 hours at room temperature. The reaction mixture was diluted with water and ethyl acetate. The organic layer was removed and dried over MgSO4, filtered and concentrated under reduced pressure. Further purification was carried out using preparative LC-MS. The resulting product fractions were concentrated under reduced pressure to give aqueous solutions which were extracted with ethyl acetate. The organic extracts were dried over MgSO$_4$, filtered and concentrated under reduced pressure to afford the title compound.

LC-MS: Rt 1.36 mins; MS m/z 530 [M+H]+; Method 2minLowpH_v01

Step 5: 3,5-dichlorobenzyl 4-(2-((2-(1H-1,2,3-triazol-4-yl)ethyl)amino)-2-oxoethyl)piperidine-1-carboxylate 3,5-dichlorobenzyl 4-(2-((2-(1-benzyl-1H-1,2,3-triazol-4-yl)ethyl)amino)-2-oxoethyl)piperidine-1-carboxylate (81.5 mg, 0.154 mmol) was dissolved in ethanol (4 ml). The solution was then submitted to continuous flow hydrogenation using H-cube hydrogenation apparatus, at 70° C. and 30 bar hydrogen pressure for 2 hours. The resultant solution was concentrated under reduced pressure. Purification was carried out using preparative LC-MS. Product fractions were collected, concentrated under reduced pressure, diluted with ethyl acetate, and washed with water. The organic portion was separated, dried over MgSO4, filtered, and concentrated under reduced pressure to give the title compound.

1H NMR (400 MHz, MeOD) δ 7.60 (1H, s), 7.40 (1H, s), 7.35 (2H, s), 5.10 (2H, s), 4.10 (2H, d), 3.50 (2H, m), 2.90, (4H, m), 2.10 (2H, m), 1.90 (1H, m), 1.65 (2H, m), 1.15 (2H, m).

LC-MS: Rt: 3.68 mins; MS m/z 440 [M+H]+; Method 8minLowpHv01

Example 62

3-methyl-5-(trifluoromethyl)benzyl 4-(4-(1H-1,2,3-triazol-4-yl)butanamido)piperidine-1-carboxylate

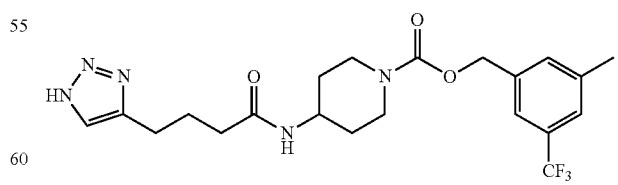

Step 1: 4-(1H-1,2,3-triazol-4-yl)butanoyl chloride

To a stirred suspension of 4-(1H-1,2,3-triazol-4-yl)butanoic acid (Example 17, step 4) (0.088 g, 0.57 mmol) in DCM (5 mL) at RT under nitrogen was added thionyl chloride (0.499 mL, 6.84 mmol) and the reaction mixture stirred at RT for 2 hours. The reaction mixture was concentrated under reduced pressure to afford the crude title product.

Step 2:
(3-methyl-5-(trifluoromethyl)phenyl)methanol

To a stirred suspension of 3-methyl-5-(trifluoromethyl) benzoic acid (1 g, 4.90 mmol) in THF (5 ml) at −78° C. under nitrogen was added dropwise over 10 mins borane tetrahydrofuran complex 1M in THF (24.49 ml, 24.49 mmol). The reaction mixture was then allowed to warm to RT over 20 hours. On cooling in an ice/water bath the reaction mixture was quenched dropwise with MeOH (10 ml) and then 1M HCl until effervescence ceased. Water was added and the reaction mixture stirred at RT for 30 mins and the THF was removed under reduced pressure. EtOAc was added and the organic portion dried over MgSO₄, filtered and concentrated under reduced pressure. Purification was carried out by chromatography on silica using 0-50% EtOAc in Hexanes as eluent to afford the title product;
LC-MS: Rt 1.21 mins; MS m/z 214.1 [M+Na]+; Method 2minLowPHv03

Step 3: 3-methyl-5-(trifluoromethyl)benzyl 4-((tert-butoxycarbonyl)amino)piperidine-1-carboxylate To a stirred solution of (3-methyl-5-(trifluoromethyl)phenyl)methanol (250 mg, 1.315 mmol) in DMF (5 mL) at RT under nitrogen was added CU (213 mg, 1.315 mmol). The reaction mixture was allowed to heat at 50° C. for 20 hours. Tert-butyl piperidin-4yl carbamate (263 mg, 1.315 mmol) was added and the reaction mixture stirred at 50° C. for 3 hours. On cooling to RT the reaction mixture was diluted with DCM and washed with a saturated solution of sodium bicarbonate, a saturated solution of brine, then was dried (MgSO₄), filtered and concentrated under reduced pressure. Purification was carried out by chromatography on silica using 0-100% EtOAc in Hexanes as eluent to afford the title product;
LC-MS: Rt 1.53 mins; MS m/z 317.2 [M-Boc]+; Method 2minLowPHv03

Step 4: 3-methyl-5-(trifluoromethyl)benzyl 4-aminopiperidine-1-carboxylate

To a stirred solution of 3-methyl-5-(trifluoromethyl)benzyl 4-((tert-butoxycarbonyl)amino)piperidine-1-carboxylate (237 mg, 0.569 mmol) in DCM (5 ml) at RT under nitrogen was added 4M HCl in Dioxane (1.423 ml, 5.69 mmol) and the reaction mixture stirred at RT for 3 hours. The reaction mixture was concentrated under reduced pressure to afford the title product as the hydrochloride salt;
LC-MS: Rt: 0.85 mins; MS m/z 316.9 M+H]+; Method 2minLowPHv03

Step 5: 3-methyl-5-(trifluoromethyl)benzyl 4-(4-(1H-1,2,3-triazol-4-yl)butanamido)piperidine-1-carboxylate To a stirred suspension of 3-methyl-5-(trifluoromethyl) benzyl 4-aminopiperidine-1-carboxylate hydrochloride salt (201 mg, 0.570 mmol) in DCM (5 mL) at RT under nitrogen was added Huenig's Base (0.199 mL, 1.140 mmol). 4-(1H-1,2,3,-triazol-4-yl)butanoyl chloride (99 mg, 0.570 mmol) in DCM (2 mL) was added and the reaction mixture stirred at RT for 2 hours. The reaction mixture was diluted with DCM and washed with a 10% solution of citric acid, and saturated brine solution, before the organic portion was dried over MgSO₄, filtered and concentrated under reduced pressure. Purification was carried out by chromatography on silica using 0-10% MeOH in DCM as eluent to afford the title product;
LC-MS: Rt 1.18 mins; MS m/z 454.7, 455.4 [M+H]+; Method 2minLowPHv03

Example 63

3-bromo-5-(trifluoromethyl)benzyl 4-(4-(1H-1,2,3-triazol-4-yl)butanamido)piperidine-1-carboxylate

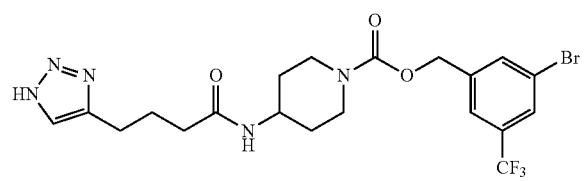 [SMILES: O=C(CCCc1c[nH]nn1)NC1CCN(C(=O)OCc2cc(Br)cc(C(F)(F)F)c2)CC1]

Step 1:
(3-bromo-5-(trifluoromethyl)phenyl)methanol

To a stirred solution of 3-bromo-5-(trifluoromethyl)benzoic acid (1 g, 3.72 mmol) in THF (5 ml) at −78° C. with stirring under nitrogen was added dropwise over 10 mins borane tetrahydrofuran complex 1M in THF (18.59 ml, 18.59 mmol) and then the reaction mixture was warmed to RT over 20 hours. The reaction mixture was cooled in an ice/water bath and quenched dropwise with MeOH (10 ml) followed by 1M HCl until effervescence ceased. Water was added and stirred at RT for 30 mins. THF was removed under reduced pressure, and the compound extracted into EtOAc. The organic portion was dried over MgSO₄, filtered and concentrated under reduced pressure. Purification was carried out by chromatography on silica using 0-50% EtOAc in Hexanes as eluent to afford the title product.
1H NMR (400 MHz, d6-DMSO): δ 7.83 (s, 1H), 7.83 (s, 1H) 7.69 (s, 1H), 5.54-5.51 (t, 1H), 4.60-4.59 (d, 2H)

Step 2: 3-bromo-5-(trifluoromethyl)benzyl 4-((tert-butoxycarbonyl)amino)piperidine-1-carboxylate To a stirred solution of (3-bromo-5-(trifluoromethyl)phenyl)methanol (567 mg, 2.223 mmol) in DMF (5 mL) at RT under nitrogen was added CU (360 mg, 2.223 mmol) and the reaction mixture heated at 50° C. for 20 hours. Tert-butyl piperidin-4-yl carbamate (445 mg, 2.223 mmol) was added and the reaction mixture stirred at 50° C. for 3 hours. On cooling to RT the mixture was diluted with DCM and washed with a saturated solution of sodium bicarbonate, a saturated solution of brine, and the organic portion was dried over MgSO₄ filtered and concentrated under reduced pressure. Purification was carried out by chromatography on silica using 0-100% EtOAc in Hexanes as eluent to afford the title product;
LC-MS: Rt 1.59 mins; MS m/z 427.2 [M-tBu]+; Method 2minLowPHv03

Step 3: 3-bromo-5-(trifluoromethyl)benzyl 4-aminopiperidine-1-carboxylate

To a stirred solution of 3-bromo-5-(trifluoromethyl)benzyl 4-(tertbutoxycarbonyl)amino)piperidine-1-carboxylate (100 mg, 0.208 mmol) in DCM (5 ml) at RT under nitrogen was added 4M HCl in Dioxane (0.519 ml, 2.078 mmol) and the reaction mixture stirred at rt for 1 hour. The reaction mixture was concentrated under reduced pressure to afford the title product as the hydrochloride salt;

LC-MS: Rt: 0.86 mins; MS m/z 383.2 [M+H]+; Method 2minLowPHv03

Step 4: 3-bromo-5-(trifluoromethyl)benzyl 4-(4-(1H-1,2,3-triazol-4-yl)butanamido)piperidine-1-carboxylate To a stirred suspension of 3-bromo-5-(trifluoromethyl)benzyl 4-aminopiperidine-1-carboxylate hydrochloride salt (92 mg, 0.220 mmol) in DCM (5 mL) at RT under nitrogen was added Huenig's Base (0.077 mL, 0.441 mmol). 4-(1H-1,2,3-triazol-4-yl)butanoyl chloride (38.2 mg, 0.220 mmol) in DCM (2 mL) was added and the reaction mixture stirred for 2 hours. The reaction mixture was diluted with DCM and washed with a 10% solution of citric acid, a saturated solution of brine, and the organic portion was then dried over MgSO₄, filtered and concentrated under reduced pressure. Purification was carried out by chromatography on silica using 0-10% MeOH/DCM as eluent to afford the title compound;

LC-MS: Rt 1.25 mins; MS m/z 520.2 [M+H]+; Method 2minLowPHv03

Example 64

3-chloro-5-cyanobenzyl 4-(5-(1H-1,2,3-triazol-4-yl)pentanamido)piperidine-1-carboxylate

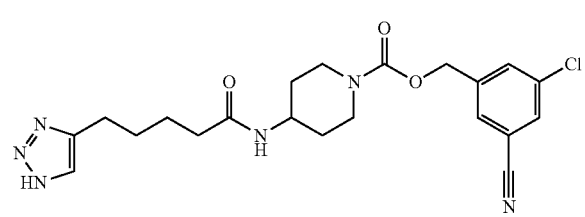 [SMILES: N#Cc1cc(Cl)cc(COC(=O)N2CCC(NC(=O)CCCCc3c[nH]nn3)CC2)c1]

Step 1: 5-(1H-1,2,3-triazol-4-yl)pentanoyl chloride

To a suspension of 5-(1H-1,2,3-triazol-4-yl)pentanoic acid (Example 20, step 3) (100 mg, 0.591 mmol) in DCM (5 mL) at RT under nitrogen was added thionyl chloride (0.518 mL, 7.09 mmol). The reaction mixture was stirred at rt for 2 hours and concentrated under reduced pressure to afford the title product.

Step 2: 3-chloro-5-cyanobenzyl 4-((tert-butoxycarbonyl)amino)piperidine-1-carboxylate To a solution of tert-butyl piperidin-4-ylcarbamate (1.045 g, 5.22 mmol) in DCM (25 mL) at RT was added a saturated solution of sodium bicarbonate (5.6 ml). 3-Chloro-5-cyanobenzyl carbonochloridate (Example 36, step 4) (1.2 g, 5.22 mmol) was then added in DCM (2 ml) and the reaction mixture stirred at RT for 2 hours. The layers were separated and the organic portion was washed with a saturated solution of brine, dried over MgSO₄, filtered and concentrated under reduced pressure to afford the title product;

LC-MS: Rt 1.38 mins; MS m/z 294.2 [M-Boc]+H+; Method 2minLowPHv03

Step 3: 3-chloro-5-cyanobenzyl 4-aminopiperidine-1-carboxylate

To a solution of 3-chloro-5-cyanobenzyl 4-((tert-butoxycarbonyl)amino)piperidine-1-carboxylate (1.846 g, 4.69 mmol) in EtOAc (30 ml) at RT under nitrogen was added 4M HCl in Dioxane (11.72 ml, 46.9 mmol) and the suspension stirred for 20 hours. After 3 hours a further 5 ml of 4M HCl in Dioxan was added. The solid was filtered off and dried to afford the title product as the hydrochloride salt;

LC-MS: Rt 0.69 mins; MS m/z 294.2, 296.2 [M+H]+; Method 2minLowPHv03

Step 4: 3-chloro-5-cyanobenzyl 4-(5-(1H-1,2,3-triazol-4-yl)pentanamido)piperidine-1-carboxylate To a suspension of 3-chloro-5-cyanobenzyl 4-aminopiperidine-1-carboxylate hydrochloride salt (195 mg, 0.591 mmol) in DCM (5 mL) at RT under nitrogen was added Huenig's Base (0.206 mL, 1.182 mmol). 5-(1H-1,2,3-Triazol-4-yl)pentanoyl chloride (111 mg, 0.591 mmol) in DCM (2 mL) was then added and the reaction mixture stirred for 20 hours. The reaction mixture was diluted with DCM and washed with a 10% solution of citric acid, a saturated solution of brine and the organic portion was then dried over MgSO₄, filtered and concentrated under reduced pressure. Purification was carried out by chromatography on silica using 0-10% MeOH in DCM to afford the title product.

LC-MS: Rt 1.1 mins; MS m/z 445.3, 447.3 [M+H]+; Method 2minLowPHv03

Example 65

3-chloro-5-cyanobenzyl 4-(3-(1H-1,2,3-triazol-4-yl)propanamido)piperidine-1-carboxylate

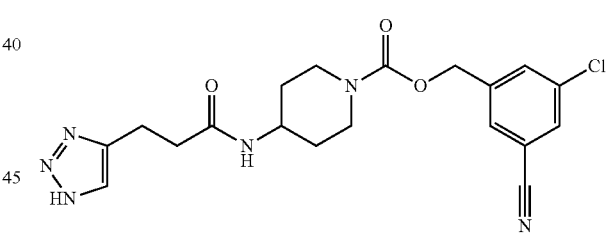

Step 1: 3-(1H-1,2,3-triazol-4-yl)propanoyl chloride

To a solution of 3-(1H-1,2,3-triazol-4-yl)propanoic acid (Example 19, step 2) (100 mg, 0.709 mmol) in DCM (5 mL) at RT under nitrogen was added thionyl chloride (0.621 mL, 8.50 mmol) and the reaction mixture stirred for 2 hours. The reaction mixture was concentrated under reduced pressure to afford the title product.

Step 2: 3-chloro-5-cyanobenzyl 4-(3-(1H-1,2,3-triazol-4-yl)propanamido)piperidine-1-carboxylate To a suspension of 3-chloro-5-cyanobenzyl 4-aminopiperidine-1-carboxylate HCl salt (Example 64, step 3) (234 mg, 0.709 mmol) in DCM (5 mL) at RT under nitrogen was added Huenig's Base (0.248 mL, 1.418 mmol). 3-(1H-1,2,3-Triazol-4-yl)propanoyl chloride (113 mg, 0.709 mmol) in DCM (2 mL) was then added and the mixture stirred for 1 hour. The reaction mixture was diluted with DCM and washed with a 10% solution of citric acid, a saturated solution of brine and then the organic portion was dried over MgSO₄, filtered and concentrated under reduced pressure. Purification was carried out by chromatography on silica using 0-10% MeOH in DCM as eluent to afford the title product;

LC-MS: Rt 1.01 mins; MS m/z 417.2, 419.1 [M+H]+; Method 2minLowPHv03

Example 66

3-cyano-5-(trifluoromethyl)benzyl 4-(4-(1H-1,2,3-triazol-4-yl)butanamido)piperidine-1-carboxylate

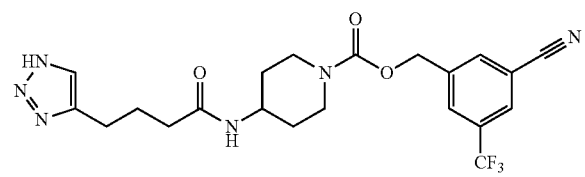 [SMILES: N#Cc1cc(COC(=O)N2CCC(NC(=O)CCCc3c[nH]nn3)CC2)cc(C(F)(F)F)c1]

Step 1: 3-cyano-5-(trifluoromethyl)benzyl 4-((tert-butoxycarbonyl)amino)piperidine-1-carboxylate 3-Bromo-5-(trifluoromethyl)benzyl 4-((tert-butoxycarbonyl)amino)piperidine-1-carboxylate (Example 63, step 2) (214 mg, 0.445 mmol), zinc cyanide (26.1 mg, 0.222 mmol) and Pd(PPh₃)₄ (20.5 mg, 0.018 mmol) were dissolved in DMF (4 ml) and the vial flushed with nitrogen. The mixture was heated in the microwave at 150° C. for 10 mins, then cooled and diluted with EtOAc (30 ml). This was washed with a saturated solution of brine, dried over MgSO4, filtered and concentrated under reduced pressure. Purification by chromatography on a 4 g silica column using 0-50% EtOAC/hexanes as eluent gave the title compound.

LC-MS: Rt 1.42 mins; MS m/z 328.2 [M-BOC+H]+; Method 2minLowPHv03

Step 2: 3-cyano-5-(trifluoromethyl)benzyl 4-aminopiperidine-1-carboxylate

3-Cyano-5-(trifluoromethyl)benzyl 4-((tert-butoxycarbonyl)amino)piperidine-1-carboxylate (119 mg, 0.278 mmol) was dissolved in DCM (5 ml) and 4M HCl in Dioxane (0.696 ml, 2.78 mmol) was added with stirring at RT under nitrogen. After 3 hrs, the mixture was concentrated in vacuo to give the title compound as the hydrochloride salt.

LC-MS: Rt 0.73 mins; MS m/z 328.2 [M+H]+; Method 2minLowPHv03

Step 3: 3-Cyano-5-(trifluoromethyl)benzyl 4-(4-(1H-1,2,3-triazol-4-yl)butanamido)piperidine-1-carboxylate 3-Cyano-5-(trifluoromethyl)benzyl 4-aminopiperidine-1-carboxylate hydrochloride (50 mg, 0.137 mmol) and 4-(1H-1,2,3-triazol-4-yl)butanoic acid (25.6 mg, 0.165 mmol) were suspended in EtOAc (5 mL) and triethylamine (0.067 mL, 0.481 mmol) was added. After 5 mins at RT, T3P, 50% in EtOAC (0.164 mL, 0.275 mmol) was added and the mixture allowed to stir at RT for 20 hours. EtOAc (30 ml) was added and the mixture washed with a 10% solution of citric acid and a saturated solution of brine. The organics were dried over MgSO4, filtered and concentrated in vacuo. Purification via silica chromatography eluting with 0-10% MeOH/DCM gave the title compound.

LC-MS: Rt 1.09 mins; MS m/z 465.2 [M+H]+; Method 2minLowPHv03

Example 67

3,5-dichlorobenzyl 4-(6-(1H-1,2,3-triazol-4-yl)hexanamido)piperidine-1-carboxylate

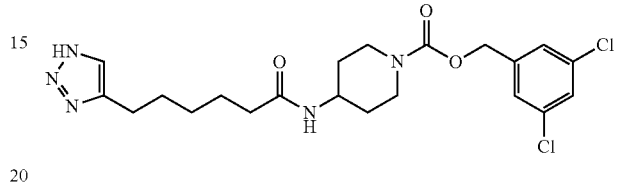

Step 1: 6-(1-benzyl-1H-1,2,3-triazol-4-yl)hexan-1-ol

Oct-7-yn-1-ol (0.948 g, 7.51 mmol) was dissolved in tBuOH (100 mL) and water (100 mL) to give a colourless solution. (Azidomethyl)benzene (1 g, 7.51 mmol), copper (II) acetate (0.136 g, 0.751 mmol) and sodium L-ascorbate (0.298 g, 1.502 mmol) were added. The reaction was left to stir overnight at room temperature, then was acidified to pH1 using 6M HCl. The mixture was saturated with solid NaCl and concentrated under pressure to give a green slurry. This was extracted with EtOAc, and the organics were separated, dried over MgSO4, and concentrated under reduced pressure. The resulting oil was dissolved in methanol and stirred with celite/charcoal. The mixture was filtered and the filtrate concentrated under reduced pressure to give the title compound.

1H NMR (400 MHz, DMSO-d6) δ 7.9 (1H, s) 7.35 5H, m). 5.5 (2H, s), 4.4 (1H, t), 4.1 (4H, m), 3.5 (2H, t), 2.6 (2H, t), 1.6 2H, t), 1.4 (2H, t)

Step 2: 6-(1-benzyl-1H-1,2,3-triazol-4-yl)hexanoic acid 6-(1-Benzyl-1H-1,2,3-triazol-4-yl)hexan-1-ol (100 mg, 0.386 mmol), sodium periodate (330 mg, 1.542 mmol), and ruthenium trichloride (1.6 mg, 7.7 µmol) were taken up in water (640 µl), ethyl acetate (320 µl) and acetonitrile (320 µl) to give a brown suspension. The reaction was stirred overnight at room temperature under nitrogen. The mixture was diluted with ethyl acetate and water and the black precipitate formed was removed by filtration. The organics were dried with MgSO4, filtered and concentrated under reduced pressure to give the crude title product.

1H NMR (400 MHz, DMSO-d6) δ 12.0 (1H, s), 7.9 (1H, s), 7.4 (5H, m), 5.5 (2H, s), 3.4 (2H, bs), 2.6 (2H, t), 2.2 (2H, t), 1.55 (4H, m)

Step 3: Tert-butyl 4-(6-(1-benzyl-1H-1,2,3-triazol-4-yl)hexanamido)piperidine-1-carboxylate 6-(1-Benzyl-1H-1,2,3-triazol-4-yl)hexanoic acid (100 mg, 0.366 mmol), tert-butyl 4-aminopiperidine-1-carboxylate (81 mg, 0.402 mmol), HATU (278 mg, 0.732 mmol) and triethylamine (153 µl, 1.098 mmol) were dissolved in DMF (1220 µl) to give an orange solution. The reaction mixture was stirred at RT for 72 hrs, then concentrated under reduced pressure to yield a slurry. This was diluted with water and ethyl acetate. The organics were separated and washed with water, then concentrated under reduced pressure to yield the title compound.

LC-MS: Rt 1.24 mins; MS m/z 456 [M+H]+; 2minLowpHv03

Step 4: Tert-butyl 4-(6-(1H-1,2,3-triazol-4-yl)hexanamido)piperidine-1-carboxylate Tert-butyl 4-(6-(1-benzyl-1H-1,2,3-triazol-4-yl)hexanamido)piperidine-1-carboxylate (187 mg, 0.410 mmol) was dissolved in ethanol (10 ml) to give a yellow solution. The solution was then submitted to continuous flow hydrogenation using H-cube hydrogenation apparatus, at 70° C. and 30 bar hydrogen pressure for 2 hours. The resultant solution was concentrated under reduced pressure to yield the title compound.

LC-MS: Rt 0.96 mins; MS m/z 366.4 [M+H]+; Method 2minLowpHv03

Step 5: N-(Piperidin-4-yl)-6-(1H-1,2,3-triazol-4-yl)hexanamide

Tert-butyl 4-(6-(1H-1,2,3-triazol-4-yl)hexanamido)piperidine-1-carboxylate (135 mg, 0.369 mmol) in 1,4-dioxane (1.2 ml) was treated with 4M HCl in dioxane (1.8 ml, 7.39 mmol). The reaction mixture was allowed to stir at RT for 3 hours. Concentration yielded the title compound as a hydrochloride salt.

LC-MS: Rt 0.3 mins; MS m/z 265 [M+H]+; Method 2minLowpHv03

Step 6: 3,5-Dichlorobenzyl 4-(6-(1H-1,2,3-triazol-4-yl)hexanamido)piperidine-1-carboxylate N-(Piperidin-4-yl)-6-(1H-1,2,3-triazol-4-yl)hexanamide (135 mg, 0.509 mmol) in DCM (50 ml) was treated with 3,5-dichlorobenzyl carbonochloridate (134 mg, 0.560 mmol) and 2M sodium hydroxide (25 ml, 50 mmol). The reaction mixture was stirred at room temperature for 5 hrs. The organics were removed, dried over MgSO4, filtered and concentrated under reduced pressure. The residue was purified by mass directed preparative LC to give the title compound, after concentration of the relevant fractions.

LC-MS: Rt 1.24 mins; MS m/z 468.2 [M+H]+; Method 2minLowpHv03

Biological Data:

The compounds of the invention are suitable as ATX inhibitors and may be tested in the following assays.

Reagents—

LPC (oleoyl (18:1)) was purchased from Avant: Polar Lipids (Alabaster, Ala.) and solubilized in methanol to 20 mM. Amplex Red was obtained from Invitrogen Life Technologies (Paisley, UK) and dissolved in DMSO to 10 mM. Choline oxidase and horseradish peroxidase (HRP) were obtained from Sigma Aldrich (Dorset, UK) and dissolved in HBSS to 20 U/ml and 200 U/ml respectively. AH reagents were stored at −20° C. in single use aliquots. All experimental measurements were performed in assay buffer made up immediately prior to use (HBSS, 0.01% BSA essentially fatty acid free).

Protein—

Recombinant human ATX was prepared at Novartis (Basel, CH) in a human embryonic kidney (HEK) cell preparation, and stored in single use aliquots of 26 mg/ml (26 μM) stocks stored at −80° C.

Method—

All experimental measurements were performed in black 384 well polystyrene (low volume, round bottom, Corning (3676)) plates. PerkinElmer EnVision (Fluorescence Intensity/Absorbance Monochromator) or Tecan Infinite 200 PRO series plate reader was used to detect change in fluorescent intensity.

Assessing ATX Inhibition—

ATX activity was determined by measurement of released choline in reactions containing ATX (10 nM), choline oxidase (0.1 U/ml), HRP (100 U/ml), amplex red (50 μM) and LPC 18:1 (10 μM). Compounds of the invention were prepared as 10 point serial dilutions from 1 μM in duplicate and pre-incubated with ATX at 37° C. for 20 minutes prior to the addition of remaining reagents. The liberated choline was measured from changes in fluorescence intensity ($\lambda$ex 530 nm, $\lambda$em 590 nm) of the product resurofin at 37° C. every 2 minutes over a 40-minute period. ATX activity was measured as a slope of the linear portion of the progress curve, typically between 14 to 24 minutes.

Data Analysis—

Slope data was exported to Graphpad prism (Graphpad software, San Diego, Calif.) where data was fitted to equation 1.

$$Y = \text{Bottom} + (\text{Top} - \text{Bottom})/(1 + 10^{((\log IC50 - X) * \text{Hill-Slope})})$$ Equation 1:

$IC_{50}$ values are determined from the concentration of compound that reduced the total activity by 50% and represent the mean of n 2.

TABLE 1

Table 1: The following table gives the $IC_{50}$ values for the exemplified compounds as measured in the above assay

| Example no. | Compound | $IC_{50}$ (μM) |
|---|---|---|
| 1 | 3,5-dichlorobenzyl 4-(2-(3-hydroxy-N-methylisoxazole-5-carboxamido)ethyl)piperidine-1-carboxylate; | 0.644 |
| 2 | 3,5-dichlorobenzyl 4-(2-((2-methoxy-3,4-dioxocyclobut-1-en-1-yl)(methyl)amino)ethyl)piperidine-1-carboxylate; | 0.248 |
| 3 | 3,5-dichlorobenzyl 4-(2-((2-ethoxy-3,4-dioxocyclobut-1-en-1-yl)amino)ethyl)piperidine-1-carboxylate; | 0.445 |
| 4 | 3,5-dichlorobenzyl 4-(2-((2-hydroxy-3,4-dioxocyclobut-1-en-1-yl)amino)ethyl)piperidine-1-carboxylate; | 0.728 |
| 5 | 3,5-dichlorobenzyl 4-((3-(3-hydroxyisoxazol-5-yl)propanamido)methyl)-2-methylpiperidine-1-carboxylate; | 0.313 |
| 6 | 3,5-dichlorobenzyl 4-(2-(N-methyl-2-(1H-1,2,3-triazol-4-yl)acetamido)ethyl)piperidine-1-carboxylate; | 0.062 |
| 7 | 3,5-dichlorobenzyl 4-(2-(2-(1H-1,2,3-triazol-4-yl)acetamido)ethyl)piperidine-1-carboxylate; | 0.028 |
| 8 | 3,5-dichlorobenzyl 4-(2-(N,5-dimethyl-2-oxo-2,3-dihydrooxazole-4-carboxamido)ethyl)piperidine-1-carboxylate; | 0.36 |
| 9 | (E)-3,5-dichlorobenzyl 4-(3-(1H-imidazol-4-yl)acrylamido)piperidine-1-carboxylate; | 0.109 |
| 10 | 6-((1-(((3,5-Dichlorobenzyl)oxy)carbonyl)piperidin-4-yl)amino)-6-oxohexanoic acid; | 0.543 |
| 11 | 3,5-dichlorobenzyl 2-(2-((2-ethoxy-3,4-dioxocyclobut-1-en-1-yl)amino)ethyl)morpholine-4-carboxylate; | 0.051 |
| 12 | 3,5-dichlorobenzyl 2-(2-(2-oxo-2,3-dihydrooxazole-5-carboxamido)ethyl)morpholine-4-carboxylate; | 0.52 |
| 13 | 3,5-dichlorobenzyl 2-(2-(N-methyl-2-oxo-2,3-dihydrooxazole-5-carboxamido)ethyl)morpholine-4-carboxylate; | 0.828 |

TABLE 1-continued

Table 1: The following table gives the IC₅₀ values for the exemplified compounds as measured in the above assay

| Example no. | Compound | IC$_{50}$ (μM) |
|---|---|---|
| 14 | 3,5-dichlorobenzyl 2-(2-((2-ethoxy-3,4-dioxocyclobut-1-en-1-yl)(methyl)amino)ethyl)morpholine-4-carboxylate; | 0.54 |
| 15 | 3,5-dichlorobenzyl 4-(2-(N-methyl-2-oxo-2,3-dihydrothiazole-5-carboxamido)ethyl)piperidine-1-carboxylate; | 0.029 |
| 16 | 3,5-dichlorobenzyl 4-(2-(2H-tetrazole-5-carboxamido)ethyl)piperidine-1-carboxylate; | 0.596 |
| 17 | 3,5-dichlorobenzyl 4-(4-(1H-1,2,3-triazol-4-yl)butanamido)piperidine-1-carboxylate; | 0.002 |
| 18 | 3,5-dichlorobenzyl 4-(N-methyl-4-(1H-1,2,3-triazol-4-yl)butanamido)piperidine-1-carboxylate; | 0.094 |
| 19 | 3,5-dichlorobenzyl 4-(3-(1H-1,2,3-triazol-4-yl)propanamido)piperidine-1-carboxylate; | 0.003 |
| 20 | 3,5-dichlorobenzyl 4-(5-(1H-1,2,3-triazol-4-yl)pentanamido)piperidine-1-carboxylate; | 0.004 |
| 21 | 3,5-dichlorobenzyl 4-(2-(2-oxo-2,3-dihydrooxazole-5-carboxamido)ethyl)piperidine-1-carboxylate; | 0.106 |
| 22 | 3,5-dichlorobenzyl 4-(2-(3-(3-hydroxyisoxazol-5-yl)propanamido)ethyl)piperidine-1-carboxylate; | 0.586 |
| 23 | 3,5-dichlorobenzyl 4-(3-(3-hydroxyisoxazol-5-yl)propanamido)piperidine-1-carboxylate; | 0.396 |
| 24 | 3,5-dichlorobenzyl 4-(2-(N-methyl-2-oxo-2,3-dihydrooxazole-4-carboxamido)ethyl)piperidine-1-carboxylate; | 0.624 |
| 25 | 3,5-dichlorobenzyl 4-(2-(5-hydroxy-N-methyl-1H-pyrazole-3-carboxamido)ethyl)piperidine-1-carboxylate; | 0.52 |
| 26 | 3,5-dichlorobenzyl 4-(3-(N-methyl-2-oxo-2,3-dihydrooxazole-5-carboxamido)propyl)piperazine-1-carboxylate; | 0.156 |
| 27 | 3,5-dichlorobenzyl 4-(2-(2-oxo-2,3-dihydrooxazole-5-carboxamido)ethyl)piperazine-1-carboxylate; | 0.375 |
| 28 | 3,5-dichlorobenzyl 4-(2-(N-methyl-5-oxo-4,5-dihydro-1,2,4-oxadiazole-3-carboxamido)ethyl)piperidine-1-carboxylate; | 0.786 |
| 29 | 3,5-dichlorobenzyl 4-(2-(N-methyl-2H-tetrazole-5-carboxamido)ethyl)piperidine-1-carboxylate; | 0.541 |
| 30 | (E)-N-(2-(1-(3-(3,5-dichlorophenyl)acryloyl)piperidin-4-yl)ethyl)-N-methyl-2-oxo-2,3-dihydrooxazole-5-carboxamide; | 0.274 |
| 31 | (E)-N-(2-(1-(3-(3,5-dichlorophenyl)acryloyl)piperidin-4-yl)ethyl)-2-oxo-2,3-dihydrooxazole-5-carboxamide; | 0.387 |
| 32 | 3,5-dichlorobenzyl 4-(2-(N-methyl-2-oxo-2,3-dihydrooxazole-5-carboxamido)ethyl)piperidine-1-carboxylate; | 0.068 |
| 33 | 3,5-dichlorobenzyl 4-((3-(3-hydroxyisoxazol-5-yl)propanamido)methyl)piperidine-1-carboxylate; | 0.131 |
| 34 | 3,5-dichlorobenzyl 4-(3-(1H-1,2,3-triazole-4-carboxamido)propyl)piperazine-1-carboxylate; | 0.282 |
| 35 | 3,5-dichlorobenzyl 4-(2-(N-methyl-1H-1,2,3-triazole-4-carboxamido)ethyl)piperidine-1-carboxylate; | 0.175 |
| 36 | 3-Chloro-5-cyanobenzyl 4-(2-(N-methyl-1H-1,2,3-triazole-4-carboxamido)ethyl) piperidine-1-carboxylate; | 1.0 |
| 37 | 3-Chloro-5-fluorobenzyl 4-(4-(1H-1,2,3-triazol-4-yl)butanamido)piperidine-1-carboxylate; | 0.055 |
| 38 | (E)-N-(1-(3-(3,5-Dichlorophenyl)acryloyl)piperidin-4-yl)-4-(1H-1,2,3-triazol-4-yl)butanamide; | 0.021 |
| 39 | (E)-N-(1-(3-(2,4-Dichlorophenyl)acryloyl)piperidin-4-yl)-4-(1H-1,2,3-triazol-4-yl)butanamide; | 0.077 |
| 40 | 8-((1-(((3,5-Dichlorobenzyl)oxy)carbonyl)piperidin-4-yl)amino)-8-oxooctanoic acid; | 0.135 |
| 41 | 3,5-Dichlorobenzyl 4-((4-(1H-1,2,3-triazol-5-yl)butanamido)methyl)piperidine-1-carboxylate; | 0.018 |
| 42 | N-(1-(3-(3,5-Dichlorophenyl)propanoyl)piperidin-4-yl)-4-(1H-1,2,3-triazol-4-yl)butanamide; | 0.119 |
| 43 | N-(1-(3-(2,4-Dichlorophenyl)propanoyl)piperidin-4-yl)-4-(1H-1,2,3-triazol-4-yl)butanamide; | 0.113 |
| 44 | 3-Chloro-5-cyanobenzyl 4-(4-(1H-1,2,3-triazol-4-yl)butanamido)piperidine-1-carboxylate; | 0.008 |
| 45 | 3,5-Dichlorobenzyl 3-(4-(1H-1,2,3-triazol-4-yl)butanamido)-8-azabicyclo[3.2.1]octane-8-carboxylate; | 0.555 |
| 46 | 3,5-Dichlorobenzyl 4-(4-(1H-1,2,3-triazol-4-yl)butanamido)azepane-1-carboxylate; | 0.731 |
| 47 | 3,5-Dichlorobenzyl (8-(4-(1H-1,2,3-triazol-4-yl)butanoyl)-8-azabicyclo[3.2.1]octan-3-yl)carbamate; | 3.161 |
| 48 | 3,5-Dichlorobenzyl (1-(4-(1H-1,2,3-triazol-4-yl)butanoyl)azepan-4-yl)carbamate; | 0.791 |
| 49 | 3,5-Dichlorobenzyl 3-(4-(1H-1,2,3-triazol-4-yl)butanamido)pyrrolidine-1-carboxylate; | 0.048 |
| 49a | (S)-or (R)-3,5-Dichlorobenzyl 3-(4-(1H-1,2,3-triazol-4-yl)butanamido)pyrrolidine-1-carboxylate; | >1 |
| 49b | (S)-or (R)-3,5-Dichlorobenzyl 3-(4-(1H-1,2,3-triazol-4-yl)butanamido)pyrrolidine-1-carboxylate; | 0.263 |
| 50 | 3,5-Dichlorobenzyl 3-(4-(1H-1,2,3-triazol-4-yl)butanamido)azetidine-1-carboxylate; | 0.012 |
| 51 | 3,5-Dimethylbenzyl 4-(4-(1H-1,2,3-triazol-4-yl)butanamido)piperidine-1-carboxylate; | 0.006 |
| 52 | 3,5-Dichlorobenzyl (1-(5-(1H-1,2,3-triazol-4-yl)pentanoyl)piperidin-4-yl)carbamate; | 0.042 |
| 53 | 4-(Trifluoromethyl)benzyl 4-(4-(1H-1,2,3-triazol-4-yl)butanamido)piperidine-1-carboxylate; | 0.04 |
| 54 | 4-(1H-1,2,3-Triazol-4-yl)-N-(1-(3-(4-(trifluoromethyl)phenyl)propanoyl)piperidin-4-yl)butanamide; | 0.087 |
| 55 | N-(1-(2-(3,5-Dichlorophenoxy)acetyl)piperidin-4-yl)-4-(1H-1,2,3-triazol-4-yl)butanamide; | 0.154 |
| 56 | 3-Chloro-5-methylbenzyl 4-(4-(1H-1,2,3-triazol-4-yl)butanamido)piperidine-1-carboxylate; | 0.01 |
| 57 | 3,5-Dichlorobenzyl 4-((3-(1H-1,2,3-triazol-5-yl)propanamido)methyl)piperidine-1-carboxylate; | 0.017 |
| 58 | 2,4-Dichlorobenzyl 4-(4-(1H-1,2,3-triazol-4-yl)butanamido)piperidine-1-carboxylate; | 0.206 |
| 59 | 3,5-Dichlorophenethyl 4-(4-(1H-1,2,3-triazol-4-yl)butanamido)piperidine-1-carboxylate; | 0.024 |
| 60 | 3,5-dichlorobenzyl 4-(3-(((1H-1,2,3-triazol-4-yl)methyl)amino)-3-oxopropyl)piperidine-1-carboxylate; | 0.007 |
| 61 | 3,5-dichlorobenzyl 4-(2-((2-(1H-1,2,3-triazol-4-yl)ethyl)amino)-2-oxoethyl)piperidine-1-carboxylate; | 0.015 |
| 62 | 3-methyl-5-(trifluoromethyl)benzyl 4-(4-(1H-1,2,3-triazol-4-yl)butanamido)piperidine-1-carboxylate; | 0.005 |
| 63 | 3-bromo-5-(trifluoromethyl)benzyl 4-(4-(1H-1,2,3-triazol-4-yl)butanamido)piperidine-1-carboxylate; | 0.003 |
| 64 | 3-chloro-5-cyanobenzyl 4-(5-(1H-1,2,3-triazol-4-yl)pentanamido)piperidine-1-carboxylate; | 0.008 |
| 65 | 3-chloro-5-cyanobenzyl 4-(3-(1H-1,2,3-triazol-4-yl)propanamido)piperidine-1-carboxylate; | 0.026 |
| 66 | 3-cyano-5-(trifluoromethyl)benzyl 4-(4-(1H-1,2,3-triazol-4-yl)butanamido)piperidine-1-carboxylate | 0.004 |
| 67 | 3,5-dichlorobenzyl 4-(6-(1H-1,2,3-triazol-4-yl)hexanamido)piperidine-1-carboxylate | 0.004 |

The invention claimed is:
1. A compound of formula (I)

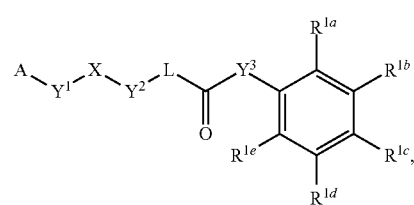

or a pharmaceutically acceptable salt thereof, wherein

A is selected from

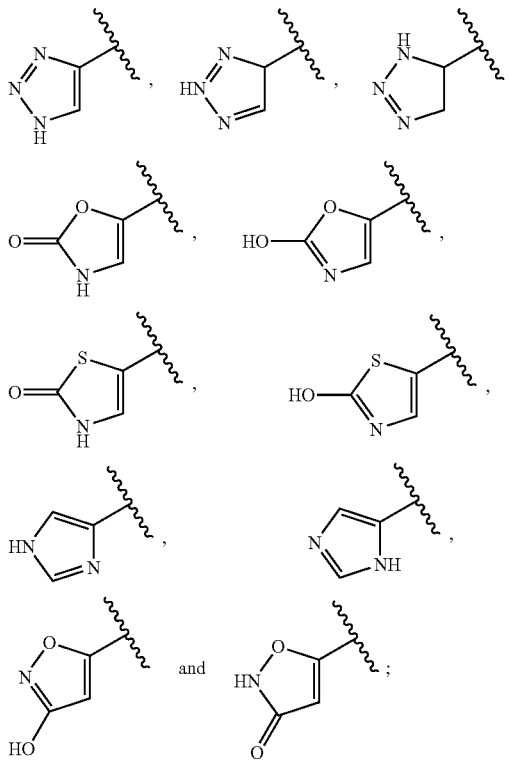

and

Y¹ is —(CR$^{2b}$R$^{2c}$)$_m$— or —CH=CH—;
X is selected from —C(=O)—, —N(R³)—C(=O)— and —C(=O)—N(R³)—;
Y² is —(CR$^{4a}$R$^{4b}$)$_n$—;
m is selected from 0, 1, 2, 3, 4 and 5;
n is selected from 0, 1, 2, 3, 4 and 5;
wherein when Y¹ is —(CR$^{2b}$R$^{2c}$)$_m$— the sum of m and n is not less than 2 and no more than 5; or
A-Y¹—X— is L is selected from W is CH or N;
Z is selected from CH$_2$, O and NR$^{5c}$;
Y³ is selected from —O—(CR$^{6a}$R$^{6b}$)—, —(CR$^{6c}$R$^{6d}$)—O—, —CH=CH—, —CR$^{6e}$R$^{6f}$—CR$^{6g}$R$^{6h}$—, and —O—(CR$^{6i}$R$^{6j}$—CR$^{6k}$R$^{6l}$)—;
R$^{1a}$, R$^{1b}$, R$^{1c}$, R$^{1d}$ and R$^{1e}$ are defined according to any one of
(a) R$^{1b}$ is halogen; R$^{1d}$ is halogen, CN, C$_{1-4}$haloalkyl or C$_{1-4}$haloalkoxy; and R$^{1a}$, R$^{1c}$ and R$^{1e}$ are H;
(b) R$^{1b}$ is halogen; R$^{1d}$ is halogen, CN, C$_{1-4}$haloalkyl or C$_{1-4}$haloalkoxy; R$^{1c}$ is halogen; and R$^{1a}$ and R$^{1e}$ are H;
(c) R$^{1b}$ is C$_{1-4}$alkyl; R$^{1d}$ is C$_{1-4}$alkyl, C$_{1-4}$haloalkoxy or CN; R$^{1a}$, R$^{1c}$ and R$^{1e}$ are H;
(d) R$^{1b}$ is CN; R$^{1d}$ is C$_{1-4}$haloalkyl or C$_{1-4}$haloalkoxy; and R$^{1a}$, R$^{1c}$ and R$^{1e}$ are H;
(e) R$^{1b}$ is C$_{1-4}$haloalkyl or C$_{1-4}$haloalkoxy; and R$^{1a}$, R$^{1c}$ and R$^{1e}$ are H; and R$^{1d}$ is H or CN;
(f) R$^{1a}$ is halogen; R$^{1c}$ is halogen, CN, C$_{1-4}$haloalkyl or C$_{1-4}$haloalkoxy; and R$^{1b}$, R$^{1d}$ and R$^{1e}$ are H;
(g) R$^{1c}$ is halogen, CN, C$_{1-4}$haloalkyl or C$_{1-4}$haloalkoxy; and R$^{1a}$, R$^{1b}$ and R$^{1e}$ are H; and R$^{1d}$ is halogen, CN, C$_{1-4}$haloalkyl, C$_{1-4}$haloalkoxy, or H;
R$^{2a}$, R$^{2b}$, R$^{2c}$, R$^{3}$, R$^{4a}$, R$^{4b}$, R$^{4c}$, R$^{4d}$, R$^{5a}$, R$^{5b}$, R$^{5c}$, R$^{6a}$, R$^{6b}$, R$^{6c}$, R$^{6d}$, R$^{6e}$, R$^{6f}$, R$^{6g}$, R$^{6h}$, R$^{6i}$, R$^{6j}$, R$^{6k}$ and R$^{6l}$ are independently selected from H and C$_{1-4}$alkyl.

2. The compound or salt according to claim 1, wherein R$^{1a}$, R$^{1b}$, R$^{1c}$, R$^{1d}$ and R$^{1e}$ are defined according to any one of
(a) R$^{1b}$ is fluoro, chloro or bromo; R$^{1d}$ is fluoro, chloro, bromo, CN, methyl, trifluoromethyl or trifluoromethoxy; and R$^{1a}$, R$^{1c}$ and R$^{1e}$ are H;

(c) $R^{1b}$ is methyl; $R^{1d}$ is methyl, trfluoromethyl, trifluoromethoxy or CN; $R^{1a}$, $R^{1c}$ and $R^{1e}$ are H;

(f) $R^{1a}$ is fluoro, chloro or bromo; $R^{1c}$ is fluoro, chloro, bromo, CN, methyl, trifluoromethyl or trifluoromethoxy; and $R^{1b}$, $R^{1d}$ and $R^{1e}$ are H; and (g) $R^{1c}$ is fluoro, chloro, bromo, CN, methyl, trifluoromethyl or trifluoromethoxy; and $R^{1a}$, $R^{1b}$ and $R^{1e}$ are H; and $R^{1d}$ is fluoro, chloro, bromo, CN, methyl, trifluoromethyl, trifluoromethoxy, or H.

3. The compound or salt according to claim 1, wherein $Y^3$ is

—O—($CR^{6a}R^{6b}$))— or —($CR^{6c}R^{6d}$)—O—.

4. The compound or salt according to claim 1, wherein X is selected from —N($R^3$)—C(=O)— and —C(=O)—N($R^3$)—.

5. The compound or salt according to claim 1, wherein the compound is of formula (II)

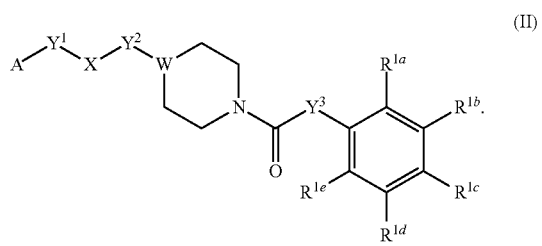

(II)

6. The compound or salt according to claim 1, wherein —$Y^1$—X—$Y^2$— is selected from

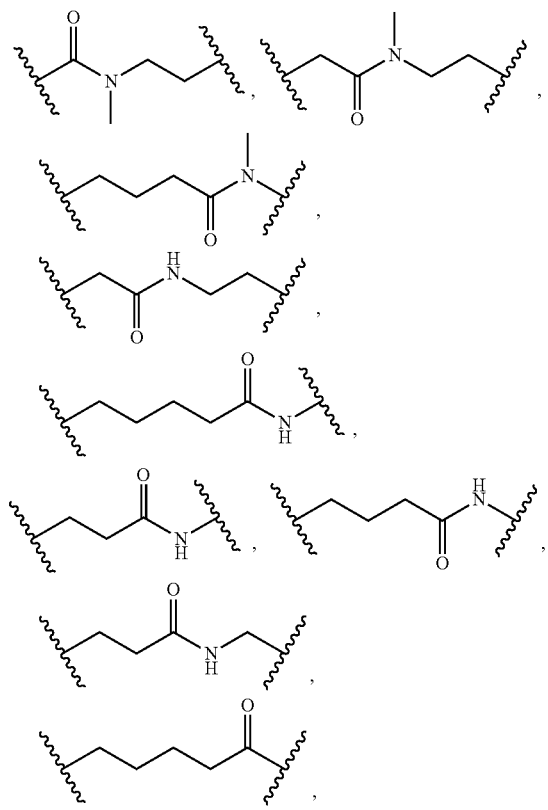

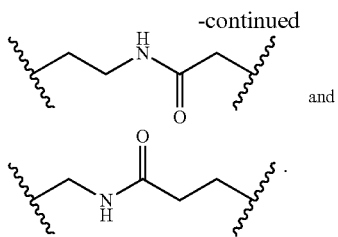

and

7. A pharmaceutical composition comprising a compound according to claim 1, or a pharmaceutically acceptable salt thereof, and a pharmaceutically acceptable carrier.

8. A pharmaceutical combination comprising a therapeutically effective amount of the compound according to claim 1, or a pharmaceutically acceptable salt thereof, and one or more therapeutically active co-agent.

9. The compound of claim 1, selected from the group consisting of:
- 3,5-dichlorobenzyl 4-(2-(3-hydroxy-N-methylisoxazole-5-carboxamido)ethyl)piperidine-1-carboxylate;
- 3,5-dichlorobenzyl 4-(2-((2-methoxy-3,4-dioxocyclobut-1-en-1-yl)(methyl)amino)ethyl)piperidine-1-carboxylate;
- 3,5-dichlorobenzyl 4-(2-((2-ethoxy-3,4-dioxocyclobut-1-en-1-yl)amino)ethyl)piperidine-1-carboxylate;
- 3,5-dichlorobenzyl 4-(2-((2-hydroxy-3,4-dioxocyclobut-1-en-1-yl)amino)ethyl)piperidine-1-carboxylate;
- 3,5-dichlorobenzyl 4-((3-(3-hydroxyisoxazol-5-yl)propanamido)methyl)-2-methylpiperidine-1-carboxylate;
- 3,5-dichlorobenzyl 4-(2-(N-methyl-2-(1H-1,2,3-triazol-4-yl)acetamido)ethyl)piperidine-1-carboxylate;
- 3,5-dichlorobenzyl 4-(2-(2-(1H-1,2,3-triazol-4-yl)acetamido)ethyl)piperidine-1-carboxylate;
- (E)-3,5-dichlorobenzyl 4-(3-(1H-imidazol-4-yl)acrylamido)piperidine-1-carboxylate;
- 3,5-dichlorobenzyl 2-(2-((2-ethoxy-3,4-dioxocyclobut-1-en-1-yl)amino)ethyl)morpholine-4-carboxylate;
- 3,5-dichlorobenzyl 2-(2-(2-oxo-2,3-dihydrooxazole-5-carboxamido)ethyl)morpholine-4-carboxylate;
- 3,5-dichlorobenzyl 2-(2-(N-methyl-2-oxo-2,3-dihydrooxazole-5-carboxamido)ethyl)morpholine-4-carboxylate;
- 3,5-dichlorobenzyl 2-(2-((2-ethoxy-3,4-dioxocyclobut-1-en-1-yl)(methyl)amino)ethyl)morpholine-4-carboxylate;
- 3,5-dichlorobenzyl 4-(2-(N-methyl-2-oxo-2,3-dihydrothiazole-5-carboxamido)ethyl)piperidine-1-carboxylate;
- 3,5-dichlorobenzyl 4-(4-(1H-1,2,3-triazol-4-yl)butanamido)piperidine-1-carboxylate;
- 3,5-dichlorobenzyl 4-(N-methyl-4-(1H-1,2,3-triazol-4-yl)butanamido)piperidine-1-carboxylate;
- 3,5-dichlorobenzyl 4-(3-(1H-1,2,3-triazol-4-yl)propanamido)piperidine-1-carboxylate;
- 3,5-dichlorobenzyl 4-(5-(1H-1,2,3-triazol-4-yl)pentanamido)piperidine-1-carboxylate;
- 3,5-dichlorobenzyl 4-(2-(2-oxo-2,3-dihydrooxazole-5-carboxamido)ethyl)piperidine-1-carboxylate;
- 3,5-dichlorobenzyl 4-(2-(3-(3-hydroxyisoxazol-5-yl)propanamido)ethyl)piperidine-1-carboxylate;
- 3,5-dichlorobenzyl 4-(3-(3-hydroxyisoxazol-5-yl)propanamido)piperidine-1-carboxylate;
- 3,5-dichlorobenzyl 4-(2-(N-methyl-2-oxo-2,3-dihydrooxazole-4-carboxamido)ethyl)piperidine-1-carboxylate;

3,5-dichlorobenzyl 4-(3-(N-methyl-2-oxo-2,3-dihydrooxazole-5-carboxamido)propyl)piperazine-1-carboxylate;

3,5-dichlorobenzyl 4-(2-(2-oxo-2,3-dihydrooxazole-5-carboxamido)ethyl)piperazine-1-carboxylate;

(E)-N-(2-(1-(3-(3,5-dichlorophenyl)acryloyl)piperidin-4-yl)ethyl)-N-methyl-2-oxo-2,3-dihydrooxazole-5-carboxamide;

(E)-N-(2-(1-(3-(3,5-dichlorophenyl)acryloyl)piperidin-4-yl)ethyl)-2-oxo-2,3-dihydrooxazole-5-carboxamide;

3,5-dichlorobenzyl 4-(2-(N-methyl-2-oxo-2,3-dihydrooxazole-5-carboxamido)ethyl)piperidine-1-carboxylate;

3,5-dichlorobenzyl 4-(3-(3-hydroxyisoxazol-5-yl)propanamido)methyl)piperidine-1-carboxylate;

3,5-dichlorobenzyl 4-(3-(1H-1,2,3-triazole-4-carboxamido)propyl)piperazine-1-carboxylate;

3,5-dichlorobenzyl 4-(2-(N-methyl-1H-1,2,3-triazole-4-carboxamido)ethyl)piperidine-1-carboxylate;

3-Chloro-5-cyanobenzyl 4-(2-(N-methyl-1H-1,2,3-triazole-4-carboxamido)ethyl)piperidine-1-carboxylate;

3-Chloro-5-fluorobenzyl 4-(4-(1H-1,2,3-triazol-4-yl)butanamido)piperidine-1-carboxylate;

(E)-N-(1-(3-(3,5-Dichlorophenyl)acryloyl)piperidin-4-yl)-4-(1H-1,2,3-triazol-4-yl)butanamide;

(E)-N-(1-(3-(2,4-Dichlorophenyl)acryloyl)piperidin-4-yl)-4-(1H-1,2,3-triazol-4-yl)butanamide;

3,5-Dichlorobenzyl 4-((4-(1H-1,2,3-triazol-5-yl)butanamido)methyl)piperidine-1-carboxylate;

N-(1-(3-(3,5-Dichlorophenyl)propanoyl)piperidin-4-yl)-4-(1H-1,2,3-triazol-4-yl)butanamide;

N-(1-(3-(2,4-Dichlorophenyl)propanoyl)piperidin-4-yl)-4-(1H-1,2,3-triazol-4-yl)butanamide;

3-Chloro-5-cyanobenzyl 4-(4-(1H-1,2,3-triazol-4-yl)butanamido)piperidine-1-carboxylate;

3,5-Dichlorobenzyl 3-(4-(1H-1,2,3-triazol-4-yl)butanamido)-8-azabicyclo[3.2.1]octane-8-carboxylate;

3,5-Dichlorobenzyl 4-(4-(1H-1,2,3-triazol-4-yl)butanamido)azepane-1-carboxylate;

3,5-Dichlorobenzyl(8-(4-(1H-1,2,3-triazol-4-yl)butanoyl)-8-azabicyclo[3.2.1]octan-3-yl)carbamate;

3,5-Dichlorobenzyl(1-(4-(1H-1,2,3-triazol-4-yl)butanoyl)azepan-4-yl)carbamate;

3,5-Dichlorobenzyl 3-(4-(1H-1,2,3-triazol-4-yl)butanamido)pyrrolidine-1-carboxylate;

(S)- or (R)-3,5-Dichlorobenzyl 3-(4-(1H-1,2,3-triazol-4-yl)butanamido)pyrrolidine-1-carboxylate;

(S)- or (R)-3,5-Dichlorobenzyl 3-(4-(1H-1,2,3-triazol-4-yl)butanamido)pyrrolidine-1-carboxylate;

3,5-Dichlorobenzyl 3-(4-(1H-1,2,3-triazol-4-yl)butanamido)azetidine-1-carboxylate;

3,5-Dimethylbenzyl 4-(4-(1H-1,2,3-triazol-4-yl)butanamido)piperidine-1-carboxylate;

3,5-Dichlorobenzyl(1-(5-(1H-1,2,3-triazol-4-yl)pentanoyl)piperidin-4-yl)carbamate;

4-(Trifluoromethyl)benzyl 4-(4-(1H-1,2,3-triazol-4-yl)butanamido)piperidine-1-carboxylate;

4-(1H-1,2,3-Triazol-4-yl)-N-(1-(3-(4-(trifluoromethyl)phenyl)propanoyl)piperidin-4-yl)butanamide;

N-(1-(2-(3,5-Dichlorophenoxy)acetyl)piperidin-4-yl)-4-(1H-1,2,3-triazol-4-yl)butanamide;

3-Chloro-5-methylbenzyl 4-(4-(1H-1,2,3-triazol-4-yl)butanamido)piperidine-1-carboxylate;

3,5-Dichlorobenzyl 4-((3-(1H-1,2,3-triazol-5-yl)propanamido)methyl)piperidine-1-carboxylate;

2,4-Dichlorobenzyl 4-(4-(1H-1,2,3-triazol-4-yl)butanamido)piperidine-1-carboxylate;

3,5-Dichlorophenethyl 4-(4-(1H-1,2,3-triazol-4-yl)butanamido)piperidine-1-carboxylate;

3,5-dichlorobenzyl 4-(3-(((1H-1,2,3-triazol-4-yl)methyl)amino)-3-oxopropyl)piperidine-1-carboxylate;

3,5-dichlorobenzyl 4-(2-((2-(1H-1,2,3-triazol-4-yl)ethyl)amino)-2-oxoethyl)piperidine-1-carboxylate;

3-methyl-5-(trifluoromethyl)benzyl 4-(4-(1H-1,2,3-triazol-4-yl)butanamido)piperidine-1-carboxylate;

3-bromo-5-(trifluoromethyl)benzyl 4-(4-(1H-1,2,3-triazol-4-yl)butanamido)piperidine-1-carboxylate;

3-chloro-5-cyanobenzyl 4-(5-(1H-1,2,3-triazol-4-yl)pentanamido)piperidine-1-carboxylate;

3-chloro-5-cyanobenzyl 4-(3-(1H-1,2,3-triazol-4-yl)propanamido)piperidine-1-carboxylate;

3-cyano-5-(trifluoromethyl)benzyl 4-(4-(1H-1,2,3-triazol-4-yl)butanamido)piperidine-1-carboxylate;

3,5-dichlorobenzyl 4-(6-(1H-1,2,3-triazol-4-yl)hexanamido)piperidine-1-carboxylate;

or a pharmaceutically acceptable salt thereof.

10. A compound which is 3,5-dichlorobenzyl 4-(3-(1H-1,2,3-triazole-4-carboxamido)propyl)piperazine-1-carboxylate.

11. A compound which is 3-Cyano-5-(trifluoromethyl)benzyl 4-(4-(1H-1,2,3-triazol-4-yl)butanamido)piperidine-1-carboxylate.

* * * * *